US012790351B2

(12) United States Patent
Burnett et al.

(10) Patent No.: US 12,790,351 B2
(45) Date of Patent: Nov. 10, 2026

(54) COVALENT Ras INHIBITORS AND USES THEREOF

(71) Applicant: Revolution Medicines, Inc., Redwood City, CA (US)

(72) Inventors: G. Leslie Burnett, Redwood City, CA (US); Anne V. Edwards, San Mateo, CA (US); Adrian L. Gill, Atherton, CA (US); John E. Knox, Emerald Hills, CA (US); Elena S. Koltun, Foster City, CA (US); Jennifer Pitzen, Fremont, CA (US)

(73) Assignee: Revolution Medicines, Inc., Redwood City, CA (US)

(*) Notice: Subject to any disclaimer, the term of this patent is extended or adjusted under 35 U.S.C. 154(b) by 377 days.

(21) Appl. No.: 18/501,211

(22) Filed: Nov. 3, 2023

(65) Prior Publication Data

US 2024/0262847 A1 Aug. 8, 2024

Related U.S. Application Data

(63) Continuation of application No. PCT/US2022/027773, filed on May 5, 2022.

(60) Provisional application No. 63/184,500, filed on May 5, 2021.

(51) Int. Cl.

*C07D 519/00* (2006.01)
*A61K 31/55* (2006.01)
*A61K 47/64* (2017.01)

(52) U.S. Cl.

CPC ............ *C07D 519/00* (2013.01); *A61K 31/55* (2013.01); *A61K 47/64* (2017.08)

(58) Field of Classification Search

CPC ....... C07D 519/00; A61K 31/55; A61K 47/64
See application file for complete search history.

(56) References Cited

U.S. PATENT DOCUMENTS

| | | | |
|---|---|---|---|
| 9,428,845 | B1 | 8/2016 | Verdine et al. |
| 9,989,535 | B2 | 6/2018 | Verdine et al. |
| 10,039,839 | B2 | 8/2018 | Verdine et al. |
| 10,203,323 | B2 | 2/2019 | Verdine et al. |
| 10,466,249 | B2 | 11/2019 | Verdine et al. |
| 10,533,016 | B2 | 1/2020 | Verdine et al. |
| 10,948,495 | B2 | 3/2021 | Verdine et al. |
| 10,989,710 | B2 | 4/2021 | Verdine et al. |
| 11,059,830 | B2 | 7/2021 | Verdine et al. |
| 11,566,007 | B2 | 1/2023 | Koltun et al. |
| 11,608,346 | B2 | 3/2023 | Koltun et al. |
| 11,644,460 | B2 | 5/2023 | Verdine et al. |
| 11,690,915 | B2 | 7/2023 | Aay et al. |
| 11,739,074 | B2 | 8/2023 | Aggen et al. |
| 11,952,352 | B2 | 4/2024 | Gill et al. |
| 11,987,590 | B2 | 5/2024 | Verdine et al. |
| 12,202,845 | B2 | 1/2025 | Knox et al. |
| 12,252,497 | B2 | 3/2025 | Burnett et al. |
| 12,280,113 | B2 | 4/2025 | Koltun et al. |
| 2015/0250896 | A1 | 9/2015 | Zhao |
| 2017/0097359 | A1 | 4/2017 | Verdine et al. |
| 2020/0199102 | A1 | 6/2020 | Mulvihill et al. |
| 2021/0285955 | A1 | 9/2021 | Mulvihill et al. |
| 2021/0405060 | A1 | 12/2021 | Verdine et al. |
| 2022/0143202 | A1 | 5/2022 | Verdine et al. |
| 2022/0144849 | A1 | 5/2022 | Verdine et al. |
| 2022/0396589 | A1 | 12/2022 | Buckl et al. |
| 2023/0100838 | A1 | 3/2023 | Pitzen et al. |
| 2023/0106174 | A1 | 4/2023 | Koltun et al. |
| 2023/0226186 | A1 | 7/2023 | Aay et al. |
| 2023/0233569 | A1 | 7/2023 | Singh et al. |
| 2023/0234929 | A1 | 7/2023 | Gill et al. |
| 2024/0108630 | A1 | 4/2024 | Corcoran et al. |
| 2024/0139185 | A1 | 5/2024 | Jin et al. |
| 2024/0262847 | A1 | 8/2024 | Burnett et al. |
| 2024/0277796 | A1 | 8/2024 | Seamon |
| 2024/0352036 | A1 | 10/2024 | Li et al. |
| 2024/0352038 | A1 | 10/2024 | Li et al. |
| 2024/0368190 | A1 | 11/2024 | Li et al. |
| 2024/0383920 | A1 | 11/2024 | Li et al. |
| 2024/0400523 | A1 | 12/2024 | Koltun et al. |
| 2024/0426833 | A1 | 12/2024 | Mulvihill et al. |
| 2025/0009753 | A1 | 1/2025 | Blaj et al. |
| 2025/0041295 | A1 | 2/2025 | Jiang et al. |
| 2025/0049810 | A1 | 2/2025 | Jiang et al. |
| 2025/0074923 | A1 | 3/2025 | Knox et al. |
| 2025/0076289 | A1 | 3/2025 | Verdine et al. |

(Continued)

FOREIGN PATENT DOCUMENTS

| | | | |
|---|---|---|---|
| WO | WO-2015/054572 | A1 | 4/2015 |
| WO | WO-2015/184349 | A2 | 12/2015 |

(Continued)

OTHER PUBLICATIONS

KRAS G12D inhibitor 18, PubChem SID: 485510480 from MedChemexpress MCE, External ID: HY-156819, available to the public on Dec. 14, 2023 (Year: 2023).*

McGregor et al., "Expanding the Scope of Electrophiles Capable of Targeting K-Ras Oncogenes," Biochem. 56(25) (Jun. 2017) (Supporting Information Included) (30 Pages).

International Search Report and Written Opinion for International Patent Application No. PCT/US2022/027773, mailed Jul. 7, 2022 (9 pages).

Ostrem et al., "K-Ras(G12C) inhibitors allosterically control GTP affinity and effector interactions," Nature 503(7477):548-551 (methods and data included) (Nov. 2013) (14 pages).

(Continued)

*Primary Examiner* — Erich A Leeser
(74) *Attorney, Agent, or Firm* — Clark + Elbing LLP

(57) ABSTRACT

The disclosure features compounds, or pharmaceutically acceptable salts thereof, alone and in combination with other therapeutic agents, pharmaceutical compositions, and protein conjugates thereof, capable of modulating biological processes including Ras, and their uses in the treatment of cancers.

14 Claims, No Drawings

Specification includes a Sequence Listing.

(56) References Cited

U.S. PATENT DOCUMENTS

| | | | |
|---|---|---|---|
| 2025/0085291 | A1 | 3/2025 | Verdine et al. |
| 2025/0101031 | A1 | 3/2025 | Verdine et al. |
| 2025/0115551 | A1 | 4/2025 | Li et al. |
| 2025/0121077 | A1 | 4/2025 | Verdine et al. |
| 2025/0129097 | A1 | 4/2025 | Cregg et al. |
| 2025/0145643 | A1 | 5/2025 | Koltun et al. |
| 2025/0154171 | A1 | 5/2025 | Knox et al. |
| 2025/0186590 | A1 | 6/2025 | Koltun et al. |
| 2025/0195662 | A1 | 6/2025 | Koltun et al. |
| 2025/0197423 | A1 | 6/2025 | Koltun et al. |
| 2025/0206715 | A1 | 6/2025 | Mulvihill et al. |

FOREIGN PATENT DOCUMENTS

| | | | |
|---|---|---|---|
| WO | WO-2016/044772 | A1 | 3/2016 |
| WO | WO-2016/112279 | A1 | 7/2016 |
| WO | WO-2016/112295 | A1 | 7/2016 |
| WO | WO-2016/164675 | A1 | 10/2016 |
| WO | WO-2017/059207 | A1 | 4/2017 |
| WO | WO-2017/181061 | A1 | 10/2017 |
| WO | WO-2017/201161 | A1 | 11/2017 |
| WO | WO-2018/187401 | A1 | 10/2018 |
| WO | WO-2018/187423 | A1 | 10/2018 |
| WO | WO-2018/206539 | A1 | 11/2018 |
| WO | WO-2018/218071 | A1 | 11/2018 |
| WO | WO-2019/051084 | A1 | 3/2019 |
| WO | WO-2019/110751 | A1 | 6/2019 |
| WO | WO-2019/215203 | A1 | 11/2019 |
| WO | WO-2020/097537 | A2 | 5/2020 |
| WO | WO-2020/132597 | A1 | 6/2020 |
| WO | WO-2021/041671 | A1 | 3/2021 |
| WO | WO-2021/091956 | A1 | 5/2021 |
| WO | WO-2021/091967 | A1 | 5/2021 |
| WO | WO-2021/091982 | A1 | 5/2021 |
| WO | WO-2021/106231 | A1 | 6/2021 |
| WO | WO-2021/107160 | A1 | 6/2021 |
| WO | WO-2021/108683 | A1 | 6/2021 |
| WO | WO-2021/215544 | A1 | 10/2021 |
| WO | WO-2022/002102 | A1 | 1/2022 |
| WO | WO-2022/015375 | A1 | 1/2022 |
| WO | WO-2022/031678 | A1 | 2/2022 |
| WO | WO-2022/042630 | A1 | 3/2022 |
| WO | WO-2022/060836 | A1 | 3/2022 |
| WO | WO-2022/066646 | A1 | 3/2022 |
| WO | WO-2022/072783 | A1 | 4/2022 |
| WO | WO-2022/212894 | A1 | 10/2022 |
| WO | WO-2022/235864 | A1 | 11/2022 |
| WO | WO-2022/235866 | A1 | 11/2022 |
| WO | WO-2022/235870 | A1 | 11/2022 |
| WO | WO-2022/251292 | A1 | 12/2022 |
| WO | WO-2023/060253 | A1 | 4/2023 |
| WO | WO-2023/133543 | A1 | 7/2023 |

OTHER PUBLICATIONS

PubChem SID 485510480, “Kras G12D inhibitor 18,” National Center for Biotechnology Information, <https://pubchem.ncbi.nlm.nih.gov/substance/485510480>, modified Dec. 14, 2023, retrieved on Jun. 16, 2025 (5 pages).

Wikipedia contributors (Nov. 1, 2018). Covalent radius. In Wikipedia, The Free Encyclopedia. Retrieved Aug. 8, 2025, from https://en.wikipedia.org/w/index.php?title=Covalent_radius&oldid=866771454 (3 pages).

* cited by examiner

COVALENT Ras INHIBITORS AND USES THEREOF

CROSS-REFERENCE TO RELATED APPLICATION

The present application is a continuation application of International Patent Application No. PCT/US2022/027773, filed on May 5, 2022, which claims the benefit of priority to U.S. Provisional Patent Application No. 63/184,500, filed on May 5, 2021, which is hereby incorporated by reference in its entirety.

SEQUENCE LISTING

The instant application contains a Sequence Listing which has been submitted electronically in XML format and is hereby incorporated by reference in its entirety. Said XML copy, created on Nov. 2, 2023, is named '51432-015002_Sequence_Listing_11_2_23' and is 4,013 bytes in size.

BACKGROUND OF THE INVENTION

The vast majority of small molecule drugs act by binding a functionally important pocket on a target protein, thereby modulating the activity of that protein. For example, cholesterol-lowering drugs known as statins bind the enzyme active site of HMG-COA reductase, thus preventing the enzyme from engaging with its substrates. The fact that many such drug/target interacting pairs are known may have misled some into believing that a small molecule modulator could be discovered for most, if not all, proteins provided a reasonable amount of time, effort, and resources. This is far from the case. Current estimates are that only about 10% of all human proteins are targetable by small molecules. Bojadzic and Buchwald, Curr Top Med Chem 18(8): 674-699 (2019). The other 90% are currently considered refractory or intractable toward above-mentioned small molecule drug discovery. Such targets are commonly referred to as "undruggable." These undruggable targets include a vast and largely untapped reservoir of medically important human proteins. Thus, there exists a great deal of interest in discovering new molecular modalities capable of modulating the function of such undruggable targets.

It has been well established in literature that Ras proteins (K-Ras, H-Ras and N-Ras) play an essential role in various human cancers and are therefore appropriate targets for anticancer therapy. Dysregulation of Ras proteins by activating mutations, overexpression or upstream activation is common in human tumors, and activating mutations in Ras are frequently found in human cancer. See, e.g., Prior et al., Cancer Res 72(10): 2457-2467 (2012). Of the Ras proteins, K-Ras is the most frequently mutated and is therefore an important target for cancer therapy. Despite extensive small molecule drug discovery efforts against Ras during the last several decades, a drug directly targeting Ras is still not available for clinical use. However, the reputation of the "undruggability" of Ras proteins by small molecules has been challenged of late (see, e.g., Ostrem et al., Nature 503(7477), 548-551 (2013). Additional efforts are needed to uncover new medical treatments for cancers driven by Ras mutations, such as by identifying new small molecule Ras inhibitors.

SUMMARY OF THE INVENTION

Covalent drugs bond covalently to their biological target. Covalent drugs have a long history in medicine and will continue to impact drug discovery and human health into the future. Biological targets with nucleophilic functional groups such as —SH, —OH, —$NH_2$, —COOH and others are potentially amenable to a covalent drug discovery approach. For example, the irreversibly covalent drug ibrutinib was approved by the FDA in 2013 for the treatment of mantle cell lymphoma, and its label has since been expanded.

Provided herein are compounds which are capable of binding to a Ras protein to form a conjugate by reacting as electrophiles and forming a covalent bond with a nucleophilic Ras amino acid of a Ras protein. Conjugate formation via covalent binding of a compound of the present invention may disrupt downstream signaling of Ras. The Ras protein may be wild type or a mutant Ras protein. The amino acid may, for example, be an aspartic acid or a glutamic acid of a Ras protein, or other acidic residue. In some embodiments, compounds of the invention form a covalent bond with an aspartic acid or a glutamic acid at the 12 position or the 13 position of a mutant K-Ras, H-Ras or N-Ras protein. In some embodiments, compounds disclosed herein form a covalent bond with the aspartic acid residue at position 12 of K-Ras G12D. In some embodiments, compounds disclosed herein form a covalent bond with the aspartic acid residue at position 13 of K-Ras G13D. In some embodiments, compounds disclosed herein form a covalent bond with the glutamic acid residue at position 12 of K-Ras G12E. In some embodiments, compounds disclosed herein form a covalent bond with the glutamic acid residue at position 13 of K-Ras G13E. In some embodiments, a compound of the present invention may be useful in the treatment of diseases and disorders in which Ras, particularly mutated Ras, play a role, such as cancer. Additional aspects of the foregoing are further described herein.

In some embodiments, a compound, or a pharmaceutically acceptable salt thereof, has the structure of Formula (I), Formula (II), Formula (III) or Formula (IV):

(I)

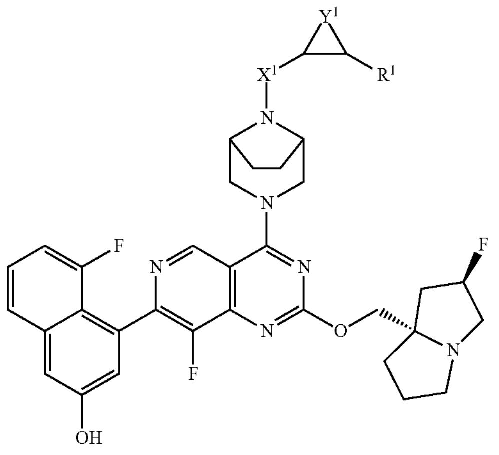

-continued (II)

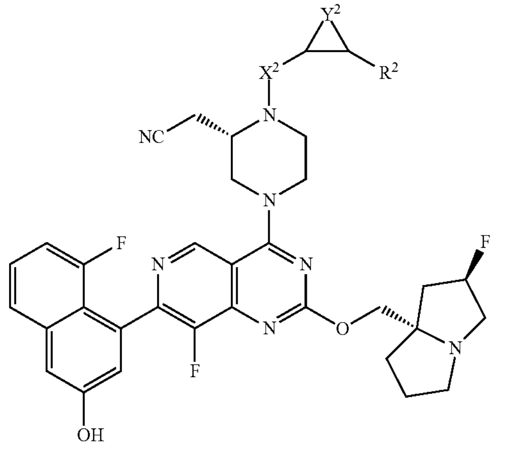

(III)

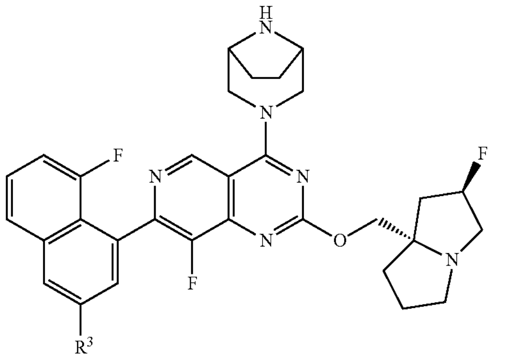

(IV)

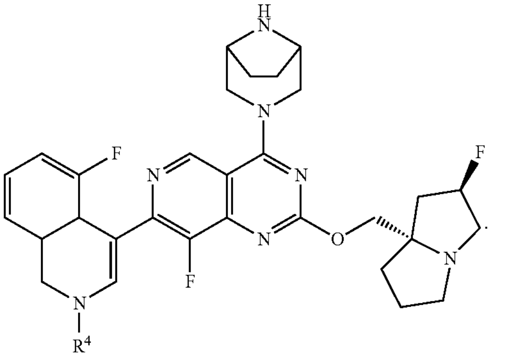

Also provided is a pharmaceutical composition comprising a compound of the present invention, or a pharmaceutically acceptable salt thereof, and a pharmaceutically acceptable excipient.

Further provided is a conjugate, or salt thereof, comprising a Ras protein covalently bound to a compound of the present invention.

Further provided is a Ras protein comprising a covalent bond to a compound of the present invention. In some embodiments, an inhibited Ras protein covalently bonded to a compound of the present invention is provided. In some embodiments, a wild-type Ras protein covalently bonded to a compound of the present invention is provided. In some embodiments, a mutated Ras protein covalently bonded to a compound of the present invention is provided.

Also provided is a method of producing a conjugate comprising contacting a Ras protein with a compound of the present invention, or a pharmaceutically acceptable salt thereof, or a pharmaceutical composition comprising such a compound or salt, under conditions sufficient for the compound to react covalently with the Ras protein, or under conditions suitable to permit conjugate formation. Conjugates produced by such methods are also provided.

Further provided is a method of treating cancer in a subject in need thereof, the method comprising administering to the subject a therapeutically effective amount of a compound of the present invention, or a pharmaceutically acceptable salt thereof, or a pharmaceutical composition comprising such a compound or salt.

Also provided is a method of inhibiting a Ras protein in a cell, the method comprising contacting the cell with an effective amount of a compound of the present invention, or a pharmaceutically acceptable salt thereof, or a pharmaceutical composition comprising such a compound or salt.

In some embodiments, a method of treating a Ras protein-related disorder in a subject in need thereof is provided, the method comprising administering to the subject a therapeutically effective of a compound of the present invention, or a pharmaceutically acceptable salt thereof, or a pharmaceutical composition comprising such a compound or salt.

DETAILED DESCRIPTION OF THE INVENTION

Definitions

In this application, unless otherwise clear from context, (i) the term "a" is understood to mean "at least one"; (ii) the term "or" is understood to mean "and/or"; (iii) the terms "comprising" and "including" are understood to encompass itemized components or steps whether presented by themselves or together with one or more additional components or steps; and (iv) where ranges are provided, endpoints are included.

As used herein, the term "about" is used to indicate that a value includes the standard deviation of error for the device or method being employed to determine the value.

As used herein, the term "adjacent" in the context of describing adjacent atoms refers to bivalent atoms that are directly connected by a covalent bond.

It will be understood that the term "binding" as used herein, typically refers to association (e.g., non-covalent or covalent, hydrogen bonds, van der Waals interaction, hydrophobic interactions, magnetism, and combinations thereof) between or among two or more entities. "Direct" binding involves physical contact between entities or moieties; indirect binding involves physical interaction by way of physical contact with one or more intermediate entities. Binding between two or more entities can typically be assessed in any of a variety of contexts—including where interacting entities or moieties are studied in isolation or in the context of more complex systems (e.g., while covalently or otherwise associated with a carrier entity or in a biological system or cell).

As used herein, the term "corresponding to" is often used to designate a structural element or moiety in a compound of interest that shares a position (e.g., in three-dimensional space or relative to another element or moiety) with one present in an appropriate reference compound. For example, in some embodiments, the term is used to refer to position/identity of a residue in a polymer, such as an amino acid residue in a polypeptide or a nucleotide residue in a nucleic acid. Those of ordinary skill will appreciate that, for purposes of simplicity, residues in such a polymer are often designated using a canonical numbering system based on a reference related polymer, so that a residue in a first polymer "corresponding to" a residue at position 190 in the reference polymer, for example, need not actually be the 190th residue in the first polymer but rather corresponds to the residue found at the 190th position in the reference polymer; those of ordinary skill in the art readily appreciate how to identify "corresponding" amino acids, including through use of one or more commercially-available algorithms specifically designed for polymer sequence comparisons.

As used herein, the term "inhibitor" refers to a compound that i) inhibits, decreases or reduces the effects of a protein, such as a Ras protein; or ii) inhibits, decreases, reduces, or delays one or more biological events. The term "inhibiting" or any variation thereof, includes any measurable decrease or complete inhibition to achieve a desired result. For example, there may be a decrease of about, at most about, or at least about 5%, 10%, 15%, 20%, 25%, 30%, 35%, 40%, 45%, 50%, 55%, 60%, 65%, 70%, 75%, 80%, 85%, 90%, 95%, 99%, or more, or any range derivable therein, reduction of activity (e.g., Ras activity) compared to normal.

The term "pure" means substantially pure or free of unwanted components (e.g., other compounds), material defilement, admixture or imperfection.

Those skilled in the art will appreciate that certain compounds described herein can exist in one or more different isomeric (e.g., stereoisomers, geometric isomers, tautomers) and/or isotopic (e.g., in which one or more atoms has been substituted with a different isotope of the atom, such as hydrogen substituted for deuterium) forms. Unless otherwise indicated or clear from context, a depicted structure can be understood to represent any such isomeric or isotopic form, individually or in combination.

Compounds described herein can be asymmetric (e.g., having one or more stereocenters). All stereoisomers, such as enantiomers and diastereomers, are intended unless otherwise indicated. Compounds of the present disclosure that contain asymmetrically substituted carbon atoms can be isolated in optically active or racemic forms. Methods on how to prepare optically active forms from optically active starting materials are known in the art, such as by resolution of racemic mixtures or by stereoselective synthesis. Many geometric isomers of olefins, C═N double bonds, and the like can also be present in the compounds described herein, and all such stable isomers are contemplated in the present disclosure. Cis and trans geometric isomers of the compounds of the present disclosure are described and may be isolated as a mixture of isomers or as separated isomeric forms.

In some embodiments, one or more compounds depicted herein may exist in different tautomeric forms. As will be clear from context, unless explicitly excluded, references to such compounds encompass all such tautomeric forms. In some embodiments, tautomeric forms result from the swapping of a single bond with an adjacent double bond and the concomitant migration of a proton. In certain embodiments, a tautomeric form may be a prototropic tautomer, which is an isomeric protonation states having the same empirical formula and total charge as a reference form. Examples of moieties with prototropic tautomeric forms are ketone—enol pairs, amide—imidic acid pairs, lactam—lactim pairs, amide—imidic acid pairs, enamine—imine pairs, and annular forms where a proton can occupy two or more positions of a heterocyclic system, such as, 1H- and 3H-imidazole, 1H-, 2H- and 4H-1,2,4-triazole, 1H- and 2H-isoindole, and 1H- and 2H-pyrazole. In some embodiments, tautomeric forms can be in equilibrium or sterically locked into one form by appropriate substitution. In certain embodiments, tautomeric forms result from acetal interconversion.

Those skilled in the art will appreciate that, in some embodiments, isotopes of compounds described herein may be prepared or utilized in accordance with the present invention. "Isotopes" refers to atoms having the same atomic number but different mass numbers resulting from a different number of neutrons in the nuclei. For example, isotopes of hydrogen include tritium and deuterium. Other isotopes include, e.g., $^{2}H$, $^{3}H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$. In some embodiments, an isotopic substitution (e.g., substitution of hydrogen with deuterium) may alter the physicochemical properties of the molecules, such as metabolism, the distribution of metabolites, or the rate of racemization of a chiral center. Methods of incorporating one or more of such isotopes into compounds are known to those of skill in the art.

A non-limiting example of a moiety of the present invention containing deuterium atom substitution includes, e.g.,

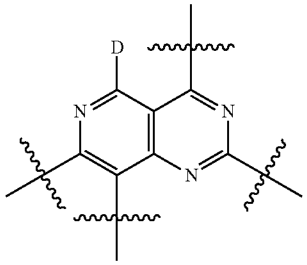 [SMILES: *c1nc(*)c2c([2H])nc(*)c(*)c2n1]

Additionally, the following moieities are further examples that may contain one or more deuterium substitutions in compounds of the present invention, where any position "R" may be deuterium (D):

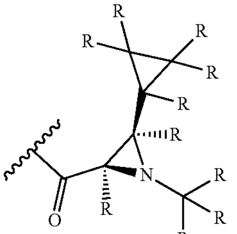
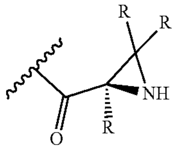
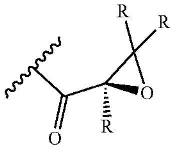
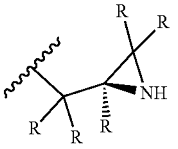
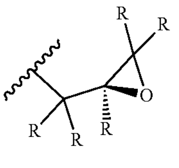
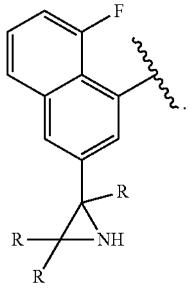

As is known in the art, many chemical entities can adopt a variety of different solid forms such as, for example, amorphous forms or crystalline forms (e.g., polymorphs, hydrates, solvate). In some embodiments, compounds of the present invention may be utilized in any such form, including in any solid form. In some embodiments, compounds described or depicted herein may be provided or utilized in hydrate or solvate form.

The term "optionally substituted X" (e.g., "optionally substituted alkyl") is intended to be equivalent to "X, wherein X is optionally substituted" (e.g., "alkyl, wherein said alkyl is optionally substituted"). It is not intended to mean that the feature "X" (e.g., alkyl) per se is optional. As described herein, certain compounds of interest may contain one or more "optionally substituted" moieties. In general, the term "substituted", whether preceded by the term "optionally" or not, means that one or more hydrogens of the designated moiety are replaced with a suitable substituent, e.g., any of the substituents or groups described herein. Unless otherwise indicated, an "optionally substituted" group may have a suitable substituent at each substitutable position of the group, and when more than one position in any given structure may be substituted with more than one substituent selected from a specified group, the substituent may be either the same or different at every position. For example, in the term "optionally substituted $C_1$-$C_6$ alkyl-$C_2$-$C_9$ heteroaryl," the alkyl portion, the heteroaryl portion, or both, may be optionally substituted. Combinations of substituents envisioned by the present disclosure are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group may be, independently, deuterium; halogen; —$(CH_2)_{0-4}R^\circ$; —$(CH_2)_{0-4}OR^\circ$; —$O(CH_2)_{0-4}R^\circ$; —O—$(CH_2)_{0-4}C(O)OR^\circ$; —$(CH_2)_{0-4}CH(OR^\circ)_2$; —$(CH_2)_{0-4}SR^\circ$; —$(CH_2)_{0-4}Ph$, which may be substituted with $R^\circ$; —$(CH_2)_{0-4}O(CH_2)_{0-1}Ph$ which may be substituted with $R^\circ$; —CH═CHPh, which may be substituted with $R^\circ$; —$(CH_2)_{0-4}O(CH_2)_{0-1}$-pyridyl which may be substituted with $R^\circ$; 4-11 membered saturated or unsaturated heterocycloalkyl (e.g., 4-8 membered saturated or unsaturated heterocycloalkyl (e.g., pyridyl)) which may be further optionally substituted (e.g., with a methyl); 3-8 membered saturated or unsaturated cycloalkyl (e.g., cyclopropyl, cyclobutyl, or cyclopentyl); —$NO_2$; —CN; —$N_3$; —$(CH_2)_{0-4}N(R^\circ)_2$; —$(CH_2)_{0-4}N(R^\circ)C(O)R^\circ$; —$N(R^\circ)C(S)R^\circ$; —$(CH_2)_{0-4}N(R^\circ)C(O)NR^\circ_2$; —$N(R^\circ)C(S)NR^\circ_2$; —$(CH_2)_{0-4}N(R^\circ)C(O)OR^\circ$; —$N(R^\circ)N(R^\circ)C(O)R^\circ$; —$N(R^\circ)N(R^\circ)C(O)NR^\circ_2$; —$N(R^\circ)N(R^\circ)C(O)OR^\circ$; —$(CH_2)_{0-4}C(O)R^\circ$; —$C(S)R^\circ$; —$(CH_2)_{0-4}C(O)OR^\circ$; —$(CH_2)_{0-4}$—C(O)—$N(R^\circ)_2$; —$(CH_2)_{0-4}$—C(O)—$N(R^\circ)$—$S(O)_2$—$R^\circ$; —$C(NCN)NR^\circ_2$; —$(CH_2)_{0-4}C(O)SR^\circ$; —$(CH_2)_{0-4}C(O)OSiR^\circ_3$; —$(CH_2)_{0-4}OC(O)R^\circ$; —$OC(O)(CH_2)_{0-4}SR^\circ$; —$SC(S)SR^\circ$; —$(CH_2)_{0-4}SC(O)R^\circ$; —$(CH_2)_{0-4}C(O)NR^\circ_2$; —$C(S)NR^\circ_2$; —$C(S)SR^\circ$; —$(CH_2)_{0-4}OC(O)NR^\circ_2$; —$C(O)N(OR^\circ)R^\circ$; —$C(O)C(O)R^\circ$; —$C(O)CH_2C(O)R^\circ$; —$C(NOR^\circ)R^\circ$; —$(CH_2)_{0-4}SSR^\circ$; —$(CH_2)_{0-4}S(O)_2R^\circ$; —$(CH_2)_{0-4}S(O)_{2}0R^\circ$; —$(CH_2)_{0-4}OS(O)_2R^\circ$; —$S(O)_2NR^\circ_2$; —$(CH_2)_{0-4}S(O)R^\circ$; —$N(R^\circ)S(O)_2NR^\circ_2$; —$N(R^\circ)S(O)_2R^\circ$; —$N(OR^\circ)R^\circ$; —$C(NOR^\circ)NR^\circ_2$; —$C(NH)NR^\circ_2$; —$P(O)_2R^\circ$; —$P(O)R^\circ_2$; —$P(O)(OR^\circ)_2$; —$OP(O)R^\circ_2$; —$OP(O)(OR^\circ)_2$; —$OP(O)(OR^\circ)R^\circ$, —$SiR^\circ_3$; —($C_{1-4}$ straight or branched alkylene)O—$N(R^\circ)_2$; or —($C_{1-4}$ straight or branched alkylene)C(O)O—$N(R^\circ)_2$, wherein each $R^\circ$ may be substituted as defined below and is independently hydrogen, —$C_{1-6}$ aliphatic, —$CH_2Ph$, —$O(CH_2)_{0-1}Ph$, —$CH_2$-(5-6 membered heteroaryl ring), or a 3-6-membered saturated, partially unsaturated, or aryl ring having 0-4 heteroatoms independently selected from nitrogen, oxygen, or sulfur, or, notwithstanding the definition above, two independent occurrences of $R^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^\circ$ (or the ring formed by taking two independent occurrences of $R^\circ$ together with their intervening atoms), may be, independently, halogen, —$(CH_2)_{0-2}R^\bullet$, -(halo$R^\bullet$), —$(CH_2)_{0-2}OH$, —$(CH_2)_{0-2}0R^\bullet$, —$(CH_2)_{0-2}CH(OR^\bullet)_2$; —O(halo$R^\bullet$), —CN, —$N_3$, —$(CH_2)_{0-2}C(O)R^\bullet$, —$(CH_2)_{0-2}C(O)OH$, —$(CH_2)_{0-2}C(O)OR^\bullet$, —$(CH_2)_{0-2}SR^\bullet$, —$(CH_2)_{0-2}SH$, —$(CH_2)_{0-2}NH_2$, —$(CH_2)_{0-2}NHR^\bullet$, —$(CH_2)_{0-2}NR^\bullet_2$, —$NO_2$, —$SiR^\bullet_3$, —$OSiR^\bullet_3$, —$C(O)SR^\bullet$, —($C_{1-4}$ straight or branched alkylene)$C(O)OR^\bullet$, or —$SSR^\bullet$ wherein each $R^\bullet$ is unsubstituted or where preceded by "halo" is substituted only with one or more halogens, and is independently selected from $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R^\circ$ include ═O and ═S.

Suitable divalent substituents on a saturated carbon atom of an "optionally substituted" group include the following: ═O, ═S, ═$NNR^\bullet_2$, ═$NNHC(O)R^\bullet$, ═$NNHC(O)OR^\bullet$, ═$NNHS(O)_2R^\bullet$, ═$NR^\bullet$, ═$NOR^\bullet$, —$O(C(R^\bullet_2))_{2-3}O$—, or —$S(C(R^\bullet_2))_{2-3}S$—, wherein each independent occurrence of $R^\bullet$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —$O(CR^\bullet_2)_{2-3}O$—, wherein each independent occurrence of $R^\bullet$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of $R^\bullet$ include halogen, —$R^\bullet$, -(halo$R^\bullet$), —OH, —$OR^\bullet$, —O(halo$R^\bullet$), —CN, —C(O)OH, —$C(O)OR^\bullet$, —$NH_2$, —$NHR^\bullet$, —$NR^\bullet_2$, or —$NO_2$, wherein each $R^\bullet$ is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —$R^\dagger$, —$NR^\dagger_2$, —$C(O)R^\dagger$, —$C(O)OR^\dagger$, —$C(O)C(O)R^\dagger$, —$C(O)CH_2C(O)R^\dagger$, —$S(O)_2R^\dagger$, —$S(O)_2NR^\dagger_2$, —$C(S)NR^\dagger_2$, —$C(NH)NR^\dagger_2$, or —$N(R^\dagger)S(O)_2R^\dagger$; wherein each $R^\dagger$ is independently hydrogen, $C_{1-6}$ aliphatic which may be substituted as defined below, unsubstituted —OPh, or an unsubstituted 3-6-membered saturated, partially unsaturated, or aryl ring having 0-4 heteroatoms independently selected from nitrogen, oxygen, or sulfur, or, notwithstanding the definition above, two independent occurrences of $R^†$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on an aliphatic group of $R^†$ are independently halogen, —$R^•$, -(halo$R^•$), —OH, —$OR^•$, —O(halo$R^•$), —CN, —C(O)OH, —C(O)$OR^•$, —$NH_2$, —$NHR^•$, —$NR^•_2$, or —$NO_2$, wherein each $R^•$ is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R^†$ include =O and =S.

The term "alkoxy," as used herein, refers to a —O—$C_1$-$C_{20}$ alkyl group, wherein the alkoxy group is attached to the remainder of the compound through an oxygen atom.

The term "alkyl," as used herein, refers to a saturated, straight or branched monovalent hydrocarbon group containing from 1 to 20 (e.g., from 1 to 10 or from 1 to 6) carbons. In some embodiments, an alkyl group is unbranched (i.e., is linear); in some embodiments, an alkyl group is branched. Alkyl groups are exemplified by, but not limited to, methyl, ethyl, n- and iso-propyl, n-, sec-, iso- and tert-butyl, and neopentyl.

The term "alkylene," as used herein, represents a saturated divalent hydrocarbon group derived from a straight or branched chain saturated hydrocarbon by the removal of two hydrogen atoms, and is exemplified by methylene, ethylene, isopropylene, and the like. The term "$C_x$-$C_y$ alkylene" represents alkylene groups having between x and y carbons. Exemplary values for x are 1, 2, 3, 4, 5, and 6, and exemplary values for y are 2, 3, 4, 5, 6, 7, 8, 9, 10, 12, 14, 16, 18, or 20 (e.g., $C_1$-$C_6$, $C_1$-$C_{10}$, $C_2$-$C_{20}$, $C_2$-$C_6$, $C_2$-$C_{10}$, or $C_2$-$C_{20}$ alkylene). In some embodiments, the alkylene can be further substituted with 1, 2, 3, or 4 substituent groups as defined herein.

The term "alkenyl," as used herein, represents monovalent straight or branched chain groups of, unless otherwise specified, from 2 to 20 carbons (e.g., from 2 to 6 or from 2 to 10 carbons) containing one or more carbon-carbon double bonds and is exemplified by ethenyl, 1-propenyl, 2-propenyl, 2-methyl-1-propenyl, 1-butenyl, and 2-butenyl. Alkenyls include both cis and trans isomers. The term "alkenylene," as used herein, represents a divalent straight or branched chain groups of, unless otherwise specified, from 2 to 20 carbons (e.g., from 2 to 6 or from 2 to 10 carbons) containing one or more carbon-carbon double bonds.

The term "alkynyl," as used herein, represents monovalent straight or branched chain groups from 2 to 20 carbon atoms (e.g., from 2 to 4, from 2 to 6, or from 2 to 10 carbons) containing a carbon-carbon triple bond and is exemplified by ethynyl, and 1-propynyl.

The term "amino," as used herein, represents —$N(R^†)_2$, e.g., —$NH_2$ and —$N(CH_3)_2$.

The term "aminoalkyl," as used herein, represents an alkyl moiety substituted on one or more carbon atoms with one or more amino moieties.

The term "amino acid," as described herein, refers to a molecule having a side chain, an amino group, and an acid group (e.g., —$CO_2H$ or —$SO_3H$), wherein the amino acid is attached to the parent molecular group by the side chain, amino group, or acid group (e.g., the side chain). As used herein, the term "amino acid" in its broadest sense, refers to any compound or substance that can be incorporated into a polypeptide chain, e.g., through formation of one or more peptide bonds. In some embodiments, an amino acid has the general structure $H_2N$—C(H)(R)—COOH. In some embodiments, an amino acid is a naturally-occurring amino acid. In some embodiments, an amino acid is a synthetic amino acid; in some embodiments, an amino acid is a D-amino acid; in some embodiments, an amino acid is an L-amino acid. "Standard amino acid" refers to any of the twenty standard L-amino acids commonly found in naturally occurring peptides. Exemplary amino acids include alanine, arginine, asparagine, aspartic acid, cysteine, glutamic acid, glutamine, glycine, histidine, optionally substituted hydroxylnorvaline, isoleucine, leucine, lysine, methionine, norvaline, ornithine, phenylalanine, proline, pyrrolysine, selenocysteine, serine, taurine, threonine, tryptophan, tyrosine, and valine.

The term "aryl" or "ara" as used herein, represents a monovalent monocyclic, bicyclic, or multicyclic ring system formed by carbon atoms, wherein the ring attached to the pendant group is aromatic. Examples of aryl groups are phenyl, naphthyl, phenanthrenyl, and anthracenyl. An aryl ring can be attached to its pendant group at any heteroatom or carbon ring atom that results in a stable structure and any of the ring atoms can be optionally substituted unless otherwise specified.

The terms "carbocyclic" and "carbocyclyl," as used herein, refer to a monovalent, optionally substituted $C_3$-$C_{12}$ monocyclic, bicyclic, or tricyclic ring structure, which may be bridged, fused or spirocyclic, in which all the rings are formed by carbon atoms and at least one ring is non-aromatic. Carbocyclic structures include cycloalkyl, cycloalkenyl, and cycloalkynyl groups. Examples of carbocyclyl groups are cyclohexyl, cyclohexenyl, cyclooctynyl, 1,2-dihydronaphthyl, 1,2,3,4-tetrahydronaphthyl, fluorenyl, indenyl, indanyl, decalinyl, and the like. A carbocyclic ring can be attached to its pendant group at any ring atom that results in a stable structure and any of the ring atoms can be optionally substituted unless otherwise specified.

The term "carbonyl," as used herein, represents a C(O) group, which can also be represented as C=O.

The term "carboxyl," as used herein, means —$CO_2H$, (C=O)(OH), COOH, or C(O)OH or the unprotonated counterparts.

The term "cyano," as used herein, represents a —CN group.

The term "cycloalkyl," as used herein, represents a monovalent saturated cyclic hydrocarbon group, which may be bridged, fused or spirocyclic having from three to eight ring carbons, unless otherwise specified, and is exemplified by cyclopropyl, cyclobutyl, cyclopentyl, cyclohexyl, cycloheptyl, and cycloheptyl.

The term "cycloalkenyl," as used herein, represents a monovalent, non-aromatic, saturated cyclic hydrocarbon group, which may be bridged, fused or spirocyclic having from three to eight ring carbons, unless otherwise specified, and containing one or more carbon-carbon double bonds.

The term "diastereomer," as used herein, means stereoisomers that are not mirror images of one another and are non-superimposable on one another.

The term "enantiomer," as used herein, means each individual optically active form of a compound of the invention, having an optical purity or enantiomeric excess (as determined by methods standard in the art) of at least 80% (i.e., at least 90% of one enantiomer and at most 10% of the other enantiomer), preferably at least 90% and more preferably at least 98%.

The term "isomer," as used herein, means any tautomer, stereoisomer, enantiomer, or diastereomer of any compound of the invention. It is recognized that the compounds of the invention can have one or more chiral centers or double bonds and, therefore, exist as stereoisomers, such as double-bond isomers (i.e., geometric E/Z isomers) or diastereomers (e.g., enantiomers (i.e., (+) or (−)) or cis/trans isomers). According to the invention, the chemical structures depicted herein, and therefore the compounds of the invention, encompass all the corresponding stereoisomers, that is, both the stereomerically pure form (e.g., geometrically pure, enantiomerically pure, or diastereomerically pure) and enantiomeric and stereoisomeric mixtures, e.g., racemates. Enantiomeric and stereoisomeric mixtures of compounds of the invention can typically be resolved into their component enantiomers or stereoisomers by well-known methods, such as chiral-phase gas chromatography, chiral-phase high performance liquid chromatography, crystallizing the compound as a chiral salt complex, or crystallizing the compound in a chiral solvent. Enantiomers and stereoisomers can also be obtained from stereomerically or enantiomerically pure intermediates, reagents, and catalysts by well-known asymmetric synthetic methods.

The term "stereoisomer," as used herein, refers to all possible different isomeric as well as conformational forms which a compound may possess (e.g., a compound of any formula described herein), in particular all possible stereochemically and conformationally isomeric forms, all diastereomers, enantiomers or conformers of the basic molecular structure. Some compounds of the present invention may exist in different tautomeric forms, all of the latter being included within the scope of the present invention.

The term "haloacetyl," as used herein, refers to an acetyl group wherein at least one of the hydrogens has been replaced by a halogen.

The term "haloalkyl," as used herein, represents an alkyl moiety substituted on one or more carbon atoms with one or more of the same of different halogen moieties.

The term "halogen," as used herein, represents a halogen selected from bromine, chlorine, iodine, or fluorine.

The term "heteroalkyl," as used herein, refers to an "alkyl" group, as defined herein, in which at least one carbon atom has been replaced with a heteroatom (e.g., an O, N, or S atom). The heteroatom may appear in the middle or at the end of the radical.

The term "heteroaryl," as used herein, represents a monovalent, monocyclic or polycyclic ring structure that contains at least one fully aromatic ring: i.e., they contain 4n+2 pi electrons within the monocyclic or polycyclic ring system and contains at least one ring heteroatom selected from N, O, or S in that aromatic ring. Exemplary unsubstituted heteroaryl groups are of 1 to 12 (e.g., 1 to 11, 1 to 10, 1 to 9, 2 to 12, 2 to 11, 2 to 10, or 2 to 9) carbons. The term "heteroaryl" includes bicyclic, tricyclic, and tetracyclic groups in which any of the above heteroaromatic rings is fused to one or more, aryl or carbocyclic rings, e.g., a phenyl ring, or a cyclohexane ring. Examples of heteroaryl groups include, but are not limited to, pyridyl, pyrazolyl, benzooxazolyl, benzoimidazolyl, benzothiazolyl, imidazolyl, thiazolyl, quinolinyl, tetrahydroquinolinyl, and 4-azaindolyl. A heteroaryl ring can be attached to its pendant group at any ring atom that results in a stable structure and any of the ring atoms can be optionally substituted unless otherwise specified. In some embodiment, the heteroaryl is substituted with 1, 2, 3, or 4 substituents groups.

The term "heterocycloalkyl," as used herein, represents a monovalent monocyclic, bicyclic or polycyclic ring system, which may be bridged, fused or spirocyclic, wherein at least one ring is non-aromatic and wherein the non-aromatic ring contains one, two, three, or four heteroatoms independently selected from the group consisting of nitrogen, oxygen, and sulfur. The 5-membered ring has zero to two double bonds, and the 6- and 7-membered rings have zero to three double bonds. Exemplary unsubstituted heterocycloalkyl groups are of 1 to 12 (e.g., 1 to 11, 1 to 10, 1 to 9, 2 to 12, 2 to 11, 2 to 10, or 2 to 9) carbons. The term "heterocycloalkyl" also represents a heterocyclic compound having a bridged multicyclic structure in which one or more carbons or heteroatoms bridges two non-adjacent members of a monocyclic ring, e.g., a quinuclidinyl group. The term "heterocycloalkyl" includes bicyclic, tricyclic, and tetracyclic groups in which any of the above heterocyclic rings is fused to one or more aromatic, carbocyclic, heteroaromatic, or heterocyclic rings, e.g., an aryl ring, a cyclohexane ring, a cyclohexene ring, a cyclopentane ring, a cyclopentene ring, a pyridine ring, or a pyrrolidine ring. Examples of heterocycloalkyl groups are pyrrolidinyl, piperidinyl, 1,2,3,4-tetrahydroquinolinyl, decahydroquinolinyl, dihydropyrrolopyridine, and decahydronapthyridinyl. A heterocycloalkyl ring can be attached to its pendant group at any ring atom that results in a stable structure and any of the ring atoms can be optionally substituted unless otherwise specified.

The term "hydroxy," as used herein, represents a —OH group.

The term "hydroxyalkyl," as used herein, represents an alkyl moiety substituted on one or more carbon atoms with one or more —OH moieties.

The term "sulfonyl," as used herein, represents an $—S(O)_2—$ group.

Those of ordinary skill in the art, reading the present disclosure, will appreciate that certain compounds described herein may be provided or utilized in any of a variety of forms such as, for example, salt forms, protected forms, pro-drug forms, ester forms, isomeric forms (e.g., optical or structural isomers), isotopic forms, etc. In some embodiments, reference to a particular compound may relate to a specific form of that compound. In some embodiments, reference to a particular compound may relate to that compound in any form. In some embodiments, for example, a preparation of a single stereoisomer of a compound may be considered to be a different form of the compound than a racemic mixture of the compound; a particular salt of a compound may be considered to be a different form from another salt form of the compound; a preparation containing one conformational isomer ((Z) or (E)) of a double bond may be considered to be a different form from one containing the other conformational isomer ((E) or (Z)) of the double bond; a preparation in which one or more atoms is a different isotope than is present in a reference preparation may be considered to be a different form; etc.

The term "Ras protein" means a protein from the Ras family of related GTPase proteins including K-Ras, H-Ras, and N-Ras. A Ras protein may be a wild-type protein or a mutant protein. In some embodiments, a Ras protein is not a wild-type protein.

K-Ras is encoded by the K-RAS gene. The term "K-Ras" also refers to natural variants of the wild-type K-Ras protein, such as proteins having at least 85% identity (e.g., 85%, 86%, 87%, 88%, 89%, 90%, 91%, 92%, 93%, 94%, 95%, 96%, 97%, 98%, 99%, 99.9% identity, or more) to the amino acid sequence of wild-type K-Ras, which is set forth in SEQ ID NO: 1.

SEQ ID NO: 1

```
MTEYKLVVVG AGGVGKSALT IQLIQNHFVD EYDPTIEDSY

RKQVVIDGET CLLDILDTAG QEEYSAMRDQ YMRTGEGFLC

VFAINNTKSF EDIHHYREQI KRVKDSEDVP MVLVGNKCDL

PSRTVDTKQA QDLARSYGIP FIETSAKTRQ RVEDAFYTLV

REIRQYRLKK ISKEEKTPGC VKIKKCIIM
```

H-Ras is encoded by the H-RAS gene. The term "H-Ras" also refers to natural variants of the wild-type H-Ras protein, such as proteins having at least 85% identity (e.g., 85%, 86%, 87%, 88%, 89%, 90%, 91%, 92%, 93%, 94%, 95%, 96%, 97%, 98%, 99%, 99.9% identity, or more) to the amino acid sequence of wild-type H-Ras, which is set forth in SEQ ID NO: 2.

SEQ ID NO: 2

```
MTEYKLVVVG AGGVGKSALT IQLIQNHFVD EYDPTIEDSY

RKQVVIDGET CLLDILDTAG QEEYSAMRDQ YMRTGEGFLC

VFAINNTKSF EDIHQYREQI KRVKDSDDVP MVLVGNKCDL

AARTVESRQA QDLARSYGIP YIETSAKTRQ GVEDAFYTLV

REIRQHKLRK LNPPDESGPG CMSCKCVLS
```

N-Ras is encoded by the N-RAS gene. The term "N-Ras" also refers to natural variants of the wild-type N-Ras protein, such as proteins having at least 85% identity (e.g., 85%, 86%, 87%, 88%, 89%, 90%, 91%, 92%, 93%, 94%, 95%, 96%, 97%, 98%, 99%, 99.9% identity, or more) to the amino acid sequence of wild-type N-Ras, which is set forth in SEQ ID NO: 3.

SEQ ID NO: 3

```
MTEYKLVVVG AGGVGKSALT IQLIQNHFVD EYDPTIEDSY

RKQVVIDGET CLIDILDTAG QEEYSAMRDQ YMRTGEGFLC

VFAINNSKSF ADINLYREQI KRVKDSDDVP MVLVGNKCDL

PTRTVDTKQA HELAKSYGIP FIETSAKTRQ GVEDAFYTLV

REIRQYRMKK LNSSDDGTQG CMGLPCVVM
```

A given Ras protein may be bound to GDP or GTP. In response to exposure of the cell to certain growth promoting stimuli, RAS is induced to exchange its bound GDP for a GTP. With GTP bound, RAS is "switched on" and is able to interact with and activate other proteins (its "downstream targets"). Ras itself has a very low intrinsic ability to hydrolyze GTP back to GDP, thus turning itself into the off state. Switching R as off requires extrinsic proteins termed GTPase-activating proteins (GAPs) that interact with RAS and greatly accelerate the conversion of GTP to GDP. Any mutation in Ras which affects its ability to interact with GAP or to convert GTP back to GDP will result in a prolonged activation of the protein and consequently a prolonged signal to the cell telling it to continue to grow and divide. Because these signals result in cell growth and division, overactive RAS signaling may ultimately lead to cancer. Methods of determining the GDP or GTP binding state of a Ras protein are known in the art.

As used herein, the term "mutant Ras protein" means a Ras protein that comprises at least one mutation in which an amino acid in the corresponding wild-type Ras protein is mutated to a different amino acid, e.g., a glycine is mutated to an aspartic acid, serine, or cysteine. The term "mutation" as used herein indicates any modification of a nucleic acid or polypeptide which results in an altered nucleic acid or polypeptide. The term "mutation" may include, for example, point mutations, deletions or insertions of single or multiple residues in a polynucleotide, which includes alterations arising within a protein-encoding region of a gene as well as alterations in regions outside of a protein-encoding sequence, such as, but not limited to, regulatory or promoter sequence, as well as amplifications or chromosomal breaks or translocations.

Examples of mutant Ras proteins include, but are not limited to, K-Ras G12D, K-Ras G13D, K-Ras G12E and K-Ras G13E; N-Ras G12D, N-Ras G13D, N-Ras G12E and N-Ras G13E; and H-Ras G12D, H-Ras G13D, H-Ras G12E and H-Ras G13E, and combinations thereof. In some embodiments, mutations contemplated by the present invention include those associated with oncogenic activity.

Compounds and Conjugates of the Present Invention

Provided herein are compounds which are capable of binding to a Ras protein to form a conjugate by reacting as electrophiles and forming a covalent bond with a nucleophilic Ras amino acid of a Ras protein. In some embodiments, a compound of the present invention may be useful in the treatment of diseases and disorders in which Ras, particularly mutated Ras, play a role, such as cancer. Compounds described or depicted herein, whether expressly stated or not, may be provided or utilized in salt form, e.g., a pharmaceutically acceptable salt form, unless expressly stated to the contrary.

Covalent binding of a compound of the present invention to Ras can be reversible or irreversible. Irreversible covalent binding to GDP-bound Ras or GTP-bound Ras can be determined by methods known to those skilled in the art, for example by mass spectrometry. For example, to determine binding to GTP or GDP-Ras, a compound of the present invention may be incubated with Ras loaded with the appropriate nucleotide, then cross-linking is determined by mass spectrometry. An example protocol is provided in the Examples below.

Moreover, covalent binding of a compound of the present invention to Ras may perturb the conformation of Ras such that it modulates or disrupts binding of Ras to its effector proteins (including SOS and RAF). Ras-RAF disruption assays are known by those skilled in the art, as described for example by Lim et al., Angew. Chem. Int. Ed. 53:199 (2014). By disrupting Ras binding to its effector proteins, compounds may disrupt downstream signaling, resulting in growth inhibition or the induction of apoptosis. These effects can be measured in cell culture following compound treatment by monitoring the activation state of downstream effectors (such as the phosphorylation state of ERK), performing a cellular viability assay, and by measuring the activity of caspase-3 in a cell lysate.

Some compounds disclosed herein may form reversible covalent bonds with Ras, including boronic acids and trifluoromethyl ketones. Boronic acids are known to interact with serine and threonine residues, as described for example by Adams et al., Cancer Invest. 22:304 (2004). By extension, aspartate residues could also form reversible covalent bonds with boronic acids or other electrophiles such as trifluoromethyl ketones.

In some embodiments, upon contacting a compound of the present invention, or a pharmaceutically acceptable salt thereof, with sample containing a Ras protein, at least 20% of the Ras protein in the sample covalently reacts with the compound, or a pharmaceutically acceptable salt thereof, to form a conjugate. In some embodiments, upon contacting the compound, or a pharmaceutically acceptable salt thereof, with a sample containing a Ras protein, at least 20% (e.g., at least 30%, at least 40%, at least 50%, at least 60%, at least 70%, at least 80%, at least 90%, at least 95%, at least 99%) of the Ras protein in the sample covalently reacts (e.g., forms a conjugate including the Ras binding moiety, the linker, and the Ras protein) with the compound, or a pharmaceutically acceptable salt thereof, to form a conjugate.

Ras proteins are described herein. Accordingly, a Ras protein may be wild-type or mutant. A Ras protein may be a human Ras protein. A wild-type Ras protein may be K-Ras, H-Ras, or N-Ras. In some embodiments, a Ras protein is not a wild-type protein. In some embodiments, a Ras protein is a mutant Ras protein, such as K-Ras G12D, K-Ras G13D. Other Ras mutants are described herein. In some embodiments, the sample containing Ras protein is a sample including isolated Ras protein in a solution, e.g., a buffer solution. In some embodiments, the sample containing Ras protein is a sample including cells expressing Ras protein.

In some embodiments, a compound of the present invention binds to the GDP-bound form of a Ras protein. In some embodiments, a compound of the present invention binds to the GTP-bound form of a Ras protein. In some embodiments, a compound of the present invention binds to the GDP-bound form and the GTP-bound form of a Ras protein.

In some embodiments, a compound, or a pharmaceutically acceptable salt thereof, of Formula (0) is provided, Formula (0)

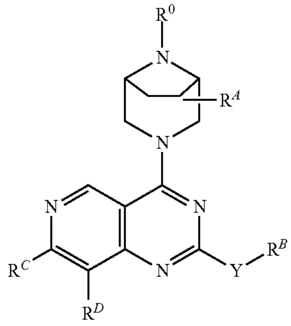

wherein:

$R^0$ is hydrogen,

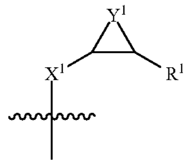

or

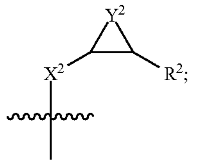

$R^A$ is hydrogen, hydroxy, halogen, $C_1$-$C_3$ cyanoalkyl, $C_1$-$C_3$ hydroxyalkyl, HC(O)—, —$CO_2R^5$, —$CO_2N(R^5)_2$, or a 5-6 membered heteroaryl; $R^B$ is hydrogen, —$N(R^5)_2$, heterocyclyl, $C_1$-$C_6$ alkyl, -L-heterocyclyl, -L-aryl, -L-heteroaryl, -L-cycloalkyl, -L-$N(R^5)_2$, -L-NHC(═NH)$NH_2$, -L-C(O)$N(R^5)_2$, -L-$C_1$-$C_6$ haloalkyl, -L-$OR^5$, -L-($CH_2OR^5$)($CH_2$)n$OR^5$ wherein n is 1-5, -L-$NR^5$C(O)-aryl, -L-COOH, or -LC(O)O$C_1$-$C_6$ alkyl, wherein the heterocyclyl and the aryl portion of -L-$NR^5$C(O)-aryl and the heterocyclyl portion of -L-heterocyclyl and the cycloalkyl portion of the -L-cycloalkyl may be optionally substituted with one or more $R^6$, and wherein the aryl or heteroaryl of the -L-aryl and the -L-heteroaryl may be optionally substituted with one or more $R^7$; each L is independently a $C_1$-$C_4$ alkylene optionally substituted with hydroxy, $C_1$-$C_4$ hydroxyalkyl or heteroaryl; $R^C$ is aryl or heteroaryl, wherein the aryl or the heteroaryl is optionally substituted with one or more $R^8$; $R^D$ is hydrogen, halogen, or $C_1$-$C_3$ alkyl; $R^1$ is hydrogen or cyclopropyl; $R^2$ is hydrogen or cyclopropyl; $X^1$ is —$CH_2$— or —C(O)—; Y is a bond, —O— or —$NR^5$—; $Y^1$ is —O— or —NH—; $Y^2$ is —O— or —NH—; each $R^5$ is independently hydrogen or $C_1$-$C_3$ alkyl; each $R^6$ is independently halogen, hydroxy, $C_1$-$C_3$ hydroxyalkyl, $C_1$-$C_3$ alkyl, $C_1$-$C_3$ haloalkyl, $C_1$-$C_3$ alkoxy, cyano, -Q-phenyl, -Q-phenyl$SO_2F$, —NHC(O)phenyl, —NHC(O)phenyl$SO_2F$, $C_1$-$C_3$ alkyl substituted with pyrazolyl, ara$C_1$-$C_3$ alkyl-, tert-butyldimethylsilyloxy$CH_2$—, —$N(R^5)_2$, ($C_1$-$C_3$ alkoxy)$C_1$-$C_3$ alkyl-, ($C_1$-$C_3$)C(O)—, oxo, ($C_1$-$C_3$ haloalkyl)C(O)—, —$SO_2F$, ($C_1$-$C_3$ alkoxy)$C_1$-$C_3$ alkoxy, —$CH_2$OC(O)$N(R^5)_2$, —$CH_2$NHC(O)O$C_1$-$C_6$ alkyl, —$CH_2$NHC(O)$N(R^5)_2$, —$CH_2$NHC(O)$C_1$-$C_6$ alkyl, —$CH_2$(pyrazolyl), —$CH_2NHSO_2C_1$-$C_6$ alkyl, —$CH_2$OC(O)heterocyclyl, —OC(O)$N(R^5)_2$, —OC(O)NH($C_1$-$C_3$ alkyl)O($C_1$-$C_3$), —OC(O)NH($C_1$-$C_3$ alkyl)O($C_1$-$C_3$ alkyl)phenyl($C_1$-$C_3$ alkyl)$N(CH_3)_2$, —OC(O)NH($C_1$-$C_3$ alkyl)O($C_1$-$C_3$ alkyl)phenyl or —OC(O)heterocycyl, —$CH_2$heterocyclyl, wherein the phenyl of —NHC(O)phenyl or —OC(O)NH($C_1$-$C_3$ alkyl)O($C_1$-$C_3$ alkyl)phenyl is optionally substituted with —C(O)H or OH and wherein the heterocyclyl of —$CH_2$heterocyclyl is optionally substituted with oxo; Q is a bond or —O—; each $R^7$ is independently halogen, hydroxy, HC(O)—, $C_1$-$C_4$ alkyl, $C_1$-$C_4$ alkoxy, $C_1$-$C_4$ haloalkyl, $C_1$-$C_4$ hydroxyalkyl, or —$N(R^5)_2$; and each $R^8$ is independently halogen, cyano, hydroxy, $C_1$-$C_4$ alkyl, —S—$C_1$-$C_3$ alkyl, $C_2$-$C_4$ alkenyl, $C_2$-$C_4$ alkynyl, $C_2$-$C_4$ hydroxyalkynyl, $C_1$-$C_3$ cyanoalkyl, triazolyl, $C_1$-$C_3$ haloalkyl, —O—$C_1$-$C_3$ haloalkyl, —S—$C_1$-$C_3$ haloalkyl, $C_1$-$C_3$ alkoxy, hydroxy$C_1$-$C_3$ alkyl, —$CH_2$C(O)$N(R^5)_2$, —$C_3$-$C_4$ alkynyl($NR^5$)$_2$, —$N(R^5)_2$, deutero$C_2$-$C_4$ alkynyl, ($C_1$-$C_3$ alkoxy)halo$C_1$-$C_3$ alkyl, or $C_3$-$C_6$ cycloalkyl, wherein said $C_3$-$C_6$ cycloalkyl is optionally substituted with halogen or $C_1$-$C_3$ alkyl, wherein at least one of $R^0$, $R^A$, $R^B$, $R^C$ and $R^D$ comprises an optionally substituted aziridine or an optionally substituted epoxide. In some embodiments, only one of $R^0$, $R^A$, $R^B$, $R^C$ and $R^D$ comprises an optionally substituted aziridine or an optionally substituted epoxide. In some embodiments, only one of $R^0$, $R^A$, $R^B$, $R^C$ and $R^D$ comprises an aziridine, an epoxide, or an aziridinyl-oxiranyl moiety.

In some embodiments regarding Formula (0), $R^A$, $R^B$, $R^C$ and $R^D$ are as defined as $R^1$, $R^2$, $R^3$ and $R^4$, respectively, in WO 2021/041671, incorporated herein by reference in its entirety. In some embodiments, a compound of the present invention is any compound of Formula (I) in WO 2021/041671, including any of compounds 1-458 therein, modified with an aziridine or an epoxide. Preparation of such modified compounds is known to those of skill in the art in view of the teachings of WO 2021/041671 and the teachings herein.

Provided herein is a compound, or a pharmaceutically acceptable salt thereof, having the structure of Formula (I0), Formula (II0), Formula (III0) or Formula (IV0):

(I0)

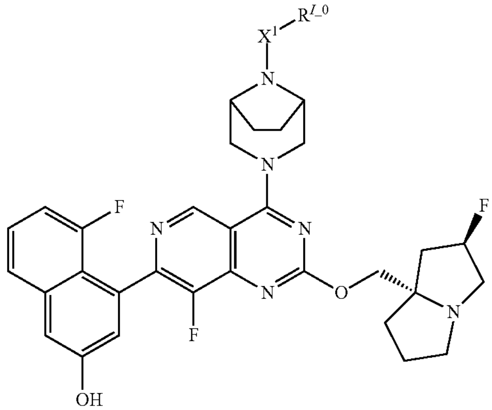

(II0)

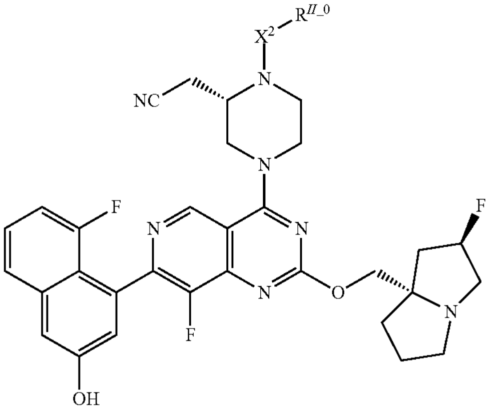

(III0)

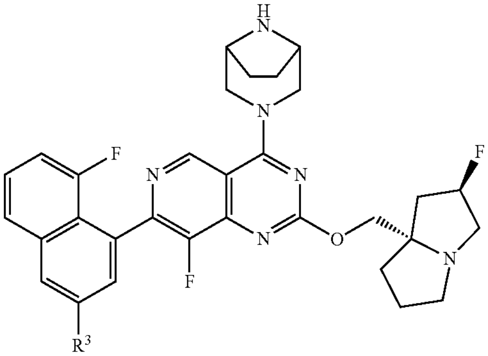

(IV0)

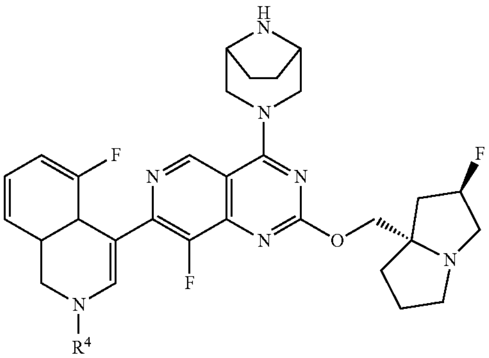

wherein:

$R^{I\_0}$ is optionally substituted aziridine or optionally substituted epoxide; $R^{II\_0}$ is optionally substituted aziridine or optionally substituted epoxide; $X^1$ is selected from —C(O)— and —$CH_2$—; $X^2$ is selected from —C(O)— and —$CH_2$—; $Y^1$ is selected from —O— and —NH—; $Y^2$ is selected from —O— and —NH—; $R^3$ is optionally substituted aziridine or optionally substituted epoxide; and $R^4$ is optionally substituted aziridine or optionally substituted epoxide. In some embodiments, $R^{I\_0}$, $R^{II\_0}$, $R^3$ and $R^4$ is each independently selected from the following, or a stereoisomer thereof:

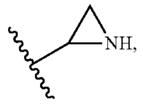 , 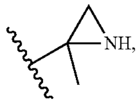 , 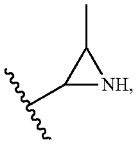 ,

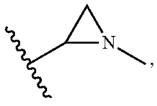 , 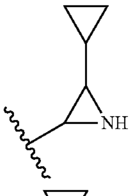 , 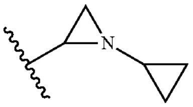 ,

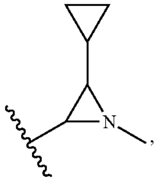 , 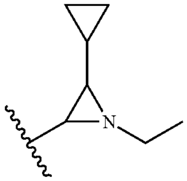 , 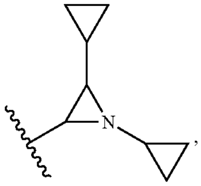 ,

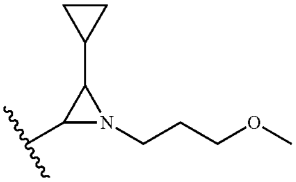 ,

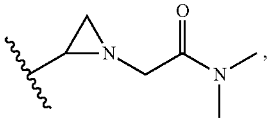 , 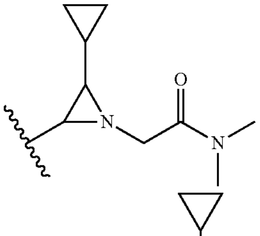 ,

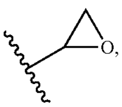 , 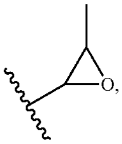 , and 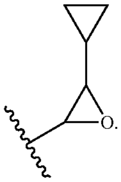 .

In some embodiments, a compound, or a pharmaceutically acceptable salt thereof, having the structure of Formula (I0) is provided. In some embodiments, a compound, or a pharmaceutically acceptable salt thereof, having the structure of Formula (II0) is provided. In some embodiments, a compound, or a pharmaceutically acceptable salt thereof, having the structure of Formula (III0) is provided. In some embodiments, a compound, or a pharmaceutically acceptable salt thereof, having the structure of Formula (IV0) is provided.

In some embodiments, a compound, or a pharmaceutically acceptable salt thereof, of Formula (I0), Formula (II0), Formula (III0) or Formula (IV0) is provided, having the structure of Formula (I), Formula (II), Formula (III) or Formula (IV):

(I)

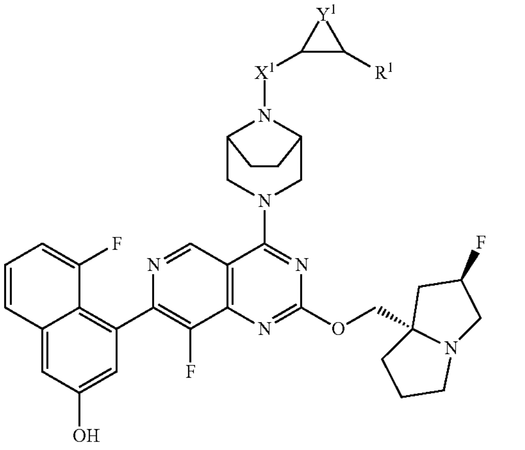

(II)

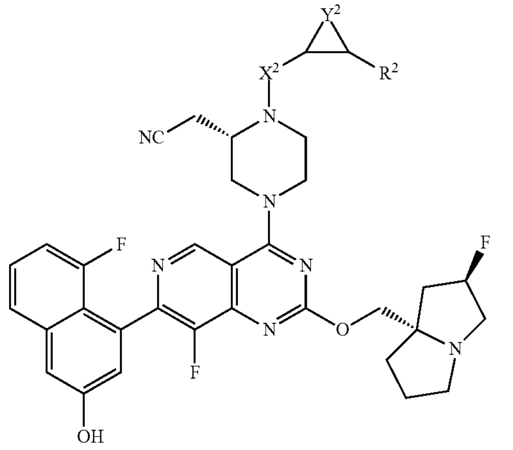

(III)

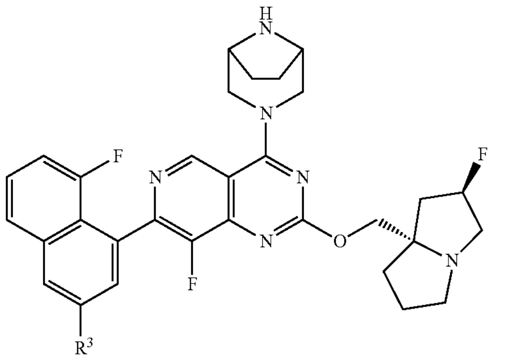

(IV)

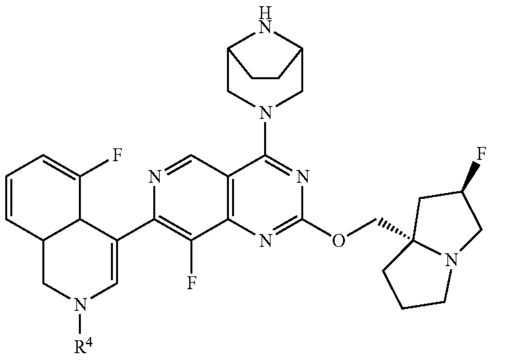

wherein:

$R^1$ is selected from H and cyclopropyl; $R^2$ is selected from H and cyclopropyl; $X^1$ is selected from —C(O)— and —$CH_2$—; $X^2$ is selected from —C(O)— and —$CH_2$—; $Y^1$ is selected from —O—, —NH—, —N($CH_3$), —N($CH_2CH_3$), —N(cyclopropyl), —N($C_1$-$C_6$ heteroalkyl); $Y^2$ is selected from —O—, —NH—, —N($CH_3$), —N($CH_2CH_3$), —N(cyclopropyl), —N($C_1$-$C_6$ heteroalkyl); $R^3$ is selected from

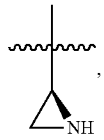
,
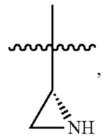
,
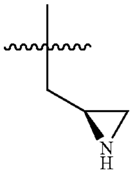
and

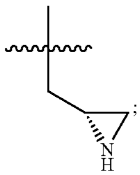
;

and $R^4$ is selected from

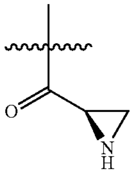
and
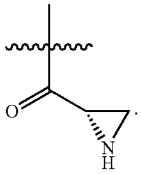
.

Also provided is a compound, or a pharmaceutically acceptable salt thereof, having the structure of Formula (I), Formula (II), Formula (III) or Formula (IV):

(I)

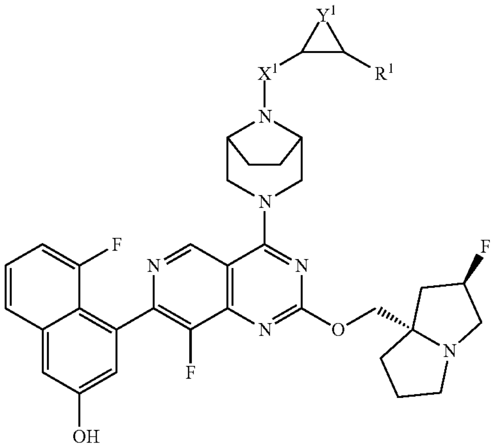

-continued (II)

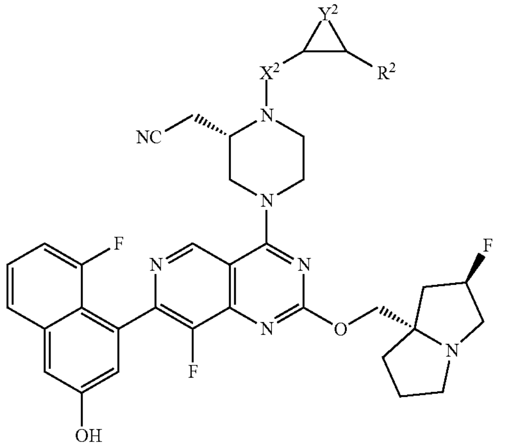

(III)

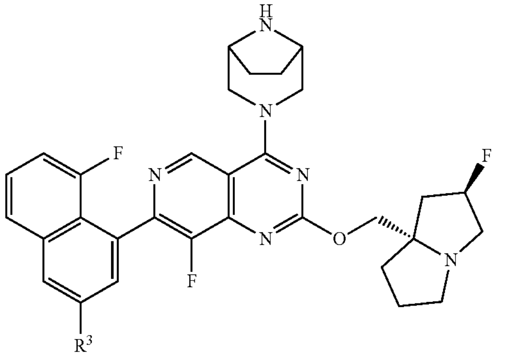

(IV)

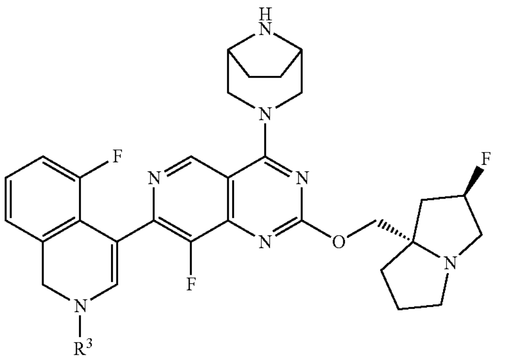

wherein:

$R^1$ is selected from H and cyclopropyl; $R^2$ is selected from H and cyclopropyl; $X^1$ is selected from —C(O)— and —$CH_2$—; $X^2$ is selected from —C(O)— and —$CH_2$—; $Y^2$ is selected from —O— and —NH—; $Y^2$ is selected from —O— and —NH—; $R^3$ is selected from

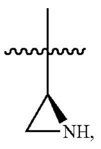, 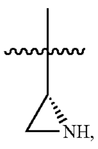, 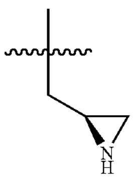 and 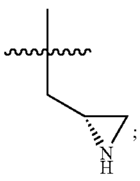;

and $R^4$ is selected from

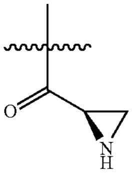 and 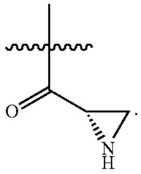.

In some embodiments, a compound, or a pharmaceutically acceptable salt thereof, having the structure of Formula (I) is provided. In some embodiments, a compound, or a pharmaceutically acceptable salt thereof, having the structure of Formula (II) is provided. In some embodiments, a compound, or a pharmaceutically acceptable salt thereof, having the structure of Formula (III) is provided. In some embodiments, a compound, or a pharmaceutically acceptable salt thereof, having the structure of Formula (IV) is provided.

In some embodiments, $R^1$ is H. In some embodiments, $R^1$ is cyclopropyl. In some embodiments, $R^1$ is

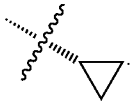.

In some embodiments, $R^1$ is

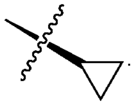.

In some embodiments, $R^2$ is H. In some embodiments, $R^2$ is cyclopropyl. In some embodiments, $R^2$ is

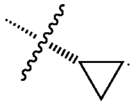.

In some embodiments, $R^2$ is

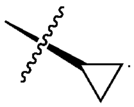.

In some embodiments, $X^1$ is —C(O)—. In some embodiments, $X^1$ is —$CH_2$—. In some embodiments, $X^2$ is —C(O)—. In some embodiments, $X^2$ is —$CH_2$—.

In some embodiments, a compound, or a pharmaceutically acceptable salt thereof, is selected from a compound of Table 1.

Also provided is a pharmaceutical composition comprising a compound of the present invention, or a pharmaceutically acceptable salt thereof, and a pharmaceutically acceptable excipient.

Further provided is a conjugate, or salt thereof, comprising a Ras protein covalently bound to a compound of the present invention. In some embodiments of a conjugate, an acidic residue at position 12 or 13 of the Ras protein is covalently bound to the compound. In some embodiments of a conjugate, the acidic residue is asparatic acid. In some embodiments of a conjugate, the acidic residue is glutamic acid.

Further provided is a method of producing a conjugate comprising contacting a Ras protein with a compound of the present invention, or a pharmaceutically acceptable salt thereof, or a pharmaceutical composition thereof, under conditions sufficient for the compound to react covalently with the Ras protein. In some embodiments, an acidic residue at position 12 or 13 of the Ras protein reacts covalently with the compound to produce the conjugate. In some embodiments, the acidic residue is asparatic acid. In some embodiments, the acidic residue is glutamic acid. Further provided is a conjugate, or salt thereof, produced by such a method.

Also provided herein is a method of treating cancer in a subject in need thereof, the method comprising administering to the subject a therapeutically effective amount of a compound of the present invention, or a pharmaceutically acceptable salt thereof, or a pharmaceutical composition thereof. Also provided is a method of treating a Ras protein-related disorder in a subject in need thereof, the method comprising administering to the subject a therapeutically effective amount of a compound of the present invention, or a pharmaceutically acceptable salt thereof, or a pharmaceutical composition thereof. Also provided is a method of inhibiting a Ras protein in a cell, the method comprising contacting the cell with an effective amount of a compound of the present invention, or a pharmaceutically acceptable salt thereof, or a pharmaceutical composition thereof. In any such method, the cell may be a cancer cell. The cell may be in vitro. The cell may be in vivo. In any such method, the method may further comprise administering an additional anticancer therapy.

A method of cross-linking K-Ras(GDP) G12D to form a conjugate is also provided, comprising contacting K-Ras (GDP) G12D with the following compound:

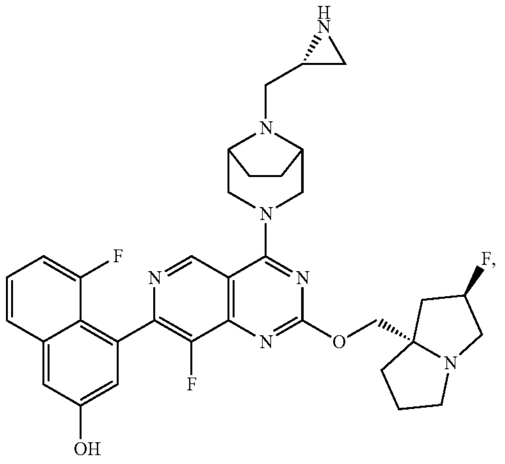 [SMILES: Oc1cc(-c2ncc3c(N4CC5CCC(C4)N5C[C@H]4CN4)nc(OC[C@@]45CCCN4C[C@H](F)C5)nc3c2F)c2c(F)cccc2c1]

wherein a conjugate is formed.

In some embodiments, a compound of Table 1 is provided, or a pharmaceutically acceptable salt thereof. In some embodiments, a compound of the present invention is selected from Table 1, or a pharmaceutically acceptable salt or atropisomer thereof.

TABLE 1

| Chain Compounds of the Present Invention | |
|---|---|
| # | Structure |
| B1 | 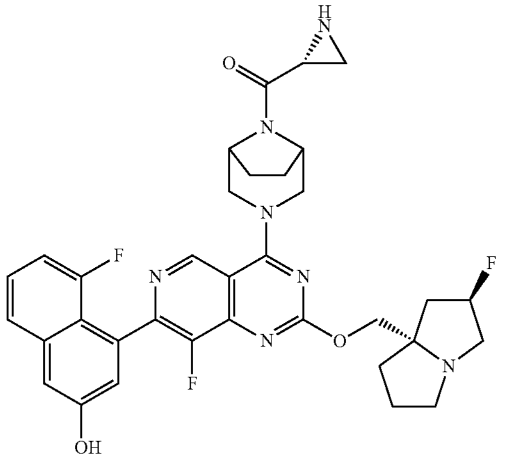 [SMILES: O=C([C@H]1CN1)N1C2CCC1CN(c1nc(OC[C@@]34CCCN3C[C@H](F)C4)nc3c(F)c(-c4cc(O)cc5cccc(F)c45)ncc13)C2] |
| B2 | 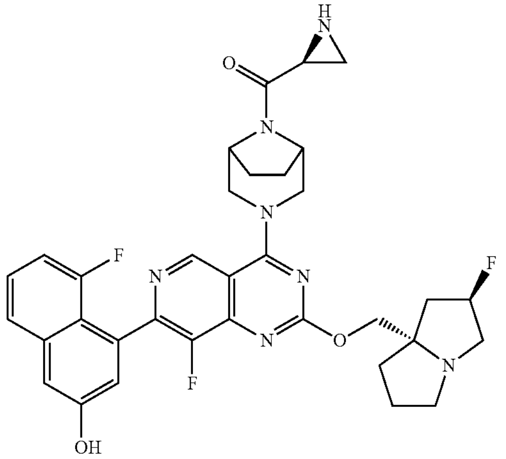 [SMILES: O=C([C@@H]1CN1)N1C2CCC1CN(c1nc(OC[C@@]34CCCN3C[C@H](F)C4)nc3c(F)c(-c4cc(O)cc5cccc(F)c45)ncc13)C2] |
| B3 | 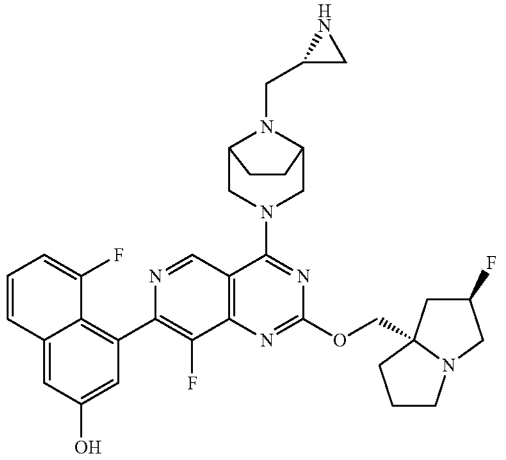 [SMILES: Oc1cc(-c2ncc3c(N4CC5CCC(C4)N5C[C@H]4CN4)nc(OC[C@@]45CCCN4C[C@H](F)C5)nc3c2F)c2c(F)cccc2c1] |

TABLE 1-continued
| Chain Compounds of the Present Invention | |
|---|---|
| # | Structure |
| B4 | 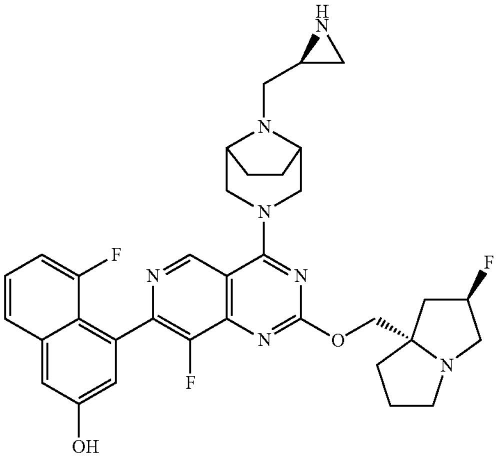 [SMILES: Oc1cc(-c2ncc3c(N4CC5CCC(C4)N5C[C@@H]4CN4)nc(OC[C@@]45CCCN4C[C@H](F)C5)nc3c2F)c2c(F)cccc2c1] |
| B5 | 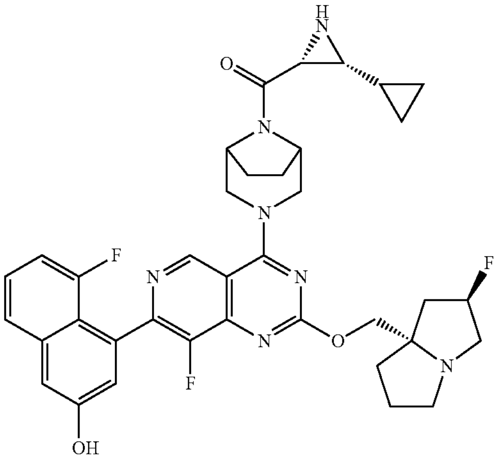 [SMILES: O=C([C@@H]1N[C@@H]1C1CC1)N1C2CCC1CN(c1nc(OC[C@@]34CCCN3C[C@H](F)C4)nc3c(F)c(-c4cc(O)cc5cccc(F)c45)ncc13)C2] |
| B6 | 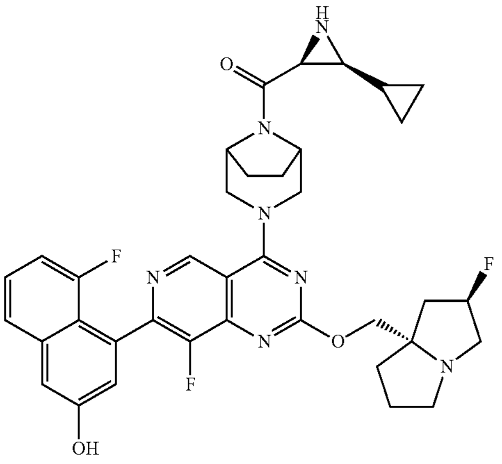 [SMILES: O=C([C@H]1N[C@H]1C1CC1)N1C2CCC1CN(c1nc(OC[C@@]34CCCN3C[C@H](F)C4)nc3c(F)c(-c4cc(O)cc5cccc(F)c45)ncc13)C2] |
TABLE 1-continued
| Chain Compounds of the Present Invention | |
|---|---|
| # | Structure |
| B7 | 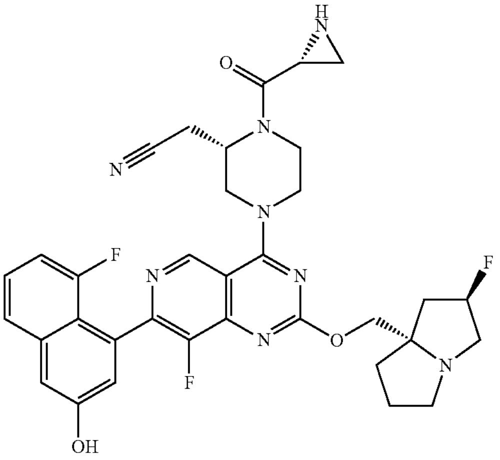 [SMILES: N#CC[C@H]1CN(c2nc(OC[C@@]34CCCN3C[C@H](F)C4)nc3c(F)c(-c4cc(O)cc5cccc(F)c45)ncc23)CCN1C(=O)[C@H]1CN1] |
| B8 | 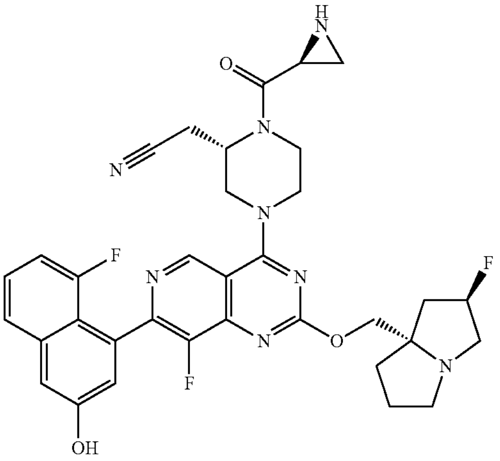 [SMILES: N#CC[C@H]1CN(c2nc(OC[C@@]34CCCN3C[C@H](F)C4)nc3c(F)c(-c4cc(O)cc5cccc(F)c45)ncc23)CCN1C(=O)[C@@H]1CN1] |
| B9 | 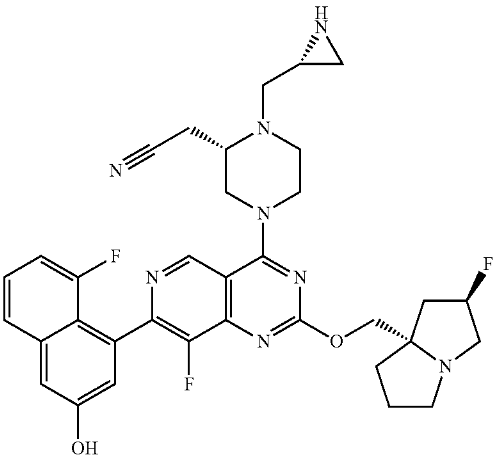 [SMILES: N#CC[C@H]1CN(c2nc(OC[C@@]34CCCN3C[C@H](F)C4)nc3c(F)c(-c4cc(O)cc5cccc(F)c45)ncc23)CCN1C[C@H]1CN1] |

TABLE 1-continued
Chain Compounds of the Present Invention
| # | Structure |
| --- | --- |
| B10 | 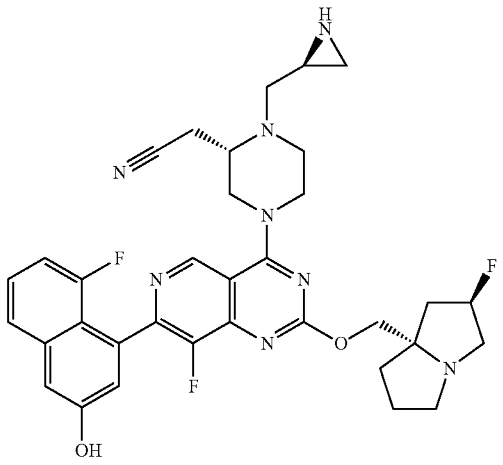 [SMILES: N#CC[C@H]1CN(c2nc(OC[C@@]34CCCN3C[C@H](F)C4)nc3c(F)c(-c4cc(O)cc5cccc(F)c45)ncc23)CCN1C[C@@H]1CN1] |
| B11 | 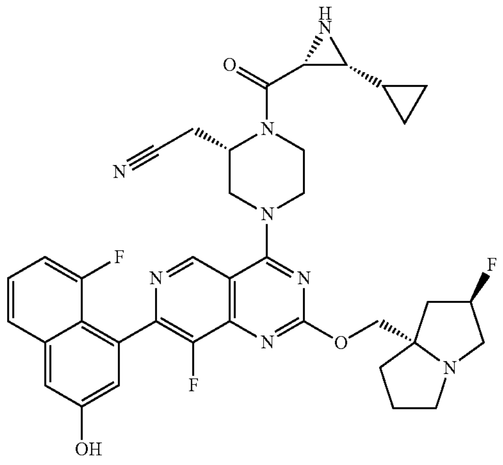 [SMILES: N#CC[C@H]1CN(c2nc(OC[C@@]34CCCN3C[C@H](F)C4)nc3c(F)c(-c4cc(O)cc5cccc(F)c45)ncc23)CCN1C(=O)[C@@H]1N[C@@H]1C1CC1] |
| B12 | 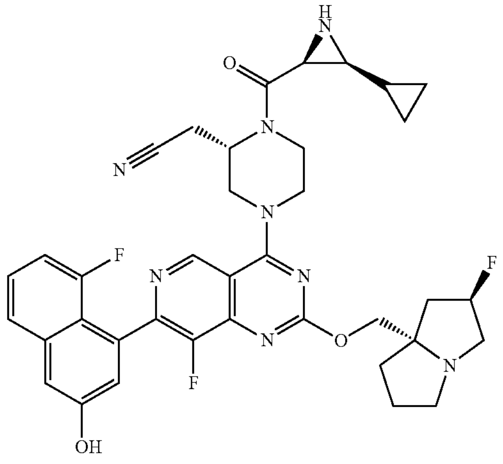 [SMILES: N#CC[C@H]1CN(c2nc(OC[C@@]34CCCN3C[C@H](F)C4)nc3c(F)c(-c4cc(O)cc5cccc(F)c45)ncc23)CCN1C(=O)[C@H]1N[C@H]1C1CC1] |
| B13 | 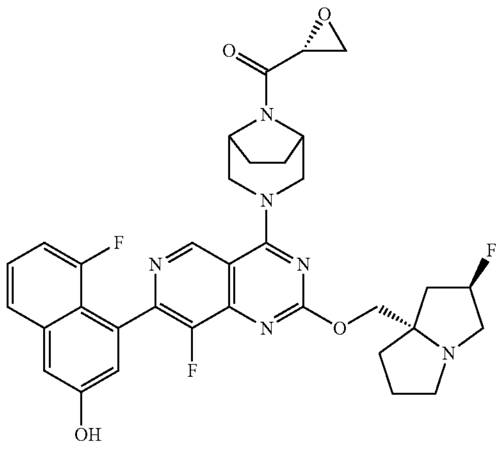 [SMILES: O=C([C@H]1CO1)N1C2CCC1CN(c1nc(OC[C@@]34CCCN3C[C@H](F)C4)nc3c(F)c(-c4cc(O)cc5cccc(F)c45)ncc13)C2] |
| B14 | 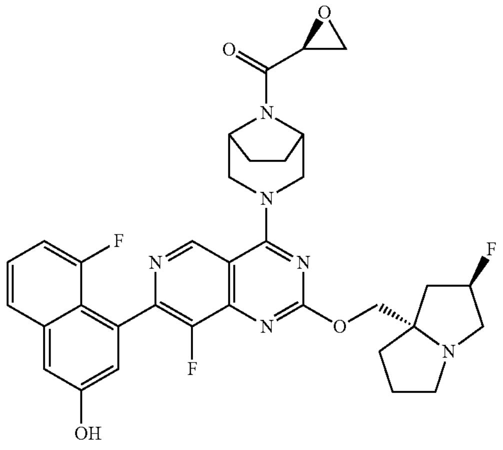 [SMILES: O=C([C@@H]1CO1)N1C2CCC1CN(c1nc(OC[C@@]34CCCN3C[C@H](F)C4)nc3c(F)c(-c4cc(O)cc5cccc(F)c45)ncc13)C2] |
| B15 | 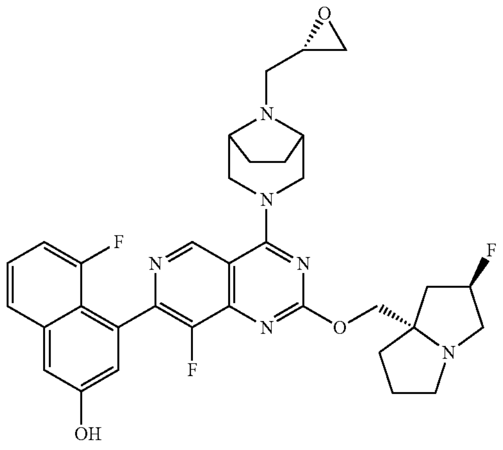 [SMILES: Oc1cc(-c2ncc3c(N4CC5CCC(C4)N5C[C@H]4CO4)nc(OC[C@@]45CCCN4C[C@H](F)C5)nc3c2F)c2c(F)cccc2c1]

TABLE 1-continued
| Chain Compounds of the Present Invention | |
|---|---|
| # | Structure |
| B16 | 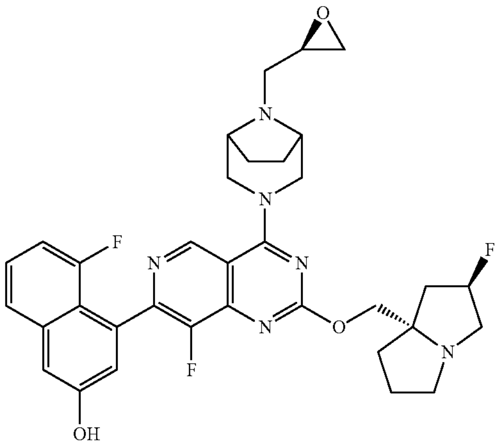 [SMILES: Oc1cc(-c2ncc3c(N4CC5CCC(C4)N5C[C@@H]4CO4)nc(OC[C@@]45CCCN4C[C@H](F)C5)nc3c2F)c2c(F)cccc2c1] |
| B17 | 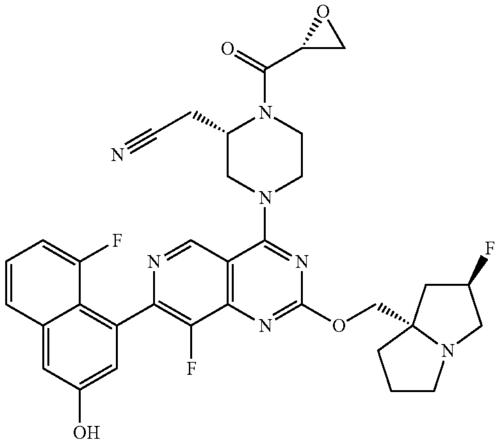 [SMILES: N#CC[C@H]1CN(c2nc(OC[C@@]34CCCN3C[C@H](F)C4)nc3c(F)c(-c4cc(O)cc5cccc(F)c45)ncc23)CCN1C(=O)[C@H]1CO1] |
| B18 | 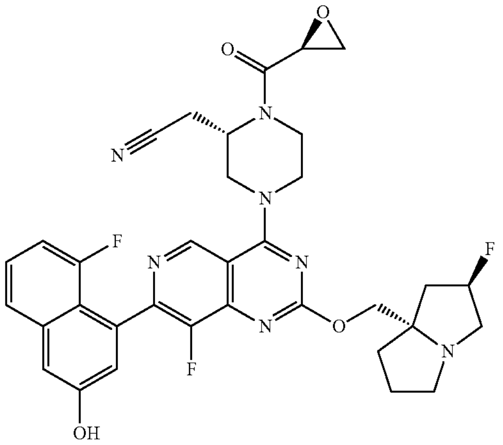 [SMILES: N#CC[C@H]1CN(c2nc(OC[C@@]34CCCN3C[C@H](F)C4)nc3c(F)c(-c4cc(O)cc5cccc(F)c45)ncc23)CCN1C(=O)[C@@H]1CO1] |
TABLE 1-continued
| Chain Compounds of the Present Invention | |
|---|---|
| # | Structure |
| B19 | 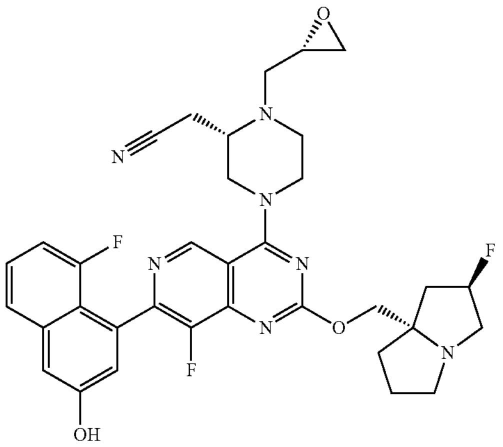 [SMILES: N#CC[C@H]1CN(c2nc(OC[C@@]34CCCN3C[C@H](F)C4)nc3c(F)c(-c4cc(O)cc5cccc(F)c45)ncc23)CCN1C[C@H]1CO1] |
| B20 | 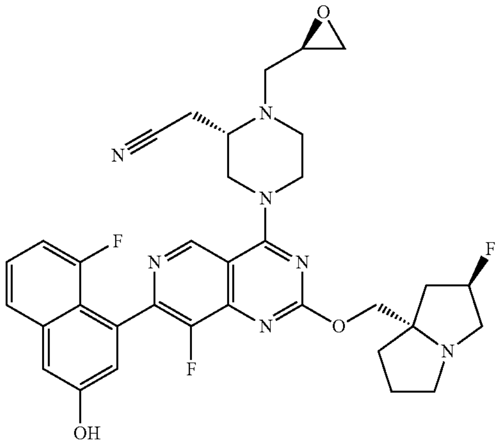 [SMILES: N#CC[C@H]1CN(c2nc(OC[C@@]34CCCN3C[C@H](F)C4)nc3c(F)c(-c4cc(O)cc5cccc(F)c45)ncc23)CCN1C[C@@H]1CO1] |
| B21 | 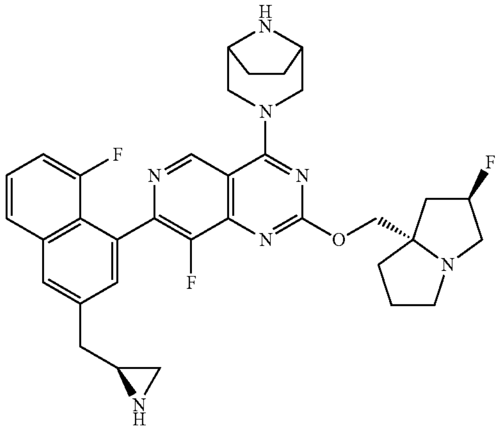 [SMILES: Fc1c(-c2cc(C[C@H]3CN3)cc3cccc(F)c23)ncc2c(N3CC4CCC(C3)N4)nc(OC[C@@]34CCCN3C[C@H](F)C4)nc12] |

TABLE 1-continued

| Chain Compounds of the Present Invention | |
|---|---|
| # | Structure |
| B22 | 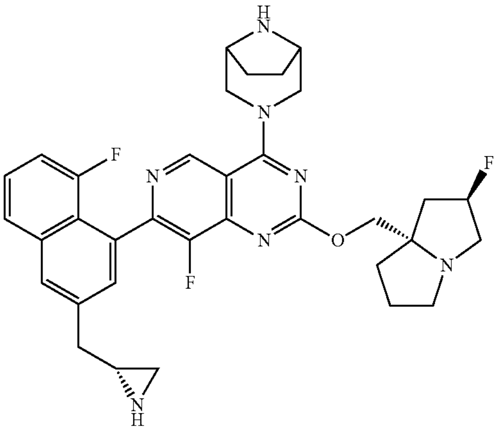 [SMILES: Fc1c(-c2cc(C[C@@H]3CN3)cc3cccc(F)c23)ncc2c(N3CC4CCC(C3)N4)nc(OC[C@@]34CCCN3C[C@H](F)C4)nc12] |
| B23 | 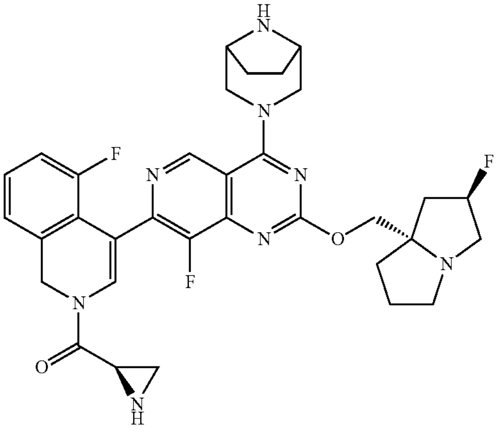 [SMILES: O=C([C@H]1CN1)N1C=C(c2ncc3c(N4CC5CCC(C4)N5)nc(OC[C@@]45CCCN4C[C@H](F)C5)nc3c2F)c2c(F)cccc2C1] |
| B24 | 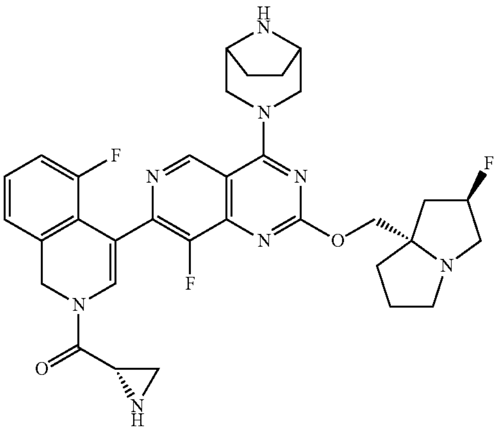 [SMILES: O=C([C@@H]1CN1)N1C=C(c2ncc3c(N4CC5CCC(C4)N5)nc(OC[C@@]45CCCN4C[C@H](F)C5)nc3c2F)c2c(F)cccc2C1] |

TABLE 1-continued

| Chain Compounds of the Present Invention | |
|---|---|
| # | Structure |
| B25 | 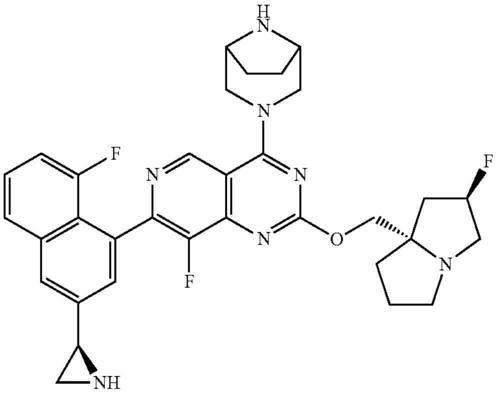 [SMILES: Fc1c(-c2cc([C@@H]3CN3)cc3cccc(F)c23)ncc2c(N3CC4CCC(C3)N4)nc(OC[C@@]34CCCN3C[C@H](F)C4)nc12] |
| B26 | 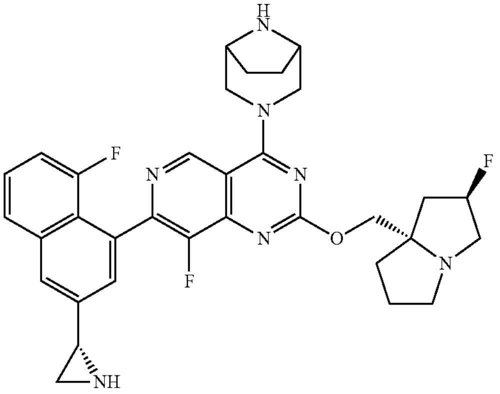 [SMILES: Fc1c(-c2cc([C@H]3CN3)cc3cccc(F)c23)ncc2c(N3CC4CCC(C3)N4)nc(OC[C@@]34CCCN3C[C@H](F)C4)nc12] |

In some embodiments, a compound of the present invention is any Ras inhibitor disclosed in WO 2022/072783, WO 2022/066646, WO 2022/042630, WO 2022/031678, WO 2022/015375, WO 2022/002102, WO 2021/215544, WO 2021/107160, and WO 2021/106231, each incorporated herein by reference in its entirety, modified with an optionally substituted aziridine or an optionally substituted epoxide, such as described herein. Preparation of such modified compounds is known to those of skill in the art in view of the teachings of WO 2022/072783, WO 2022/066646, WO 2022/042630, WO 2022/031678, WO 2022/015375, WO 2022/002102, WO 2021/215544, WO 2021/107160, and WO 2021/106231, and the teachings herein.

Further provided is a Ras protein comprising a covalent bond to a compound of the present invention. In some embodiments regarding a conjugate or salt thereof, a compound of the present invention is bound to the Ras protein through a covalent bond to a carboxyl group of a Ras protein, such as a human mutant K-Ras protein, human mutant H-Ras protein, or human mutant N-Ras protein. In some embodiments, the carboxyl group of a residue of the Ras protein is the carboxyl group of an aspartic acid residue at the mutated position corresponding to position 12 or 13 of human wild-type K-Ras, N-Ras or H-Ras. In some embodiments, the carboxyl group of a residue of the Ras protein is the carboxyl group of a glutamic acid residue at the mutated position corresponding to position 12 or 13 of human wild-type K-Ras, N-Ras or H-Ras.

Further provided is a method of producing a conjugate comprising contacting a Ras protein with a compound of the present invention, or a pharmaceutically acceptable salt thereof, or a pharmaceutical composition of such a compound or salt, under conditions sufficient for the compound to react covalently with the Ras protein. Also provided is method of producing a conjugate, the method comprising contacting a Ras protein with a compound of the present invention, or a pharmaceutically acceptable salt thereof, or a pharmaceutical composition of such a compound or salt, under conditions suitable to permit conjugate formation. Conjugates produced by such methods are also provided.

Methods of Synthesis

The compounds described herein may be made from commercially available starting materials or synthesized using known organic, inorganic, or enzymatic processes.

The compounds of the present invention can be prepared in a number of ways well known to those skilled in the art of organic synthesis. By way of example, compounds of the disclosure can be synthesized using the methods described below and the Intermediates as set forth in the Examples, together with synthetic methods known in the art of synthetic organic chemistry, or variations thereon as appreciated by those skilled in the art. See, e.g., WO 2021041671, incorporated herein by reference in its entirety, regarding synthetic preparations of various aspects corresponding to compounds of the present invention. These methods include but are not limited to those methods described below as well as in the Examples section.

Reaction Scheme 1

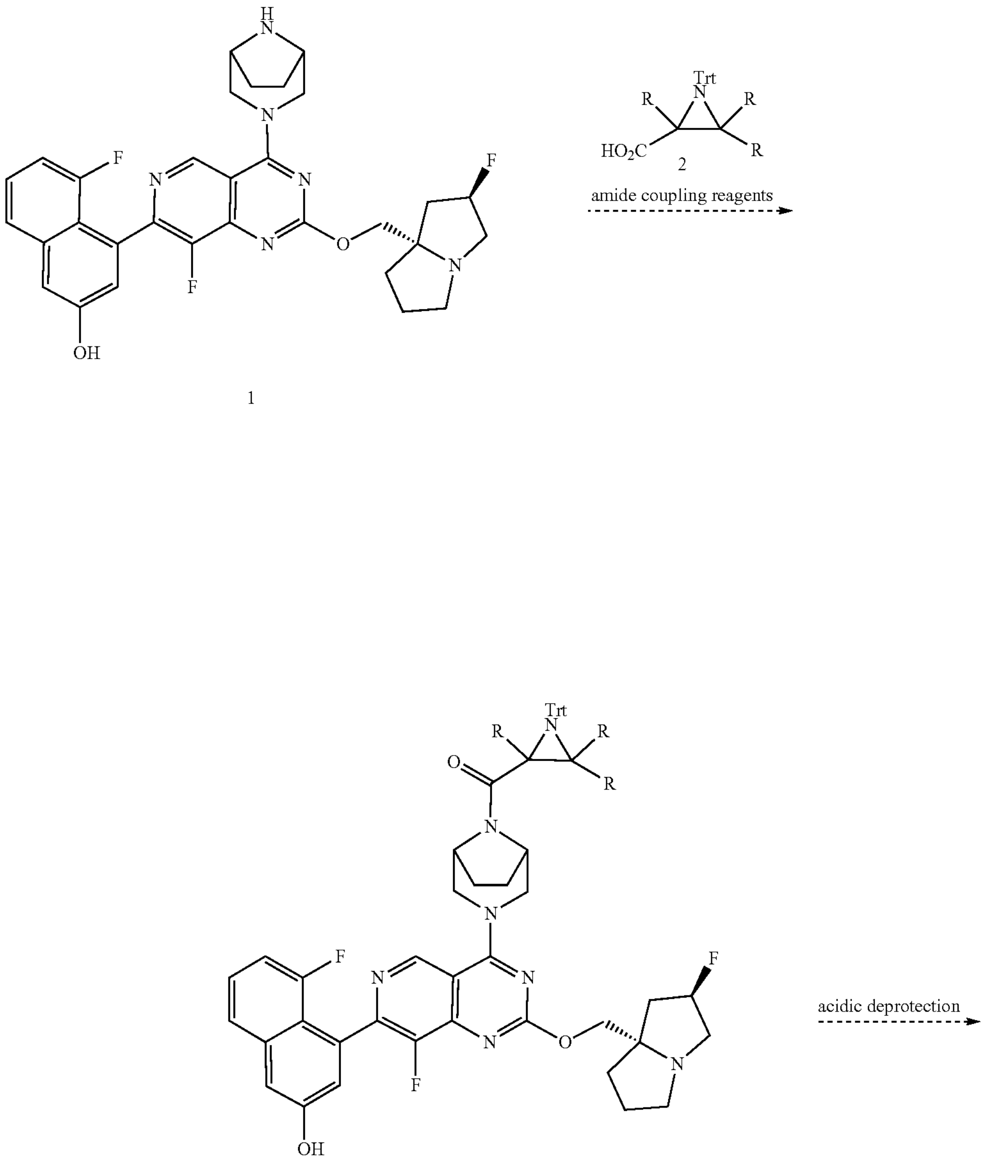

1

2

3

-continued
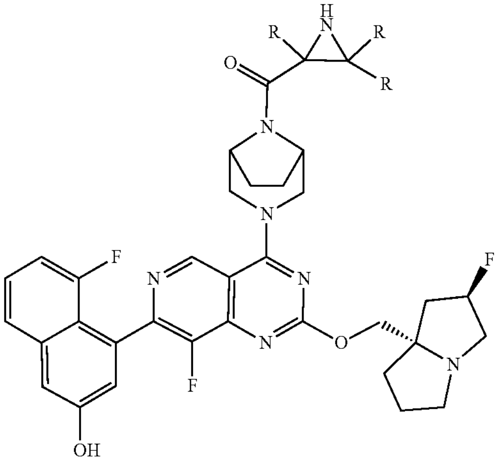
4
As shown in Scheme 1, compounds of type 4 may be prepared by the reaction of an appropriate amine such as compound 1 with a carboxylic acid such as compound 2 in the presence of standard amide coupling reagents (e.g., HOBt, HATU), followed by trityl deprotection under acidic conditions.
Reaction Scheme 2
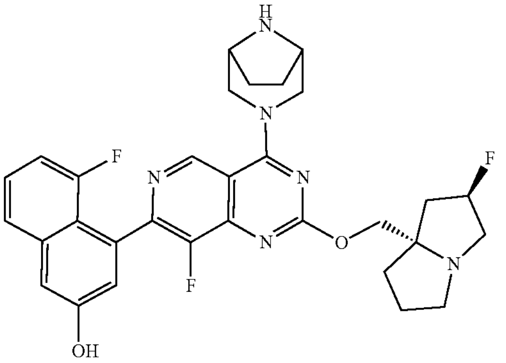
1
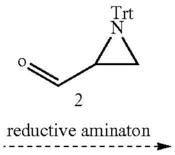
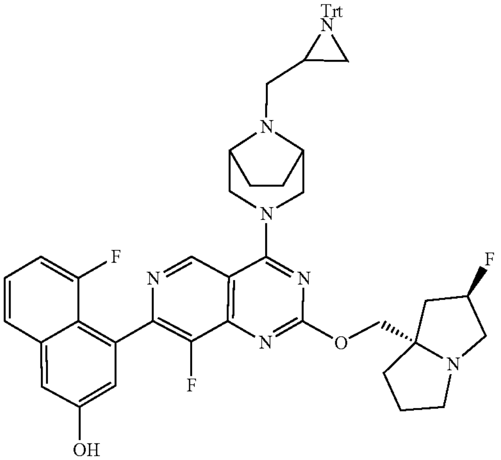
3
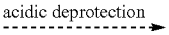

-continued
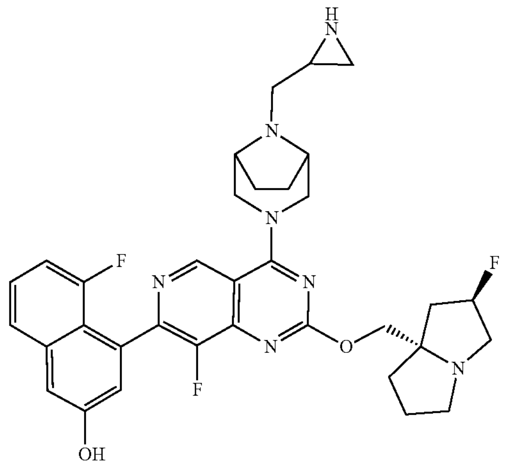
4
As shown in Scheme 2, compounds of type 4 may be prepared by the reductive amination of an appropriate amine such as compound 1 with an aldehyde such as compound 2, followed by trityl deprotection under acidic conditions.
Reaction Scheme 3
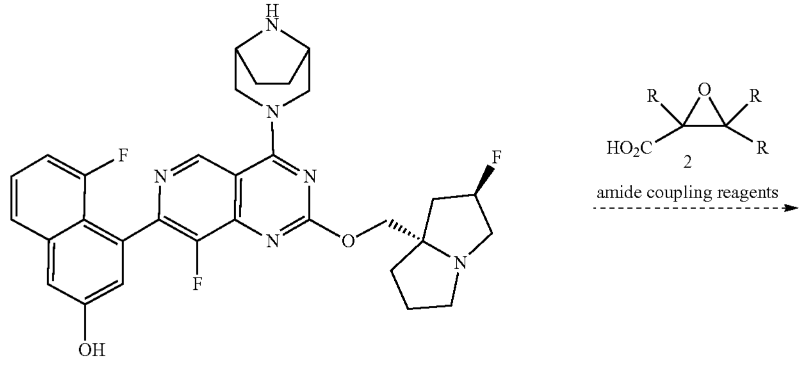
1
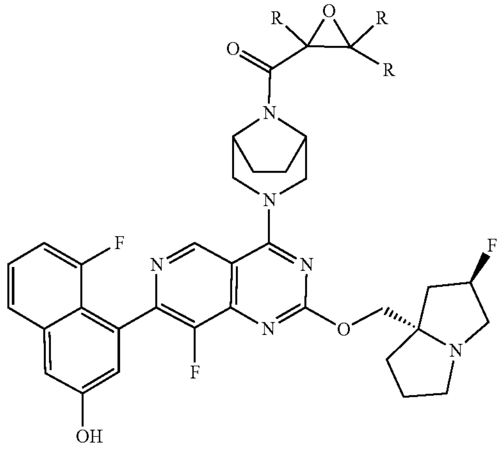
3

As shown in Scheme 3, compounds of type 3 may be prepared by the reaction of an appropriate amine such as compound 1 with a carboxylic acid such as compound 2 in the presence of standard amide coupling reagents (e.g., HOBt, HATU).

Reaction Scheme 4

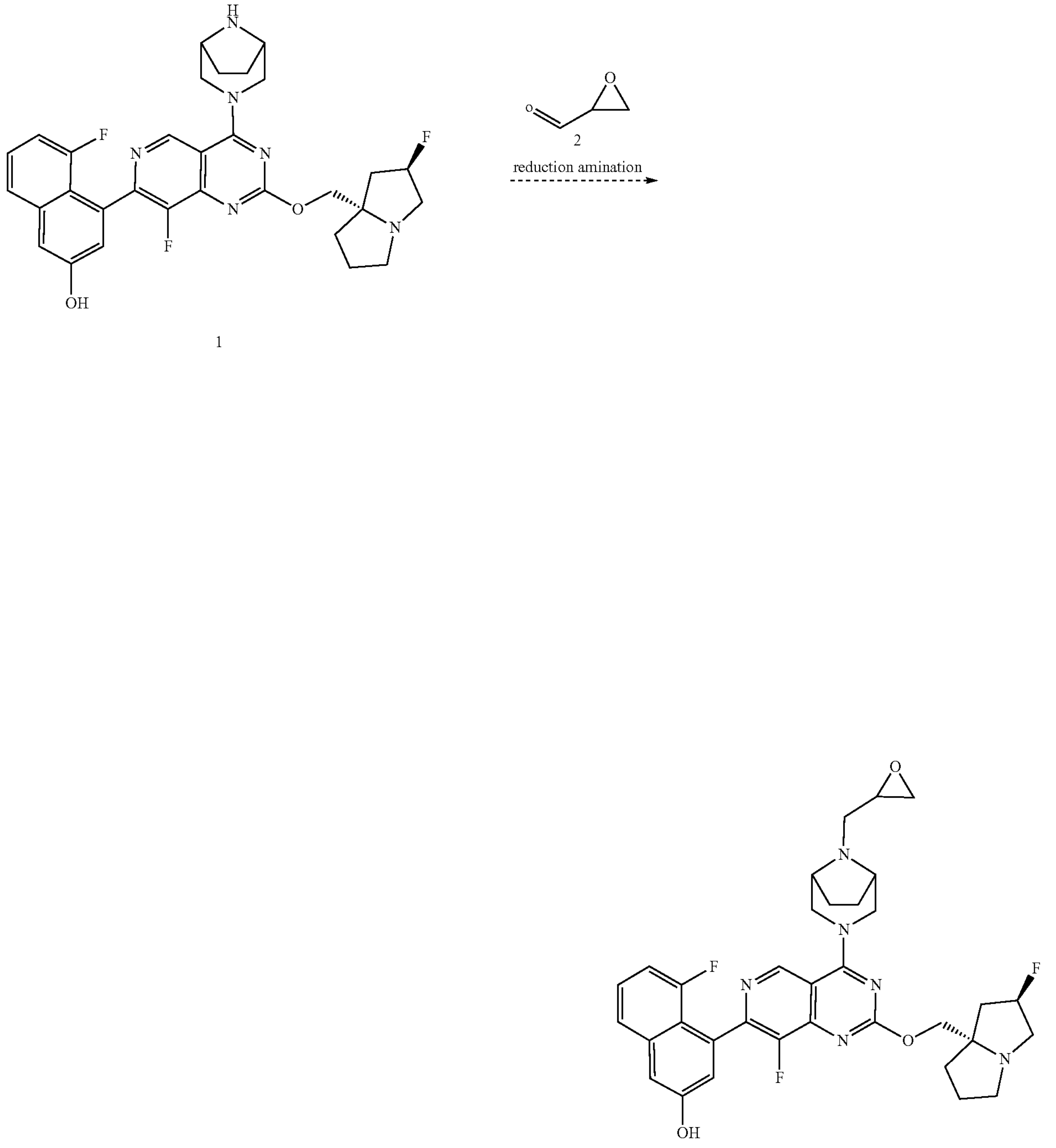

1

2

3

As shown in Scheme 4, compounds of type 3 may be prepared by the reductive amination of an appropriate amine such as compound 1 with an aldehyde such as compound 2.

Reaction Scheme 5
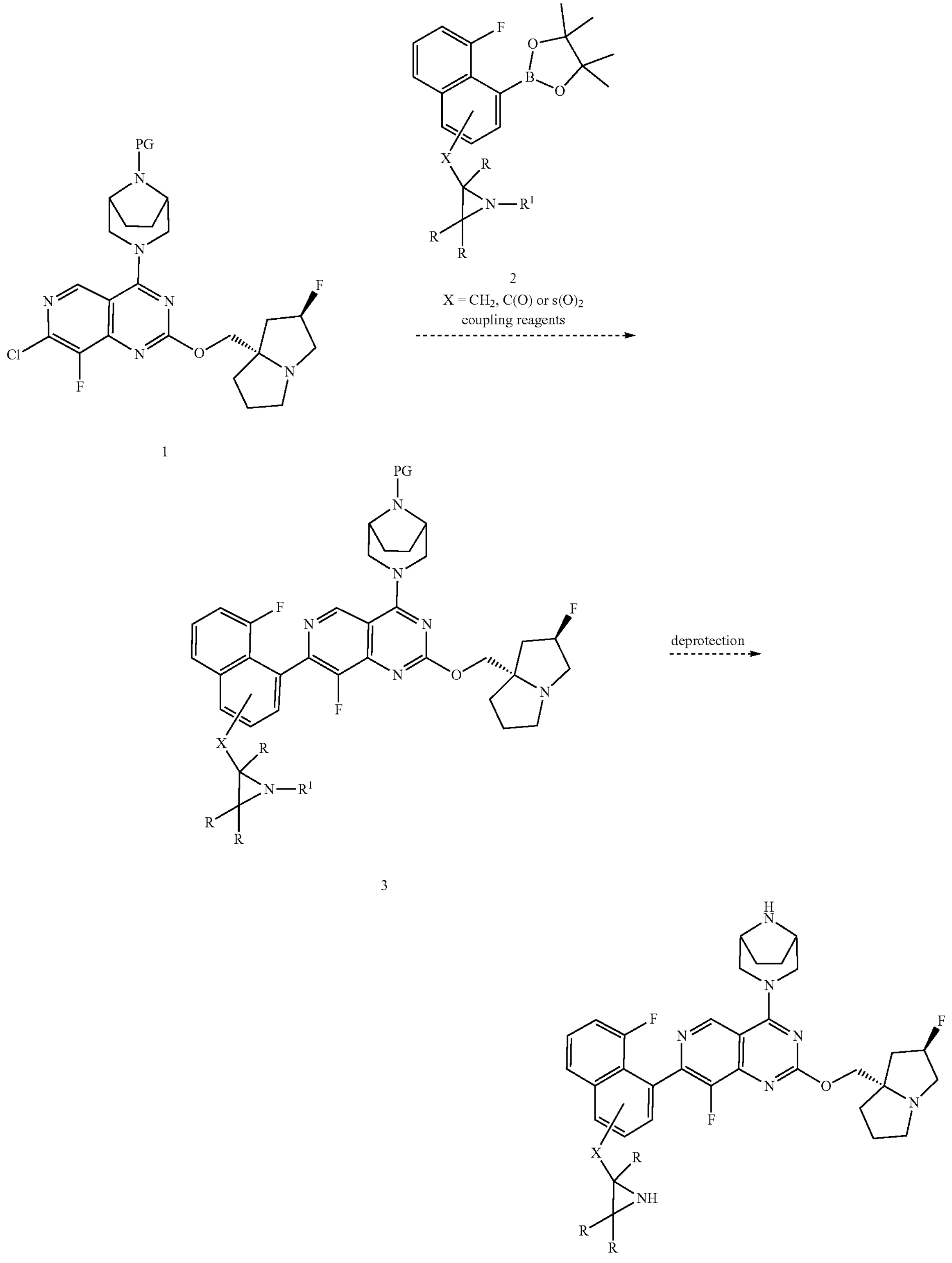
1
2
3
4

As shown in Scheme 5, compounds of type 4 may be prepared by the reaction of an appropriate aryl halide (1) with an aryl boronate (2) in the presence of standard coupling reagents (e.g., a Pd(0) complex) to give 3, followed by deprotection of the amine, and deprotection of the aziridine if $R^1$ is a protecting group.
Reaction Scheme 6
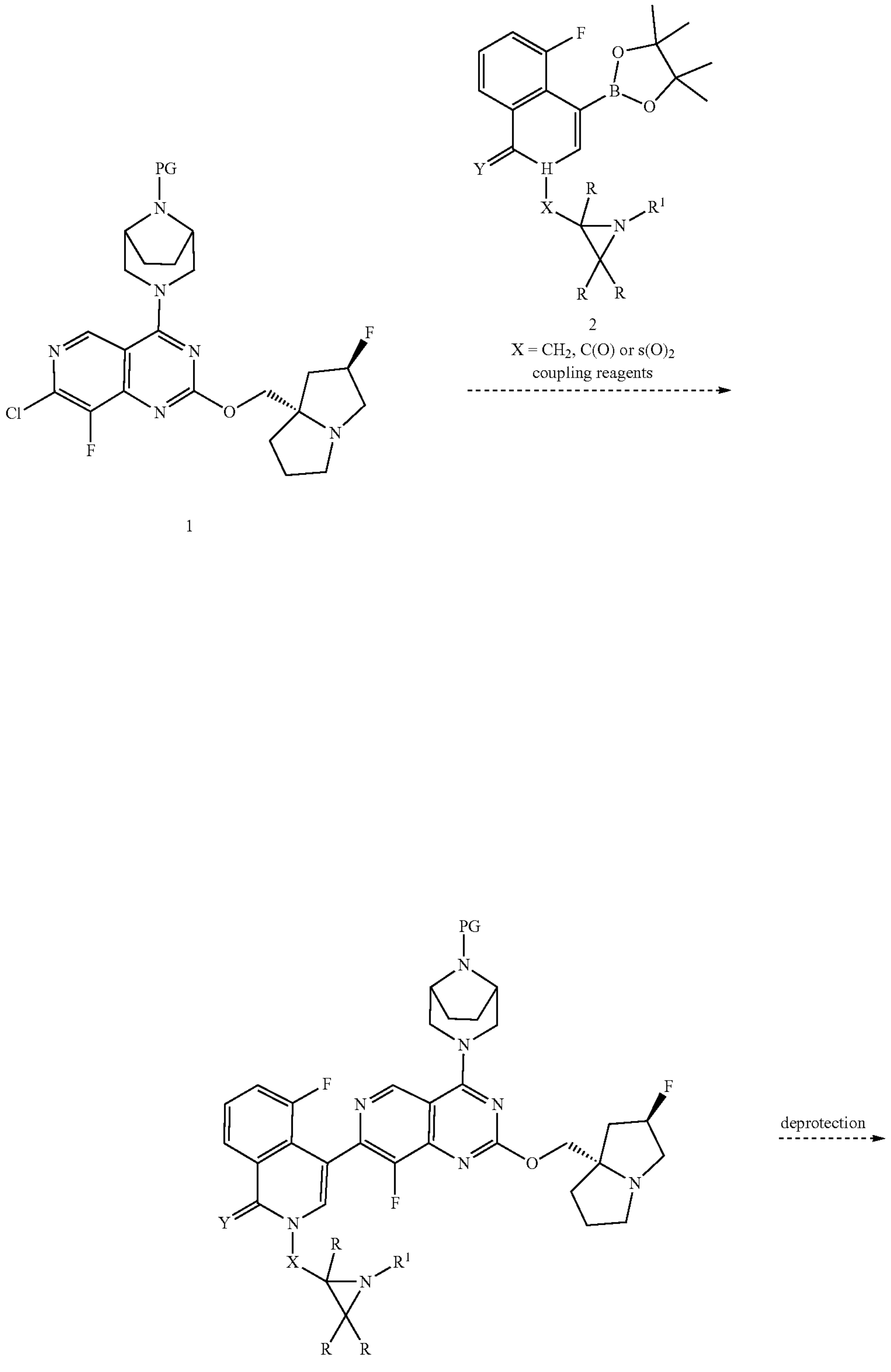
1
3

-continued

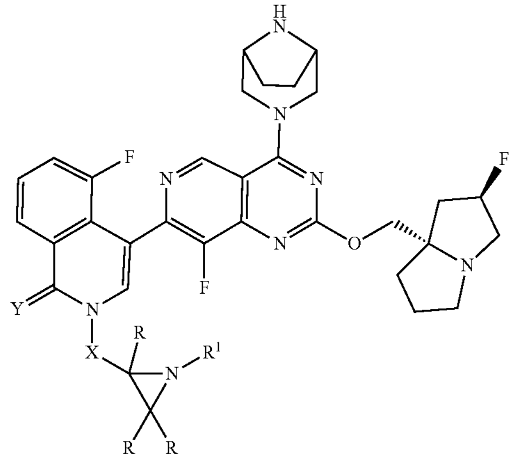

4

As shown in Scheme 6, compounds of type 4 may be prepared by the reaction of an appropriate aryl halide (1) with an aryl boronate (2) in the presence of standard coupling reagents (e.g., a Pd(0) complex) to give 3, followed by deprotection of the amine, and deprotection of the aziridine if $R^1$ is a protecting group.

Pharmaceutical Compositions and Methods of Administration

As used herein, the term "pharmaceutical composition" refers to an active compound, formulated together with one or more pharmaceutically acceptable excipients. In some embodiments, a compound is present in unit dose amount appropriate for administration in a therapeutic regimen that shows a statistically significant probability of achieving a predetermined therapeutic effect when administered to a relevant population. In some embodiments, pharmaceutical compositions may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream, or foam; sublingually; ocularly; transdermally; or nasally, pulmonary, and to other mucosal surfaces.

A "pharmaceutically acceptable excipient," as used herein, refers any inactive ingredient (for example, a vehicle capable of suspending or dissolving the active compound) having the properties of being nontoxic and non-inflammatory in a subject. Typical excipients include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, or waters of hydration. Excipients include, but are not limited to: butylated optionally substituted hydroxyltoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, optionally substituted hydroxylpropyl cellulose, optionally substituted hydroxylpropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, stearic acid, sucrose, talc, titanium dioxide, vitamin A, vitamin E, vitamin C, and xylitol. Those of ordinary skill in the art are familiar with a variety of agents and materials useful as excipients.

Compounds described or depicted herein, whether expressly stated or not, may be provided or utilized in salt form, e.g., a pharmaceutically acceptable salt form, unless expressly stated to the contrary. The term "pharmaceutically acceptable salt," as use herein, refers to those salts of the compounds described here that are, within the scope of sound medical judgment, suitable for use in contact with the tissues of humans and animals without undue toxicity, irritation, allergic response and the like and are commensurate with a reasonable benefit/risk ratio. Pharmaceutically acceptable salts are well known in the art. For example, pharmaceutically acceptable salts are described in: Berge et al., *J. Pharmaceutical Sciences* 66:1-19, 1977 and in *Pharmaceutical Salts: Properties, Selection, and Use*, (Eds. P. H. Stahl and C. G. Wermuth), Wiley-VCH, 2008. The salts can be prepared in situ during the final isolation and purification of the compounds described herein or separately by reacting the free base group with a suitable organic acid.

The compounds of the invention may have ionizable groups so as to be capable of preparation as pharmaceutically acceptable salts. These salts may be acid addition salts involving inorganic or organic acids or the salts may, in the case of acidic forms of the compounds of the invention be prepared from inorganic or organic bases. Frequently, the compounds are prepared or used as pharmaceutically acceptable salts prepared as addition products of pharmaceutically acceptable acids or bases. Suitable pharmaceutically acceptable acids and bases are well-known in the art, such as hydrochloric, sulfuric, hydrobromic, acetic, lactic, citric, or tartaric acids for forming acid addition salts, and potassium hydroxide, sodium hydroxide, ammonium hydroxide, caffeine, various amines, and the like for forming basic salts. Methods for preparation of the appropriate salts are well-established in the art.

Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-optionally substituted hydroxyl-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts and the like. Representative alkali or alkaline earth metal salts include sodium, lithium, potassium, calcium, magnesium and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine and the like.

As used herein, the term "subject" refers to any member of the animal kingdom. In some embodiments, "subject" refers to humans, at any stage of development. In some embodiments, "subject" refers to a human patient. In some embodiments, "subject" refers to non-human animals, at any stage of development. In some embodiments, the non-human animal is a mammal (e.g., a rodent, a mouse, a rat, a rabbit, a monkey, a dog, a cat, a sheep, cattle, a primate, or a pig). In some embodiments, subjects include, but are not limited to, mammals, birds, reptiles, amphibians, fish, or worms. In some embodiments, a subject may be a transgenic animal, genetically-engineered animal, or a clone.

As used herein, the term "dosage form" refers to a physically discrete unit of an active compound (e.g., a therapeutic or diagnostic agent) for administration to a subject. Each unit contains a predetermined quantity of active agent. In some embodiments, such quantity is a unit dosage amount (or a whole fraction thereof) appropriate for administration in accordance with a dosing regimen that has been determined to correlate with a desired or beneficial outcome when administered to a relevant population (i.e., with a therapeutic dosing regimen). Those of ordinary skill in the art appreciate that the total amount of a therapeutic composition or compound administered to a particular subject is determined by one or more attending physicians and may involve administration of multiple dosage forms.

As used herein, the term "dosing regimen" refers to a set of unit doses (typically more than one) that are administered individually to a subject, typically separated by periods of time. In some embodiments, a given therapeutic compound has a recommended dosing regimen, which may involve one or more doses. In some embodiments, a dosing regimen comprises a plurality of doses each of which are separated from one another by a time period of the same length; in some embodiments, a dosing regimen comprises a plurality of doses and at least two different time periods separating individual doses. In some embodiments, all doses within a dosing regimen are of the same unit dose amount. In some embodiments, different doses within a dosing regimen are of different amounts. In some embodiments, a dosing regimen comprises a first dose in a first dose amount, followed by one or more additional doses in a second dose amount different from the first dose amount. In some embodiments, a dosing regimen comprises a first dose in a first dose amount, followed by one or more additional doses in a second dose amount same as the first dose amount. In some embodiments, a dosing regimen is correlated with a desired or beneficial outcome when administered across a relevant population (i.e., is a therapeutic dosing regimen).

A "therapeutic regimen" refers to a dosing regimen whose administration across a relevant population is correlated with a desired or beneficial therapeutic outcome.

The term "treatment" (also "treat" or "treating"), in its broadest sense, refers to any administration of a substance (e.g., provided compositions) that partially or completely alleviates, ameliorates, relives, inhibits, delays onset of, reduces severity of, or reduces incidence of one or more symptoms, features, or causes of a particular disease, disorder, or condition. In some embodiments, such treatment may be administered to a subject who does not exhibit signs of the relevant disease, disorder or condition or of a subject who exhibits only early signs of the disease, disorder, or condition. Alternatively, or additionally, in some embodiments, treatment may be administered to a subject who exhibits one or more established signs of the relevant disease, disorder or condition. In some embodiments, treatment may be of a subject who has been diagnosed as suffering from the relevant disease, disorder, or condition. In some embodiments, treatment may be of a subject known to have one or more susceptibility factors that are statistically correlated with increased risk of development of the relevant disease, disorder, or condition.

The term "therapeutically effective amount" means an amount that is sufficient, when administered to a population suffering from or susceptible to a disease, disorder, or condition in accordance with a therapeutic dosing regimen, to treat the disease, disorder, or condition. In some embodiments, a therapeutically effective amount is one that reduces the incidence or severity of, or delays onset of, one or more symptoms of the disease, disorder, or condition. Those of ordinary skill in the art will appreciate that the term "therapeutically effective amount" does not in fact require successful treatment be achieved in a particular individual. Rather, a therapeutically effective amount may be that amount that provides a particular desired pharmacological response in a significant number of subjects when administered to patients in need of such treatment. It is specifically understood that particular subjects may, in fact, be "refractory" to a "therapeutically effective amount." To give but one example, a refractory subject may have a low bioavailability such that clinical efficacy is not obtainable. In some embodiments, reference to a therapeutically effective amount may be a reference to an amount as measured in one or more specific tissues (e.g., a tissue affected by the disease, disorder or condition) or fluids (e.g., blood, saliva, serum, sweat, tears, urine). Those of ordinary skill in the art will appreciate that, in some embodiments, a therapeutically effective amount may be formulated or administered in a single dose. In some embodiments, a therapeutically effective amount may be formulated or administered in a plurality of doses, for example, as part of a dosing regimen.

For use as treatment of subjects, the compounds of the invention, or a pharmaceutically acceptable salt thereof, can be formulated as pharmaceutical or veterinary compositions. Depending on the subject to be treated, the mode of administration, and the type of treatment desired, e.g., prevention, prophylaxis, or therapy, the compounds, or a pharmaceutically acceptable salt thereof, are formulated in ways consonant with these parameters. A summary of such techniques may be found in *Remington: The Science and Practice of*

*Pharmacy,* 21$^{st}$ Edition, Lippincott Williams & Wilkins, (2005); and *Encyclopedia of Pharmaceutical Technology*, eds. J. Swarbrick and J. C. Boylan, 1988-1999, Marcel Dekker, New York, each of which is incorporated herein by reference.

Compounds, or a pharmaceutically acceptable salt thereof, described herein may be present in amounts totaling 1-95% by weight of the total weight of a composition, such as a pharmaceutical composition. The composition may be provided in a dosage form that is suitable for intraarticular, oral, parenteral (e.g., intravenous, intramuscular), rectal, cutaneous, subcutaneous, topical, transdermal, sublingual, nasal, vaginal, intravesicular, intraurethral, intrathecal, epidural, aural, or ocular administration, or by injection, inhalation, or direct contact with the nasal, genitourinary, reproductive or oral mucosa. Thus, the pharmaceutical composition may be in the form of, e.g., tablets, capsules, pills, powders, granulates, suspensions, emulsions, solutions, gels including hydrogels, pastes, ointments, creams, plasters, drenches, osmotic delivery devices, suppositories, enemas, injectables, implants, sprays, preparations suitable for iontophoretic delivery, or aerosols. The compositions may be formulated according to conventional pharmaceutical practice.

Compounds of the invention, or a pharmaceutically acceptable salt thereof, may be prepared and used as pharmaceutical compositions comprising a therapeutically effective amount of a compound, or a pharmaceutically acceptable salt thereof, described herein and a pharmaceutically acceptable carrier or excipient, as is well known in the art. In some embodiments, a composition includes at least two different pharmaceutically acceptable excipients or carriers.

As used herein, the term "administration" refers to the administration of a composition (e.g., a compound, or a preparation that includes a compound as described herein) to a subject or system. Administration to an animal subject (e.g., to a human) may be by any appropriate route. For example, in some embodiments, administration may be bronchial (including by bronchial instillation), buccal, enteral, interdermal, intra-arterial, intradermal, intragastric, intramedullary, intramuscular, intranasal, intraperitoneal, intrathecal, intravenous, intraventricular, mucosal, nasal, oral, rectal, subcutaneous, sublingual, topical, tracheal (including by intratracheal instillation), transdermal, vaginal and vitreal.

Formulations may be prepared in a manner suitable for systemic administration or topical or local administration. Systemic formulations include those designed for injection (e.g., intramuscular, intravenous or subcutaneous injection) or may be prepared for transdermal, transmucosal, or oral administration. A formulation will generally include a diluent as well as, in some cases, adjuvants, buffers, preservatives and the like. Compounds, or a pharmaceutically acceptable salt thereof, can be administered also in liposomal compositions or as microemulsions.

For injection, formulations can be prepared in conventional forms as liquid solutions or suspensions or as solid forms suitable for solution or suspension in liquid prior to injection or as emulsions. Suitable excipients include, for example, water, saline, dextrose, glycerol and the like. Such compositions may also contain amounts of nontoxic auxiliary substances such as wetting or emulsifying agents, pH buffering agents and the like, such as, for example, sodium acetate, sorbitan monolaurate, and so forth.

Various sustained release systems for drugs have also been devised. See, for example, U.S. Pat. No. 5,624,677, which is herein incorporated by reference.

Systemic administration may also include relatively non-invasive methods such as the use of suppositories, transdermal patches, transmucosal delivery and intranasal administration. Oral administration is also suitable for compounds of the invention, or a pharmaceutically acceptable salt thereof. Suitable forms include syrups, capsules, and tablets, as is understood in the art.

Each compound, or a pharmaceutically acceptable salt thereof, of a combination therapy, as described herein, may be formulated in a variety of ways that are known in the art. For example, the first and second agents of the combination therapy may be formulated together or separately.

The individually or separately formulated agents can be packaged together as a kit. Non-limiting examples include, but are not limited to, kits that contain, e.g., two pills, a pill and a powder, a suppository and a liquid in a vial, two topical creams, etc. The kit can include optional components that aid in the administration of the unit dose to subjects, such as vials for reconstituting powder forms, syringes for injection, customized IV delivery systems, inhalers, etc. Additionally, the unit dose kit can contain instructions for preparation and administration of the compositions. The kit may be manufactured as a single use unit dose for one subject, multiple uses for a particular subject (at a constant dose or in which the individual compounds, or a pharmaceutically acceptable salt thereof, may vary in potency as therapy progresses); or the kit may contain multiple doses suitable for administration to multiple subjects ("bulk packaging"). The kit components may be assembled in cartons, blister packs, bottles, tubes, and the like.

Formulations for oral use include tablets containing the active ingredient(s) in a mixture with non-toxic pharmaceutically acceptable excipients. These excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, optionally substituted hydroxylpropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

Two or more compounds may be mixed together in a tablet, capsule, or other vehicle, or may be partitioned. In one example, the first compound is contained on the inside of the tablet, and the second compound is on the outside, such that a substantial portion of the second compound is released prior to the release of the first compound.

Formulations for oral use may also be provided as chewable tablets, or as hard gelatin capsules wherein the active ingredient is mixed with an inert solid diluent (e.g., potato starch, lactose, microcrystalline cellulose, calcium carbonate, calcium phosphate or kaolin), or as soft gelatin capsules wherein the active ingredient is mixed with water or an oil medium, for example, peanut oil, liquid paraffin, or olive oil. Powders, granulates, and pellets may be prepared using the ingredients mentioned above under tablets and capsules in a conventional manner using, e.g., a mixer, a fluid bed apparatus or a spray drying equipment.

Dissolution or diffusion-controlled release can be achieved by appropriate coating of a tablet, capsule, pellet, or granulate formulation of compounds, or by incorporating the compound, or a pharmaceutically acceptable salt thereof, into an appropriate matrix. A controlled release coating may include one or more of the coating substances mentioned above or, e.g., shellac, beeswax, glycowax, castor wax, carnauba wax, stearyl alcohol, glyceryl monostearate, glyceryl distearate, glycerol palmitostearate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-optionally substituted hydroxylmethacrylate, methacrylate hydrogels, 1,3 butylene glycol, ethylene glycol methacrylate, or polyethylene glycols. In a controlled release matrix formulation, the matrix material may also include, e.g., hydrated methylcellulose, carnauba wax and stearyl alcohol, carbopol 934, silicone, glyceryl tristearate, methyl acrylate-methyl methacrylate, polyvinyl chloride, polyethylene, or halogenated fluorocarbon.

The liquid forms in which the compounds, or a pharmaceutically acceptable salt thereof, and compositions of the present invention can be incorporated for administration orally include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Generally, when administered to a human, the oral dosage of any of the compounds, or a pharmaceutically acceptable salt thereof, of the combination of the invention will depend on the nature of the compound, and can readily be determined by one skilled in the art. Typically, such dosage is normally about 0.001 mg to 2000 mg per day, desirably about 1 mg to 1000 mg per day, and more desirably about 5 mg to 500 mg per day. Dosages up to 200 mg per day may be necessary.

In some embodiments, the pharmaceutical composition may further comprise an additional compound having anti-proliferative activity. Depending on the mode of administration, compounds, or a pharmaceutically acceptable salt thereof, will be formulated into suitable compositions to permit facile delivery. Each compound, or a pharmaceutically acceptable salt thereof, of a combination therapy may be formulated in a variety of ways that are known in the art. For example, the first and second agents of the combination therapy may be formulated together or separately. Desirably, the first and second agents are formulated together for the simultaneous or near simultaneous administration of the agents.

It will be appreciated that the compounds and pharmaceutical compositions of the present invention can be formulated and employed in combination therapies, that is, the compounds and pharmaceutical compositions can be formulated with or administered concurrently with, prior to, or subsequent to, one or more other desired therapeutics or medical procedures. The particular combination of therapies (therapeutics or procedures) to employ in a combination regimen will take into account compatibility of the desired therapeutics or procedures and the desired therapeutic effect to be achieved. It will also be appreciated that the therapies employed may achieve a desired effect for the same disorder, or they may achieve different effects (e.g., control of any adverse effects).

Administration of each drug in a combination therapy, as described herein, can, independently, be one to four times daily for one day to one year, and may even be for the life of the subject. Chronic, long-term administration may be indicated.

Methods of Use

In some embodiments, the invention discloses a method of treating a disease or disorder that is characterized by aberrant Ras activity due to a Ras mutant. In some embodiments, the disease or disorder is a cancer. In some embodiments, the cancer is colorectal cancer, non-small cell lung cancer, or small cell lung cancer. In some embodiments, the aberrant Ras activity is due to Ras G12D mutation. In some embodiments, the aberrant Ras activity is due to a K-Ras G12D mutation. In some embodiments, the aberrant Ras activity is due to Ras G13D mutation. In some embodiments, the aberrant Ras activity is due to a K-Ras G13D mutation. In some embodiments, the aberrant Ras activity is due to Ras G12E mutation. In some embodiments, the aberrant Ras activity is due to a K-Ras G12E mutation. In some embodiments, the aberrant Ras activity is due to Ras G13E mutation. In some embodiments, the aberrant Ras activity is due to a K-Ras G13E mutation. Other Ras mutations are described herein.

Also provided is a method of treating cancer in a subject in need thereof, the method comprising administering to the subject a therapeutically effective amount of a compound of the present invention, or a pharmaceutically acceptable salt thereof, or a pharmaceutical composition comprising such a compound or salt. In some embodiments, the cancer is colorectal cancer, non-small cell lung cancer, pancreatic cancer, appendiceal cancer, melanoma, acute myeloid leukemia, small bowel cancer, ampullary cancer, germ cell cancer, cervical cancer, cancer of unknown primary origin, endometrial cancer, esophagogastric cancer, GI neuroendocrine cancer, ovarian cancer, sex cord stromal tumor cancer, hepatobiliary cancer, or bladder cancer. Also provided is a method of treating a Ras protein-related disorder in a subject in need thereof, the method comprising administering to the subject a therapeutically effective amount of a compound of the present invention, or a pharmaceutically acceptable salt thereof, or a pharmaceutical composition comprising such a compound or salt. In some embodiments, the cancer comprises a Ras mutation, such as a Ras mutation described herein.

In some embodiments, the compounds of the present invention or pharmaceutically acceptable salts thereof, pharmaceutical compositions comprising such compounds or salts, and methods provided herein may be used for the treatment of a wide variety of cancers including tumors such as lung, prostate, breast, brain, skin, cervical carcinomas, testicular carcinomas, etc. More particularly, cancers that may be treated by the compounds or salts thereof, pharmaceutical compositions comprising such compounds or salts, and methods of the invention include, but are not limited to tumor types such as astrocytic, breast, cervical, colorectal, endometrial, esophageal, gastric, head and neck, hepatocellular, laryngeal, lung, oral, ovarian, prostate and thyroid carcinomas and sarcomas. Other cancers include, for example:

Cardiac, for example: sarcoma (angiosarcoma, fibrosarcoma, rhabdomyosarcoma, liposarcoma), myxoma, rhabdomyoma, fibroma, lipoma and teratoma;

Lung, for example: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma;

Gastrointestinal, for example: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma);

Genitourinary tract, for example: kidney (adenocarcinoma, Wilm's tumor (nephroblastoma), lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma);

Liver, for example: hepatoma (hepatocellular carcinoma), cholangiocarcinoma, hepatoblastoma, angiosarcoma, hepatocellular adenoma, hemangioma;

Biliary tract, for example: gall bladder carcinoma, ampullary carcinoma, cholangiocarcinoma;

Bone, for example: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors;

Nervous system, for example: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma (pinealoma), glioblastoma multiform, oligodendroglioma, schwannoma, retinoblastoma, congenital tumors, neurofibromatosis type 1, spinal cord neurofibroma, meningioma, glioma, sarcoma;

Gynecological, for example: uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma);

Hematologic, for example: blood (myeloid leukemia (acute and chronic), acute lymphoblastic leukemia, chronic lymphocytic leukemia, myeloproliferative diseases (e.g., myelofibrosis and myeloproliferative neoplasms), multiple myeloma, myelodysplastic syndrome), Hodgkin's disease, non-Hodgkin's lymphoma (malignant lymphoma);

Skin, for, example: malignant melanoma, basal cell carcinoma, squamous cell carcinoma, Kaposi's sarcoma, moles dysplastic nevi, lipoma, angioma, dermatofibroma, keloids, psoriasis; and Adrenal glands, for example: neuroblastoma.

Also provided is a method of inhibiting a Ras protein in a cell, the method comprising contacting the cell with an effective amount of a compound of the present invention, or a pharmaceutically acceptable salt thereof. The cell may be in vitro or in vivo. A method of inhibiting RAF-Ras binding, the method comprising contacting the cell with an effective amount of a compound of the present invention, or a pharmaceutically acceptable salt thereof. The cell may be a cancer cell. The cancer cell may be, for example, a colorectal cancer cell, a non-small cell lung cancer cell, a pancreatic cancer cell, a appendiceal cancer cell, a melanoma cell, an acute myeloid leukemia cell, a small bowel cancer cell, an ampullary cancer cell, a germ cell cancer cell, a cervical cancer cell, a cancer cell of unknown primary origin, an endometrial cancer cell, an esophagogastric cancer cell, a GI neuroendocrine cancer cell, an ovarian cancer cell, a sex cord stromal tumor cancer cell, a hepatobiliary cancer cell, or a bladder cancer cell. In some embodiments, the cancer is appendiceal, endometrial or melanoma.

Combination Therapy

The present disclosure also provides methods for combination therapies in which an agent known to modulate other pathways, or other components of the same pathway, or even overlapping sets of targets, are used in combination with a compound of the present disclosure, or a pharmaceutically acceptable salt thereof. In one aspect, such therapy includes but is not limited to the combination of one or more compounds of the disclosure with antiproliferative agents, chemotherapeutic agents, therapeutic antibodies, and radiation treatment, to provide a synergistic or additive therapeutic effect. An example of other pharmaceuticals to combine with the compounds, or a pharmaceutically acceptable salt thereof, described herein would include pharmaceuticals for the treatment of the same indication. Another example of a potential pharmaceutical to combine with compounds, or a pharmaceutically acceptable salt thereof, described herein would include pharmaceuticals for the treatment of different yet associated or related symptoms or indications.

As used herein, the term "combination therapy" refers to those situations in which a subject is simultaneously exposed to two or more therapeutic regimens (e.g., two or more compounds, such as compounds of this invention). In some embodiments, two or more compounds may be administered simultaneously; in some embodiments, such compounds may be administered sequentially; in some embodiments, such compounds are administered in overlapping dosing regimens. In some embodiments, a combination therapeutic regimen employs two therapeutic agents, one compound of the present invention and a second selected from the therapeutic agents described herein. In some embodiments, a combination therapeutic regimen employs three therapeutic agents, one compound of the present invention and two selected from the therapeutic agents described herein. In some embodiments, a combination therapeutic regiment employs four or more therapeutic agents, one compound of the present invention and three selected from the therapeutic agents described herein. For example, a combination therapy may entail a Ras inhibitor as described herein, a MEK inhibitor, and a SHP2 inhibitor; a Ras inhibitor as described herein, a MEK inhibitor, and a SOS1 inhibitor; or a RAS inhibitor, a PD-L1 inhibitor, and a SHP2 inhibitor.

In this Combination Therapy section, all references are incorporated by reference for the agents described, whether explicitly stated as such or not.

In some embodiments, a compound of the present invention is used in combination with an EGFR inhibitor. In some embodiments, a compound of the present invention may be used in combination with an inhibitor of a member downstream of a Receptor Tyrosine Kinase (RTK)/Growth Factor Receptor, such a SHP2 inhibitor, a SOS1 inhibitor, a Raf inhibitor, a MEK inhibitor, an ERK inhibitor, a PI3K inhibitor, a PTEN inhibitor, an AKT inhibitor, or an mTORC1 inhibitor. Examples of these inhibitors are provided below.

In some embodiments, a compound of the present invention may be used in combination with a second Ras inhibitor. In some embodiments, the Ras inhibitor targets Ras in its active, or GTP-bound state (Ras(ON)). In some embodiments, the Ras(ON) inhibitor is RMC-6291, RMC-6236, RMC-9805 or RMC-8839. In some embodiments, the Ras inhibitor is a RAS(ON) inhibitor disclosed in WO 2021091956, WO 2021091967, WO 2021091982, WO 2022060836, or WO 2020132597, or a pharmaceutically acceptable salt, solvate, isomer (e.g., stereoisomer), prodrug, or tautomer thereof, incorporated herein by reference in their entireties. In some embodiments, the Ras inhibitor targets Ras in its inactive, or GDP-bound state. In some embodiments, the Ras inhibitor is an inhibitor of K-Ras G12C, such as AMG 510, MRTX1257, MRTX849, JNJ-74699157 (ARS-3248), LY3499446, ARS-1620, ARS-853, BPI-421286, LY3537982, JDQ443, ERAS-3490, JAB-21000, RMC-6291 or GDC-6036. In some embodiments, the Ras inhibitor is an inhibitor of K-Ras G12D, such as ERAS-4, MRTX1133, RMC-9805 or JAB-22000. In some embodiments, the Ras inhibitor is a K-Ras G12V inhibitor, such as JAB-23000. In some embodiments, the Ras inhibitor is an inhibitor of K-Ras G12C, such as RMC-8839. In some embodiments, the Ras inhibitor is RMC-6236.

Many chemotherapeutics are presently known in the art and can be used in combination with the compounds of the disclosure. In some embodiments, the chemotherapeutic is selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, and anti-androgens. Non-limiting examples are chemotherapeutic agents, cytotoxic agents, and non-peptide small molecules such as Gleevec® (Imatinib Mesylate), Kyprolis® (carfilzomib), Velcade® (bortezomib), Casodex™ (bicalutamide), Iressa® (gefitinib), and Adriamycin as well as a host of chemotherapeutic agents. Non-limiting examples of chemotherapeutic agents include alkylating agents such as thiotepa and cyclosphosphamide (CYTOXANTM™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, Casodex™, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifiuridine, enocitabine, floxuridine, androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfomithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g., paclitaxel and docetaxel; retinoic acid; esperamicins; capecitabine; and pharmaceutically acceptable salts, acids or derivatives of any of the above.

Also included as suitable chemotherapeutic cell conditioners are anti-hormonal agents that act to regulate or inhibit hormone action on tumors such as anti-estrogens including for example tamoxifen, (Nolvadex™), raloxifene, aromatase inhibiting 4(5)-imidazoles, 4-hydroxy tamoxifen, trioxifene, keoxifene, LY 117018, onapristone, and toremifene (Fareston); and anti-androgens such as flutamide, nilutamide, bicalutamide, leuprolide, and goserelin; chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; Xeloda®; ibandronate; camptothecin-11 (CPT-11); topoisomerase inhibitor RFS 2000; difluoromethylomithine (DMFO).

Where desired, the compounds or pharmaceutical composition of the present disclosure can be used in combination with commonly prescribed anti-cancer drugs such as Herceptin®, Avastin®, Erbitux®, Rituxan®, Taxol®, Arimidex®, Taxotere®, ABVD, AVICINE, Abagovomab, Acridine carboxamide, Adecatumumab, 17-N-Allylamino-17-demethoxygeldanamycin, Alpharadin, Alvocidib, 3-Aminopyridine-2-carboxaldehyde thiosemicarbazone, Amonafide, Anthracenedione, Anti-CD22 immunotoxins, Antineoplastic, Antitumorigenic herbs, Apaziquone, Atiprimod, Azathioprine, Belotecan, Bendamustine, BIBW 2992, Biricodar, Brostallicin, Bryostatin, Buthionine sulfoximine, CBV (chemotherapy), Calyculin, cell-cycle nonspecific antineoplastic agents, Dichloroacetic acid, Discodermolide, Elsamitrucin, Enocitabine, Epothilone, Eribulin, Everolimus, Exatecan, Exisulind, Ferruginol, Forodesine, Fosfestrol, ICE chemotherapy regimen, IT-101, Imexon, Imiquimod, Indolocarbazole, Irofulven, Laniquidar, Larotaxel, Lenalidomide, Lucanthone, Lurtotecan, Mafosfamide, Mitozolomide, Nafoxidine, Nedaplatin, Olaparib, Ortataxel, PAC-1, Pawpaw, Pixantrone, Proteasome inhibitor, Rebeccamycin, Resiquimod, Rubitecan, SN-38, Salinosporamide A, Sapacitabine, Stanford V, Swainsonine, Talaporfin, Tariquidar, Tegafur-uracil, Temodar, Tesetaxel, Triplatin tetranitrate, Tris(2-chloroethyl)amine, Troxacitabine, Uramustine, Vadimezan, Vinflunine, ZD6126 or Zosuquidar.

This disclosure further relates to a method for using the compounds or pharmaceutical compositions provided herein, in combination with radiation therapy for inhibiting abnormal cell growth or treating the hyperproliferative disorder in the mammal. Techniques for administering radiation therapy are known in the art, and these techniques can be used in the combination therapy described herein. The administration of the compound of the disclosure in this combination therapy can be determined as described herein.

Radiation therapy can be administered through one of several methods, or a combination of methods, including without limitation external-beam therapy, internal radiation therapy, implant radiation, stereotactic radiosurgery, systemic radiation therapy, radiotherapy and permanent or temporary interstitial brachy therapy. The term "brachy therapy," as used herein, refers to radiation therapy delivered by a spatially confined radioactive material inserted into the body at or near a tumor or other proliferative tissue disease site. The term is intended without limitation to include exposure to radioactive isotopes (e.g., At-211, 1-131, 1-125, Y-90, Re-186, Re-188, Sm-153, Bi-212, P-32, and radioactive isotopes of Lu). Suitable radiation sources for use as a cell conditioner of the present disclosure include both solids and liquids. By way of non-limiting example, the radiation source can be a radionuclide, such as 1-125, 1-131, Yb-169, Ir-192 as a solid source, 1-125 as a solid source, or other radionuclides that emit photons, beta particles, gamma radiation, or other therapeutic rays. The radioactive material can also be a fluid made from any solution of radionuclide(s), e.g., a solution of 1-125 or 1-131, or a radioactive fluid can be produced using a slurry of a suitable fluid containing small particles of solid radionuclides, such as Au-198, Y-90. Moreover, the radionuclide(s) can be embodied in a gel or radioactive micro spheres.

The compounds or pharmaceutical compositions of the disclosure can be used in combination with an amount of one or more substances selected from anti-angiogenesis agents, signal transduction inhibitors, antiproliferative agents, glycolysis inhibitors, or autophagy inhibitors.

Anti-angiogenesis agents, such as MMP-2 (matrix-metalloproteinase 2) inhibitors, MMP-9 (matrix-metalloprotienase 9) inhibitors, and COX-11 (cyclooxygenase 11) inhibitors, can be used in conjunction with a compound of the disclosure and pharmaceutical compositions described herein. Anti-angiogenesis agents include, for example, rapamycin, temsirolimus (CCI-779), everolimus (RAD001), sorafenib, sunitinib, and bevacizumab. Examples of useful COX-II inhibitors include alecoxib, valdecoxib, and rofecoxib. Examples of useful matrix metalloproteinase inhibitors are described in WO 96/33172, WO 96/27583, EP0818442, EP1004578, WO 98/07697, WO 98/03516, WO 98/34918, WO 98/34915, WO 98/33768, WO 98/30566, EP606046, WO 90/05719, WO 99/52910, WO 99/52889, WO 99/29667, WO1999007675, EP1786785, EP1181017, US20090012085, U.S. Pat. Nos. 5,863,949, 5,861,510, and EP0780386. Preferred MMP-2 and MMP-9 inhibitors are those that have little or no activity inhibiting MMP-1. More preferred, are those that selectively inhibit MMP-2 or AMP-9 relative to the other matrix-metalloproteinases (i.e., MAP-1, MMP-3, MMP-4, MMP-5, MMP-6, MMP-7, MMP-8, MMP-10, MMP-11, MMP-12, and MMP-13). Some specific examples of MMP inhibitors useful in the disclosure are AG-3340, RO 32-3555, and RS 13-0830.

The present compounds may also be used in co-therapies with other anti-neoplastic agents, such as acemannan, aclarubicin, aldesleukin, alemtuzumab, alitretinoin, altretamine, amifostine, aminolevulinic acid, amrubicin, amsacrine, anagrelide, anastrozole, ANCER, ancestim, ARGLABIN, arsenic trioxide, BAM 002 (Novelos), bexarotene, bicalutamide, broxuridine, capecitabine, celmoleukin, cetrorelix, cladribine, clotrimazole, cytarabine ocfosfate, DA 3030 (Dong-A), daclizumab, denileukin diftitox, deslorelin, dexrazoxane, dilazep, docetaxel, docosanol, doxercalciferol, doxifluridine, doxorubicin, bromocriptine, carmustine, cytarabine, fluorouracil, HIT diclofenac, interferon alfa, daunorubicin, doxorubicin, tretinoin, edelfosine, edrecolomab, eflornithine, emitefur, epirubicin, epoetin beta, etoposide phosphate, exemestane, exisulind, fadrozole, filgrastim, finasteride, fludarabine phosphate, formestane, fotemustine, gallium nitrate, gemcitabine, gemtuzumab zogamicin, gimeracil/oteracil/tegafur combination, glycopine, goserelin, heptaplatin, human chorionic gonadotropin, human fetal alpha fetoprotein, ibandronic acid, idarubicin, (imiquimod, interferon alfa, interferon alfa, natural, interferon alfa-2, interferon alfa-2a, interferon alfa-2b, interferon alfa-NI, interferon alfa-n3, interferon alfacon-1, interferon alpha, natural, interferon beta, interferon beta-Ia, interferon beta-Ib, interferon gamma, natural interferon gamma-Ia, interferon gamma-Ib, interleukin-1 beta, iobenguane, irinotecan, irsogladine, Ianreotide, LC 9018 (Yakult), leflunomide, lenograstim, lentinan sulfate, letrozole, leukocyte alpha interferon, leuprorelin, levamisole+fluorouracil, liarozole, lobaplatin, Ionidamine, lovastatin, masoprocol, melarsoprol, metoclopramide, mifepristone, miltefosine, mirimostim, mismatched double stranded RNA, mitoguazone, mitolactol, mitoxantrone, molgramostim, nafarelin, naloxone+pentazocine, nartograstim, nedaplatin, nilutamide, noscapine, novel erythropoiesis stimulating protein, NSC 631570 octreotide, oprelvekin, osaterone, oxaliplatin, paclitaxel, pamidronic acid, pegaspargase, peginterferon alfa-2b, pentosan polysulfate sodium, pentostatin, picibanil, pirarubicin, rabbit antithymocyte polyclonal antibody, polyethylene glycol interferon alfa-2a, porfimer sodium, raloxifene, raltitrexed, rasburiembodiment, rhenium Re 186 etidronate, RII retinamide, rituximab, romurtide, samarium (153 Sm) lexidronam, sargramostim, sizofiran, sobuzoxane, sonermin, strontium-89 chloride, suramin, tasonermin, tazarotene, tegafur, temoporfin, temozolomide, teniposide, tetrachlorodecaoxide, thalidomide, thymalfasin, thyrotropin alfa, topotecan, toremifene, tositumomab-iodine 131, trastuzumab, treosulfan, tretinoin, trilostane, trimetrexate, triptorelin, tumor necrosis factor alpha, natural, ubenimex, bladder cancer vaccine, Maruyama vaccine, melanoma lysate vaccine, valrubicin, verteporfin, vinorelbine, VIRULIZIN, zinostatin stimalamer, or zoledronic acid; abarelix; AE 941 (Aeterna), ambamustine, antisense oligonucleotide, bcl-2 (Genta), APC 8015 (Dendreon), cetuximab, decitabine, dexaminoglutethimide, diaziquone, EL 532 (Elan), EM 800 (Endorecherche), eniluracil, etanidazole, fenretinide, filgrastim SDO1 (Amgen), fulvestrant, galocitabine, gastrin 17 immunogen, HLA-B7 gene therapy (Vical), granulocyte macrophage colony stimulating factor, histamine dihydrochloride, ibritumomab tiuxetan, ilomastat, IM 862 (Cytran), interleukin-2, iproxifene, LDI 200 (Milkhaus), leridistim, lintuzumab, CA 125 MAb (Biomira), cancer MAb (Japan Pharmaceutical Development), HER-2 and Fc MAb (Medarex), idiotypic 105AD7 MAb (CRC Technology), idiotypic CEA MAb (Trilex), LYM-1-iodine 131 MAb (Techni clone), polymorphic epithelial mucin-yttrium 90 MAb (Antisoma), marimastat, menogaril, mitumomab, motexafin gadolinium, MX 6 (Galderma), nelarabine, nolatrexed, P 30 protein, pegvisomant, pemetrexed, porfiromycin, prinomastat, RL 0903 (Shire), rubitecan, satraplatin, sodium phenylacetate, sparfosic acid, SRL 172 (SR Pharma), SU 5416 (SUGEN), TA 077 (Tanabe), tetrathiomolybdate, thaliblastine, thrombopoietin, tin ethyl etiopurpurin, tirapazamine, cancer vaccine (Biomira), melanoma vaccine (New York University), melanoma vaccine (Sloan Kettering Institute), melanoma oncolysate vaccine (New York Medical College), viral melanoma cell lysates vaccine (Royal Newcastle Hospital), or valspodar.

In some embodiments, the anti-cancer agent is a HER2 inhibitor. Non-limiting examples of HER2 inhibitors include monoclonal antibodies such as trastuzumab (Herceptin®) and pertuzumab (Perjeta®); small molecule tyrosine kinase inhibitors such as gefitinib (Iressa®), erlotinib (Tarceva®), pilitinib, CP-654577, CP-724714, canertinib (CI 1033), HKI-272, lapatinib (GW-572016; Tykerb®), PKI-166, AEE788, BMS-599626, HKI-357, BIBW 2992, ARRY-334543, and JNJ-26483327.

The compounds of the invention may further be used with VEGFR inhibitors. Other compounds described in the following patents and patent applications can be used in combination therapy: U.S. Pat. No. 6,258,812, US 2003/0105091, WO 01/37820, U.S. Pat. No. 6,235,764, WO 01/32651, U.S. Pat. Nos. 6,630,500, 6,515,004, 6,713,485, 5,521,184, 5,770,599, 5,747,498, WO 02/68406, WO 02/66470, WO 02/55501, WO 04/05279, WO 04/07481, WO 04/07458, WO 04/09784, WO 02/59110, WO 99/45009, WO 00/59509, WO 99/61422, U.S. Pat. No. 5,990,141, WO 00/12089, and WO 00/02871.

In some embodiments, the combination comprises a composition of the present invention in combination with at least one anti-angiogenic agent. Agents are inclusive of, but not limited to, in vitro synthetically prepared chemical compositions, antibodies, antigen binding regions, radionuclides, and combinations and conjugates thereof. An agent can be an agonist, antagonist, allosteric modulator, toxin or, more generally, may act to inhibit or stimulate its target (e.g., receptor or enzyme activation or inhibition), and thereby promote cell death or arrest cell growth.

Exemplary anti-angiogenic agents include ERBITUX™ (IMC-C225), KDR (kinase domain receptor) inhibitory agents (e.g., antibodies and antigen binding regions that specifically bind to the kinase domain receptor), anti-VEGF agents (e.g., antibodies or antigen binding regions that specifically bind VEGF, or soluble VEGF receptors or a ligand binding region thereof) such as AVASTIN™ or VEGF-TRAP™, and anti-VEGF receptor agents (e.g., antibodies or antigen binding regions that specifically bind thereto), EGFR inhibitory agents (e.g., antibodies or antigen binding regions that specifically bind thereto) such as Vectibix (panitumumab), IRESSA™ (gefitinib), TARCEVA™ (erlotinib), anti-Angl and anti-Ang2 agents (e.g., antibodies or antigen binding regions specifically binding thereto or to their receptors, e.g., Tie2/Tek), and anti-Tie2 kinase inhibitory agents (e.g., antibodies or antigen binding regions that specifically bind thereto). The pharmaceutical compositions of the present invention can also include one or more agents (e.g., antibodies, antigen binding regions, or soluble receptors) that specifically bind and inhibit the activity of growth factors, such as antagonists of hepatocyte growth factor (HGF, also known as Scatter Factor), and antibodies or antigen binding regions that specifically bind its receptor “c-met”.

Other anti-angiogenic agents include Campath, IL-8, B-FGF, Tek antagonists (US2003/0162712; U.S. Pat. No. 6,413,932), anti-TWEAK agents (e.g., specifically binding antibodies or antigen binding regions, or soluble TWEAK receptor antagonists; see U.S. Pat. No. 6,727,225), ADAM distintegrin domain to antagonize the binding of integrin to its ligands (US 2002/0042368), specifically binding anti-eph receptor or anti-ephrin antibodies or antigen binding regions (U.S. Pat. Nos. 5,981,245; 5,728,813; 5,969,110; 6,596,852; 6,232,447; 6,057,124 and patent family members thereof), and anti-PDGF-BB antagonists (e.g., specifically binding antibodies or antigen binding regions) as well as antibodies or antigen binding regions specifically binding to PDGF-BB ligands, and PDGFR kinase inhibitory agents (e.g., antibodies or antigen binding regions that specifically bind thereto).

Additional anti-angiogenic/anti-tumor agents include: SD-7784 (Pfizer, USA); cilengitide. (Merck KGaA, Germany, EPO 770622); pegaptanib octasodium, (Gilead Sciences, USA); Alphastatin, (BioActa, UK); M-PGA, (Celgene, USA, U.S. Pat. No. 5,712,291); ilomastat, (Arriva, USA, U.S. Pat. No. 5,892,112); emaxanib, (Pfizer, USA, U.S. Pat. No. 5,792,783); vatalanib, (Novartis, Switzerland); 2-methoxyestradiol, (EntreMed, USA); TLC ELL-12, (Elan, Ireland); anecortave acetate, (Alcon, USA); alpha-D148 Mab, (Amgen, USA); CEP-7055, (Cephalon, USA); anti-Vn Mab, (Crucell, Netherlands) DACantiangiogenic, (ConjuChem, Canada); Angiocidin, (InKine Pharmaceutical, USA); KM-2550, (Kyowa Hakko, Japan); SU-0879, (Pfizer, USA); CGP-79787, (Novartis, Switzerland, EP 970070); ARGENT technology, (Ariad, USA); YIGSR-Stealth, (Johnson & Johnson, USA); fibrinogen-E fragment, (BioActa, UK); angiogenesis inhibitor, (Trigen, UK); TBC-1635, (Encysive Pharmaceuticals, USA); SC-236, (Pfizer, USA); ABT-567, (Abbott, USA); Metastatin, (EntreMed, USA); angiogenesis inhibitor, (Tripep, Sweden); maspin, (Sosei, Japan); 2-methoxyestradiol, (Oncology Sciences Corporation, USA); ER-68203-00, (IV AX, USA); Benefin, (Lane Labs, USA); Tz-93, (Tsumura, Japan); TAN-1120, (Takeda, Japan); FR-111142, (Fujisawa, Japan, JP 02233610); platelet factor 4, (RepliGen, USA, EP 407122); vascular endothelial growth factor antagonist, (Borean, Denmark); bevacizumab (pINN), (Genentech, USA); angiogenesis inhibitors, (SUGEN, USA); XL 784, (Exelixis, USA); XL 647, (Exelixis, USA); MAb, alpha5beta3 integrin, second generation, (Applied Molecular Evolution, USA and MedImmune, USA); gene therapy, retinopathy, (Oxford BioMedica, UK); enzastaurin hydrochloride (USAN), (Lilly, USA); CEP 7055, (Cephalon, USA and Sanofi-Synthelabo, France); BC 1, (Genoa Institute of Cancer Research, Italy); angiogenesis inhibitor, (Alchemia, Australia); VEGF antagonist, (Regeneron, USA); rBPI 21 and BPI-derived antiangiogenic, (XOMA, USA); PI 88, (Progen, Australia); cilengitide (pINN), (Merck KGaA, German; Munich Technical University, Germany, Scripps Clinic and Research Foundation, USA); cetuximab (INN), (Aventis, France); AVE 8062, (Ajinomoto, Japan); AS 1404, (Cancer Research Laboratory, New Zealand); SG 292, (Telios, USA); Endostatin, (Boston Childrens Hospital, USA); ATN 161, (Attenuon, USA); ANGIOSTATIN, (Boston Childrens Hospital, USA); 2-methoxyestradiol, (Boston Childrens Hospital, USA); ZD 6474, (AstraZeneca, UK); ZD 6126, (Angiogene Pharmaceuticals, UK); PPI 2458, (Praecis, USA); AZD 9935, (AstraZeneca, UK); AZD 2171, (AstraZeneca, UK); vatalanib (pINN), (Novartis, Switzerland and Schering AG, Germany); tissue factor pathway inhibitors, (EntreMed, USA); pegaptanib (Pinn), (Gilead Sciences, USA); xanthorrhizol, (Yonsei University, South Korea); vaccine, gene-based, VEGF-2, (Scripps Clinic and Research Foundation, USA); SPV5.2, (Supratek, Canada); SDX 103, (University of California at San Diego, USA); PX 478, (ProlX, USA); METASTATIN, (EntreMed, USA); troponin I, (Harvard University, USA); SU 6668, (SUGEN, USA); OXI 4503, (OXiGENE, USA); o-guanidines, (Dimensional Pharmaceuticals, USA); motuporamine C, (British Columbia University, Canada); CDP 791, (Celltech Group, UK); atiprimod (pINN), (GlaxoSmithKline, UK); E 7820, (Eisai, Japan);

CYC 381, (Harvard University, USA); AE 941, (Aeterna, Canada); vaccine, angiogenesis, (EntreMed, USA); urokinase plasminogen activator inhibitor, (Dendreon, USA); oglufanide (pINN), (Melmotte, USA); HIF-lalfa inhibitors, (Xenova, UK); CEP 5214, (Cephalon, USA); BAY RES 2622, (Bayer, Germany); Angiocidin, (InKine, USA); A6, (Angstrom, USA); KR 31372, (Korea Research Institute of Chemical Technology, South Korea); GW 2286, (GlaxoSmithKline, UK); EHT 0101, (ExonHit, France); CP 868596, (Pfizer, USA); CP 564959, (OSI, USA); CP 547632, (Pfizer, USA); 786034, (GlaxoSmithKline, UK); KRN 633, (Kirin Brewery, Japan); drug delivery system, intraocular, 2-methoxyestradiol, (EntreMed, USA); anginex, (Maastricht University, Netherlands, and Minnesota University, USA); ABT 510, (Abbott, USA); AAL 993, (Novartis, Switzerland); VEGI, (ProteomTech, USA); tumor necrosis factor-alpha inhibitors, (National Institute on Aging, USA); SU 11248, (Pfizer, USA and SUGEN USA); ABT 518, (Abbott, USA); YH16, (Yantai Rongchang, China); S-3APG, (Boston Childrens Hospital, USA and EntreMed, USA); MAb, KDR, (ImClone Systems, USA); MAb, alpha5 betal, (Protein Design, USA); KDR kinase inhibitor, (Celltech Group, UK, and Johnson & Johnson, USA); GFB 116, (South Florida University, USA and Yale University, USA); CS 706, (Sankyo, Japan); combretastatin A4 prodrug, (Arizona State University, USA); chondroitinase AC, (IBEX, Canada); BAY RES 2690, (Bayer, Germany); AGM 1470, (Harvard University, USA, Takeda, Japan, and TAP, USA); AG 13925, (Agouron, USA); Tetrathiomolybdate, (University of Michigan, USA); GCS 100, (Wayne State University, USA) CV 247, (Ivy Medical, UK); CKD 732, (Chong Kun Dang, South Korea); MAb, vascular endothelium growth factor, (Xenova, UK); irsogladine (INN), (Nippon Shinyaku, Japan); RG 13577, (Aventis, France); WX 360, (Wilex, Germany); squalamine (pINN), (Genaera, USA); RPI 4610, (Sirna, USA); cancer therapy, (Marinova, Australia); heparanase inhibitors, (InSight, Israel); KL 3106, (Kolon, South Korea); Honokiol, (Emory University, USA); ZK CDK, (Schering AG, Germany); ZK Angio, (Schering AG, Germany); ZK 229561, (Novartis, Switzerland, and Schering AG, Germany); XMP 300, (XOMA, USA); VGA 1102, (Taisho, Japan); VEGF receptor modulators, (Pharmacopeia, USA); VE-cadherin-2 antagonists, (ImClone Systems, USA); Vasostatin, (National Institutes of Health, USA); vaccine, Flk-1, (ImClone Systems, USA); TZ 93, (Tsumura, Japan); TumStatin, (Beth Israel Hospital, USA); truncated soluble FLT 1 (vascular endothelial growth factor receptor 1), (Merck & Co, USA); Tie-2 ligands, (Regeneron, USA); and, thrombospondin 1 inhibitor, (Allegheny Health, Education and Research Foundation, USA).

Autophagy inhibitors include, but are not limited to chloroquine, 3-methyladenine, hydroxychloroquine (Plaquenil™), bafilomycin Al, 5-amino-4-imidazole carboxamide riboside (AICAR), okadaic acid, autophagy-suppressive algal toxins which inhibit protein phosphatases of type 2A or type 1, analogues of cAMP, and drugs which elevate cAMP levels such as adenosine, LY204002, N6-mercaptopurine riboside, and vinblastine. In addition, antisense or siRNA that inhibits expression of proteins including but not limited to ATG5 (which are implicated in autophagy), may also be used.

Additional pharmaceutically active compounds/agents that can be used in the treatment of cancers and that can be used in combination with one or more compound of the present invention include: epoetin alfa; darbepoetin alfa; panitumumab; pegfilgrastim; palifermin; filgrastim; denosumab; ancestim; AMG 102; AMG 386; AMG 479; AMG 655; AMG 745; AMG 951; and AMG 706, or a pharmaceutically acceptable salt thereof.

In certain embodiments, a composition provided herein is conjointly administered with a chemotherapeutic agent. Suitable chemotherapeutic agents may include, natural products such as vinca alkaloids (e.g., vinblastine, vincristine, and vinorelbine), paclitaxel, epidipodophyllotoxins (e.g., etoposide and teniposide), antibiotics (e.g., dactinomycin (actinomycin D), daunorubicin, doxorubicin, and idarubicin), anthracyclines, mitoxantrone, bleomycins, plicamycin (mithramycin), mitomycin, enzymes (e.g., L-asparaginase which systemically metabolizes L-asparagine and deprives cells which do not have the capacity to synthesize their own asparagine), antiplatelet agents, antiproliferative/antimitotic alkylating agents such as nitrogen mustards (e.g., mechlorethamine, cyclophosphamide and analogs, melphalan, and chlorambucil), ethylenimines and methylmelamines (e.g., hexaamethylmelaamine and thiotepa), CDK inhibitors (e.g., ribociclib, abemaciclib, palbociclib, seliciclib, UCN-01, P1446A-05, PD-0332991, dinaciclib, P27-00, AT-7519, RGB286638, and SCH727965), alkyl sulfonates (e.g., busulfan), nitrosoureas (e.g., carmustine (BCNU) and analogs, and streptozocin), trazenes-dacarbazinine (DTIC), antiproliferative/antimitotic antimetabolites such as folic acid analogs (e.g., methotrexate), pyrimidine analogs (e.g., fluorouracil, floxuridine, and cytarabine), purine analogs and related inhibitors (e.g., mercaptopurine, thioguanine, pentostatin and 2-chlorodeoxyadenosine), aromatase inhibitors (e.g., anastrozole, exemestane, and letrozole), and platinum coordination complexes (e.g., cisplatin and carboplatin), procarbazine, hydroxyurea, mitotane, aminoglutethimide, histone deacetylase (HDAC) inhibitors (e.g., trichostatin, sodium butyrate, apicidan, suberoyl anilide hydroamic acid, vorinostat, LBH 589, romidepsin, ACY-1215, and panobinostat), mTOR inhibitors (e.g., temsirolimus, everolimus, ridaforolimus, and sirolimus; see also below), KSP(Eg5) inhibitors (e.g., Array 520), DNA binding agents (e.g., Zalypsis), PI3K delta inhibitor (e.g., GS-1101 and TGR-1202), PI3K delta and gamma inhibitor (e.g., CAL-130), multi-kinase inhibitor (e.g., TGO2 and sorafenib), hormones (e.g., estrogen) and hormone agonists such as leutinizing hormone releasing hormone (LHRH) agonists (e.g., goserelin, leuprolide and triptorelin), BAFF-neutralizing antibody (e.g., LY2127399), IKK inhibitors, p38MAPK inhibitors, anti-IL-6 (e.g., CNT0328), telomerase inhibitors (e.g., GRN 163L), aurora kinase inhibitors (e.g., MLN8237), cell surface monoclonal antibodies (e.g., anti-CD38 (HUMAX-CD38), anti-CSI (e.g., elotuzumab), HSP90 inhibitors (e.g., 17 AAG and KOS 953), P13K/Akt inhibitors (e.g., perifosine), Akt inhibitor (e.g., GSK-2141795), PKC inhibitors (e.g., enzastaurin), FTIs (e.g., Zarnestra™), anti-CD138 (e.g., BT062), Torcl/2 specific kinase inhibitor (e.g., INK128), kinase inhibitor (e.g., GS-1101), ER/UPR targeting agent (e.g., MKC-3946), cFMS inhibitor (e.g., ARRY-382), JAK1/2 inhibitor (e.g., CYT387), PARP inhibitor (e.g., olaparib and veliparib (ABT-888)), and BCL-2 antagonist. Other chemotherapeutic agents may include mechlorethamine, camptothecin, ifosfamide, tamoxifen, raloxifene, gemcitabine, navelbine, sorafenib, or any analog or derivative variant of the foregoing.

Other mTOR inhibitors that may be combined with compounds of the present invention include, but are not limited to, ATP-competitive mTORC1/mTORC2 inhibitors, e.g., PI-103, PP242, PP30; Torin 1; FKBP12 enhancers; 4H-1-benzopyran-4-one derivatives; and rapamycin (also known as sirolimus) and derivatives thereof, including: temsirolimus (Torisel®); everolimus (Afinitor®; WO94/09010);

ridaforolimus (also known as deforolimus orAP23573); rapalogs, e.g., as disclosed in WO98/02441 and WOO1/14387, e.g. AP23464 and AP23841; 40-(2-hydroxyethyl) rapamycin; 40-[3-hydroxy(hydroxymethyl)methylpropanoate]-rapamycin (also known as CC1779); 40-epi-(tetrazolyt)-rapamycin (also called ABT578); 32-deoxorapamycin; 16-pentynyloxy-32(S)-dihydrorapanycin; derivatives disclosed in WO05/005434; derivatives disclosed in U.S. Pat. Nos. 5,258,389, 5,118,677, 5,118,678, 5,100,883, 5,151,413, 5,120,842, and 5,256,790, and in WO94/090101, WO92/05179, WO93/111130, WO94/02136, WO94/02485, WO95/14023, WO94/02136, WO95/16691, WO96/41807, WO96/41807, and WO2018204416; and phosphorus-containing rapamycin derivatives (e.g., WO05/016252). In some embodiments, the mTOR inhibitor is a bisteric inhibitor (see, e.g., WO2018204416, WO2019212990 and WO2019212991), such as RMC-5552.

The compounds of the present invention may also be used in combination with radiation therapy, hormone therapy, surgery and immunotherapy, which therapies are well known to those skilled in the art.

In certain embodiments, a pharmaceutical composition provided herein is conjointly administered with a steroid. Suitable steroids may include, but are not limited to, 21-acetoxypregnenolone, alclometasone, algestone, amcinonide, beclomethasone, betamethasone, budesonide, chloroprednisone, clobetasol, clocortolone, cloprednol, corticosterone, cortisone, cortivazol, deflazacort, desonide, desoximetasone, dexamethasone, diflorasone, diflucortolone, difuprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, hydrocortisone, loteprednol etabonate, mazipredone, medrysone, meprednisone, methylprednisolone, mometasone furoate, paramethasone, prednicarbate, prednisolone, prednisolone 25-diethylaminoacetate, prednisolone sodium phosphate, prednisone, prednival, prednylidene, rimexolone, tixocortol, triamcinolone, triamcinolone acetonide, triamcinolone benetonide, triamcinolone hexacetonide, and salts or derivatives thereof. In a particular embodiment, the compounds of the present invention can also be used in combination with additional pharmaceutically active agents that treat nausea. Examples of agents that can be used to treat nausea include: dronabinol; granisetron; metoclopramide; ondansetron; and prochlorperazine; or a pharmaceutically acceptable salt thereof.

The compounds of the present invention may also be used in combination with an additional pharmaceutically active compound that disrupts or inhibits RAS-RAF-ERK or PI3K-AKT-TOR signaling pathways. In some combinations, the additional pharmaceutically active compound is a PD-1 or PD-L1 antagonist. The compounds or pharmaceutical compositions of the disclosure can also be used in combination with an amount of one or more substances selected from EGFR inhibitors, MEK inhibitors, PI3K inhibitors, AKT inhibitors, TOR inhibitors, Mcl-1 inhibitors, BCL-2 inhibitors, SHP2 inhibitors, proteasome inhibitors, and immune therapies, including monoclonal antibodies, immunomodulatory imides (IMiDs), anti-PD-1, anti-PD-L1, anti-CTLA4, anti-LAGI, and anti-OX40 agents, GITR agonists, CAR-T cells, and BiTEs.

EGFR inhibitors include, but are not limited to, small molecule antagonists, antibody inhibitors, or specific antisense nucleotide or siRNA. Useful antibody inhibitors of EGFR include cetuximab (Erbitux®), panitumumab (Vectibix®), zalutumumab, nimotuzumab, and matuzumab. Small molecule antagonists of EGFR include gefitinib, erlotinib (Tarceva®), osimertinib (Tagrisso®), and lapatinib (TykerB®). See e.g., Yan L, et. al, Pharmacogenetics and Pharmacogenomics In Oncology Therapeutic Antibody Development, BioTechniques 2005; 39(4): 565-8, and Paez J G, et. al, EGFR Mutations In Lung Cancer Correlation With Clinical Response To Gefitinib Therapy, Science 2004; 304(5676): 1497-500.

Non-limiting examples of small molecule EGFR inhibitors include any of the EGFR inhibitors described in the following patent publications, and all pharmaceutically acceptable salts and solvates of said EGFR inhibitors: European Patent Application EP 520722, published Dec. 30, 1992; European Patent Application EP 566226, published Oct. 20, 1993; PCT International Publication WO 96/33980, published Oct. 31, 1996; U.S. Pat. No. 5,747,498, issued May 5, 1998; PCT International Publication WO 96/30347, published Oct. 3, 1996; European Patent Application EP 787772, published Aug. 6, 1997; PCT International Publication WO 97/30034, published Aug. 21, 1997; PCT International Publication WO 97/30044, published Aug. 21, 1997; PCT International Publication WO 97/38994, published Oct. 23, 1997; PCT International Publication WO 97/49688, published Dec. 31, 1997; European Patent Application EP 837063, published Apr. 22, 1998; PCT International Publication WO 98/02434, published Jan. 22, 1998; PCT International Publication WO 97/38983, published Oct. 23, 1997; PCT International Publication WO 95/19774, published Jul. 27, 1995; PCT International Publication WO 95/19970, published Jul. 27, 1995; PCT International Publication WO 97/13771, published Apr. 17, 1997; PCT International Publication WO 98/02437, published Jan. 22, 1998; PCT International Publication WO 98/02438, published Jan. 22, 1998; PCT International Publication WO 97/32881, published Sep. 12, 1997; German Application DE 19629652, published Jan. 29, 1998; PCT International Publication WO 98/33798, published Aug. 6, 1998; PCT International Publication WO 97/32880, published Sep. 12, 1997; PCT International Publication WO 97/32880 published Sep. 12, 1997; European Patent Application EP 682027, published Nov. 15, 1995; PCT International Publication WO 97/02266, published January 23, 197; PCT International Publication WO 97/27199, published Jul. 31, 1997; PCT International Publication WO 98/07726, published Feb. 26, 1998; PCT International Publication WO 97/34895, published Sep. 25, 1997; PCT International Publication WO 96/31510, published Oct. 10, 1996; PCT International Publication WO 98/14449, published Apr. 9, 1998; PCT International Publication WO 98/14450, published Apr. 9, 1998; PCT International Publication WO 98/14451, published Apr. 9, 1998; PCT International Publication WO 95/09847, published Apr. 13, 1995; PCT International Publication WO 97/19065, published May 29, 1997; PCT International Publication WO 98/17662, published Apr. 30, 1998; U.S. Pat. No. 5,789,427, issued Aug. 4, 1998; U.S. Pat. No. 5,650,415, issued Jul. 22, 1997; U.S. Pat. No. 5,656,643, issued Aug. 12, 1997; PCT International Publication WO 99/35146, published Jul. 15, 1999; PCT International Publication WO 99/35132, published Jul. 15, 1999; PCT International Publication WO 99/07701, published Feb. 18, 1999; and PCT International Publication WO 92/20642 published Nov. 26, 1992. Additional non-limiting examples of small molecule EGFR inhibitors include any of the EGFR inhibitors described in Traxler, P., 1998, Exp. Opin. Ther. Patents 8(12): 1599-1625. In some embodiments, an EGFR inhibitor is an ERBB inhibitor. In humans, the ERBB family contains HER1 (EGFR, ERBB1), HER2 (NEU, ERBB2), HER3 (ERBB3), and HER (ERBB4).

Antibody-based EGFR inhibitors include any anti-EGFR antibody or antibody fragment that can partially or completely block EGFR activation by its natural ligand. Non-limiting examples of antibody-based EGFR inhibitors include those described in Modjtahedi, H., et al, 1993, Br. J. Cancer 67:247-253; Teramoto, T., et al, 1996, Cancer 77:639-645; Goldstein et al, 1995, Clin. Cancer Res. 1: 1311-1318; Huang, S. M., et al., 1999, Cancer Res. 15:59(8): 1935-40; and Yang, X., et al., 1999, Cancer Res. 59: 1236-1243. Thus, the EGFR inhibitor can be monoclonal antibody Mab E7.6.3 (Yang, 1999 supra), or Mab C225 (ATCC Accession No. HB-8508), or an antibody or antibody fragment having the binding specificity thereof.

MEK inhibitors include, but are not limited to, cobimetinib, trametinib, and binimetinib.

PI3K inhibitors include, but are not limited to, wortmannin, 17-hydroxywortmannin analogs described in WO 06/044453, 4-[2-(IH-Indazol-4-yl)-6-[[4-(methylsulfonyl)piperazin-1-yl]methyl]thieno[3,2-d]pyrimidin-4-yl]morpholine (also known as GDC 0941 and described in PCT Publication Nos. WO 09/036,082 and WO 09/055,730), 2-Methyl-2-[4-[3-methyl-2-oxo-8-(quinolin-3-yl)-2,3-dihydroimidazo[4,5-c]quinolin-1-yl]phenyl]propionitrile (also known as BEZ 235 or NVP-BEZ 235, and described in PCT Publication No. WO 06/122806), (S)-l-(4-((2-(2-aminopyrinddin-5-yl)-7-methyl-4-morpholinothieno[3,2-d]pyriiTddin-6-yl)methyl)piperazin-1-yl)-2-hydroxypropan-1-one (described in PCT Publication No. WO 2008/070740), LY294002 (2-(4-Morpholinyl)-8-phenyl-4H-1-benzopyran-4-one available from Axon Medchem), PI 103 hydrochloride (3-[4-(4-morpholinylpyrido-[3',2':4,5]furo[3,2-d]pyrimidin-2-yl] phenol hydrochloride available from Axon Medchem), PIK 75 (N'-[(IE)-(6-bromoinddazo[1,2-a]pyridin-3-yl)methylene]-N,2-dimethyl-5-nitrobenzenesulfono-hydrazide hydrochloride available from Axon Medchem), PIK 90 (N-(7,8-dimethoxy-2,3-dihydro-imidazo[1,2-c]quinazolin-5-yl)-nicotinamide available from Axon Medchem), GDC-0941 bismesylate (2-(IH-Indazol-4-yl)-6-(4-methanesulfonyl-piperazin-1-ylmethyl)-4-moholin-4-yl-thieno[3,2-d]pyrimidine bismesylate available from Axon Medchem), AS-252424 (5-[1-[5-(4-Fluoro-2-hydroxy-phenyl)-furan-2-yl]-meth-(Z)-ylidene]-thiazolidine-2,4-dione available from Axon Medchem), and TGX-221 (7-Methyl-2-(4-morpholinyl)-9-[I-(phenylamino)ethyl]-4H-pyrido-[1,2-a]pyrirnidin-4-one available from Axon Medchem), XL-765, and XL-147. Other PI3K inhibitors include demethoxyviridin, perifosine, CAL101, PX-866, BEZ235, SF1126, INK1117, IPI-145, BKM120, XL147, XL765, Palomid 529, GSK1059615, ZSTK474, PWT33597, IC87114, TGI 00-115, CAL263, PI-103, GNE-477, CUDC-907, and AEZS-136.

AKT inhibitors include, but are not limited to, Akt-1-1 (inhibits Aktl) (Barnett et al. (2005) Biochem. J., 385 (Pt. 2), 399-408); Akt-1-1,2 (inhibits Akl and 2) (Barnett et al. (2005) Biochem. J. 385 (Pt. 2), 399-408); API-59CJ-Ome (e.g., Jin et al. (2004) Br. J. Cancer 91, 1808-12); I-H-imidazo[4,5-c]pyridinyl compounds (e.g., WO05011700); indole-3-carbinol and derivatives thereof (e.g., U.S. Pat. No. 6,656,963; Sarkar and Li (2004) J Nutr. 134(12 Suppl), 3493S-3498S); perifosine (e.g., interferes with Akt membrane localization; Dasmahapatra et al. (2004) Clin. Cancer Res. 10(15), 5242-52, 2004); phosphatidylinositol ether lipid analogues (e.g., Gills and Dennis (2004) Expert. Opin. Investig. Drugs 13, 787-97); and triciribine (TCN or API-2 or NCI identifier: NSC 154020; Yang et al. (2004) Cancer Res. 64, 4394-9).

TOR inhibitors include, but are not limited to, inhibitors include AP-23573, CCI-779, everolimus, RAD-001, rapamycin, temsirolimus, ATP-competitive TORC1/TORC2 inhibitors, including PI-103, PP242, PP30 and Torin 1. Other TOR inhibitors in FKBP12 enhancer; rapamycins and derivatives thereof, including: CCI-779 (temsirolimus), RAD001 (Everolimus; WO 9409010) and AP23573; rapalogs, e.g., as disclosed in WO 98/02441 and WO 01/14387, e.g., AP23573, AP23464, or AP23841; 40-(2-hydroxyethyl) rapamycin, 40-[3-hydroxy(hydroxymethyl)methylpropanoate]-rapamycin (also called CC1779), 40-epi-(tetrazolyt)-rapamycin (also called ABT578), 32-deoxorapamycin, 16-pentynyloxy-32(S)-dihydrorapanycin, and other derivatives disclosed in WO 05005434; derivatives disclosed in U.S. Pat. No. 5,258,389, WO 94/090101, WO 92/05179, U.S. Pat. Nos. 5,118,677, 5,118,678, 5,100,883, 5,151,413, 5,120,842, WO 93/111130, WO 94/02136, WO 94/02485, WO 95/14023, WO 94/02136, WO 95/16691, WO 96/41807, WO 96/41807 and U.S. Pat. No. 5,256,790; phosphorus-containing rapamycin derivatives (e.g., WO 05016252); 4H-1-benzopyran-4-one derivatives (e.g., WO 2005/056014).

Optional BRAF inhibitors that may be used in combination include, for example, vemurafenib, dabrafenib, and encorafenib.

In some embodiments, an anti-cancer agent is an ALK inhibitor. Non-limiting examples of ALK inhibitors include ceritinib, TAE-684 (NVP-TAE694), PF02341066 (crizotinib or 1066), alectinib; brigatinib; entrectinib; ensartinib (X-396); lorlatinib; ASP3026; CEP-37440; 4SC-203; TL-398; PLB1003; TSR-011; CT-707; TPX-0005, and AP26113. Additional examples of ALK kinase inhibitors are described in examples 3-39 of WO05016894.

In some embodiments, an anti-cancer agent is an inhibitor of a member downstream of a Receptor Tyrosine Kinase (RTK)/Growth Factor Receptor (e.g., a SHP2, a SOS1 inhibitor, a Raf inhibitor, a MEK inhibitor, an ERK inhibitor, a PI3K inhibitor, a PTEN inhibitor, an AKT inhibitor, or an mTOR inhibitor (e.g., mTORC1 inhibitor or mTORC2 inhibitor). In some embodiments, an anti-cancer agent is an additional Ras inhibitor, or a Ras vaccine, or another therapeutic modality designed to directly or indirectly decrease the oncogenic activity of Ras. In some embodiments, a therapeutic agent may be a pan-RTK inhibitor, such as afatinib.

MCI-1 inhibitors include, but are not limited to, AMG-176, MIK665, and S63845. The myeloid cell leukemia-1 (MCL-1) protein is one of the key anti-apoptotic members of the B-cell lymphoma-2 (BCL-2) protein family. Over-expression of MCL-1 has been closely related to tumor progression as well as to resistance, not only to traditional chemotherapies but also to targeted therapeutics including BCL-2 inhibitors such as ABT-263.

Proteasome inhibitors include, but are not limited to, Kyprolis® (carfilzomib), Velcade® (bortezomib), and oprozomib.

Immune therapies include, but are not limited to, anti-PD-1 agents, anti-PD-L1 agents, anti-CTLA-4 agents, anti-LAGI agents, and anti-OX40 agents.

Monoclonal antibodies include, but are not limited to, Darzalex® (daratumumab), Herceptin® (trastuzumab), Avastin® (bevacizumab), Rituxan® (rituximab), Lucentis® (ranibizumab), and Eylea® (aflibercept).

Immunomodulatory agents (IMiDs) are a class of immunomodulatory drugs (drugs that adjust immune responses) containing an imide group. The IMiD class includes thalidomide and its analogues (lenalidomide, pomalidomide, and apremilast).

A therapeutic agent may be a T-cell checkpoint inhibitor. In one embodiment, the checkpoint inhibitor is an inhibitory antibody (e.g., a monospecific antibody such as a monoclonal antibody). The antibody may be, e.g., humanized or fully human. In some embodiments, the checkpoint inhibitor is a fusion protein, e.g., an Fc-receptor fusion protein. In some embodiments, the checkpoint inhibitor is an agent, such as an antibody, that interacts with a checkpoint protein. In some embodiments, the checkpoint inhibitor is an agent, such as an antibody, that interacts with the ligand of a checkpoint protein. In some embodiments, the checkpoint inhibitor is an inhibitor (e.g., an inhibitory antibody or small molecule inhibitor) of CTLA-4 (e.g., an anti-CTLA-4 antibody or fusion a protein). In some embodiments, the checkpoint inhibitor is an inhibitor or antagonist (e.g., an inhibitory antibody or small molecule inhibitor) of PD-1. In some embodiments, the checkpoint inhibitor is an inhibitor or antagonist (e.g., an inhibitory antibody or small molecule inhibitor) of PD-L1. In some embodiments, the checkpoint inhibitor is an inhibitor or antagonist (e.g., an inhibitory antibody or Fc fusion or small molecule inhibitor) of PD-L2 (e.g., a PD-L2/Ig fusion protein). Exemplary anti-PD-1 antibodies and methods for their use are described by Goldberg et al, Blood 110(1): 186-192 (2007), Thompson et al., Clin. Cancer Res. 13(6): 1757-1761 (2007), and Korman et al, International Application No. PCT/JP2006/309606 (publication no. WO 2006/121168 A1), each of which are expressly incorporated by reference herein, include: Yervoy™ (ipilimumab) or Tremelimumab (to CTLA-4), galiximab (to B7.1), BMS-936558 (to PD-1), MK-3475 (to PD-1) (pembrolizumab), AMP224 (to B7DC), BMS-936559 (to B7-H1), MPDL3280A (to B7-H1), MEDI-570 (to ICOS), AMG557 (to B7H2), MGA271 (to B7H3), IMP321 (to LAG-3), BMS-663513 (to CD137), PF-05082566 (to CD137), CDX-1127 (to CD27), anti-OX40 (Providence Health Services), huMAbOX40L (to OX40L), Atacicept (to TACl), CP-870893 (to CD40), Lucatumumab (to CD40), Dacetuzumab (to CD40), Muromonab-CD3 (to CD3), Ipilumumab (to CTLA-4). Immune therapies also include genetically engineered T-cells (e.g., CAR-T cells) and bispecific antibodies (e.g., BiTEs).

GITR agonists include, but are not limited to, GITR fusion proteins and anti-GITR antibodies (e.g., bivalent anti-GITR antibodies), such as, a GITR fusion protein described in U.S. Pat. No. 6,111,090, European Patent No. 090505B1, U.S. Pat. No. 8,586,023, PCT Publication Nos. WO 2010/003118 and 2011/090754, or an anti-GITR antibody described, e.g., in U.S. Pat. No. 7,025,962, European Patent No. 1947183B1, U.S. Pat. Nos. 7,812,135, 8,388,967, 8,591,886, European Patent No. EP 1866339, PCT Publication No. WO 2011/028683, PCT Publication No. WO 2013/039954, PCT Publication No. WO2005/007190, PCT Publication No. WO 2007/133822, PCT Publication No. WO2005/055808, PCT Publication No. WO 99/40196, PCT Publication No. WO 2001/03720, PCT Publication No. WO99/20758, PCT Publication No. WO2006/083289, PCT Publication No. WO 2005/115451, U.S. Pat. No. 7,618,632, and PCT Publication No. WO 2011/051726.

In some embodiments, the additional therapeutic agent is a SHP2 inhibitor. SHP2 is a non-receptor protein tyrosine phosphatase encoded by the PTPN11 gene that contributes to multiple cellular functions including proliferation, differentiation, cell cycle maintenance and migration. SHP2 has two N-terminal Src homology 2 domains (N-SH2 and C—SH2), a catalytic domain (PTP), and a C-terminal tail. The two SH2 domains control the subcellular localization and functional regulation of SHP2. The molecule exists in an inactive, self-inhibited conformation stabilized by a binding network involving residues from both the N-SH2 and PTP domains. Stimulation by, for example, cytokines or growth factors acting through receptor tyrosine kinases (RTKs) leads to exposure of the catalytic site resulting in enzymatic activation of SHP2.

SHP2 is involved in signaling through the RAS-mitogen-activated protein kinase (MAPK), the JAK-STAT or the phosphoinositol 3-kinase-AKT pathways. Mutations in the PTPN11 gene and subsequently in SHP2 have been identified in several human developmental diseases, such as Noonan Syndrome and Leopard Syndrome, as well as human cancers, such as juvenile myelomonocytic leukemia, neuroblastoma, melanoma, acute myeloid leukemia and cancers of the breast, lung and colon. Some of these mutations destabilize the auto-inhibited conformation of SHP2 and promote autoactivation or enhanced growth factor driven activation of SHP2. SHP2, therefore, represents a highly attractive target for the development of novel therapies for the treatment of various diseases including cancer. A SHP2 inhibitor (e.g., RMC-4550 or SHP099) in combination with a RAS pathway inhibitor (e.g., a MEK inhibitor) have been shown to inhibit the proliferation of multiple cancer cell lines in vitro (e.g., pancreas, lung, ovarian and breast cancer). Thus, combination therapy involving a SHP2 inhibitor with a RAS pathway inhibitor could be a general strategy for preventing tumor resistance in a wide range of malignancies.

Non-limiting examples of such SHP2 inhibitors that are known in the art, include those found in the following publications: Chen et al. *Mol Pharmacol.* 2006, 70, 562; Sarver et al., *J. Med. Chem.* 2017, 62, 1793; Xie et al., *J. Med. Chem.* 2017, 60, 113734; and Igbe et al., *Oncotarget,* 2017, 8, 113734; and patent applications: WO 2022063190, WO 2022043685, WO 2022042331, WO 2022033430, WO 2022033430, WO 2022017444, WO 2022007869, WO 2021259077, WO 2021249449, WO 2021249057, WO 2021244659, WO 2021218755, WO 2021281752, WO 2021197542, WO 2021176072, WO 2021149817, WO 2021148010, WO 2021147879, WO 2021143823, WO 2021143701, WO 2021143680, WO 2021121397, WO 2021119525, WO 2021115286, WO 2021110796, WO 2021088945, WO 2021073439, WO 2021061706, WO 2021061515, WO 2021043077, WO 2021033153, WO 2021028362, WO 2021033153, WO 2021028362, WO 2021018287, WO 2020259679, WO 2020249079, WO 2020210384, WO 2020201991, WO 2020181283, WO 2020177653, WO 2020165734, WO 2020165733, WO 2020165732, WO 2020156243, WO 2020156242, WO 2020108590, WO 2020104635, WO 2020094104, WO 2020094018, WO 2020081848, WO 2020073949, WO 2020073945, WO 2020072656, WO 2020065453, WO 2020065452, WO 2020063760, WO 2020061103, WO 2020061101, WO 2020033828, WO 2020033286, WO 2020022323, WO 2019233810, WO 2019213318, WO 2019183367, WO 2019183364, WO 2019182960, WO 2019167000, WO 2019165073, WO 2019158019, WO 2019152454, WO 2019051469, WO 2019051084, WO 2018218133, WO 2018172984, WO 2018160731, WO 2018136265, WO 2018136264, WO 2018130928, WO 2018129402, WO 2018081091, WO 2018057884, WO 2018013597, WO 2017216706, WO 2017211303, WO 2017210134, WO 2017156397, WO 2017100279, WO 2017079723, WO 2017078499, WO 2016203406, WO 2016203405, WO 2016203404, WO 2016196591, WO 2016191328, WO 2015107495, WO 2015107494, WO 2015107493, WO 2014176488, WO 2014113584, US 20210085677, U.S. Ser. No. 10/858,359, U.S. Ser. No. 10/934,302, U.S. Ser. No. 10/954,243, U.S. Ser. No. 10/988,466, U.S. Ser. No. 11/001,561, U.S. Ser. No. 11/033,547, U.S. Ser. No. 11/034,705, U.S. Ser. No. 11/044,675, CN 114213417, CN 114163457, CN 113896710, CN 113248521, CN 113248449, CN 113135924, CN 113024508, CN 112920131, CN 112823796, CN 112402385, CN 111848599, CN 111704611, CN 111265529, and CN 108113848, or a pharmaceutically acceptable salt, solvate, isomer (e.g., stereoisomer), prodrug, or tautomer thereof, each of which is incorporated herein by reference.

In some embodiments, a SHP2 inhibitor binds in the active site. In some embodiments, a SHP2 inhibitor is a mixed-type irreversible inhibitor. In some embodiments, a SHP2 inhibitor binds an allosteric site e.g., a non-covalent allosteric inhibitor. In some embodiments, a SHP2 inhibitor is a covalent SHP2 inhibitor, such as an inhibitor that targets the cysteine residue (C333) that lies outside the phosphatase's active site. In some embodiments a SHP2 inhibitor is a reversible inhibitor. In some embodiments, a SHP2 inhibitor is an irreversible inhibitor. In some embodiments, the SHP2 inhibitor is SHP099. In some embodiments, the SHP2 inhibitor is TNO155. In some embodiments, the SHP2 inhibitor is RMC-4550. In some embodiments, the SHP2 inhibitor is RMC-4630. In some embodiments, the SHP2 inhibitor is JAB-3068 or JAB-3312. In some embodiments, the SHP2 inhibitor is RLY-1971, ERAS-601, SH3809, PF-07284892, or BBP-398.

The SOS1 inhibitor may be, for example, BI-1701963, SDR5, BAY-293, MRTX0902 or RMC-5845.

In some embodiments, the additional therapeutic agent is selected from the group consisting of a HER2 inhibitor, a SHP2 inhibitor, a CDK4/6 inhibitor, an mTOR inhibitor, a SOS1 inhibitor, or a PD-L1 inhibitor. See, e.g., Hallin et al., Cancer Discovery, DOI: 10.1158/2159-8290 (Oct. 28, 2019) and Canon et al., Nature, 575:217(2019). In some embodiments, the additional therapeutic agent is selected from the group consisting of an EGFR inhibitor, a second Ras inhibitor, a SHP2 inhibitor, a SOS1 inhibitor, a Raf inhibitor, a MEK inhibitor, an ERK inhibitor, a PI3K inhibitor, a PTEN inhibitor, an AKT inhibitor, an mTORC1 inhibitor, a BRAF inhibitor, a PD-L1 inhibitor, a PD-1 inhibitor, and a CDK4/6 inhibitor, a HER2 inhibitor, or a combination thereof. In some embodiments, the additional therapeutic agents are a second Ras inhibitor and a PD-L1 inhibitor (i.e., triplet therapy).

The compounds described herein can be used in combination with the agents disclosed herein or other suitable agents, depending on the condition being treated. Hence, in some embodiments the one or more compounds of the disclosure will be co-administered with other agents as described above. When used in combination therapy, the compounds described herein are administered with the second agent simultaneously or separately. This administration in combination can include simultaneous administration of the two agents in the same dosage form, simultaneous administration in separate dosage forms, and separate administration. That is, a compound described herein and any of the agents described above can be formulated together in the same dosage form and administered simultaneously. Alternatively, a compound of the disclosure and any of the agents described above can be simultaneously administered, wherein both the agents are present in separate formulations. In another alternative, a compound of the present disclosure can be administered just followed by and any of the agents described above, or vice versa. In some embodiments of the separate administration protocol, a compound of the disclosure and any of the agents described above are administered a few minutes apart, or a few hours apart, or a few days apart.

As one aspect of the present invention contemplates the treatment of the disease/conditions with a combination of pharmaceutically active compounds that may be administered separately, the invention further relates to combining separate pharmaceutical compositions in kit form. The kit comprises two separate pharmaceutical compositions: a compound of the present invention, and a second pharmaceutical compound. The kit comprises a container for containing the separate compositions such as a divided bottle or a divided foil packet. Additional examples of containers include syringes, boxes, and bags. In some embodiments, the kit comprises directions for the use of the separate components. The kit form is particularly advantageous when the separate components are preferably administered in different dosage forms (e.g., oral and parenteral), are administered at different dosage intervals, or when titration of the individual components of the combination is desired by the prescribing health care professional.

In addition, it is to be understood that any embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any embodiment of the compositions of the invention can be excluded from any one or more claims, for any reason, whether related to the existence of prior art or not.

EXAMPLES

The following examples are intended to illustrate the synthesis and use of a representative number of compounds, or a pharmaceutically acceptable salt thereof. Accordingly, the examples are intended to illustrate but not to limit the invention. Additional compounds not specifically exemplified may be synthesized using conventional methods in combination with the methods described herein.

Abbreviations

Ac Acetyl
BnNCS Benzyl isothiocyanate
Boc tert-Butyloxycarbonyl
Cbz Benzyloxycarbonyl
CbzOSu Benzyl (2,5-dioxopyrrolidin-1-yl) carbonate
COMU (1-Cyano-2-ethoxy-2-oxoethylidenaminooxy)dimethylamino-morpholino-carbenium hexafluorophosphate
DBU 1,8-Diazabicyclo[5.4.0]undec-7-ene
DCM Dichloromethane
DMA N,N-Dimethylacetamide
DMAP N,N-Dimethylamin-4-pyridine
DMF N,N-Dimethylformamide
DMSO Dimethylsulfoxide
EDC N-(3-Dimethylaminopropyl)-N'-ethyl-carbodiimide
Et Ethyl HATU N-[(Dimethylamino)-1H-1,2,3-triazolo-[4,5-b]pyridin-1-ylmethylene]-N-methylmethanaminium hexafluorophosphate N-oxide
HOBt 1-Hydroxybenzotriazole
KHMDS Potassium bis(trimethylsilyl)amide
m-CPBA meta-Chloroperoxybenzoic acid
Me Methyl
MsCl Mesyl chloride
MTBE Methyl tert-butyl ether
NCS N-chlorosuccinimide
NMM N-methylmorpholine
n-PrNCS 1-propyl isothiocyanate
$Pd_2(dba)_3$ Tris(dibenzylideneacetone)dipalladium(0)
$Pd(dppf)Cl_2$ [1,1-Bis(diphenylphosphino)ferrocene]dichloropalladium(II)
$Ph_2NTf$ N-Phenyl-bis(trifluoromethanesulfonimide)
Pr Propyl
RuPhos Dicyclohexyl(2',6'-diisopropoxy-[1,1'-biphenyl]-2-yl)phosphane
$T_3P$ Propanephosphonic acid anhydride
TBAF Tetrabutylammonium fluoride
TBDPSCl tert-Butyl(chloro)diphenylsilane
Tf Triflate
TFA Trifluoroacetic acid
THF Tetrahydrofuran
Trt Trityl
TsOH Toluenesulfonic acid

Synthesis of Intermediates

Intermediate A-1: Synthesis of (2S,3S)-1-(tert-butylsulfinyl)-3-cyclopropylaziridine-2-carboxylic acid

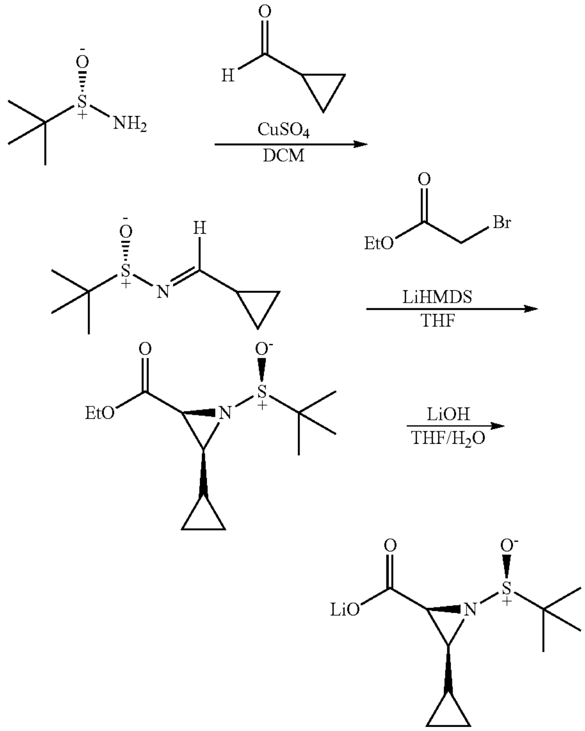

Step 1: Synthesis of (E)-N-(cyclopropylmethylene)-2-methylpropane-2-sulfinamide To a suspension of (S)-2-methylpropane-2-sulfinamide (4.0 g, 33.0 mmol) and $CuSO_4$ (15.80 g, 99.01 mmol) in DCM (200.0 mL) was added cyclopropanecarbaldehyde (4.63 g, 66.0 mmol). The resulting mixture was stirred overnight and was then filtered, the filter cake was washed with DCM (3×100 mL), and the filtrate was concentrated under reduced pressure to afford the desired product (3.5 g, 61% yield). LCMS (ESI) m/z [M+H] calcd for $C_8H_{15}NOS$: 174.10; found: 174.1.

Step 2: Synthesis of ethyl (2S,3S)-1-(tert-butylsulfinyl)-3-cyclopropylaziridine-2-carboxylate To a solution of ethyl bromoacetate (481.91 mg, 2.886 mmol) in THE (5.0 mL) at −78° C. was added LiHMDS (2.90 mL, 2.90 mmol). The resulting mixture was stirred for 2 h at −78° C. and then a solution of (E)-N-(cyclopropylmethylene)-2-methylpropane-2-sulfinamide (250.0 mg, 1.443 mmol) was added. The resulting mixture was stirred for 2 h at −78° C. and then quenched with $H_2O$ at 0° C. The aqueous layer was extracted with EtOAc (3×50 mL), and the combined organic layers were dried over $Na_2SO_4$, filtered, and concentrated under reduced pressure. The residue was purified by prep-TLC (17% EtOAc/pet. ether) to afford the desired product (250 mg, 67% yield). LCMS (ESI) m/z [M+H] calcd for $C_{12}H_{21}NO_3S$: 260.13; found: 260.1.

Step 3: Synthesis of (2S,3S)-1-(tert-butylsulfinyl)-3-cyclopropylaziridine-2-carboxylic acid A solution of ethyl (2S,3S)-1-(tert-butylsulfinyl)-3-cyclopropylaziridine-2-carboxylate (500.0 mg, 1.928 mmol) in THE (2.0 mL) and $H_2O$ (2.0 mL) at 0° C. was added $LiOH{\cdot}H_2O$ (121.34 mg, 2.89 mmol). The reaction mixture was stirred for 1 h and was then acidified to pH 6 with 1 M HCl (aq.). The resulting mixture was extracted with EtOAc (2×10 mL) and the combined organic layers were washed with brine (10 mL), dried over $Na_2SO_4$, filtered, and the filtrate was concentrated under reduced pressure to afford the desired product (400 mg, 90% yield). LCMS (ESI) m/z [M+H] calcd for $C_{10}H_{17}NO_3S$: 232.10; found: 232.0.

Intermediate A-2. Synthesis of (2R,3R)-1-((R)-tert-butylsulfinyl)-3-cyclopropylaziridine-2-carboxylic acid

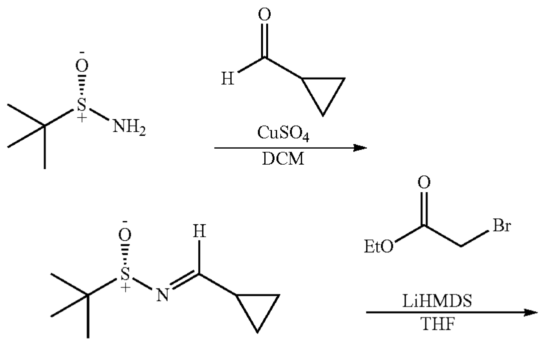

-continued

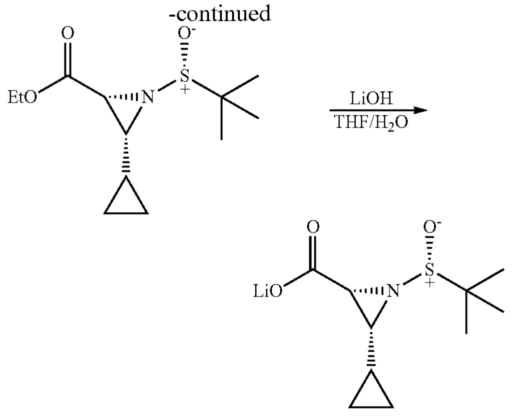

Step 1: Synthesis of (R,E)-N-(cyclopropylmethylene)-2-methylpropane-2-sulfinamide To a solution of (R)-2-methylpropane-2-sulfinamide (1.0 g, 8.25 mmol) and cyclopropanecarbaldehyde (1.16 g, 16.55 mmol) in DCM (50 mL) at room temperature was added $CuSO_4$ (3.95 g, 24.75 mmol). The resulting mixture was stirred overnight. The reaction mixture was then filtered, the filter cake washed with EtOAc, and the filtrate was concentrated under reduced pressure. The residue was purified by prep-TLC (17% EtOAc/pet. ether) to afford the desired product (1.4 g, 98% yield). LCMS (ESI) m/z: [M+H] calcd for $C_8H_{15}NOS$: 174.10; found 174.1.

Step 2: Synthesis of ethyl (2R,3R)-1-((R)-tert-butylsulfinyl)-3-cyclopropylaziridine-2-carboxylate To a solution of 1 M LiHMDS (23 mL, 23 mmol) in THE (50.0 mL) at −78° C. was added ethyl bromoacetate (3.83 g, 22.95 mmol). The resulting mixture was warmed to −70° C. and stirred for 1 h. To the reaction mixture was then added (R,E)-N-(cyclopropylmethylene)-2-methylpropane-2-sulfinamide (2.0 g, 11.48 mmol). The resulting mixture was stirred for 1 h at −70° C. The reaction mixture was warmed to 0° C. and quenched with $H_2O$. The aqueous layer was extracted with EtOAc (3×100 mL). The combined organic layers were washed with brine, dried over $Na_2SO_4$, filtered, and concentrated under reduced pressure. The residue was purified by prep-TLC (25% EtOAc/pet. ether) to afford the desired product (1.8 g, 61% yield). LCMS (ESI) m/z: [M+H] calcd for $C_{12}H_{21}N_{03}S$: 306.14; found 260.13.

Step 3: Synthesis of (2R,3R)-1-((R)-tert-butylsulfinyl)-3-cyclopropylaziridine-2-carboxylic acid To a solution of ethyl (2R,3R)-1-((R)-tert-butylsulfinyl)-3-cyclopropylaziridine-2-carboxylate (900.0 mg, 3.47 mmol) in THE (3.0 mL) and $H_2O$ (3.0 mL) at 0° C. was added $LiOH{\cdot}H_2O$ (218.4 mg, 5.21 mmol). The resulting mixture was stirred for 1 h and was then quenched by $H_2O$. The aqueous layer was extracted with EtOAc (3×50) and the combined organic layers were washed with brine, dried over $Na_2SO_4$, filtered, and concentrated under reduced pressure to afford the desired crude product (400 mg, 30% yield). LCMS (ESI) m/z: [M+H] calcd for $C_{10}H_{17}NO_3S$: 232.10; found 232.1.

Intermediate A-3: Synthesis of ethyl (2R,3R)-3-cyclopropylaziridine-2-carboxylate

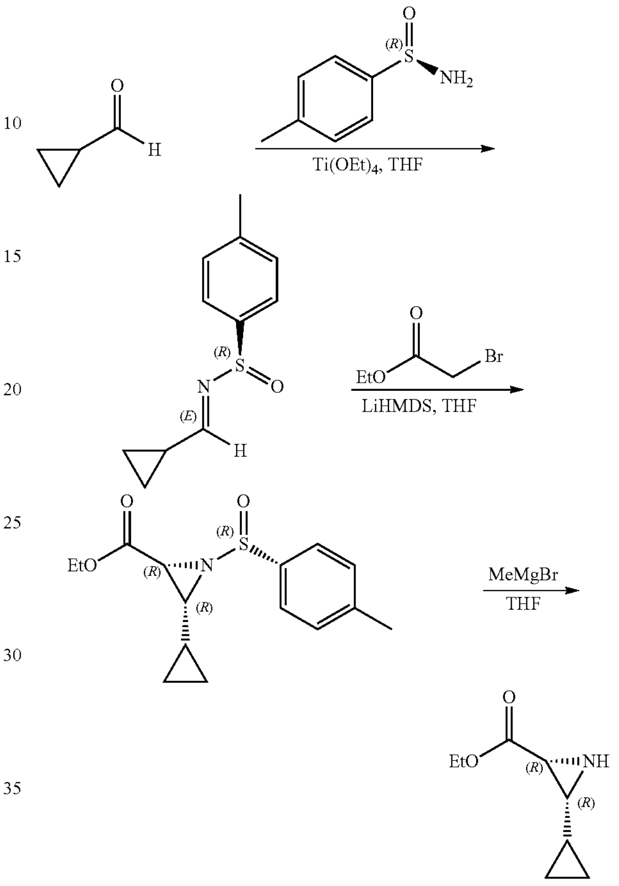

Step 1: Synthesis of (R,E)-N-(cyclopropylmethylene)-4-methylbenzenesulfinamide

To a solution of cyclopropanecarbaldehyde (6 g, 85.60 mmol) in THE (120 mL) was added (R)-4-methylbenzenesulfinamide (13.29 g, 85.60 mmol) and $Ti(OEt)_4$ (39.05 g, 171.21 mmol) at room temperature under $N_2$. The mixture was stirred at 75° C. for 2 h. The reaction mixture was poured into brine/$H_2O$ (1:1, 600 mL) at 0-15° C. The mixture was filtered through a pad of Celite and the pad was washed with EtOAc (6×200 mL). The combined filtrates were extracted with EtOAc (2×200 mL). The combined organic layers were washed with brine (200 mL), dried over $Na_2SO_4$, filtered and concentrated under reduced pressure to give a residue. The crude product was purified by silica gel column chromatography. (0→10% EtOAc/pet. ether) to give the product (14.6 g, 82% yield) as a solid.

Step 2: Synthesis of ethyl (2R,3R)-3-cyclopropyl-1-((R)-p-tolylsulfinyl)aziridine-2-carboxylate To a solution of ethyl 2-bromoacetate (23.52 g, 140.86 mmol) in THE (700 mL) was added LiHMDS (1 M, 140.86 mL) at −70° C. over 10 min under $N_2$. The mixture was stirred at −70° C. for 20 min. A solution of (R,E)-N-(cyclopropylmethylene)-4-methylbenzenesulfinamide (14.6 g, 70.43 mmol) in THE (150 mL) was added into the reaction solution at −70° C. for 10 min. Then the mixture was stirred at −70° C. for 1 h 20 min under $N_2$. The reaction mixture was poured into cold $H_2O$ (1.2 L) and stirred at room temperature for 5 min. The aqueous layer was extracted with EtOAc (3×300 mL). The combined organic layers were washed with brine (300 mL), dried over $Na_2SO_4$, filtered and concentrated under reduced pressure to give a residue. The crude product was purified by silica gel column chromatography. (0→10% EtOAc/pet. ether) to give the product (11 g, 53% yield) as an oil. LCMS (ESI) m/z [M+H] calcd for $C_{15}H_{20}NO_3S$: 294.11; found: 294.1.

Step 3: Synthesis of ethyl (2R,3R)-3-cyclopropylaziridine-2-carboxylate

Ethyl (2R,3R)-3-cyclopropyl-1-[(R)-p-tolylsulfinyl]aziridine-2-carboxylate (6 g, 20.45 mmol) was dissolved in anhydrous THE (300 mL). MeMgBr (3 M, 13.63 mL) was added dropwise at −65° C. over 40 min under $N_2$. The reaction mixture was stirred for 5 min. Sat. aq. $NH_4Cl$ (90 mL) was added dropwise at −65° C. The cooling bath was removed, and the reaction mixture was warmed to room temperature. EtOAc (300 mL) was added and the organic layer was separated and concentrated under reduced pressure. The residue was purified by silica gel column chromatography (0→50% EtOAC/pet. ether) to afford the product as an oil.

Intermediate A-4: Synthesis of lithium (2R,3R)-3-cyclopropyl-1-((R)-p-tolylsulfinyl)aziridine-2-carboxylate

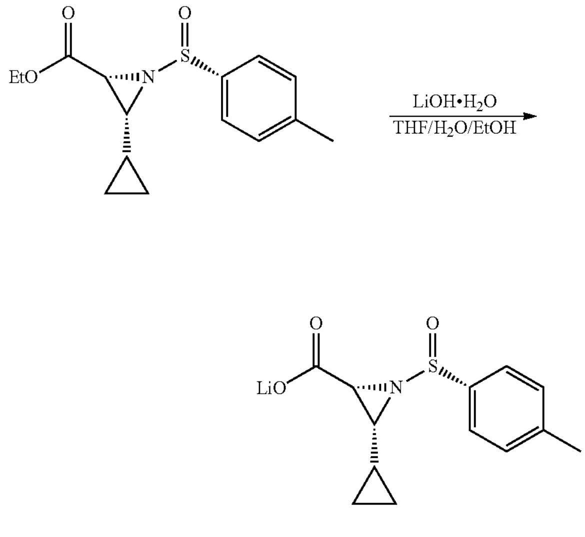

To a solution of ethyl (2R,3R)-3-cyclopropyl-1-((R)-p-tolylsulfinyl)aziridine-2-carboxylate (380 mg, 1.30 mmol) in THE (1.6 mL), $H_2O$ (1.2 mL) and EtOH (1.2 mL) was added $LiOH{\cdot}H_2O$ (163.06 mg, 3.89 mmol) at 0° C., then the mixture was stirred at room temperature for 1 h. $H_2O$ (5 mL) was added and the reaction mixture was lyophilized directly to give the product (430 mg, crude) as a solid, which was used directly in the next step. LCMS (ESI) m/z [M+H] calcd for $C_{13}H_{16}NO_3S$:266.08; found: 266.1.

Intermediate A-5: Synthesis of (2R,3R)-3-cyclopropyl-1-methylaziridine-2-carboxylic acid

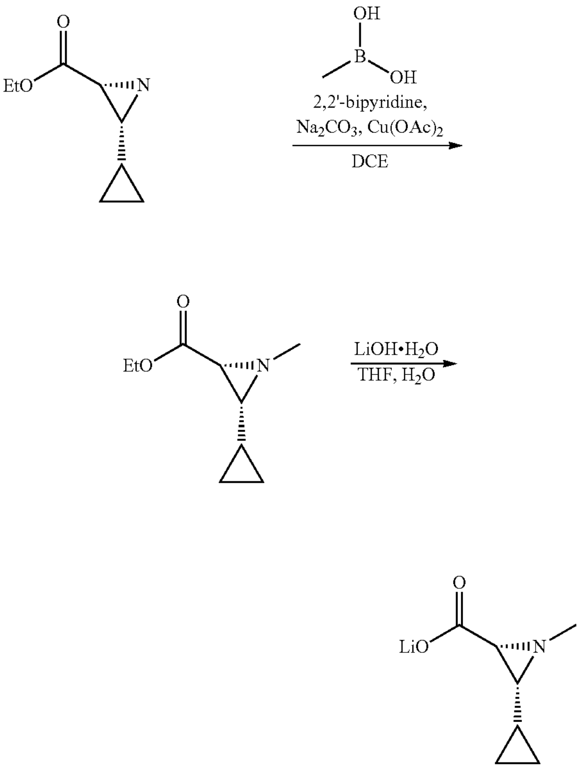

Step 1: ethyl (2R,3R)-3-cyclopropyl-1-methylaziridine-2-carboxylate

To a solution of ethyl (2R,3R)-3-cyclopropylaziridine-2-carboxylate (400 mg, 2.58 mmol) in DCE (8 mL) was added methylboronic acid (462.85 mg, 7.73 mmol), 2,2'-bipyridine (402.54 mg, 2.58 mmol), $Cu(OAc)_2$ (468.14 mg, 2.58 mmol), and $Na_2CO_3$ (819.54 mg, 7.73 mmol). The reaction mixture was stirred at 45° C. for 40 h. The mixture was poured into aq. $NH_4Cl$ (15 mL) and extracted with DCM (3×15 mL), the combined organic phases were washed with brine (20 mL), dried with anhydrous $Na_2SO_4$, filtered and concentrated under reduced pressure. The residue was purified by silica gel column chromatography (0→50% EtOAc/pet. ether) to give the product (230 mg, 53% yield) as an oil. LCMS (ESI) m/z [M+H] calcd for $CH_{16}NO_2$: 170.1; found: 170.1.

Step 2: (2R,3R)-3-cyclopropyl-1-methylaziridine-2-carboxylic acid

To a solution of ethyl (2R,3R)-3-cyclopropyl-1-methylaziridine-2-carboxylate (230 mg, 1.36 mmol) in THE (2 mL) was added a solution of $LiOH{\cdot}H_2O$ (114.07 mg, 2.72 mmol) in $H_2O$ (1 mL). The reaction mixture was stirred at room temperature for 1 h. The pH was adjusted to about 8 with 0.5 N HCl at 0° C., and the solution was lyophilized directly to give the product (230 mg, crude) as a solid.

Intermediate A-6: Synthesis of (S)-1-((benzyloxy)carbonyl)-2-methylaziridine-2-carboxylic acid

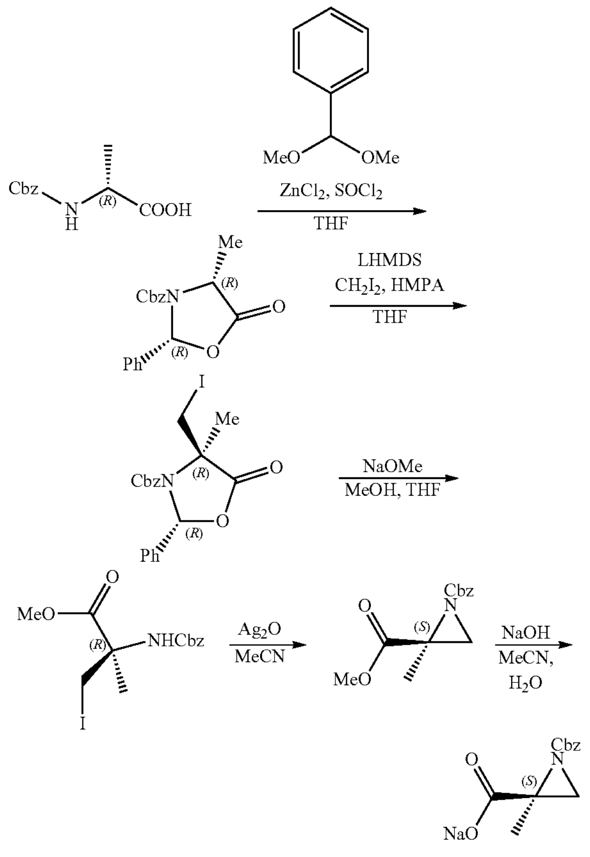

Step 1: Synthesis of benzyl (2R,4R)-4-methyl-5-oxo-2-phenyloxazolidine-3-carboxylate To a mixture of ((benzyloxy)carbonyl)-D-alanine (5 g, 22.40 mmol) and (dimethoxymethyl)benzene (3.75 g, 24.64 mmol) in THE (35 mL) was added $SOCl_2$ (2.93 g, 24.64 mmol) in one portion at 0° C. After the mixture was stirred for 10 min, $ZnCl_2$ (3.36 g, 24.64 mmol) was added to the solution. Then the mixture was stirred at 0° C. for 4 h. The reaction mixture was quenched by dropwise addition of cold $H_2O$ and adjusted to pH 5 with sat. aq. $NaHCO_3$, then extracted with EtOAc (3x50 mL). The organic layer was washed with a sat. aq. $NaHCO_3$ (30 mL) and brine (30 mL), dried over $Na_2SO_4$, and concentrated. The residue was purified by silica gel column chromatography (0→20% EtOAc/pet. ether) to afford the product (3.19 g, 46% yield) as an oil. LCMS (ESI) m/z [M+H] calcd for $C_{18}H_{18}NO_4$: 311.14; found: 312.1.

Step 2: Synthesis of benzyl (2R,4R)-4-(iodomethyl)-4-methyl-5-oxo-2-phenyloxazolidine-3-carboxylate To a mixture of THE (50 mL), HMPA (8.50 g, 47.44 mmol) was added LiHMDS (1 M, 10.55 mL) under $N_2$ at room temperature. This solution was cooled to −70° C. and a solution of benzyl (2R,4R)-4-methyl-5-oxo-2-phenyl-oxazolidine-3-carboxylate (3.19 g, 10.25 mmol) in THE (14 mL) was added dropwise. After stirring an additional 30 min, a solution of diiodomethane (8.23 g, 30.74 mmol) in THE (14 mL) was added dropwise. The mixture was stirred at −70° C. for 90 min. sat. aq. $NH_4Cl$ (50 mL) was added to the reaction mixture at 0° C. and extracted with EtOAc (3x30 mL). The combined organic layers were washed with brine (80 mL), dried over $Na_2SO_4$, filtered and concentrated under reduced pressure. The residue was purified by silica gel column chromatography (0→20% EtOAc/pet. ether) to afford the product (3.03 g, 66% yield) as an oil. LCMS (ESI) m/z [M+H] calcd for $C_{19}H_{19}INO_4$: 451.26; found: 452.0.

Step 3: Synthesis of methyl (R)-2-(((benzyloxy)carbonyl)amino)-3-iodo-2-methylpropanoate To a solution of benzyl (2R,4R)-4-(iodomethyl)-4-methyl-5-oxo-2-phenyl-oxazolidine-3-carboxylate (3 g, 6.65 mmol) in THE (50 mL) was added NaOMe (2.39 g, 13.30 mmol) in MeOH (22.5 mL) dropwise over 10 min at −40° C. under $N_2$. The mixture was stirred at −40° C. for 2 h, then warmed to room temperature and stirred for 30 min. The reaction was quenched by the addition of $H_2O$ (50 mL), and the resulting mixture was extracted with EtOAc (3x30 mL). The combined organic layers were washed with brine (80 mL), dried over $Na_2SO_4$, filtered, and concentrated under reduced pressure. The residue was purified by silica gel column chromatography (0→20% EtOAc/pet. ether) to afford the product (2.04 g, 81% yield) as an oil. LCMS (ESI) m/z [M+H] calcd for $C_{13}H_{17}INO_4$: 377.18; found: 378.0.

Step 4: Synthesis of 1-benzyl 2-methyl (S)-2-methylaziridine-1,2-dicarboxylate

To a solution of (R)-2-(((benzyloxy)carbonyl)amino)-3-iodo-2-methylpropanoate (1 g, 2.65 mmol) in MeCN (100 mL) was added $Ag_2O$ (1.84 g, 7.95 mmol) at room temperature. The mixture was heated at 90° C. for 30 min. After the reaction was cooled to room temperature the mixture was filtered through Celite and the filtrate concentrated under reduced pressure. This residue was extracted with EtOAc (100 mL), and the organic layer was filtered through Celite and concentrated under reduced pressure to afford the product (630 mg, crude) as an oil. LCMS (ESI) m/z [M+H] calcd for $C_{13}H_{16}NO_4$: 249.27; found: 250.1.

Step 5: Synthesis of (S)-1-((benzyloxy)carbonyl)-2-methylaziridine-2-carboxylic acid To a solution of 1-benzyl 2-methyl (S)-2-methylaziridine-1,2-dicarboxylate (630 mg, 2.53 mmol) in MeCN (3.2 mL) was add a solution of NaOH (151.65 mg, 3.79 mmol) in $H_2O$ (3.2 mL) at 0° C. The mixture was stirred at 0° C. for 30 min. The reaction mixture was diluted with $H_2O$ (10 mL) and lyophilized to give the product (652.65 mg, crude) as solid.

Intermediate A-7: Synthesis of (R)-1-((benzyloxy)carbonyl)-2-methylaziridine-2-carboxylic acid

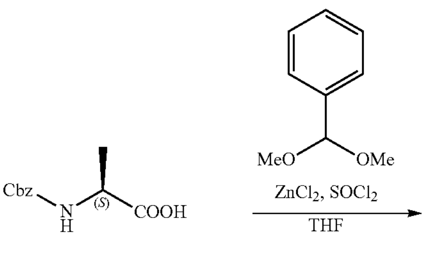

-continued

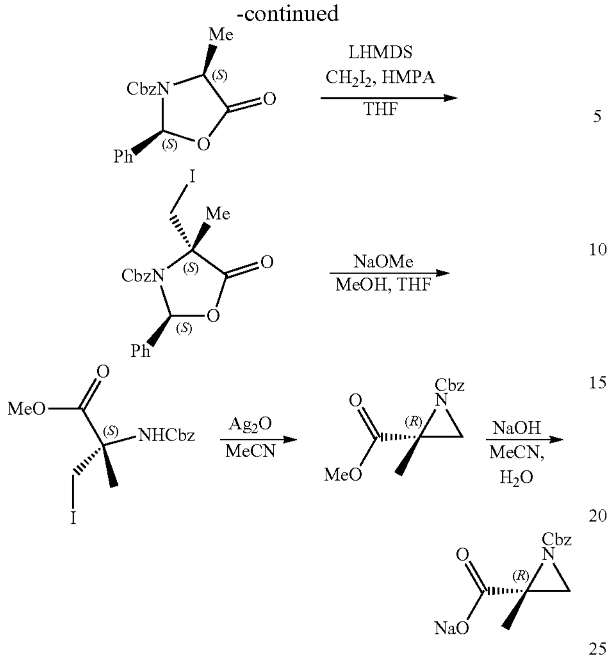

Step 1: Synthesis of benzyl (2S,4S)-4-methyl-5-oxo-2-phenyloxazolidine-3-carboxylate To a solution of ((benzyloxy)carbonyl)-L-alanine (5 g, 22.40 mmol) and (dimethoxymethyl)benzene (3.51 g, 23.07 mmol) in THF (36 mL) was added $SOCl_2$ (2.93 g, 24.64 mmol) in one portion at 0° C. The mixture was stirred for 10 min and then $ZnCl_2$ (1.15 mL, 24.64 mmol) was added. The mixture was then stirred at 0° C. for 4 h. The reaction mixture was quenched by the dropwise addition of cold $H_2O$, adjusted to pH 5 with sat. $NaHCO_3$, then extracted with EtOAc (2×30 mL). The organic phase was washed with a sat. aq. $NaHCO_3$ (30 mL) and brine (30 mL), dried with anhydrous $Na_2SO_4$, and concentrated under reduced pressure. The residue was purified by silica gel column chromatography (0→20% EtOAc/pet. ether) to afford the product (3.7 g, 53% yield) as an oil.

Step 2: Synthesis of benzyl (2S,4S)-4-(iodomethyl)-4-methyl-5-oxo-2-phenyloxazolidine-3-carboxylate A mixture of HMPA (9.33 g, 52.05 mmol) and LiHMDS (1 M, 11.58 mL) in THF (52 mL) was stirred at room temperature under $N_2$, and was then cooled to −70° C. A solution of benzyl (2S,4S)-4-methyl-5-oxo-2-phenyloxazolidine-3-carboxylate (3.5 g, 11.24 mmol) in THF (15 mL) was added dropwise. After stirring for 30 min, a solution of diiodomethane (9.03 g, 33.73 mmol) in THF (7 mL) was added dropwise. The mixture was stirred at −70° C. for 90 min, then sat. $NH_4Cl$ (50 mL) was added to the reaction mixture at 0° C. and the solution was extracted with EtOAc (3×30 mL). The combined organic layers were washed with brine (80 mL), dried over anhydrous $Na_2SO_4$, filtered and concentrated under reduced pressure. The residue was purified by column chromatography (0→20% EtOAc/pet. ether) to give the product (2.39 g, 47% yield) as an oil.

Step 3: Synthesis of methyl (S)-2-(((benzyloxy)carbonyl)amino)-3-iodo-2-methylpropanoate To a solution of benzyl (2S,4S)-4-(iodomethyl)-4-methyl-5-oxo-2-phenyloxazolidine-3-carboxylate (2.39 g, 5.30 mmol) in THF (40 mL) was added NaOMe (1.91 g, 10.59 mmol) in MeOH (19 mL) dropwise over 10 min at −40° C. under $N_2$. The mixture was stirred at −40° C. for 2 h, then warmed to −20° C. and stirred for 0.5 h. The reaction was quenched by addition of $H_2O$ (50 mL), and the resulting mixture was extracted with EtOAc (3×30 mL). The combined organic layers were washed with brine (80 mL), dried over $Na_2SO_4$, filtered, and concentrated under reduced pressure. The residue was purified by column chromatography (0→20% EtOAc/pet. ether) to give the product (1.37 g, 69% yield) as an oil.

Step 4: Synthesis of 1-benzyl 2-methyl (R)-2-methylaziridine-1,2-dicarboxylate

To a mixture of methyl (2S)-2-(benzyloxycarbonylamino)-3-iodo-2-methyl-propanoate (1.37 g, 3.63 mmol) in MeCN (14 mL) was added $Ag_2O$ (2.53 g, 10.90 mmol) in one portion at room temperature. The mixture was stirred at 90° C. for 30 min, then the mixture was vacuum filtered through Celite and the filtrate was concentrated under reduced pressure to give the product (790 mg, 87% yield) as an oil. LCMS: (ESI) m/z [M+H] calcd for $C_{13}H_{16}NO_4$: 250.10; found 250.1.

Step 5: Synthesis of (R)-1-((benzyloxy)carbonyl)-2-methylaziridine-2-carboxylic acid To a mixture of 1-benzyl 2-methyl (R)-2-methylaziridine-1,2-dicarboxylate (790 mg, 3.17 mmol) in MeCN (7.6 mL) and $H_2O$ (7.6 mL) was added NaOH (126.77 mg, 3.17 mmol) in one portion at 0° C. under $N_2$. The mixture was stirred at 0° C. for 0.5 h. The reaction was added $H_2O$ (8 mL) and lyophilized to give (R)-1-((benzyloxy)carbonyl)-2-methylaziridine-2-carboxylic acid (850 mg, crude, Na) as white solid.

Intermediate A-8: Synthesis of (2R,3R)-3-methyloxirane-2-carboxylic acid

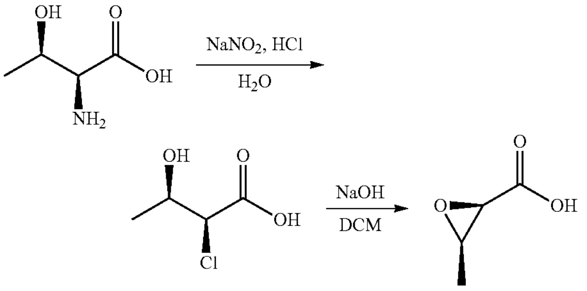

Step 1: Synthesis of (2S,3R)-2-chloro-3-hydroxybutanoic acid

To a mixture of (2S,3R)-2-amino-3-hydroxy-butanoic acid (25 g, 209.87 mmol) in HCl (148.50 g, 1.55 mol) and $H_2O$ was added $NaNO_2$ (54.30 g, 314.81 mmol) at 0° C. The reaction mixture was stirred at 0° C. for 3 h, and was then extracted with EtOAc (3×200 mL). The combined organic layer was washed with brine (100 mL), dried over $Na_2SO_4$, filtered and the filtrate was concentrated under reduced pressure to give the product (27 g, crude) as an oil, which was used directly to the next step. LCMS (ESI) m/z [M−H] calcd for $C_4H_6ClO_3$: 137.01; found: 137.0.

Step 2: Synthesis of (2R,3R)-3-methyloxirane-2-carboxylic acid

To a mixture of (2S,3R)-2-chloro-3-hydroxy-butanoic acid (27 g, 194.88 mmol) in DCM (300 mL) was added NaOH (48.99 g, 428.73 mmol) at 10° C. The mixture was stirred at 10° C. for 3 h. The aqueous layer was extracted with DCM (2×50 mL). The pH of aqueous layer was adjusted to about 1-2 by adding 25% HCl and was then extracted with EtOAc (4×100 mL). The organic layer was washed with brine (30 mL), dried over $Na_2SO_4$, filtered and the filtrate was concentrated under reduced pressure to give the product (6 g, 30% yield) as an oil, which was used directly to the next step. LCMS (ESI) m/z [M−H] calcd for $C_4H_5O_3$: 101.03; found: 101.0.

Intermediate A-9: Synthesis of lithium (2R,3R)-3-cyclopropyloxirane-2-carboxylate

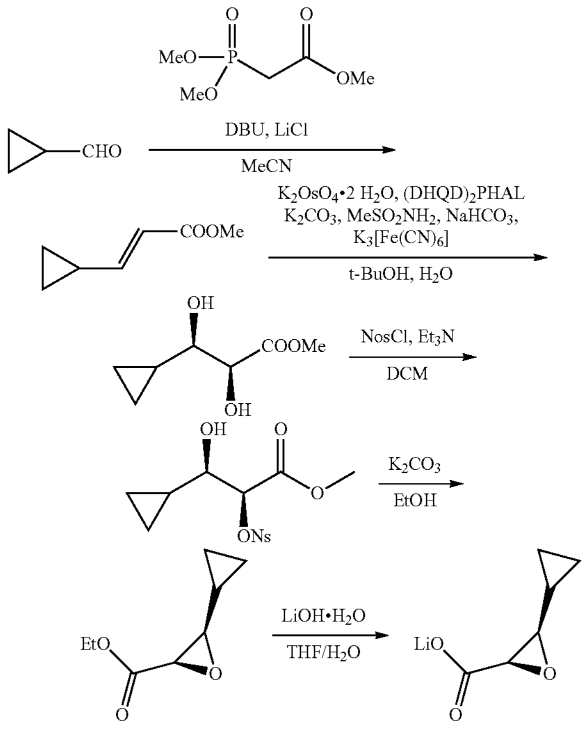

Step 1: Synthesis of methyl (E)-3-cyclopropylacrylate

To a mixture of methyl 2-(dimethoxyphosphoryl)acetate (31.18 g, 171.21 mmol) in MeCN (100 mL) was added DBU (26.06 g, 171.21 mmol) and LiCl (9.07 g, 214.01 mmol) at 0° C. followed by cyclopropanecarbaldehyde (10 g, 142.67 mmol). The mixture was stirred at room temperature for 12 h then quenched with $H_2O$ (300 mL) and extracted with EtOAc (2×150 mL). The combined organic layers were washed with brine (100 mL), dried over $Na_2SO_4$, filtered and the filtrate was concentrated under reduced pressure to give a residue. The residue was purified by silica gel column chromatography (0→20% EtOAc/pet. ether) to give the product (9 g, 50% yield) as an oil.

Step 2: Synthesis of methyl (2S,3R)-3-cyclopropyl-2,3-dihydroxypropanoate

A mixture of $K_3[Fe(CN)_6]$ (27.40 g, 83.23 mmol), $K_2CO_3$ (11.50 g, 83.23 mmol), $MeSO_2NH_2$ (2.64 g, 27.74 mmol), $NaHCO_3$(6.99 g, 83.23 mmol) in t-BuOH (210 mL) and $H_2O$ (140 mL) was stirred at room temperature for 10 min. $K_2OsO_4 \cdot 2H_2O$ (40.89 mg, 110.98 μmol) and (DHQD) $_2$PHAL (216.12 mg, 277.44 μmol) were then added. The mixture was stirred at for 30 min, then cooled to 0° C. Methyl (E)-3-cyclopropylacrylate (3.5 g, 27.74 mmol, 1 eq) in t-BuOH (70 mL) was added to the mixture and stirred at room temperature for 15 h. The mixture was quenched with sat. $Na_2S_2O_3$ (100 mL) and was then extracted with EtOAc (3×200 mL). The combined organic layers were washed with brine (100 mL) and dried over $Na_2SO_4$, filtered and the filtrate was concentrated under reduced pressure to give a residue. The residue was purified by silica gel column chromatography (0→50% EtOAc/pet. ether) to afford the product (4.2 g, 47% yield) as a solid.

Step 3: Synthesis of methyl (2S,3R)-3-cyclopropyl-3-hydroxy-2-(((4-nitrophenyl)sulfonyl) oxy)propanoate To a mixture of methyl (2S,3R)-3-cyclopropyl-2,3-dihydroxypropanoate (4 g, 24.97 mmol) and $Et_3N$ (3.79 g, 37.46 mmol) in DCM (40 mL) was added dropwise 4-nitrobenzenesulfonyl chloride (6.09 g, 27.47 mmol) in DCM (10 mL) at 0° C. and stirred at room temperature for 12 h. The mixture was poured into $H_2O$ (50 mL) and extracted with DCM (2×50 mL). The combined organic layers were washed with brine (30 mL), dried over $Na_2SO_4$, filtered and the filtrate was concentrated under reduced pressure to give a residue. The residue was purified by silica gel column chromatography (0→100% EtOAc/pet. ether) to give the product (5.82 g, 68% yield) as an oil.

Step 4: Synthesis of ethyl (2R,3R)-3-cyclopropyloxirane-2-carboxylate

To a mixture of methyl (2S,3R)-3-cyclopropyl-3-hydroxy-2-(((4-nitrophenyl)sulfonyl)oxy) propanoate (1 g, 2.90 mmol) in EtOH (20 mL) was added $K_2CO_3$ (800.44 mg, 5.79 mmol). The mixture was stirred at 15° C. for 12 h. The mixture was poured into sat. $NaHCO_3$ (50 mL) and extracted with DCM (3×40 mL). The combined organic layers were washed with brine (30 mL), dried over $Na_2SO_4$, filtered and the filtrate was concentrated under reduced pressure to give a residue. The residue was purified by silica gel column chromatography (0→30% EtOAc/pet. ether) to give the product (0.3 g, crude) as an oil, which was used directly in the next step.

Step 5: Synthesis of lithium (2R,3R)-3-cyclopropyloxirane-2-carboxylate

To a solution of ethyl (2R,3R)-3-cyclopropyloxirane-2-carboxylate (300 mg, 1.92 mmol) in THE (3 mL) was added $LiOH \cdot H_2O$ (161.20 mg, 3.84 mmol) in $H_2O$ (1.5 mL). The mixture was stirred at 0° C. for 1 h. $H_2O$ (20 mL) was added and the mixture was lyophilized directly to give the product (200 mg, crude) as solid. LCMS (ESI) m/z [M−H] calcd for $C_6H_7O_2$: 127.0; found: 127.0.

Intermediate A-10. Synthesis of (2R,3S)-3-phenylaziridine-2-carboxylic acid

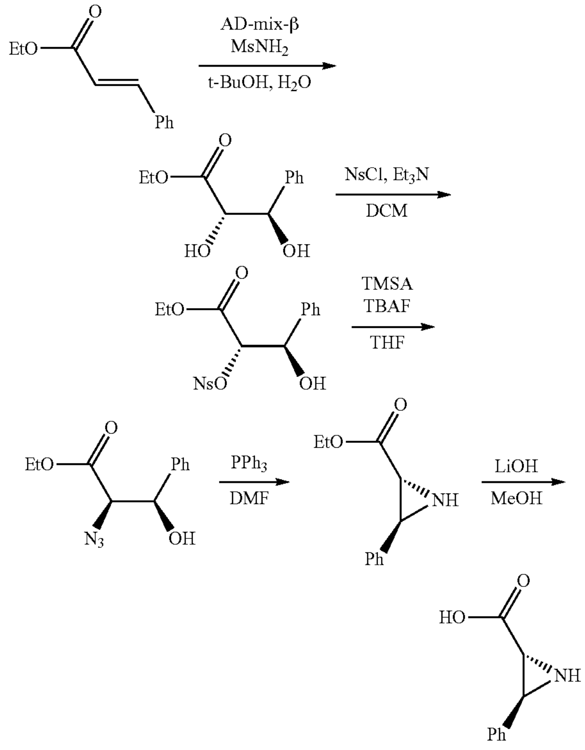

Step 1: Synthesis of ethyl (2S,3R)-2,3-dihydroxy-3-phenylpropanoate

To a solution of ethyl cinnamate (2.0 g, 11.4 mmol) in t-BuOH (35.0 mL) and $H_2O$ (35.0 mL) at 0° C. was added AD-mix-β (15.83 g, 20.32 mmol), and methanesulfonamide (1.08 g, 11.3 mmol). The reaction mixture was stirred at room temperature for 16 h. The reaction was cooled to 0° C. and quenched with aq. $KHSO_4$. The resulting mixture was extracted with EtOAc (3×100 mL) and the combined organic layers were washed with brine (2×90 mL), dried over $Na_2SO_4$, filtered, and concentrated under reduced pressure. The residue was purified by normal phase chromatography (50% EtOAc/pet. ether) to afford the desired product (2.2 g, 82% yield) as a solid.

Step 2: Synthesis of ethyl (2S,3R)-3-hydroxy-2-(((4-nitrophenyl)sulfonyl)oxy)-3-phenylpropanoate To a solution of ethyl (2S,3R)-2,3-dihydroxy-3-phenylpropanoate (2.0 g, 9.5 mmol) and $Et_3N$ (3.97 mL, 28.5 mmol) in DCM (30.0 mL) at 0° C. was added 4-nitrobenzenesulfonyl chloride (2.11 g, 9.51 mmol). The resulting mixture was stirred for 1 h and was then diluted with $H_2O$ (300 mL). The mixture was extracted with DCM (3×100 mL) and the combined organic layers were washed with brine (2×100 mL), dried over $Na_2SO_4$, filtered, and concentrated under reduced pressure. The residue was purified by prep-TLC (50% EtOAc/pet. ether) to afford the desired product (2.8 g, 67% yield) as a solid.

Step 3: Synthesis of ethyl (2R,3R)-2-azido-3-hydroxy-3-phenylpropanoate

To a solution of ethyl (2S,3R)-3-hydroxy-2-(((4-nitrophenyl)sulfonyl)oxy)-3-phenylpropanoate (2.80 g, 7.08 mmol) in THF (30 mL) at room temperature was added trimethylsilyl azide (1.63 g, 14.2 mmol) and TBAF (1M in THF, 14.16 mL, 14.16 mmol). The reaction mixture was heated to 60° C. and was stirred for 16 h. The reaction mixture was then cooled to room temperature, diluted with $H_2O$ (150 mL), 10 and extracted with EtOAc (3×50 mL). The combined organic layers were washed with brine (2×30 mL), dried over $Na_2SO_4$, filtered, and concentrated under reduced pressure. The residue was purified by normal phase chromatography (50% EtOAc/pet. ether) to afford the desired product (1.2 g, 64% yield) as an oil.

Step 4: Synthesis of ethyl (2R,3S)-3-phenylaziridine-2-carboxylate

To a solution of ethyl (2R,3R)-2-azido-3-hydroxy-3-phenylpropanoate (1.20 g, 5.10 mmol) in DMF (15.0 mL) was added $PPh_3$ (1.61 g, 6.12 mmol). The reaction mixture was stirred at room temperature for 30 min and then heated to 80° C. for an additional 16 h. The reaction mixture was then cooled to room temperature, diluted with $H_2O$ (100 mL), and extracted with EtOAc (3×40 mL). The combined organic layers were washed with brine (20 mL), dried over $Na_2SO$, filtered, and concentrated under reduced pressure. The residue was purified by normal phase chromatography (16% EtOAc/pet. ether) to afford the desired product (620 mg, 57% yield) as an oil. LCMS (ESI) m/z: [M+H] calcd for $C_{11}H_{13}NO_2$: 192.10; found 192.0.

Step 5: Synthesis of (2R,3S)-3-phenylaziridine-2-carboxylic acid

To a solution of ethyl (2R,3S)-3-phenylaziridine-2-carboxylate (0.100 g, 0.523 mmol) in MeOH (0.70 mL) at 0° C. was added a solution of LiOH (18.8 mg, 0.784 mmol) in $H_2O$ (0.70 mL). The reaction mixture was stirred for 1 h. The mixture was then diluted with MeCN (10 mL), and the resulting precipitate was collected by filtration and washed with MeCN (2×10 mL) to afford the crude desired product (70 mg) as a solid. LCMS (ESI) m/z: [M+H] calcd for $C_9H_9NO_2$: 164.07; found 164.0.

Intermediate A-11. Synthesis of (2S,3R)-3-phenylaziridine-2-carboxylic acid

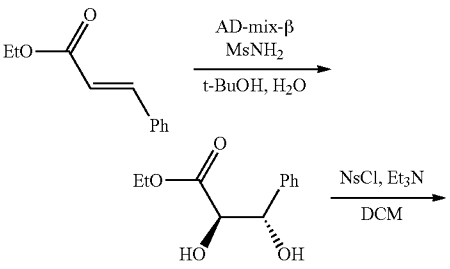

-continued

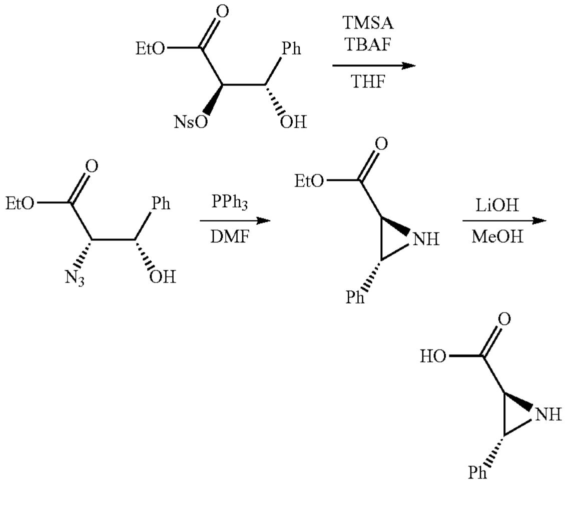

Step 1: Synthesis of ethyl (2R,3S)-2,3-dihydroxy-3-phenylpropanoate

To a solution of ethyl cinnamate (2.0 g, 11.4 mmol) in t-BuOH (35.0 mL) and $H_2O$ (35.0 mL) at 0° C. was added AD-mix-α (15.83 g, 20.32 mmol), and methanesulfonamide (1.08 g, 11.3 mmol). The reaction mixture was stirred at room temperature for 16 h. The reaction was cooled to 0° C. and quenched with aq. $KHSO_4$. The resulting mixture was extracted with EtOAc (3×100 mL) and the combined organic layers were washed with brine (2×80 mL), dried over $Na_2SO_4$, filtered, and concentrated under reduced pressure. The residue was purified by normal phase chromatography (50% EtOAc/pet. ether) to afford the desired product (2.2 g, 82% yield) as a solid.

Step 2: Synthesis of ethyl (2R,3S)-3-hydroxy-2-(((4-nitrophenyl)sulfonyl)oxy)-3-phenylpropanoate To a solution of ethyl (2R,3S)-2,3-dihydroxy-3-phenylpropanoate (2.10 g, 9.99 mmol) and $Et_3N$ (4.18 mL, 29.9 mmol) in DCM (30.0 mL) at 0° C. was added 4-nitrobenzenesulfonyl chloride (2.21 g, 9.99 mmol). The resulting mixture was stirred for 1 h and was then diluted with $H_2O$ (200 mL). The mixture was extracted with DCM (3×80 mL) and the combined organic layers were washed with brine (2×80 mL), dried over $Na_2SO_4$, filtered, and concentrated under reduced pressure. The residue was purified by prep-TLC (50% EtOAc/pet. ether) to afford the desired product (3.0 g, 68% yield) as a solid.

Step 3: Synthesis of ethyl (2S,3S)-2-azido-3-hydroxy-3-phenylpropanoate

To a solution of ethyl (2R,3S)-3-hydroxy-2-(((4-nitrophenyl)sulfonyl)oxy)-3-phenylpropanoate (3.0 g, 7.59 mmol) in THE (30 mL) at room temperature was added trimethylsilyl azide (1.75 g, 15.2 mmol) and TBAF (1M in THF, 15.18 mL, 15.18 mmol). The reaction mixture was heated to 60° C. and was stirred for 16 h. The reaction mixture was then cooled to room temperature, diluted with $H_2O$ (150 mL), and extracted with EtOAc (3×50 mL). The combined organic layers were washed with brine (2×30 mL), dried over $Na_2SO_4$, filtered, and concentrated under reduced pressure. The residue was purified by normal phase chromatography (50% EtOAc/pet. ether) to afford the desired product (1.4 g, 70% yield) as an oil.

Step 4: Synthesis of ethyl (2S,3R)-3-phenylaziridine-2-carboxylate

To a solution of ethyl (2S,3S)-2-azido-3-hydroxy-3-phenylpropanoate (1.40 g, 5.95 mmol) in DMF (20.0 mL) was added $PPh_3$ (1.87 g, 7.14 mmol). The reaction mixture was stirred at room temperature for 30 min and then heated to 80° C. for an additional 16 h. The reaction mixture was then cooled to room temperature, diluted with $H_2O$ (150 mL), and extracted with EtOAc (3×50 mL). The combined organic layers were washed with brine (40 mL), dried over $Na_2SO$, filtered, and concentrated under reduced pressure. The residue was purified by normal phase chromatography (16% EtOAc/pet. ether) to afford the desired product (720 mg, 56% yield) as an oil. LCMS (ESI) m/z: [M+H] calcd for $C_{11}H_{13}NO_2$: 192.10; found 192.0.

Step 5: Synthesis of (2S,3R)-3-phenylaziridine-2-carboxylic acid

To a solution of ethyl (2S,3R)-3-phenylaziridine-2-carboxylate (0.100 g, 0.523 mmol) in MeOH (0.70 mL) at 0° C. was added a solution of LiOH (18.8 mg, 0.784 mmol) in $H_2O$ (0.70 mL). The reaction mixture was stirred for 1 h. The mixture was then diluted with MeCN (10 mL), and the resulting precipitate was collected by filtration and washed with MeCN (2×10 mL) to afford the crude desired product (68 mg) as a solid. LCMS (ESI) m/z: [M+H] calcd for $C_9H_9NO_2$: 164.07; found 164.0.

Intermediate A-12. Synthesis of (2R,3S)-1-((R)-tert-butylsulfinyl)-3-(methoxycarbonyl)aziridine-2-carboxylic acid

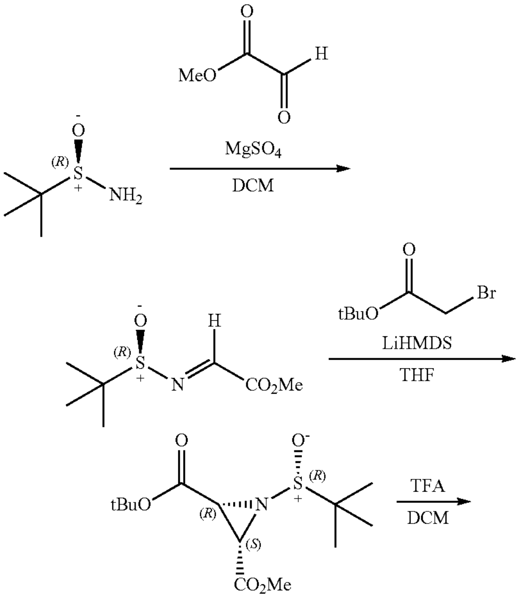

-continued

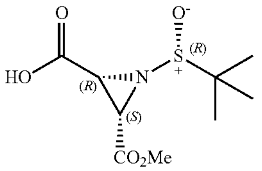

Step 1: Synthesis of methyl (R,E)-2-((tert-butylsulfinyl)imino)acetate

To a solution of (R)-2-methylpropane-2-sulfinamide (13.21 g, 109.01 mmol) and methyl 2-oxoacetate (8.0 g, 90.85 mmol) in DCM (130 mL) at room temperature was added $MgSO_4$ (54.67 g, 454.23 mmol). The resulting mixture was heated to 35° C. and stirred for 16 h. The resulting mixture was filtered, the filter cake washed with EtOAc (3×50 mL), and the filtrate was concentrated under reduced pressure. The residue was purified by normal phase chromatography (25% EtOAc/pet. ether) to afford the desired (5.8 g, 33% yield). LCMS (ESI) m/z: [M+H] calcd for $C_7H_{13}NO_3S$: 192.07; found 191.9.

Step 2: Synthesis of 2-(tert-butyl) 3-methyl (2R, 3S)-1-((R)-tert-butylsulfinyl)aziridine-2,3-dicarboxylate To a solution of 1 M LiHMDS (61.40 mL, 61.40 mmol) in THE (300.0 mL) at −78° C. was added tert-butyl 2-bromoacetate (11.83 g, 60.65 mmol). The resulting mixture was stirred for 30 min. To the reaction mixture was then added methyl methyl (R,E)-2-((tert-butylsulfinyl)imino)acetate (5.8 g, 30.33 mmol). The resulting mixture was warmed to −60° C. and stirred for 2.5 h. The reaction was warmed to 0° C. and quenched with sat. $NH_4Cl$ (aq.). The resulting mixture was extracted with EtOAc (3×200 mL). The combined organic layers were washed with brine (500 mL), dried over $Na_2SO_4$, filtered, and concentrated under reduced pressure. The residue was purified by reverse phase chromatography (10→50% MeCN/$H_2O$) to afford the desired product (1.34 g, 5% yield). LCMS (ESI) m/z: [M+H] calcd for $C_{13}H_{23}NO_5S$: 306.14; found 306.2.

Step 3: Synthesis of (2R,3S)-1-((R)-tert-butylsulfinyl)-3-(methoxycarbonyl)aziridine-2-carboxylic acid To a solution of 2-(tert-butyl) 3-methyl (2R,3S)-1-((R)-tert-butylsulfinyl)aziridine-2,3-dicarboxylate (302.0 mg, 0.99 mmol) in DCM (3.0 mL) at 0° C. was added TFA (1.50 mL). The resulting mixture was stirred for 1 h and then concentrated under reduced pressure to afford the desired crude product (300 mg). LCMS (ESI) m/z: [M+H] calcd for $C_9H_{15}NO_5S$: 250.07; found 250.1.

Intermediate A-13. Synthesis of (2S,3R)-1-((S)-tert-butylsulfinyl)-3-(methoxycarbonyl)aziridine-2-carboxylic acid

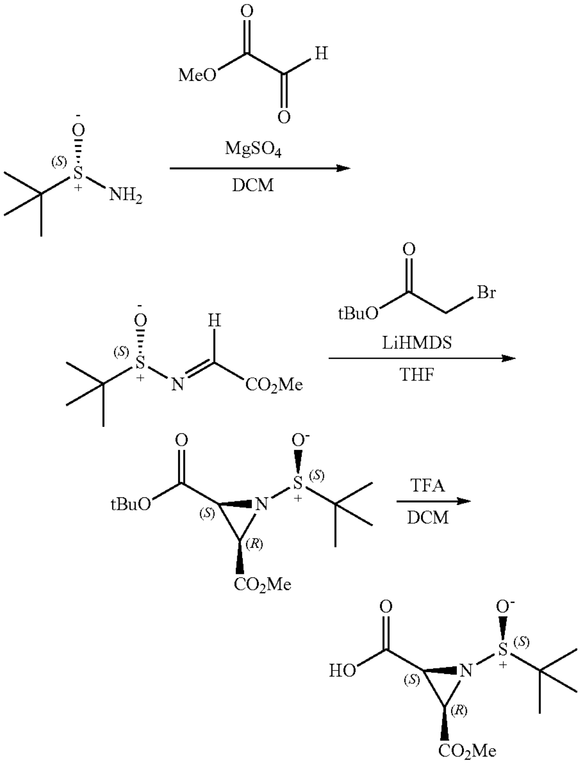

Step 1: Synthesis of methyl (S,E)-2-((tert-butylsulfinyl)imino)acetate

To a solution of (S)-2-methylpropane-2-sulfinamide (9.81 g, 80.94 mmol) and methyl 2-oxoacetate (5.94 g, 67.45 mmol) in DCM (100 mL) at room temperature was added $MgSO_4$ (40.60 g, 337.26 mmol). The resulting mixture was heated to 35° C. and stirred for 16 h. The resulting mixture was filtered, the filter cake washed with EtOAc (3×50 mL), and the filtrate was concentrated under reduced pressure. The residue was purified by normal phase chromatography (25% EtOAc/pet. ether) to afford the desired (5.68 g, 44% yield). LCMS (ESI) m/z: [M+H] calcd for $C_7H_{13}NO_3S$: 192.07; found 191.1.

Step 2: Synthesis of 2-(tert-butyl) 3-methyl (2S, 3R)-1-((S)-tert-butylsulfinyl)aziridine-2,3-dicarboxylate To a solution of 1 M LiHMDS (59.40 mL, 59.40 mmol) in THE (300.0 mL) at −78° C. was added tert-butyl 2-bromoacetate (11.59 g, 59.40 mmol). The resulting mixture was stirred for 30 min. To the reaction mixture was then added methyl methyl (S,E)-2-((tert-butylsulfinyl)imino)acetate (5.68 g, 29.70 mmol). The resulting mixture was warmed to −60° C. and stirred for 2.5 h. The reaction was warmed to 0° C. and quenched with sat. $NH_4Cl$ (aq.). The resulting mixture was extracted with EtOAc (3×200 mL). The combined organic layers were washed with brine (500 mL), dried over $Na_2SO_4$, filtered, and concentrated under reduced pressure. The residue was purified by reverse phase chromatography (10→50% MeCN/$H_2O$) to afford the desired product (1.26 g, 14% yield). LCMS (ESI) m/z: [M+H] calcd for $C_{13}H_{23}NO_5S$: 306.14; found 306.1.

Step 3: Synthesis of (2S,3R)-1-((S)-tert-butylsulfinyl)-3-(methoxycarbonyl)aziridine-2-carboxylic acid To a solution of 2-(tert-butyl) 3-methyl (2S,3R)-1-((S)-tert-butylsulfinyl)aziridine-2,3-dicarboxylate (457.0 mg, 1.50 mmol) in DCM (6.0 mL) at 0° C. was added TFA (3.0 mL). The resulting mixture was stirred for 1 h and then concentrated under reduced pressure to afford the desired crude product (450 mg). LCMS (ESI) m/z: [M+H] calcd for $C_9H_{15}NO_5S$: 250.07; found 250.1.

Intermediate A-14. Synthesis of (2R,3R)-1-((R)-tert-butylsulfinyl)-3-methylaziridine-2-carboxylic acid

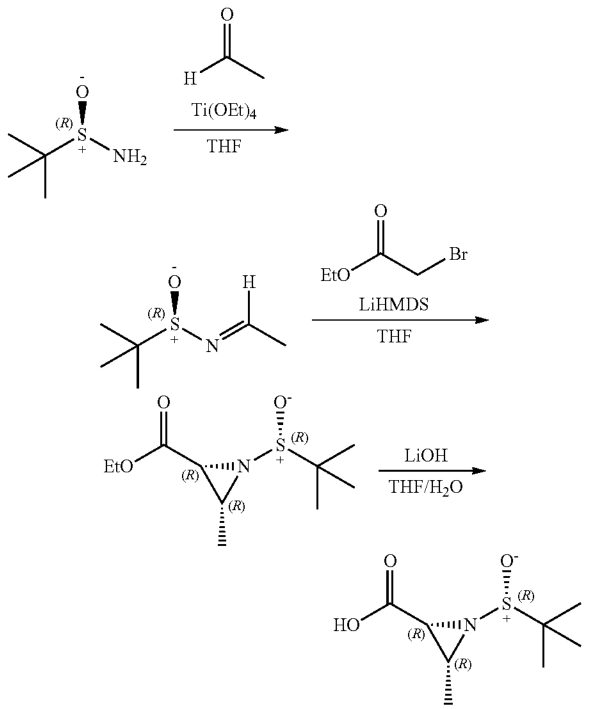

Step 1: Synthesis of (R,E)-N-ethylidene-2-methylpropane-2-sulfinamide

To a solution of (R)-2-methylpropane-2-sulfinamide (3.0 g, 24.75 mmol) and tetraethoxytitanium (1.7 g, 7.43 mmol) in THF (30 mL) at 0° C. was added acetaldehyde (218.1 mg, 4.95 mmol). The resulting mixture was stirred for 20 min and was then quenched with $H_2O$ (100 mL). The suspension was filtered, and the filter cake washed with EtOAc (3×100 mL). The aqueous layer was extracted with EtOAc (3×100 mL) and the combined organic layers were washed with brine (3×100 mL), dried over $Na_2SO_4$, filtered, and concentrated under reduced pressure. Purification by normal phase chromatography (9% EtOAc/pet. ether) afforded desired product (3 g, 82% yield). LCMS (ESI) m/z: [M+H] calcd for $C_6H_{13}NOS$: 148.08; found 148.0.

Step 2: Synthesis of ethyl (2R,3R)-1-((R)-tert-butylsulfinyl)-3-methylaziridine-2-carboxylate To a solution of 1 M LiHMDS (40.75 mL, 40.75 mmol) in THE (30.0 mL) at −78° C. was added ethyl bromoacetate (6.80 g, 40.75 mmol). The resulting mixture was stirred for 1 h. To the reaction mixture was then added (R,E)-N-ethylidene-2-methylpropane-2-sulfinamide (3.0 g, 20.38 mmol). The resulting mixture was stirred for 2 h at −78° C. and then quenched with $H_2O$ (300 mL). The aqueous layer was extracted with EtOAc (3×300 mL) and the combined organic layers were washed with brine (3×100 mL), dried over $Na_2SO_4$, filtered, and concentrated under reduced pressure. The residue was purified by reverse phase chromatography (10→50% MeCN/$H_2O$) to afford the desired product (1.4 g, 30% yield). LCMS (ESI) m/z: [M+H] calcd for $C_{10}H_{19}NO_3S$: 234.12; found 234.1.

Step 3: Synthesis of (2R,3R)-1-((R)-tert-butylsulfinyl)-3-methylaziridine-2-carboxylic acid To a solution of ethyl (2R,3R)-1-((R)-tert-butylsulfinyl)-3-methylaziridine-2-carboxylate (1.0 g, 4.29 mmol) in THE (6.4 mL) and $H_2O$ (6.4 mL) at 0° C. was added LiOH·$H_2O$ (539.5 mg, 12.86 mmol). The resulting mixture was warmed to room temperature and stirred for 2 h and was then neutralized to pH 5 with HCl (aq.) and sat. $NH_4Cl$ (aq.). The aqueous layer was extracted with EtOAc (3×10 mL) and the combined organic layers were washed with brine, dried over $Na_2SO_4$, filtered, and concentrated under reduced pressure to afford the desired crude product (489 mg, 56% yield). LCMS (ESI) m/z: [M+H] calcd for $CH_{15}NO_3S$: 206.09; found 206.0.

Intermediate A-15. Synthesis of (2S,3S)-1-(S)-tert-butylsulfinyl)-3-methylaziridine-2-carboxylic acid

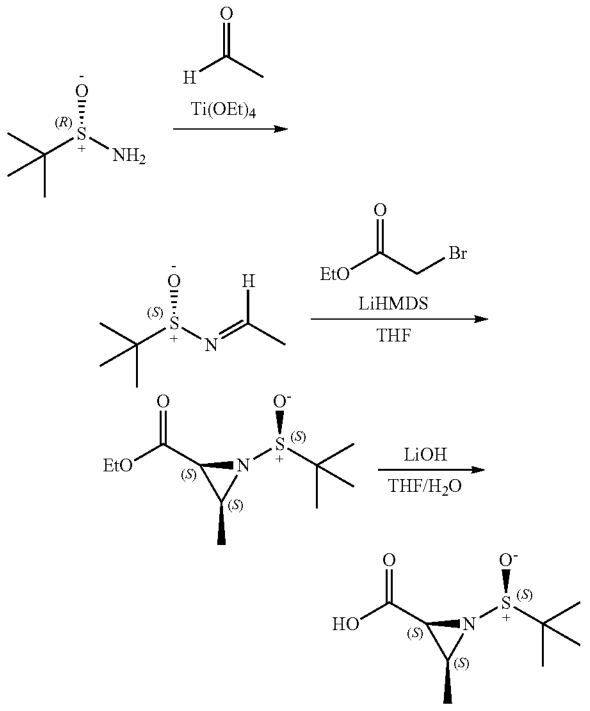

Step 1: Synthesis of (S,E)-N-ethylidene-2-methylpropane-2-sulfinamide

To a mixture of (S)-2-methylpropane-2-sulfinamide (5.0 g, 41.25 mmol) and tetraethoxytitanium (18.82 g, 82.51 mmol) at 0° C. was added acetaldehyde (3.63 g, 82.51 mmol). The resulting mixture was warmed to room temperature and stirred for 30 min and was then quenched with $H_2O$ (100 mL). The suspension was filtered, and the filter cake washed with EtOAc (3×100 mL). The aqueous layer was extracted with EtOAc (3×100 mL) and the combined organic layers were washed with brine (3×100 mL), dried over $Na_2SO_4$, filtered, and concentrated under reduced pressure to afford desired crude product (3.9 g, 64% yield). LCMS (ESI) m/z: [M+H] calcd for $C_6H_{13}NOS$: 148.08; found 148.2.

Step 2: Synthesis of ethyl (2S,3S)-1-((S)-tert-butylsulfinyl)-3-methylaziridine-2-carboxylate To a solution of 1 M LiHMDS (40.75 mL, 40.75 mmol) in THE (30.0 mL) at −78° C. was added ethyl bromoacetate (6.80 g, 40.75 mmol). The resulting mixture was stirred for 1 h. To the reaction mixture was then added (S,E)-N-ethylidene-2-methylpropane-2-sulfinamide (3.0 g, 20.38 mmol). The resulting mixture was stirred for 2 h at −78° C. and then quenched with $H_2O$. The aqueous layer was extracted with EtOAc (3×200 mL) and the combined organic layers were washed with brine (3×300 mL), dried over $Na_2SO_4$, filtered, and concentrated under reduced pressure. The residue was purified by reverse phase chromatography (10→50% MeCN/$H_2O$) to afford the desired product (2 g, 42% yield). LCMS (ESI) m/z: [M+H] calcd for $C_{10}H_{19}NO_3S$: 234.12; found 234.0.

Step 3: Synthesis of (2S,3S)-1-((S)-tert-butylsulfinyl)-3-methylaziridine-2-carboxylic acid To a solution of ethyl (2S,3S)-1-((S)-tert-butylsulfinyl)-3-methylaziridine-2-carboxylate (80.0 mg, 0.34 mmol) in THE (1.0 mL) and $H_2O$ (0.2 mL) at 0° C. was added $LiOH \cdot H_2O$ (32.9 mg, 1.37 mmol). The resulting mixture was warmed to room temperature and stirred for 4 h and was then acidified to pH 3 with HCl (aq.). The aqueous layer was extracted with EtOAc (3×10 mL) and the combined organic layers were washed with brine, dried over $Na_2SO_4$, filtered, and concentrated under reduced pressure to afford the desired crude product (70 mg, 99% yield). LCMS (ESI) m/z: [M+H] calcd for $C_8H_{15}NO_3S$: 206.09; found 206.0.

Intermediate A-16. Synthesis of (2S,3S)-1-(tert-butylsulfinyl)-3-cyclopropylaziridine-2-carboxylic acid

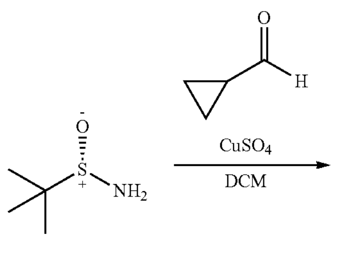

-continued

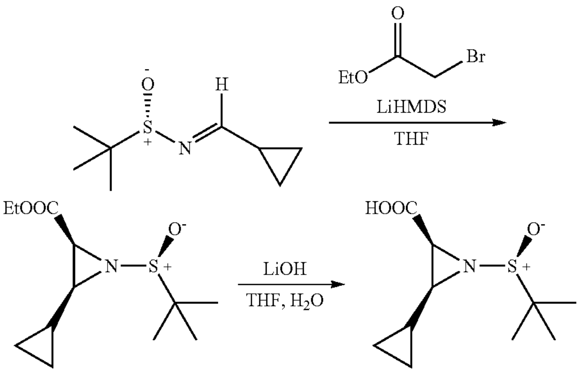

Step 1: Synthesis of (E)-N-(cyclopropylmethylene)-2-methylpropane-2-sulfinamide To a suspension of (S)-2-methylpropane-2-sulfinamide (4.0 g, 33.0 mmol) and $CuSO_4$ (15.80 g, 99.01 mmol) in DCM (200.0 mL) was added cyclopropanecarbaldehyde (4.63 g, 66.0 mmol). The resulting mixture was stirred overnight and was then filtered, the filter cake was washed with DCM (3×100 mL), and the filtrate was concentrated under reduced pressure to afford the desired product (3.5 g, 61% yield). LCMS (ESI) m/z: [M+H] calcd for $C_8H_{15}NOS$: 174.10; found 174.1.

Step 2: Synthesis of ethyl (2S,3S)-1-(tert-butylsulfinyl)-3-cyclopropylaziridine-2-carboxylate To a solution of ethyl bromoacetate (481.91 mg, 2.886 mmol) in THE (5.0 mL) at −78° C. was added LiHMDS (2.90 mL, 2.90 mmol). The resulting mixture was stirred for 2 h at −78° C. and then a solution of (E)-N-(cyclopropylmethylene)-2-methylpropane-2-sulfinamide (250.0 mg, 1.443 mmol) was added. The resulting mixture was stirred for 2 h at −78° C. and was then was then quenched with $H_2O$ at 0° C. The aqueous layer was extracted with EtOAc (3×50 mL), and the combined organic layers were dried over $Na_2SO_4$, filtered, and concentrated under reduced pressure. The residue was purified by prep-TLC (17% EtOAc/pet. ether) to afford the desired product (250 mg, 67% yield). LCMS (ESI) m/z: [M+H] calcd for $C_{12}H_{21}NO_3S$: 260.13; found 260.1.

Step 3: Synthesis of (2S,3S)-1-(tert-butylsulfinyl)-3-cyclopropylaziridine-2-carboxylic acid A solution of ethyl (2S,3S)-1-(tert-butylsulfinyl)-3-cyclopropylaziridine-2-carboxylate (500.0 mg, 1.928 mmol) in THE (2.0 mL) and $H_2O$ (2.0 mL) at 0° C. was added $LiOH \cdot H_2O$ (121.34 mg, 2.89 mmol). The reaction mixture was stirred for 1 h and was then acidified to pH 6 with 1 M HCl (aq.). The resulting mixture was extracted with EtOAc (2×10 mL) and the combined organic layers were washed with brine (10 mL), dried over $Na_2SO_4$, filtered, and the filtrate was concentrated under reduced pressure to afford the desired product (400 mg, 90% yield). LCMS (ESI) m/z: [M+H] calcd for $C_{10}H_{17}NO_3S$: 232.10; found 232.0.

Intermediate A-17. Synthesis of (2R,3R)-3-(methoxymethyl)-1-tritylaziridine-2-carboxylic acid

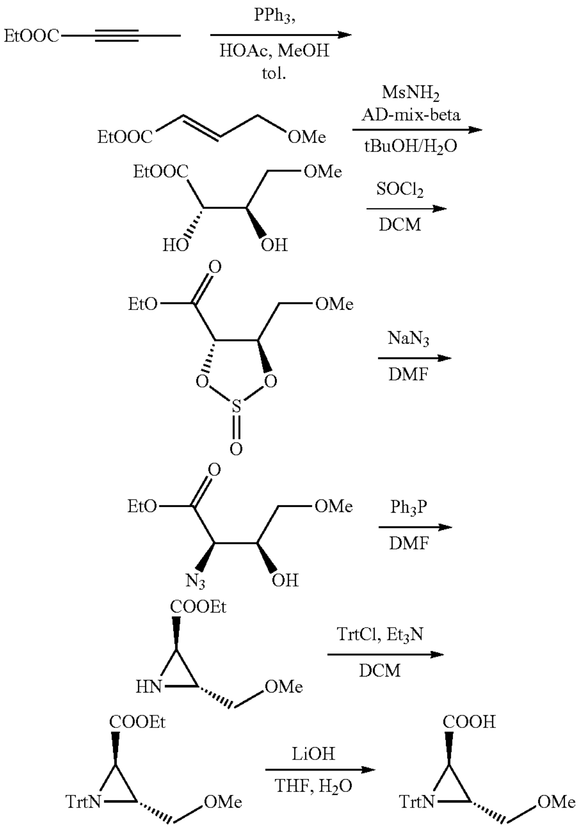

Step 1: Synthesis of ethyl (E)-4-methoxybut-2-enoate

To a solution of ethyl but-2-ynoate (10.0 g, 89.18 mmol) in MeOH (8.80 mL, 118.594 mmol) and HOAc (1.05 mL, 18.3 mmol) was added a solution of $PPh_3$ (1.20 g, 4.58 mmol) in toluene (60.0 mL). The resulting solution heated to 110° C. and stirred overnight. The reaction mixture was cooled to room temperature and was then diluted with $H_2O$ (60 mL). The resulting solution was extracted with EtOAc (2×60), and the combined organic layers were washed with brine (2×20 mL), dried over $Na_2SO_4$, filtered, and concentrated under reduced pressure. The residue was purified by silica gel column chromatography (9% EtOAc/pet. ether) to afford the desired product (4.9 g, 38% yield). LCMS (ESI) m/z: [M+H] calcd for $C_7H_{12}O_3$: 145.09; found 144.9.

Step 2: Synthesis of ethyl (2S,3R)-2,3-dihydroxy-4-methoxybutanoate

To a solution of ethyl (E)-4-methoxybut-2-enoate (5.0 g, 34.68 mmol), and methanesulfonamide (3.30 g, 34.68 mmol) in t-BuOH (150.0 mL) and $H_2O$ (100.0 mL) was added AD-mix-β (48.63 g, 62.43 mmol). The resulting solution was heated to 30° C. and stirred overnight. The solution was then cooled to room temperature and adjusted to pH 2 with $KHSO_4$. The resulting solution was extracted with EtOAc (2×100 mL) and the combined organic layers were dried over $Na_2SO_4$, filtered, and concentrated under reduced pressure to afford the desired product (1.28 g, crude). LCMS (ESI) m/z: [M+H] calcd for $C_7H_{14}O_5$: 179.09; found 179.0.

Step 3: Synthesis of ethyl (4S,5R)-5-(methoxymethyl)-1,3,2-dioxathiolane-4-carboxylate 2-oxide To a solution of ethyl (2S,3R)-2,3-dihydroxy-4-methoxybutanoate (4.10 g, 23.01 mmol) in DCM (20.0 mL) at 0° C. was added $SOCl_2$ (5.47 g, 45.9 mmol). The resulting mixture was heated to 50° C. and stirred for 3 h. The reaction mixture was then cooled to room temperature and concentrated under reduced pressure to afford the desired product (4.0 g, crude).

Step 4: Synthesis of ethyl (2R,3S)-2-azido-3-hydroxy-4-methoxybutanoate

To a solution of ethyl (4S,5R)-5-(methoxymethyl)-1,3,2-dioxathiolane-4-carboxylate 2-oxide (4.0 g crude, 17.84 mmol) in DMF (20.0 mL) at 0° C. was added $NaN_3$ (5.80 g, 89.22 mmol). The resulting mixture was heated to 35° C. and stirred overnight. The reaction mixture was then diluted with $H_2O$ (200 mL) and was extracted with EtOAc (3×50 mL). The combined organic layers were washed with brine (3×50 mL), dried over $Na_2SO_4$, filtered, and concentrated under reduced pressure. The residue was purified by silica gel column chromatography (17% EtOAc/pet. ether) to afford the desired product (1.0 g, 28% yield). LCMS (ESI) m/z: [M+H] calcd for $C_7H_{13}N_3O_4$: 204.10; found 204.0.

Step 5: Synthesis of ethyl (2R,3R)-3-(methoxymethyl)aziridine-2-carboxylate

To a solution of ethyl (2R,3S)-2-azido-3-hydroxy-4-methoxybutanoate (1.0 g, 4.92 mmol) in DMF (10 mL) at 0° C. was added $PPh_3$ (1.29 g, 4.92 mmol) in portions over 30 min. The reaction solution was then warmed to room temperature and stirred for 30 min. The reaction mixture was then heated to 85° C. and stirred until the reaction was complete. The reaction mixture was then concentrated under reduced pressure and purified by prep-TLC (33% EtOAc/pet. ether) to afford the desired product (480 mg, 61% yield). LCMS (ESI) m/z: [M+H] calcd for $C_7H_{13}NO_3$: 160.10; found 160.1.

Step 6: Synthesis of ethyl (2R,3R)-3-(methoxymethyl)-1-tritylaziridine-2-carboxylate To a solution of ethyl (2R,3R)-3-(methoxymethyl)aziridine-2-carboxylate (480.0 mg, 3.02 mmol) and $Et_3N$ (2.1 mL, 15.0 mmol) in DCM (10 mL) at 0° C. was added Trt-Cl (1.681 g, 6.031 mmol). The resulting mixture was warmed to room temperature and stirred for 2 h. The mixture was concentrated then concentrated under reduced pressure and the residue was purified by prep-TLC (5% EtOAc/pet. ether) to afford the desired product (700 mg, crude).

Step 7: Synthesis of (2R,3R)-3-(methoxymethyl)-1-tritylaziridine-2-carboxylic acid To a solution of ethyl (2R,3R)-3-(methoxymethyl)-1-(triphenylmethyl)aziridine-2-carboxylate (200.0 mg, 0.498 mmol) in THE (5.0 mL) and $H_2O$ (5 mL) was added $LiOH{\cdot}H_2O$ (41.81 mg, 0.996 mmol). The resulting solution was stirred at room temperature for 24 h. The mixture was then diluted with $H_2O$ (10 mL) and extracted with EtOAc (20 mL). The aqueous layer was then acidified to pH 7 with sat. aq. $NH_4Cl$ and extracted with EtOAc (2×10 mL). The combined organic layers were dried over $Na_2SO_4$, filtered, and concentrated under reduced pressure to afford the desired product (60 mg, 32% yield). LCMS (ESI) m/z: [M−H] calcd for $C_{24}H_{23}NO_3$: 372.16; found 372.1.

Intermediate A-18. Synthesis of (2S,3S)-1-(tert-butylsulfinyl)-3-(4-methoxyphenyl)aziridine-2-carboxylic acid

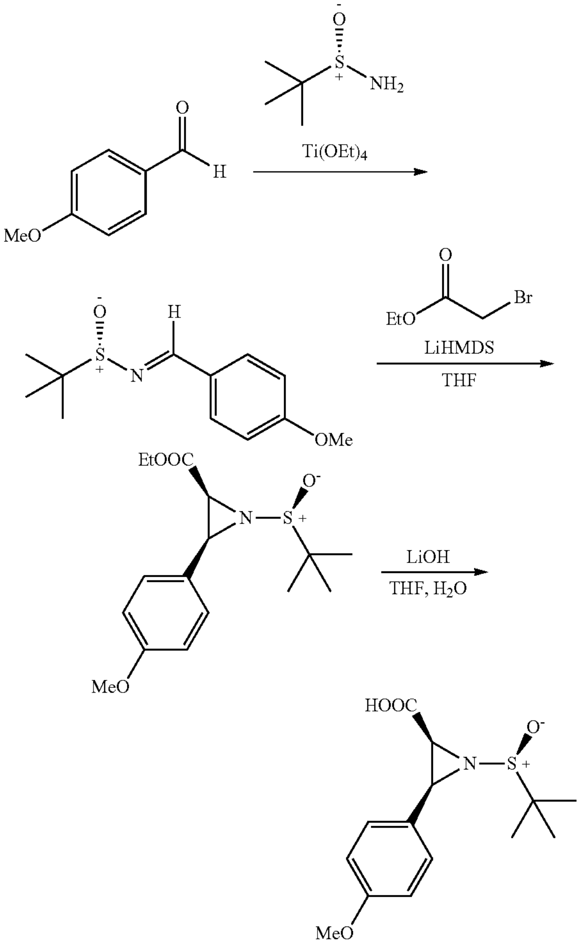

Step 1: (E)-N-(4-methoxybenzylidene)-2-methylpropane-2-sulfinamide

A solution of (S)-2-methylpropane-2-sulfinamide (2.50 g) and anisaldehyde (2.81 g) in $Ti(OEt)_4$ (20.0 mL) was stirred at 70° C. for 1 h. The resulting mixture was cooled to room temperature, diluted with EtOAc (60 mL), and then poured into $H_2O$. The mixture was filtered, and the filter cake was washed with EtOAc (3×50 mL). The resulting mixture was extracted with EtOAc (3×50 mL) and the combined organic layers were washed with brine (50 mL), dried over $Na_2SO_4$, filtered, and concentrated under reduced pressure. The residue was purified by silica gel column chromatography (25% EtOAc/pet. ether) to afford the desired product (4 g, 81% yield). LCMS (ESI) m/z: [M+H] calcd for $C_{12}H_{17}NO_2S$: 240.11; found 240.1.

Step 2: Synthesis of ethyl (2S,3S)-1-(tert-butylsulfinyl)-3-(4-methoxyphenyl)aziridine-2-carboxylate To a solution of ethyl 2-bromoacetate (5.60 g, 33.5 mmol) in THF (100 mL) at −78° C. was added LiHMDS (1 M in THF, 34 mL, 33.473 mmol). After 30 min a solution of (E)-N-(4-methoxybenzylidene)-2-methylpropane-2-sulfinamide (4 g, 16.74 mmol) in THF (20 mL) was added. The resulting mixture was stirred at −78° C. for additional 3 h. The reaction was then quenched with sat. aq. $NH_4Cl$. The mixture was extracted with EtOAc (3×100 mL) and the combined organic layers were washed with brine (50 mL), dried over $Na_2SO_4$, filtered, and concentrated under reduced pressure. The residue was purified by silica gel chromatography (25% EtOAc/pet. ether) to afford the desired product (2.7 g, 50% yield). LCMS (ESI) m/z: [M+H] calcd for $C_{16}H_{23}NO_4S$: 326.14; found 326.1.

Step 3: Synthesis of (2S,3S)-1-(tert-butylsulfinyl)-3-(4-methoxyphenyl)aziridine-2-carboxylic acid To a solution of ethyl (2S,3S)-1-(tert-butylsulfinyl)-3-(4-methoxyphenyl)aziridine-2-carboxylate (800.0 mg, 2.68 mmol) in THF (2.0 mL) at 0° C. was added a solution of $LiOH{\cdot}H_2O$ (309.46 mg, 7.38 mmol) in $H_2O$ (3.0 mL). The resulting mixture was warmed to room temperature and stirred for 4 h. The mixture was then acidified to pH 6 with sat. aq. $NH_4Cl$ and then extracted with EtOAc (3×50 mL). The combined organic layers were dried over $Na_2SO_4$, filtered. and concentrated under reduced pressure to afford the desired product (690 mg, 94% yield). LCMS (ESI) m/z: [M−H] calcd for $C_{14}H_{19}NO_4S$: 296.10; found 296.2.

Intermediate A-19. Synthesis of (2S,3R)-3-(4-methoxyphenyl)aziridine-2-carboxylic acid

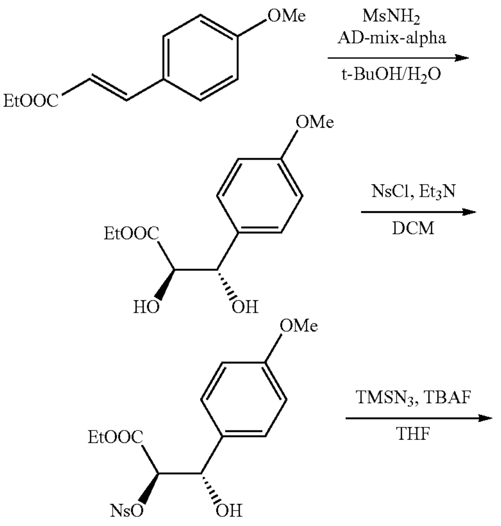

-continued

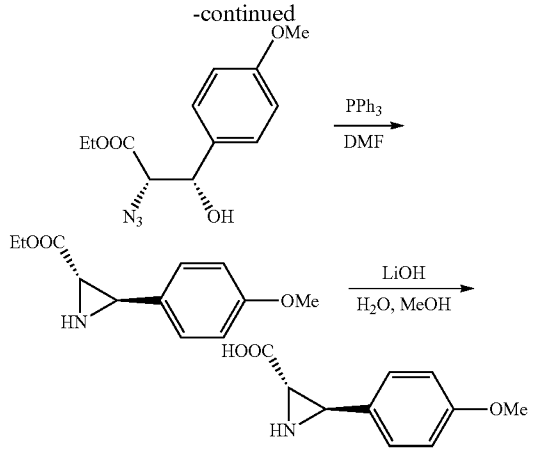

Step 1: Synthesis of ethyl (2R,3S)-2,3-dihydroxy-3-(4-methoxyphenyl)propanoate

To a solution of ethyl p-methoxycinnamate (5.0 g, 24.24 mmol) in tBuOH (70.0 mL) and $H_2O$ (70.0 mL) at 0° C. was added AD-mix-α (33.80 g, 43.39 mmol) and methanesulfonamide (2.31 mg, 0.024 mmol). The resulting mixture was warmed to room temperature and stirred overnight. The reaction was then cooled to 0° C. and quenched with $KHSO_4$ (aq.). The mixture was extracted with EtOAc (3×100 mL) and the combined organic layers were washed with brine (2×90 mL), dried over $Na_2SO_4$, filtered, and concentrated under reduced pressure. The residue was purified by silica gel chromatography (50% EtOAc/pet. ether) to afford the desired product (5.7 g, 88% yield).

Step 2: Synthesis of ethyl (2R,3S)-3-hydroxy-3-(4-methoxyphenyl)-2-(((4-nitrophenyl)sulfonyl)oxy)propanoate To a solution of ethyl (2R,3S)-2,3-dihydroxy-3-(4-methoxyphenyl)propanoate (3.0 g, 12.49 mmol) and $Et_3N$ (0.174 mL, 1.249 mmol) in DCM (30.0 mL) at 0° C. was added 4-nitrobenzenesulfonyl chloride (2.76 g, 12.49 mmol). The resulting mixture was stirred for 1 h and was then diluted with $H_2O$. The mixture was extracted with DCM (3×100 mL) and the combined organic layers were washed with brine (2×100 mL), dried over $Na_2SO_4$, filtered, and concentrated under reduced pressure. The residue was purified by prep-TLC (50% EtOAc/pet. ether) to afford the desired product (3.8 g, 68% yield). LCMS (ESI) m/z: [M+Na] calcd for $C_{18}H_{19}NO_9S$: 448.07; found 448.2.

Step 3: Synthesis of ethyl (2S,3S)-2-azido-3-hydroxy-3-(4-methoxyphenyl)propanoate To a solution of ethyl (2R,3S)-3-hydroxy-3-(4-methoxyphenyl)-2-(((4-nitrophenyl)sulfonyl)oxy)propanoate (1.20 g, 2.82 mmol) in THE at 0° C. was added TBAF (1 M in THF, 5.64 mL, 5.64 mmol) and $TMSN_3$ (648.79 mg, 5.64 mmol). The resulting mixture was heated to at 60° C. and stirred for 16 h. The reaction was then cooled to at 0° C. and quenched with sat. aq. $NH_4Cl$. The mixture was extracted with EtOAc (3×100 mL) and the combined organic layers were washed with $H_2O$ (2×100 mL), dried over $Na_2SO_4$, filtered, and concentrated under reduced pressure. The residue was purified by prep-TLC (33% EtOAc/pet. ether) to afford the desired product (540 mg, 71% yield).

Step 4: Synthesis of ethyl (2S,3R)-3-(4-methoxyphenyl)aziridine-2-carboxylate

To a solution of ethyl (2S,3S)-2-azido-3-hydroxy-3-(4-methoxyphenyl)propanoate (440.0 mg, 1.659 mmol) in DMF was added $PPh_3$ (522.06 mg, 1.99 mmol). The resulting mixture was stirred at room temperature for 30 min and was then heated to 80° C. and stirred overnight. The mixture was then extracted with EtOAc (3×100 mL), and the combined organic layers were washed with $H_2O$ (2×100 mL), dried over anhydrous $Na_2SO_4$, filtered, and concentrated under reduced pressure. The residue was purified by prep-TLC (25% EtOAc/pet. ether) to afford the desired product (200 mg, 52% yield). LCMS (ESI) m/z: [M+H] calcd for $C_{12}H_{15}NO_3$: 222.12; found 222.1.

Step 5: Synthesis of (2S,3R)-3-(4-methoxyphenyl)aziridine-2-carboxylic acid

To a solution of ethyl (2S,3R)-3-(4-methoxyphenyl)aziridine-2-carboxylate (200.0 mg, 0.904 mmol) in MeOH and $H_2O$ at 0° C. was added $LiOH \cdot H_2O$ (86.6 mg, 3.62 mmol). The resulting mixture was stirred for 1 h and was then neutralized to pH 7 with HCl (aq.). The mixture was extracted with EtOAc (3×100 mL) and the combined organic layers were washed with $H_2O$ (2×100 mL), dried over $Na_2SO_4$, filtered, and concentrated under reduced pressure to afford the desired product (180 mg, 98% yield). LCMS (ESI) m/z: [M−H] calcd for $C_{10}H_{11}NO_3$: 192.07; found 192.0.

Intermediate A-20. Synthesis of (2R,3S)-3-(4-methoxyphenyl)aziridine-2-carboxylic acid

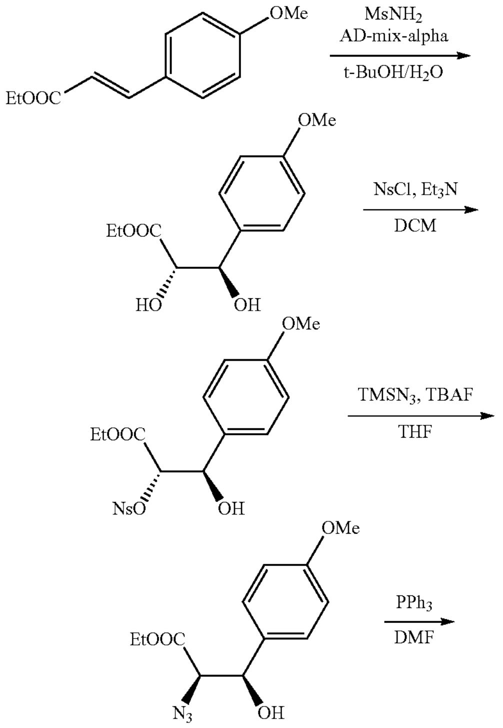

-continued

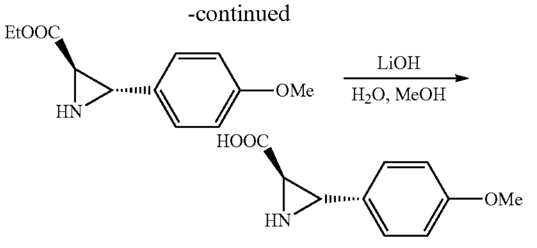

Step 1: Synthesis of ethyl (2S,3R)-2,3-dihydroxy-3-(4-methoxyphenyl)propanoate To a solution of ethyl p-methoxycinnamate (5.0 g, 24.24 mmol) in tBuOH (70.0 mL) and $H_2O$ (70.0 mL) at 0° C. was added AD-mix-β (33.80 g, 43.39 mmol) and methanesulfonamide (2.31 mg, 0.024 mmol). The resulting mixture was warmed to room temperature and stirred overnight. The reaction was then cooled to 0° C. and quenched with $KHSO_4$ (aq.). The mixture was extracted with EtOAc (3×100 mL) and the combined organic layers were washed with brine (2×90 mL), dried over $Na_2SO_4$, filtered, and concentrated under reduced pressure. The residue was purified by silica gel chromatography (50% EtOAc/pet. ether) to afford the desired product (5.7 g, 88% yield).

Step 2: Synthesis of ethyl (2S,3R)-3-hydroxy-3-(4-methoxyphenyl)-2-(((4-nitrophenyl)sulfonyl)oxy)propanoate To a solution of ethyl (2S,3R)-2,3-dihydroxy-3-(4-methoxyphenyl)propanoate (5.80 g, 24.14 mmol) and $Et_3N$ (10.1 mL, 72.42 mmol) in DCM (30.0 mL) at 0° C. was added 4-nitrobenzenesulfonyl chloride (5.34 g, 24.1 mmol). The resulting mixture was stirred for 1 h and was then diluted with $H_2O$. The mixture was extracted with DCM (3×100 mL) and the combined organic layers were washed with brine (2×100 mL), dried over $Na_2SO_4$, filtered, and concentrated under reduced pressure. The residue was purified by prep-TLC (50% EtOAc/pet. ether) to afford the desired product (7.2 g, 67% yield). LCMS (ESI) m/z: [M+H] calcd for $C_{18}H_{19}NO_9S$: 426.09; found 426.2.

Step 3: Synthesis of ethyl (2R,3R)-2-azido-3-hydroxy-3-(4-methoxyphenyl)propanoate To a solution of ethyl (2S,3R)-3-hydroxy-3-(4-methoxyphenyl)-2-(((4-nitrophenyl)sulfonyl)oxy)propanoate (5.0 g, 11.75 mmol) in THF at 0° C. was added TBAF (1 M in THF, 23.5 mL, 23.51 mmol) and $TMSN_3$ (2.7 g, 23.5 mmol). The resulting mixture was heated to at 60° C. and stirred for 16 h. The reaction was then cooled to at 0° C. and quenched with sat. aq. $NH_4Cl$. The mixture was extracted with EtOAc (3×100 mL) and the combined organic layers were washed with $H_2O$ (2×100 mL), dried over $Na_2SO_4$, filtered, and concentrated under reduced pressure. The residue was purified by prep-TLC (33% EtOAc/pet. ether) to afford the desired product (2.3 g, 70% yield).

Step 4: Synthesis of ethyl (2R,3S)-3-(4-methoxyphenyl)aziridine-2-carboxylate To a solution of ethyl (2R,3R)-2-azido-3-hydroxy-3-(4-methoxyphenyl)propanoate (2.30 g, 8.67 mmol) in DMF was added $PPh_3$ (2.73 g, 10.4 mmol). The resulting mixture was stirred at room temperature for 30 min and was then heated to 80° C. and stirred overnight. The mixture was then extracted with EtOAc (3×100 mL), and the combined organic layers were washed with $H_2O$ (2×100 mL), dried over anhydrous $Na_2SO_4$, filtered, and concentrated under reduced pressure. The residue was purified by prep-TLC (25% EtOAc/pet. ether) to afford the desired product (1.6 g, 79% yield). LCMS (ESI) m/z: [M+H] calcd for $C_{12}H_{15}NO_3$: 222.12; found 222.1.

Step 5: Synthesis of (2R,3S)-3-(4-methoxyphenyl)aziridine-2-carboxylic acid

To a solution of ethyl (2S,3R)-3-(4-methoxyphenyl)aziridine-2-carboxylate (200.0 mg, 0.904 mmol) in MeOH and $H_2O$ at 0° C. was added $LiOH \cdot H_2O$ (86.6 mg, 3.62 mmol). The resulting mixture was stirred for 1 h and was then neutralized to pH 7 with HCl (aq.). The mixture was extracted with EtOAc (3×100 mL) and the combined organic layers were washed with $H_2O$ (2×100 mL), dried over $Na_2SO_4$, filtered, and concentrated under reduced pressure to afford the desired product (180 mg, 98% yield). LCMS (ESI) m/z: [M−H] calcd for $C_{10}H_{11}NO_3$: 192.07; found 192.0.

Intermediate A-21. Synthesis of (2S,3S)-1-((S)-tert-butylsulfinyl)-3-phenylaziridine-2-carboxylic acid

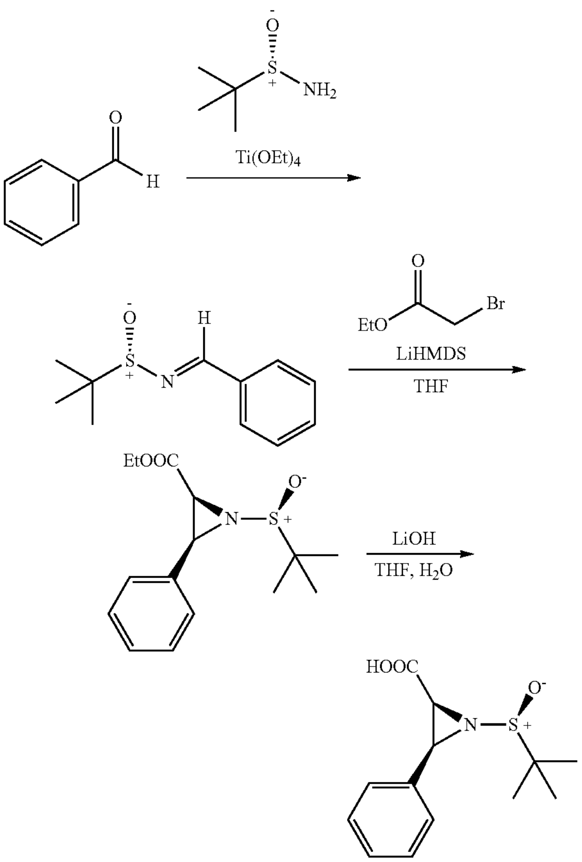

Step 1: Synthesis of (S,E)-N-benzylidene-2-methylpropane-2-sulfinamide

A solution of (S)-2-methylpropane-2-sulfinamide (2.50 g, 20.6 mmol), titanium ethoxide (9.41 g, 41.25 mmol) and benzaldehyde (2.19 g, 20.7 mmol) was heated at 70° C. for 1 h, cooled, and diluted with $H_2O$ (250 mL). The aqueous layer was extracted with EtOAc (3×80 mL) and the combined organic layers were washed with brine (2×100 mL), dried with $Na_2SO_4$, filtered and concentrated under reduced pressure to afford the desired product (4.3 g, crude) which was used without further purification. LCMS (ESI) m/z: [M+H] calcd for $C_{11}H_{15}NOS$: 210.10; found 210.2.

Step 2: Synthesis of ethyl (2S,3S)-1-((S)-tert-butylsulfinyl)-3-phenylaziridine-2-carboxylate To a solution of ethyl bromoacetate (798 mg, 4.78 mmol) in THF (15 mL) at −78° C. was added LiHMDS (1 M in THF, 4.78 mL, 4.78 mmol). After 1 h, (S,E)-N-benzylidene-2-methylpropane-2-sulfinamide (500 mg, 2.39 mmol) in THF (5 mL) was added in portions over 20 min. The reaction mixture was stirred at −78° C. for 2 h and then quenched by the addition of sat. $NH_4Cl$. The aqueous layer was extracted with EtOAc (3×40 mL) and the combined organic layers were washed with brine (2×30 mL), dried with $Na_2SO_4$, filtered, and concentrated under reduced pressure. Purification by reverse phase chromatography (30→60% MeCN/$H_2O$, 0.1% $HCO_2H$) afforded the desired product (480 mg, 61% yield).

LCMS (ESI) m/z: [M+H] calcd for $C_{15}H_{21}NO_3S$: 296.13; found 296.2.

Step 3: Synthesis (2S,3S)-1-((S)-tert-butylsulfinyl)-3-phenylaziridine-2-carboxylic acid To a solution of ethyl (2S,3S)-1-((S)-tert-butylsulfinyl)-3-phenylaziridine-2-carboxylate (600 mg, 2.03 mmol) in THF (4.0 mL) at 0° C. was added a solution of LiOH (97.2 mg, 4.06 mmol) in $H_2O$ (4.0 mL). The resulting mixture was stirred for 2 h at 0° C. and then acidified to pH 5 with 1 M HCl. The aqueous layer was extracted with EtOAc (3×40 mL) and the combined organic layers were washed with brine (2×20 mL), dried with $Na_2SO_4$, filtered, and concentrated under reduced pressure to afford the desired compound (450 mg, crude) which was used without further purification. LCMS (ESI) m/z: [M+H] calcd for $C_{13}H_{17}NO_3S$: 268.10; found 268.1.

Intermediate A-22. Synthesis of (2R,3R)-1-((R)-tert-butylsulfinyl)-3-phenylaziridine-2-carboxylic acid

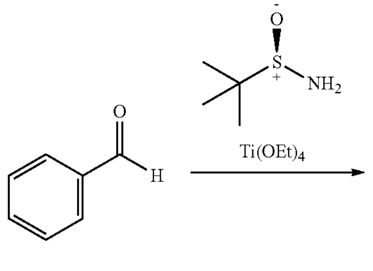

-continued

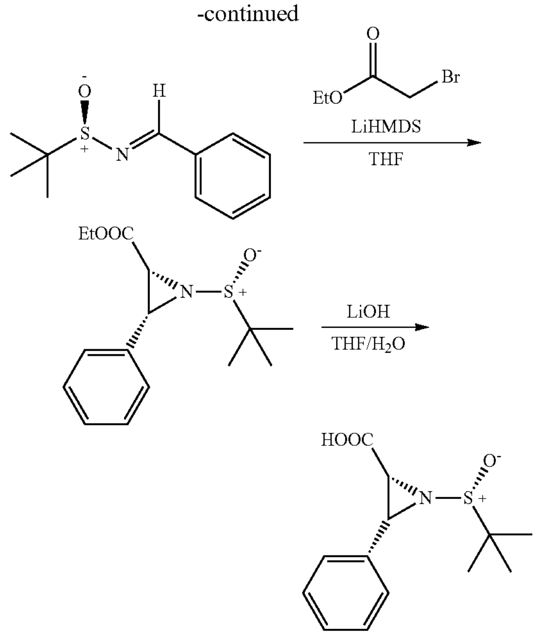

Step 1: Synthesis (R,E)-N-benzylidene-2-methylpropane-2-sulfinamide

A solution (R)-2-methylpropane-2-sulfinamide (2.50 g, 20.6 mmol), titanium tetraethoxide (9.41 g, 41.3 mmol) and benzaldehyde (2.19 g, 20.6 mmol) was heated 70° C. for 1 h, cooled, and diluted with $H_2O$ (250 mL). The aqueous layer was extracted with EtOAc (3×90 mL) and the combined organic layers were washed with brine (2×100 mL), dried with $Na_2SO_4$, filtered and concentrated under reduced pressure to afford the desired product (4.2 g, crude) which was used without further purification. LCMS (ESI) m/z: [M+H] calcd for $C_{11}H_{15}NOS$: 210.10; found 210.1.

Step 2: Synthesis of ethyl (2R,3R)-1-((R)-tert-butylsulfinyl)-3-phenylaziridine-2-carboxylate To a solution of ethyl bromoacetate (6.38 g, 38.2 mmol) in THF (150 mL) at −78° C. was added LiHMDS (1M in THF, 7.19 mL, 42.9 mmol). After 1 h, (R,E)-N-benzylidene-2-methylpropane-2-sulfinamide (4.0 g, 19.1 mmol) in THF (50 mL) was added in portions over 20 min. The reaction mixture was stirred at −78° C. for 2 h and then quenched by the addition of sat. $NH_4Cl$. The aqueous layer was extracted with EtOAc (3×80 mL) and the combined organic layers were washed with brine (2×60 mL), dried with $Na_2SO_4$, filtered and concentrated under reduced pressure. Purification by reverse phase chromatography (30→60% MeCN/$H_2O$, 0.1% $HCO_2H$) afforded the desired product (3.9 g, 62% yield). LCMS (ESI) m/z: [M+H] calcd for $C_{15}H_{21}NO_3S$: 296.13; found 296.2.

Step 3: Synthesis (2R,3R)-1-((R)-tert-butylsulfinyl)-3-phenylaziridine-2-carboxylic acid To a solution of ethyl (2R,3R)-1-((R)-tert-butylsulfinyl)-3-phenylaziridine-2-carboxylate (200 mg, 0.677 mmol) in THE (1.5 mL) at 0° C. was added a solution of LiOH (32.4 mg, 1.35 mmol) in $H_2O$ (1.3 mL). The resulting mixture was stirred for 2 h at 0° C. and then acidified to pH 5 with 1 M HCl. The aqueous layer was extracted with EtOAc (3×20 mL) and the combined organic layers were washed with brine (2×10 mL), dried with $Na_2SO_4$, filtered, and concentrated under reduced pressure to afford the desired compound (220 mg, crude) which was used without further purification. LCMS (ESI) m/z: [M+H] calcd for $C_{13}H_{17}NO_3S$: 268.10; found 268.4.

Intermediate A-23. Synthesis of (2R,3S)-3-cyclopropylaziridine-2-carboxylic acid

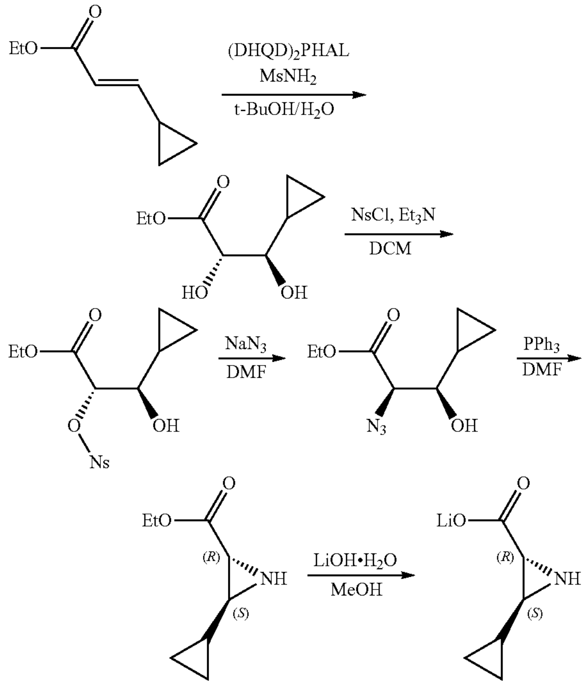

Step 1: Synthesis of ethyl (2S,3R)-3-cyclopropyl-2,3-dihydroxypropanoate

A solution of ethyl (E)-3-cyclopropylacrylate (10.4 mL, 71 mmol) in tert-BuOH (270 mL) and $H_2O$ (270 mL) was stirred at 0° C. After 5 min $MsNH_2$ (6.8 g, 71 mmol) and $(DHQD)_2PHAL$ (100 g, 130 mmol) were added and the reaction mixture was warmed to room temperature. After stirring overnight, sat. $Na_2SO_3$ was added and the mixture was stirred for 30 min. The mixture was acidified to pH 6 with $KH_2PO_4$. Purification by silica gel column chromatography (33% EtOAC/pet. ether) afforded desired product (5.5 g, 44% yield).

Step 2: Synthesis of ethyl (2S,3R)-3-cyclopropyl-3-hydroxy-2-(((4-nitrophenyl)sulfonyl)oxy)propanoate A solution of ethyl (2S,3R)-3-cyclopropyl-2,3-dihydroxypropanoate (5.40 g, 31.0 mmol) and $Et_3N$ (13.0 mL, 93.0 mmol) in DCM (20 mL) was stirred at 0° C. and a solution of 4-nitrobenzenesulfonyl chloride (6.53 g, 29.5 mmol) in DCM (10 mL) was added. The reaction mixture was stirred for 1.5 h and was then extracted with DCM (3×200 mL). The combined organic layers were washed with brine (100 mL), dried with $Na_2SO_4$, filtered, and concentrated under reduced pressure. Purification by silica gel column chromatography (33% EtOAc/pet. ether) afforded desired product (6.9 g, 62% yield).

Step 3: Synthesis of ethyl (2R,3R)-2-azido-3-cyclopropyl-3-hydroxypropanoate

A mixture of ethyl (2S,3R)-3-cyclopropyl-3-hydroxy-2-(((4-nitrophenyl)sulfonyl)oxy)propanoate (6.90 g, 19.2 mmol) and $NaN_3$ (6.24 g, 96.0 mmol) in DMF (70.0 mL) was heated to 50° C. The reaction mixture was stirred for 5 h and then extracted with EtOAc (3×200 mL). The combined organic layers were washed with brine (100 mL), dried with $Na_2SO_4$, filtered, and concentrated under reduced pressure. Purification by silica gel column chromatography (20% EtOAc/pet. ether) afforded desired product (2.8 g, 73% yield).

Step 4: Synthesis of ethyl (2R,3S)-3-cyclopropylaziridine-2-carboxylate

A mixture of triphenylphosphine (1.84 g, 7.02 mmol) in DMF (5 mL) was stirred at 0° C. After 5 min ethyl (2R,3R)-2-azido-3-cyclopropyl-3-hydroxypropanoate (1.40 g, 7.03 mmol) was added and the reaction was warmed to room temperature. The reaction mixture was heated to 80° C. and stirred for 1 h. The mixture was then cooled to room temperature and extracted with EtOAc (3×50 mL). The combined organic layers were washed with brine (50 mL), dried with $Na_2SO_4$, filtered, and concentrated under reduced pressure. Purification by silica gel column chromatography (20% EtOAc/pet. ether) afforded the desired product (230 mg, 46% yield). LCMS (ESI) m/z: [M+H] calcd for $C_8H_{13}NO_2$: 156.10; found 156.2.

Step 5: Synthesis of lithium (2R,3S)-3-cyclopropylaziridine-2-carboxylate

To a mixture of ethyl (2R,3S)-3-cyclopropylaziridine-2-carboxylate (230 mg, 1.5 mmol) in MeOH (3.0 mL) was added $LiOH \cdot H_2O$ (125 mg, 3.0 mmol). The reaction was stirred for 3 h and then filtered. The filtrate was concentrated under reduced pressure which afforded the desired product (150 mg, crude). LCMS (ESI) m/z: [M+H] calcd for $C_6H_9NO_2$: 128.07; found 128.2.

Intermediate A-24. Synthesis of (2S,3R)-3-cyclopropylaziridine-2-carboxylic acid

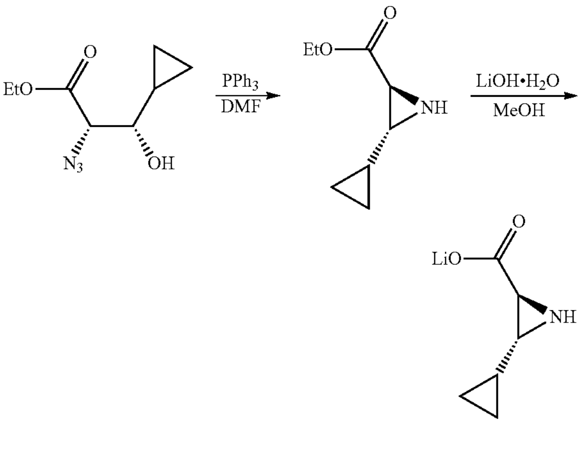

Step 1: Synthesis of ethyl (2S,3R)-3-cyclopropylaziridine-2-carboxylate

A mixture of $PPh_3$ (1.4 g, 5.4 mmol) in DMF (15.0 mL) was stirred at 0° C. After 30 min, ethyl (2S,3S)-2-azido-3-cyclopropyl-3-hydroxypropanoate (980 mg, 4.92 mmol) was added. The reaction mixture was heated to 80° C. After 2 h the reaction was quenched by the addition of $H_2O$ (20 mL) and was extracted with EtOAc (3x30 mL). Purification by silica gel column chromatography (17% EtOAc/pet. ether) afforded desired product (500 mg, 65% yield).

Step 2: Synthesis of lithium (2S,3R)-3-cyclopropylaziridine-2-carboxylate

To a solution of ethyl (2S,3R)-3-cyclopropylaziridine-2-carboxylate (450 mg, 2.9 mmol) in THE (6.0 mL) and $H_2O$ (2.0 mL) was added LiOH (90 mg, 3.8 mmol). The reaction was stirred for 2 h and then filtered.

The filtrate was concentrated under reduced pressure which afforded the desired product (300 mg, crude).

Intermediate A-25. Synthesis of potassium (S)-1-isopropylaziridine-2-carboxylate

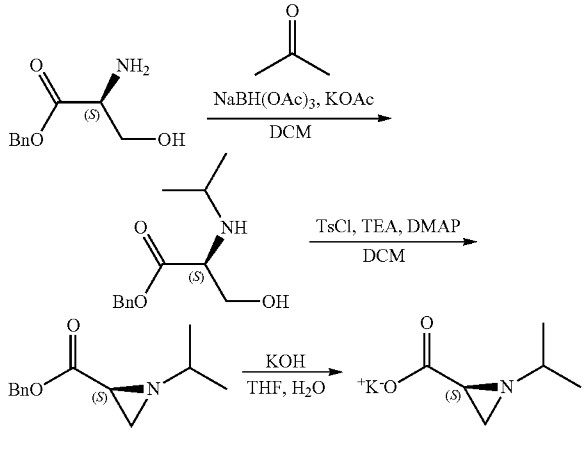

Step 1: Synthesis benzyl isopropyl-L-serinate

To a solution of benzyl L-serinate (3.65 g, 18.69 mmol), KOAc (1.83 g, 18.69 mmol), and acetone (2.5 mL, 33.66 mmol) in DCM (60.0 mL) was added $NaBH(AcO)_3$ (4.76 g, 22.436 mmol) in portions at 0° C. The resulting mixture was stirred overnight at room temperature. The reaction was quenched by the addition of sat. aq. $NaHCO_3$ (50 mL) at room temperature. The resulting mixture was extracted with DCM (3x80 mL). The combined organic layers were washed with brine (50 mL), dried over $Na_2SO_4$, filtered, and concentrated under reduced pressure. The residue was purified by silica gel chromatography (67% EtOAc/hexanes) to afford the desired product (2.7 g, 61% yield) as an off-white solid. LCMS (ESI) m/z: [M+H] calcd for $C_{13}H_{19}NO_3$: 238.14; found 238.2.

Step 2: Synthesis of benzyl (S)-1-isopropylaziridine-2-carboxylate

To a solution of benzyl isopropyl-L-serinate (2.70 g, 11.378 mmol), $Et_3N$ (4.75 mL, 34.134 mmol) and DMAP (2.57 mg, 0.021 mmol) in DCM (50.0 mL) was added a solution of TsCl (2.60 g, 13.65 mmol) in DCM dropwise at 0° C. The resulting mixture was stirred overnight at room temperature and was then stirred for 4 h at 40° C. The reaction mixture was diluted with $H_2O$ (80 mL) and was then extracted with DCM (2x50 mL). The combined organic layers were washed with brine (30 mL), dried over $Na_2SO_4$, filtered, and concentrated under reduced pressure. The residue was purified by silica gel chromatography (20% EtOAc/hexanes) to afford the desired product (2.3 g, 93% yield). LCMS (ESI) m/z: [M+H] calcd for $C_{13}H_{17}NO_2$: 220.13; found 220.1.

Step 3: Synthesis of potassium (S)-1-isopropylaziridine-2-carboxylate

To a solution of benzyl (S)-1-isopropylaziridine-2-carboxylate (800.0 mg, 3.65 mmol) and $H_2O$ (6.0 mL) and THE (8.0 mL) was added a solution of KOH (245.62 mg, 4.378 mmol) in $H_2O$ (2.0 mL) dropwise at 0° C. The resulting mixture was stirred for 2 h at room temperature. The mixture was diluted with $H_2O$ (10 mL) and the aqueous layer was washed with MTBE (3x8 mL). The aqueous layer was dried by lyophilization to afford the desired product (400 mg, crude). LCMS (ESI) m/z: [M+H] calcd for $C_6H_{11}NO_2$: 130.09; found 130.0.

Intermediate A-26. Synthesis of potassium (R)-1-isopropylaziridine-2-carboxylate

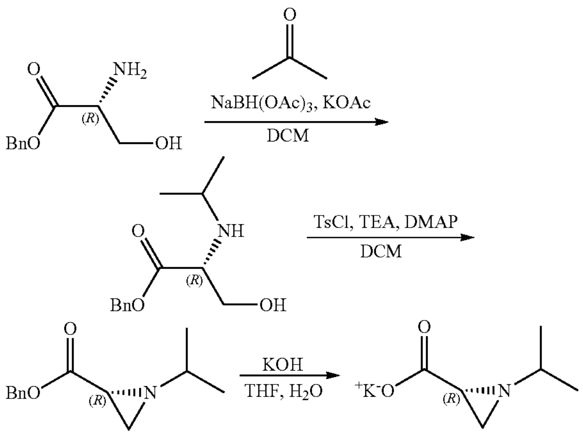

Step 1: Synthesis benzyl isopropyl-D-serinate

To a solution of benzyl D-serinate (2.10 g, 10.757 mmol), KOAc (1.06 g, 10.757 mmol), and acetone (1.2 mL, 16.136 mmol) in DCM (40.0 mL) was added a solution of $NaBH(AcO)_3$ (2.96 g, 13.984 mmol) in portions at 0° C. The resulting mixture was stirred overnight at room temperature. The reaction was quenched by the addition of sat. aq. $NaHCO_3$ (50 mL) and the mixture was extracted with DCM (3x50 mL). The combined organic layers were washed with brine (50 mL), dried over $Na_2SO_4$, filtered, and concentrated under reduced pressure. The residue was purified by silica gel chromatography (67% EtOAc/hexanes) to afford the desired product (1.7 g, 67% yield). LCMS (ESI) m/z: [M+H] calcd for $C_{13}H_{19}NO_3$: 238.14; found 238.0.

Step 2: Synthesis of benzyl (R)-1-isopropylaziridine-2-carboxylate

To a solution of benzyl isopropyl-D-serinate (1.75 g, 7.375 mmol), $Et_3N$ (2.58 mL, 18.437 mmol) and DMAP (90.09 mg, 0.737 mmol) in DCM (30.0 mL) was added a solution of TsCl (1.69 g, 8.850 mmol) in DCM dropwise at 0° C. The resulting mixture was stirred overnight at room temperature before being stirred for 4 h at 40° C. The mixture was diluted with $H_2O$ (80 mL) and then extracted with DCM (3×50 mL). The combined organic layers were washed with brine (50 mL), dried over $Na_2SO_4$, filtered, and concentrated under reduced pressure. The residue was purified by silica gel chromatography (20% EtOAc/hexanes) to afford the desired product (1.4 g, 87% yield). LCMS (ESI) m/z: [M+H] calcd for $C_{13}H_{17}NO_2$: 220.13; found 219.9.

Step 3: Synthesis of potassium (R)-1-isopropylaziridine-2-carboxylate

To a solution of benzyl (R)-1-isopropylaziridine-2-carboxylate (600.0 mg, 2.736 mmol) in $H_2O$ (3.0 mL) and THE (5.0 mL) was added a solution of KOH (184.22 mg, 3.283 mmol) in $H_2O$ (2.0 mL) dropwise at 0° C. The resulting mixture was stirred for 2 h at room temperature. The mixture was then diluted with $H_2O$ (10 mL) and the aqueous layer was washed with MTBE (3×8 mL). The aqueous layer was then dried by lyophilization to afford the desired product (260 mg, crude). LCMS (ESI) m/z: [M+H] calcd for $C_6H_{11}NO_2$: 130.09; found 130.1.

Intermediate A-27. Synthesis of (S)-1-(2-((tert-butyldiphenylsilyl)oxy)ethyl)aziridine-2-carboxylic acid

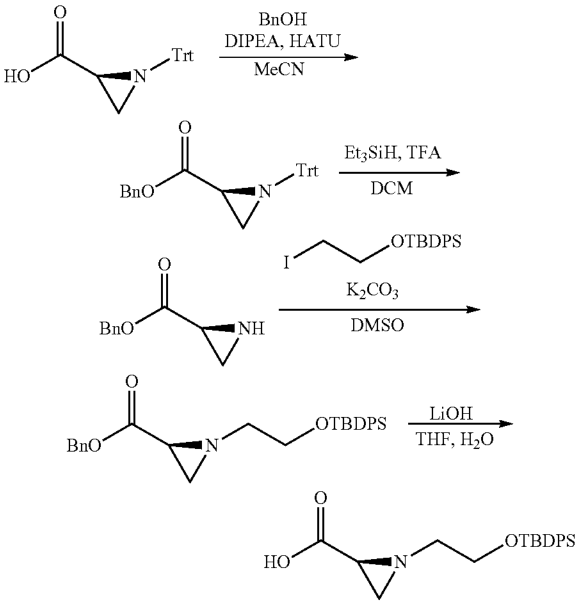

Step 1: Synthesis of benzyl (S)-1-tritylaziridine-2-carboxylate

To a solution of (S)-1-tritylaziridine-2-carboxylic acid (500.0 mg, 1.518 mmol), benzyl alcohol (246.2 mg, 2.277 mmol) and DIPEA (0.793 mL, 4.554 mmol) in MeCN (10.0 mL) was added HATU (1.73 mg, 4.554 mmol). The resulting solution was stirred for 3 h at room temperature and was then concentrated under reduced pressure. The crude residue was purified by prep-TLC (50% EtOAc/pet. ether) to afford the desired product (300 mg, 47% yield) as an off-white slid. LCMS (ESI) m/z: [M+Na] calcd for $C_{29}H_{25}NO_2$: 442.18; found 442.3.

Step 2: Synthesis of benzyl (S)-aziridine-2-carboxylate

To a solution of benzyl (S)-1-tritylaziridine-2-carboxylate (300.0 mg, 0.715 mmol) in DCM (5.0 mL) at 0° C. was added TFA (326.2 mg, 2.860 mmol) and $Et_3SiH$ (332.6 mg, 2.860 mmol). The resulting mixture was stirred at 0° C. for 3 h and was then concentrated under reduced pressure. The residue was purified by prep-TLC (10% MeOH/DCM) to afford the desired product (130 mg, 82% yield). LCMS (ESI) m/z: [M+H] calcd for $C_{10}H_{11}NO_2$: 178.09; found 178.2.

Step 3: Synthesis of benzyl (S)-1-(2-((tert-butyldiphenylsilyl)oxy)ethyl)aziridine-2-carboxylate To a solution of benzyl (S)-aziridine-2-carboxylate (400.0 mg, 2.257 mmol) and tert-butyl(2-iodoethoxy)diphenylsilane (1.85 g, 4.52 mmol) in DMSO (10.0 mL) was added $K_2CO_3$ (935.9 mg, 6.772 mmol) at room temperature. The mixture was stirred at 60° C. for 5 h. The mixture was diluted with $H_2O$ (30.0 mL) and was extracted with EtOAc (2×30 mL). The combined organic layers were washed with brine (2×50 mL), dried over $Na_2SO_4$, filtered, and concentrated under reduced pressure. The resulting residue was purified by prep-TLC (20% EtOAc/pet. ether) to afford the desired product (200 mg, 15% yield). LCMS (ESI) m/z: [M+H] calcd for $C_{28}H_{33}NO_3Si$: 460.23; found 460.0.

Step 4: Synthesis of lithium (S)-1-(2-((tert-butyldiphenylsilyl)oxy)ethyl)aziridine-2-carboxylate To a solution of benzyl (S)-1-(2-((tert-butyldiphenylsilyl)oxy)ethyl)aziridine-2-carboxylate (200.0 mg, 0.435 mmol) in MeOH (2.0 mL) was added LiOH·$H_2O$ (36.5 mg, 0.870 mmol). The resulting mixture was stirred overnight and was then concentrated under reduced pressure to afford the desired product (200 mg, crude). LCMS (ESI) m/z: [M+H] calcd for $C_{21}H_{27}NO_3Si$: 370.18; found 370.1.

Intermediate A-28. Synthesis of (R)-1-(2-((tert-butyldiphenylsilyl)oxy)ethyl)aziridine-2-carboxylic acid

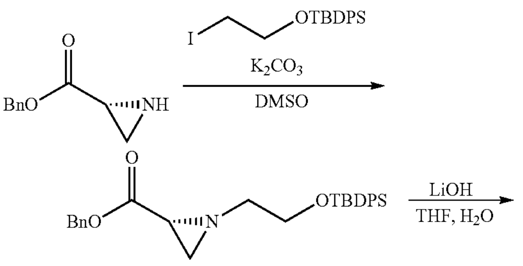

-continued

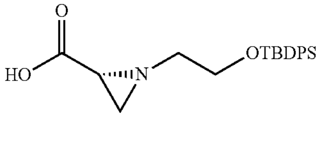

Step 1: Synthesis of methyl benzyl (R)-1-(2-((tert-butyldiphenylsilyl)oxy)ethyl)aziridine-2-carboxylate To a solution of benzyl (R)-aziridine-2-carboxylate (600.0 mg, 3.386 mmol) and $K_2CO_3$ (1.87 g, 13.544 mmol) in DMSO (8.0 mL) was added tert-butyl(2-iodoethoxy)diphenylsilane (1.39 g, 3.386 mmol) in portions at room temperature. The resulting mixture was stirred at 80° C. for 16 h. The reaction mixture was then cooled to room temperature and concentrated under reduced pressure. The residue was purified by reverse phase chromatography (60→90% MeCN/$H_2O$) to afford the desired product (150 mg, 10% yield) as a colorless solid. LCMS (ESI) m/z: [M+Na] calcd for $C_{28}H_{33}NO_3Si$: 482.21; found 482.3.

Step 2: Synthesis of (R)-1-(2-((tert-butyldiphenylsilyl)oxy)ethyl)aziridine-2-carboxylic acid To a solution of methyl benzyl (R)-1-(2-((tert-butyldiphenylsilyl)oxy)ethyl)aziridine-2-carboxylate (180.0 mg, 0.392 mmol) in $H_2O$ (2.0 mL) and THE (3.0 mL) at 0° C. was added a solution of $LiOH \cdot H_2O$ (32.87 mg, 0.392 mmol) in $H_2O$ (1.0 mL). The resulting mixture was diluted with $H_2O$ (6.0 mL) and the aqueous layer was washed with MTBE (3×4 mL). The aqueous layer was dried by lyophilization which afforded the desired product (140 mg, crude). LCMS (ESI) m/z: [M+H] calcd for $C_{21}H_{27}NO_3Si$: 370.18; found 370.0.

Intermediate A-29 and A-30. Synthesis of (2R,3S)-1-(4-methoxybenzyl)-3-(trifluoromethyl)aziridine-2-carboxylic acid and (2S,3R)-1-(4-methoxybenzyl)-3-(trifluoromethyl)aziridine-2-carboxylic acid

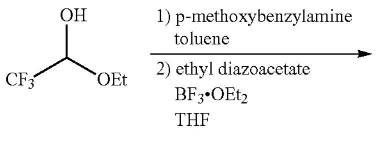

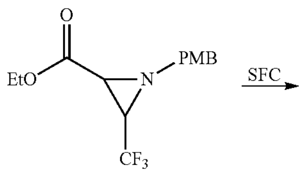

-continued

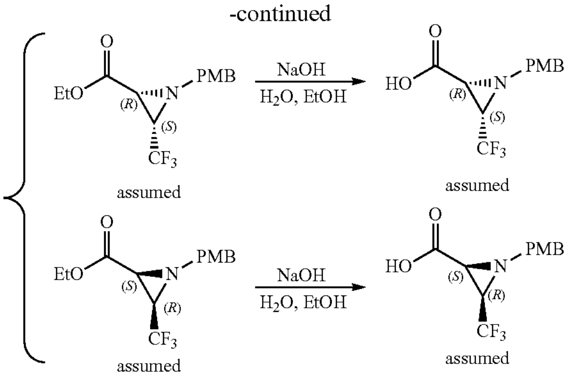

Step 1: Synthesis of ethyl 1-(4-methoxybenzyl)-3-(trifluoromethyl)aziridine-2-carboxylate A solution of 1-ethoxy-2,2,2-trifluoroethan-1-ol (2.17 mL, 18.37 mmol) and p-methoxybenzylamine (1.89 mL, 14.58 mmol) in toluene (46 mL) was refluxed for 16 h under Dean-Stark conditions. The reaction was concentrated under reduced pressure and the resulting residue was dissolved in THE (80 mL) and cooled to −78° C. $BF_3 \cdot Et_2O$ (0.360 mL, 2.92 mmol) was added to the solution, followed by dropwise addition of ethyl diazoacetate (1.83 mL, 17.50 mmol). The reaction was stirred for 4 h at room temperature. The reaction mixture was quenched by addition of aq. sat. $NaHCO_3$ (5 mL), and the resulting solution was extracted with DCM (3×50 mL). The combined organic layers were washed with $H_2O$ (20 mL) and brine (10 mL). The organic phase was dried over $Na_2SO_4$, filtered, and concentrated under reduced pressure. The residue was purified by silica gel column chromatography (1→10% EtOAc/pet. ether) afford the desired product (2 g, 45% yield).

Step 2: Synthesis of ethyl (2R,3S)-1-(4-methoxybenzyl)-3-(trifluoromethyl)aziridine-2-carboxylate and ethyl (2S,3R)-1-(4-methoxybenzyl)-3-(trifluoromethyl)aziridine-2-carboxylate Ethyl 1-(4-methoxybenzyl)-3-(trifluoromethyl)aziridine-2-carboxylate (1 g) was purified by SFC separation (column: REGIS(S,S)WHELK-O1 (250 mm*25 mm, 10 um); mobile phase: [Neu-IPA]; B %: 13%-13%, min) to afford ethyl (2R,3S)-1-(4-methoxybenzyl)-3-(trifluoromethyl)aziridine-2-carboxylate (530 mg) and ethyl (2S,3R)-1-(4-methoxybenzyl)-3-(trifluoromethyl)aziridine-2-carboxylate (470 mg).

Step 3: Synthesis of (2R,3S)-1-(4-methoxybenzyl)-3-(trifluoromethyl)aziridine-2-carboxylic acid To a solution of ethyl (2R,3S)-1-(4-methoxybenzyl)-3-(trifluoromethyl)aziridine-2-carboxylate (430 mg, 1.42 mmol) in EtOH (4 mL) and $H_2O$ (6 mL) was added NaOH (113.42 mg, 2.84 mmol). The mixture was stirred at room temperature for 5 h. The mixture was acidified with aq. HCl (2M) to pH=1-2. The reaction mixture was poured into $H_2O$ (3 mL) and the aqueous phase was extracted with EtOAc (3×3 mL). The combined organic phase was washed with brine (5 mL), dried over $Na_2SO_4$, filtered, and concentrated under reduced pressure to afford the desired product (350 mg, 89% yield). LCMS (ESI) m/z: [M+H] calcd for $C_{12}H_{11}FNO_3$: 274.08; found 274.1.

Step 4: Synthesis of (2S,3R)-1-(4-methoxybenzyl)-3-(trifluoromethyl)aziridine-2-carboxylic acid To a solution of ethyl (2S,3R)-1-(4-methoxybenzyl)-3-(trifluoromethyl)aziridine-2-carboxylate (370 mg, 1.22 mmol) in $H_2O$ (2 mL) and EtOH (4 mL) was added NaOH (97.59 mg, 2.44 mmol). The mixture was stirred at room temperature for 5 h. The mixture was brought to pH=1-2 with the addition of aq. HCl (2 M). The reaction mixture was poured into $H_2O$ (3 mL) and the aqueous phase was extracted with EtOAc (3x3 mL). The combined organic phase was washed with brine (5 mL), dried over $Na_2SO_4$, filtered, and concentrated under reduced pressure to afford the desired product (300 mg, 89% yield). LCMS (ESI) m/z: [M+H] calcd for $C_{12}H_{11}FNO_3$: 234.08; found 234.2.

Intermediate A-31 and A-32. Synthesis of (2S,3S)-1-benzyl-3-(trifluoromethyl)aziridine-2-carboxylic acid and (2R,3R)-1-benzyl-3-(trifluoromethyl)aziridine-2-carboxylic acid

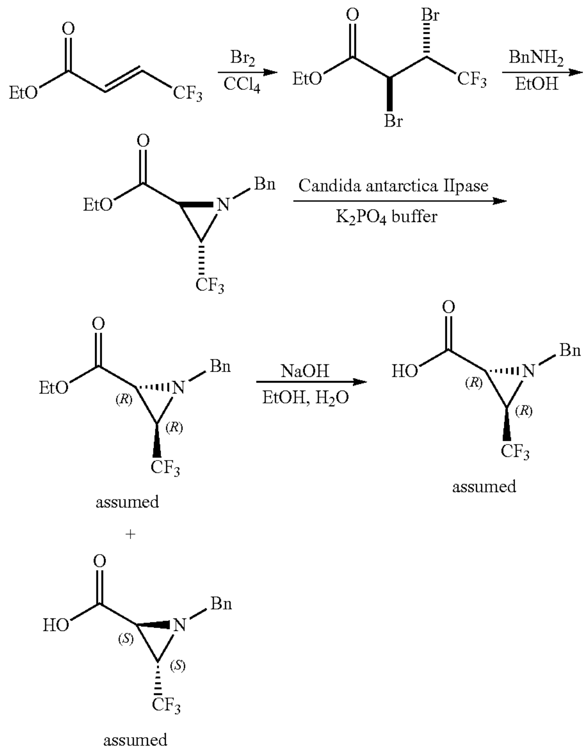

Step 1: Synthesis of ethyl (2S,3R)-2,3-dibromo-4,4,4-trifluorobutanoate

To a solution of ethyl (E)-4,4,4-trifluorobut-2-enoate (5 g, 29.74 mmol, 4.42 mL) in $CCl_4$ (90 mL) was added $Br_2$ (1.69 mL, 32.72 mmol) and the solution was stirred at 75° C. for 5 h. The reaction mixture was concentrated under reduced pressure to give the desired product (10.72 g, crude).

Step 2: Synthesis of ethyl (2S,3S)-1-benzyl-3-(trifluoromethyl)aziridine-2-carboxylate To a solution of ethyl (2S,3R)-2,3-dibromo-4,4,4-trifluorobutanoate (10.72 g, 32.69 mmol) in EtOH (30 mL) was slowly added the solution of $BnNH_2$ (12.47 mL, 114.42 mmol) in EtOH (120 mL) at −5° C. under $N_2$. The mixture was warmed to room temperature and stirred for 15 h. The mixture was concentrated under reduced pressure and EtOAc (120 mL) was added to the residue. The precipitate was filtered off and the filtrate was washed with aqueous HCl (3%, 180 mL) and $H_2O$ (100 mL), dried over $Na_2SO_4$, filtered and concentrated under reduced pressure. The residue was purified by silica gel chromatography (20% EtOAc/pet. ether) to afford the desired product (6.02 g, 67% yield).

Step 3: Synthesis of ethyl (2R,3R)-1-benzyl-3-(trifluoromethyl)aziridine-2-carboxylate and (2S,3S)-1-benzyl-3-(trifluoromethyl)aziridine-2-carboxylic acid Ethyl (2R,3R)-1-benzyl-3-(trifluoromethyl)aziridine-2-carboxylate and (2S,3S)-1-benzyl-3-(trifluoromethyl)aziridine-2-carboxylic acid were synthesized in Enzyme Screening Platform, based on the procedure in Tetrahedron Asymmetry 1999, 10, 2361.

Step 5: Synthesis of (2R,3R)-1-benzyl-3-(trifluoromethyl)aziridine-2-carboxylic acid To a solution of ethyl (2R,3R)-1-benzyl-3-(trifluoromethyl)aziridine-2-carboxylate (200 mg, 731.93 µmol) in EtOH (5 mL) was added NaOH (2 M, 548.95 µL) and the mixture was stirred at room temperature for 1 h. The reaction mixture was concentrated under reduced pressure to remove EtOH. Then to the mixture was added HCl (1 M) to adjust pH to 1, and extracted with EtOAc (3x5 mL). The combined organic layers were washed with brine (2x10 mL), dried over $Na_2SO_4$, filtered and concentrated under reduced pressure to afford the desired product (138 mg, 77% yield). LCMS (ESI) m/z: [M+H] calcd for $C_{11}H_{10}F_3NO_2$: 246.07; found 245.9.

Intermediate A-33. Synthesis of 1-(oxetan-3-yl)aziridine-2-carboxylic acid

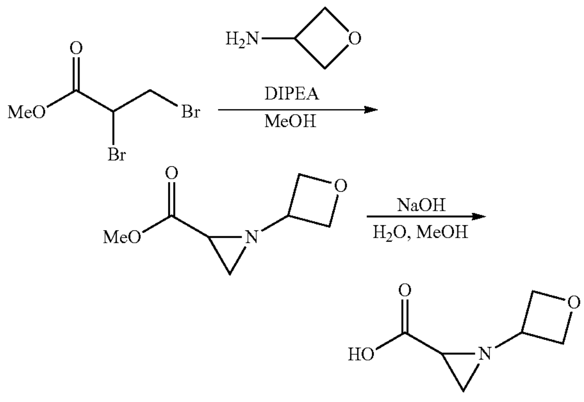

Step 1: Synthesis of methyl 1-(oxetan-3-yl)aziridine-2-carboxylate

To a solution of methyl 2,3-dibromopropanoate (515.46 µL, 4.07 mmol) in MeOH (15 mL) was added DIPEA (3.54 mL, 20.33 mmol). After addition, the mixture was stirred for 15 min, and then oxetan-3-amine (297.25 mg, 4.07 mmol)

was added dropwise. The resulting mixture was stirred at room temperature for 12 h. The reaction mixture was poured into $H_2O$ (20 mL), the aqueous phase was extracted with DCM (2×25 mL). The combined organic phase was washed with brine (20 mL), dried with $Na_2SO_4$, filtered and concentrated under reduced pressure. The residue was purified by silica gel chromatography (10%→30% EtOAc/pet. ether) to afford the desired product (380 mg, 60% yield).

Step 2: Synthesis of 1-(oxetan-3-yl)aziridine-2-carboxylic acid

To a solution of methyl 1-(oxetan-3-yl)aziridine-2-carboxylate (280 mg, 1.78 mmol) in EtOH (3 mL) was added NaOH (2 M, 1.34 mL) at room temperature and the resulting mixture was stirred for 3 h. The reaction mixture was adjusted to pH 8 by the addition of HCl (1 M), and lyophilized to afford the desired product (200 mg, 78% yield).

Intermediate A-34. Synthesis of (2S,3S)-1-((S)-tert-butylsulfinyl)-3-cyclobutylaziridine-2-carboxylic acid

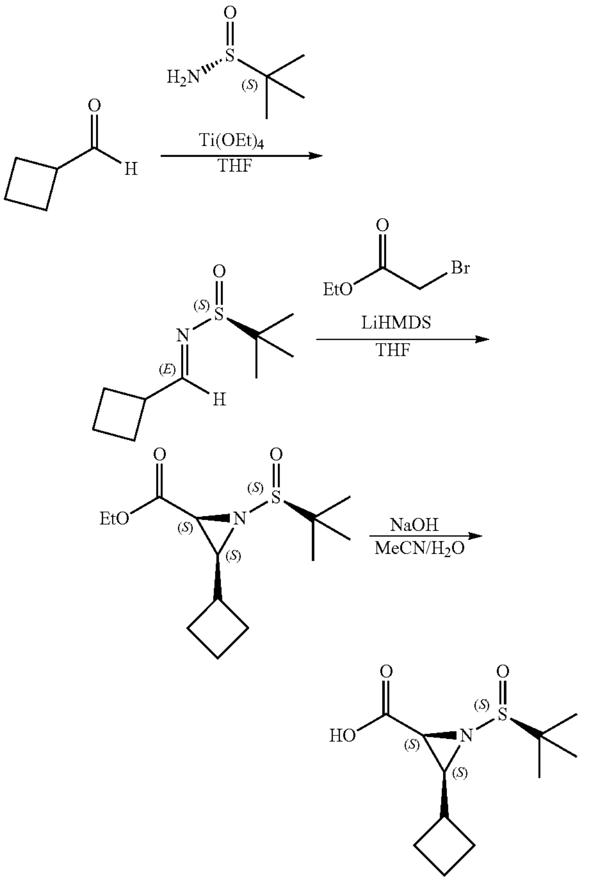

Step 1: Synthesis of (S,E)-N-(cyclobutylmethylene)-2-methylpropane-2-sulfinamide To a solution of cyclobutanecarbaldehyde (0.5 g, 5.94 mmol) in THE (10 mL) was added (S)-2-methylpropane-2-sulfinamide (792.48 mg, 6.54 mmol) and $Ti(OEt)_4$ (2.47 mL, 11.89 mmol). The mixture was stirred at 75° C. for 3 h. The reaction mixture was cooled to room temperature and quenched by addition brine (30 mL), and filtered to remove solids. The mixture was extracted with EtOAc (3×30 mL). The combined organic layers were washed with brine (2×10 mL), dried over $Na_2SO_4$, filtered and concentrated under reduced pressure to give a residue. The residue was purified by silica gel chromatography (2%→10% EtOAc/pet. ether) to afford the desired product (907.3 mg, 40% yield). LCMS (ESI) m/z: [M+H] calcd for $C_9H_{17}NOS$: 188.1; found 188.3.

Step 2: Synthesis of ethyl (2S,3S)-1-((S)-tert-butylsulfinyl)-3-cyclobutylaziridine-2-carboxylate To a solution of ethyl 2-bromoacetate (1.60 g, 9.61 mmol, 1.06 mL) in THE (9 mL) was added LiHMDS (1 M, 9.61 mL) at −78° C., after 2 min, (S,E)-N-(cyclobutylmethylene)-2-methylpropane-2-sulfinamide (0.9 g, 4.81 mmol) was added. The mixture was stirred at −78° C. for 2 h. The reaction mixture was quenched by addition $H_2O$ (25 mL) at −78° C. and warmed to room temperature, then the mixture extracted with EtOAc (3×20 mL). The combined organic layers were washed with brine (2×5 mL), dried over $Na_2SO_4$, filtered and concentrated under reduced pressure to give a residue, which was purified by silica gel chromatography (10%→20% EtOAc/pet. ether) to afford the desired product (426 mg, crude). LCMS (ESI) m/z: [M+H] calcd for $C_{13}H_{23}NO_3S$: 274.14; found 274.3.

Step 3: Synthesis of (2S,3S)-1-((S)-tert-butylsulfinyl)-3-cyclobutylaziridine-2-carboxylic acid To a solution of (2S,3S)-1-((S)-tert-butylsulfinyl)-3-cyclobutylaziridine-2-carboxylate (100 mg, 365.78 μmol) in MeCN (0.5 mL) and $H_2O$ (0.5 mL) was added NaOH (21.95 mg, 548.67 μmol) at 0° C., the mixture was warmed to room temperature and stirred for 2 h. The reaction mixture was adjusted to pH 5 by addition aq. 10% citric acid (~10 mL) and was then extracted with EtOAc (3×20 mL). The combined organic layers were washed with brine (2×5 mL), dried over $Na_2SO_4$, filtered and concentrated under reduced pressure to afford the desired product (92.6 mg, crude). LCMS (ESI) m/z: [M+H] calcd for $C_{11}H_{19}NO_3S$: 246.11; found 246.3.

Intermediate A-35. Synthesis of (2R,3R)-1-((R)-tert-butylsulfinyl)-3-cyclobutylaziridine-2-carboxylic acid

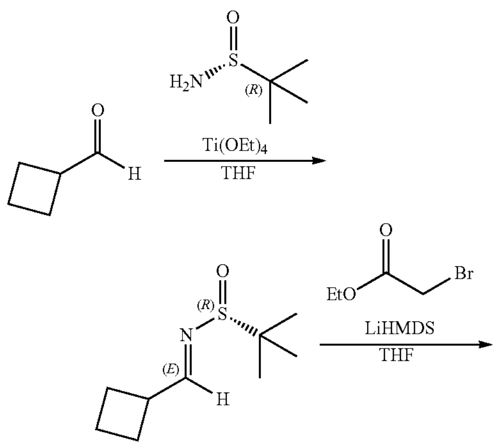

-continued

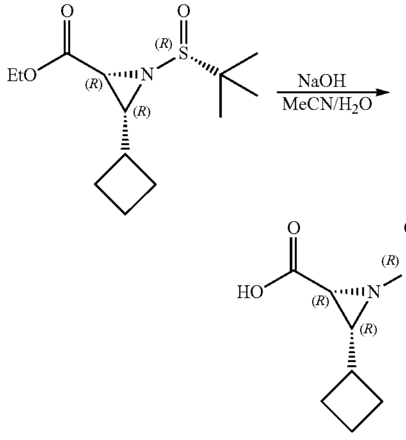

Step 1: Synthesis of (R,E)-N-(cyclobutylmethylene)-2-methylpropane-2-sulfinamide To a solution of cyclobutanecarbaldehyde (0.25 g, 2.97 mmol) in THE (5 mL) was added (R)-2-methylpropane-2-sulfinamide (396.24 mg, 3.27 mmol) and $Ti(OEt)_4$ (1.36 g, 5.94 mmol, 1.23 mL). The mixture was stirred at 75° C. for 3 h in two batches. The two batches were combined and the reaction mixture was quenched by the addition of brine (15 mL). The solution was extracted with EtOAc (3×20 mL) and the combined organic layers were washed with brine (2×5 mL), dried over $Na_2SO_4$, filtered and concentrated under reduced pressure to give a residue, which was purified by silica gel chromatography (10%→20% EtOAc/pet. ether) to afford the desired product (786.7 mg, 71% yield). LCMS (ESI) m/z: [M+H] calcd for $C_9H_{17}NOS$: 188.1; found 188.3.

Step 2: Synthesis of ethyl (2R,3R)-1-((R)-tert-butylsulfinyl)-3-cyclobutylaziridine-2-carboxylate To a solution of ethyl 2-bromoacetate (236.19 μL, 2.14 mmol) in THE (2 mL) was added LiHMDS (1 M, 2.14 mL) at −78° C., after 30 min, (R,E)-N-(cyclobutylmethylene)-2-methylpropane-2-sulfinamide (0.2 g, 1.07 mmol) was added. The mixture was warmed to −40° C. and stirred for 4 h. The reaction mixture was quenched by addition $H_2O$ (18 mL) at −40° C. and warmed to room temperature The mixture was extracted with EtOAc (3×15 mL) and the combined organic layers were washed with brine (2×5 mL), dried over $Na_2SO_4$, filtered and concentrated under reduced pressure to give a residue, which was purified by prep-TLC (20% EtOAc/pet. ether) to afford the desired product (0.1 g, crude). LCMS (ESI) m/z: [M+H] calcd for $C_{13}H_{23}NO_3S$: 274.14; found 274.3.

Step 3: Synthesis of (2R,3R)-1-((R)-tert-butylsulfinyl)-3-cyclobutylaziridine-2-carboxylic acid In two batches, to a solution ethyl (2R,3R)-1-((R)-tert-butylsulfinyl)-3-cyclobutylaziridine-2-carboxylate (25 mg, 91.44 μmol) in MeCN (0.25 mL) and $H_2O$ (0.25 mL) was added NaOH (5.49 mg, 137.17 μmol) at 0° C., the mixture was warmed to room temperature and stirred for 5 h. The reaction mixtures were combined, and adjust to pH to 5 with aq. 10% citric acid (10 mL), then extracted with EtOAc (3×20 mL). The combined organic layers were washed with brine (2×5 mL), dried over $Na_2SO_4$, filtered and concentrated under reduced pressure to afford the desired product (53 mg, crude). LCMS (ESI) m/z: [M+H] calcd for $C_1H_{19}NO_3S$: 246.11; found 246.2.

Intermediate A-36. Synthesis of lithium (R)-1-(3-methoxypropyl)aziridine-2-carboxylate

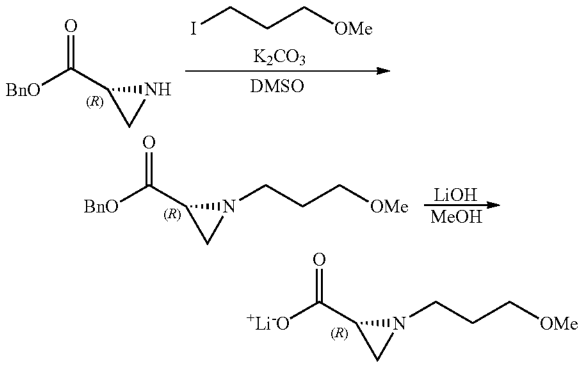

Step 1: Synthesis of benzyl (R)-1-(3-methoxypropyl)aziridine-2-carboxylate

To a mixture of benzyl (R)-aziridine-2-carboxylate (350.0 mg, 1.975 mmol) and $K_2CO_3$ (545.95 mg, 3.950 mmol) in DMSO (4 mL) at 60° C. was added 1-iodo-3-methoxypropane (790.13 mg, 3.950 mmol). The resulting mixture was stirred for 2 h and was then cooled to room temperature, diluted with brine (50 mL), and extracted with EtOAc (3×20 mL). The combined organic layers were concentrated under reduced pressure. The crude product was purified by reverse phase chromatography (30%→38% MeCN/$H_2O$) to afford the desired product (170 mg, 31% yield). LCMS (ESI) m/z: [M+H] calcd for $C_{14}H_{19}NO_3$: 250.14; found 250.2.

Step 2: Synthesis of lithium (R)-1-(3-methoxypropyl)aziridine-2-carboxylate

A mixture of benzyl (R)-1-(3-methoxypropyl)aziridine-2-carboxylate (170 mg, 0.682 mmol) and LiOH (57.23 mg, 1.364 mmol) in MeOH (2 mL) was stirred at 0° C. for 1 h. The mixture was concentrated under reduced pressure to afford the desired product (200 mg, crude). LCMS (ESI) m/z: [M+H] calcd for $C_7H_{13}NO_3$: 160.09; found 160.3.

Intermediate A-37. Synthesis of lithium (S)-1-(3-methoxypropyl)aziridine-2-carboxylate

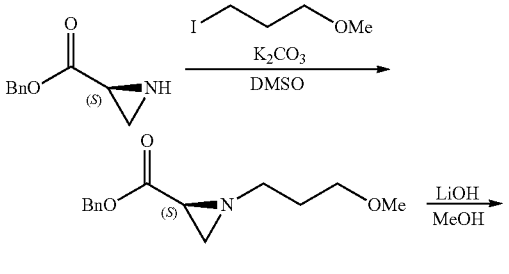

-continued

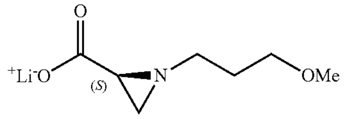

Step 1: Synthesis of benzyl (S)-1-(3-methoxypropyl)aziridine-2-carboxylate

To a mixture of benzyl (S)-aziridine-2-carboxylate (250 mg, 1.411 mmol) and $K_2CO_3$ (389.96 mg, 2.822 mmol) in DMSO (4 mL) at 60° C. was added 1-iodo-3-methoxypropane (564.38 mg, 2.822 mmol). The resulting mixture was stirred for 2 h and was then cooled to room temperature, diluted with brine (50 mL), and extracted with EtOAc (3×20 mL). The combined organic layers were concentrated under reduced pressure. The crude product was purified by reverse phase chromatography (25%→40% $H_2O$/MeCN) to afford the desired product (234 mg, 63% yield). LCMS (ESI) m/z: [M+H] calcd for $C_{14}H_{19}NO_3$: 250.14; found 250.2.

Step 2: Synthesis of lithium (S)-1-(3-methoxypropyl)aziridine-2-carboxylate

A mixture of benzyl (S)-1-(3-methoxypropyl) aziridine-2-carboxylate (230 mg, 0.923 mmol) and $LiOH{\cdot}H_2O$ (77.43 mg, 1.845 mmol) in MeOH (3 mL) was stirred for 1 h at 0° C. The resulting mixture was concentrated under reduced pressure to afford the desired product (320 mg, crude). LCMS (ESI) m/z: [M+H] calcd for $C_7H_{13}NO_3$: 160.09; found 160.1.

Intermediate A-38. Synthesis of (S)-1-((3-methyloxetan-3-yl)methyl)aziridine-2-carboxylic acid

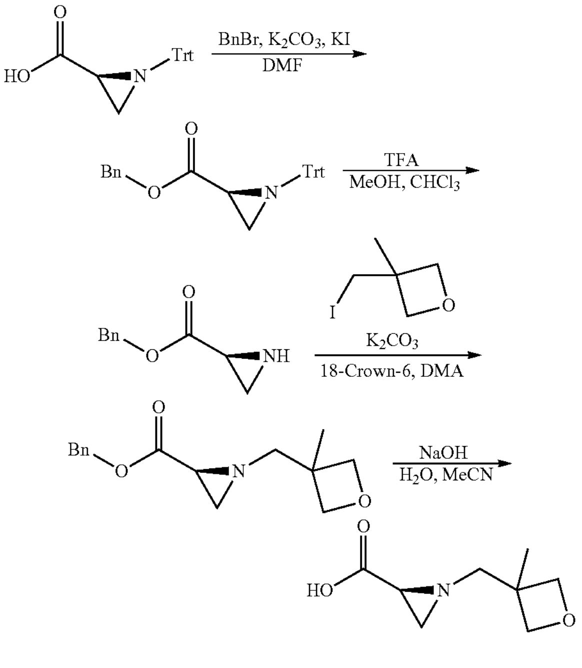

Step 1: Synthesis of benzyl (S)-1-tritylaziridine-2-carboxylate

To a mixture of (S)-1-tritylaziridine-2-carboxylic acid (3.0 g, 9.11 mmol) and benzyl bromide (2.16 mL, 18.22 mmol) in DMF (30 mL) was added $K_2CO_3$ (2.25 g, 18.22 mmol) and KI (76 mg, 455 μmol). The reaction mixture was heated to 50° C. and stirred for 30 min then was cooled to room temperature and diluted with $H_2O$ (30 mL) and EtOAc (30 mL). The aqueous layer was extracted with EtOAc (3×40 mL), and the combined organic layers were washed with brine (5×70 mL), dried over $Na_2SO_4$, filtered, and concentrated under reduced pressure to afford the desired product (4.7 g, crude).

Step 2: Synthesis of benzyl (S)-aziridine-2-carboxylate

To a mixture of benzyl (S)-1-tritylaziridine-2-carboxylate (3.4 g, 8.10 mmol) in MeOH (17.5 mL) and $CHCl_3$ (17.5 mL) at 0° C. was added TFA (9.0 mL, 122 mmol). The reaction mixture was stirred for 30 min then was poured into sat. aq. $NaHCO_3$ (50 mL), extracted into DCM (4×35 mL), dried over $Na_2SO_4$, filtered, and concentrated under reduced pressure. Purification by silica gel column chromatography (6→100% EtOAc/pet. ether) afforded the desired product (445 mg, 31% yield).

Step 3: Synthesis of benzyl (S)-1-((3-methyloxetan-3-yl)methyl)aziridine-2-carboxylate To a mixture of benzyl (S)-aziridine-2-carboxylate (440 mg, 2.48 mmol) and 3-(iodomethyl)-3-methyloxetane (2.11 g, 9.93 mmol) in DMA (5 mL) was added $K_2CO_3$ (1.72 g, 12.42 mmol) and 18-crown-6 (32.8 mg, 124 μmol). The reaction mixture was heated to 80° C. and stirred for 12 h, and was then was diluted with $H_2O$ (25 mL) and EtOAc (25 mL). The aqueous layer was extracted with EtOAc (3×20 mL), and the combined organic layers were washed with brine (5×45 mL), dried over $Na_2SO_4$, filtered, and concentrated under reduced pressure. Purification by prep-TLC (50% EtOAc/pet. ether) afforded the desired product (367 mg, 57% yield). LCMS (ESI) m/z: [M+H] calcd for $C_{15}H_{19}NO_3$: 262.14; found 262.0.

Step 4: Synthesis of (S)-1-((3-methyloxetan-3-yl)methyl)aziridine-2-carboxylic acid To a mixture of benzyl (S)-1-((3-methyloxetan-3-yl)methyl)aziridine-2-carboxylate (100 mg, 383 μmol) in MeCN (500 μL) and $H_2O$ (500 μL) at 0° C. was added NaOH (23 mg, 574 μmol). The reaction mixture was stirred at 0° C. for 1 h then was concentrated under reduced pressure to afford the desired product (100 mg, crude). LCMS (ESI) m/z: [M+H] calcd for $C_8H_{13}NO_3$: 172.10; found 172.0.

Intermediate A-39. Synthesis of (2R,3R)-1-(tert-butylsulfinyl)-3-ethylaziridine-2-carboxylic acid

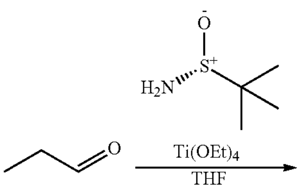

-continued

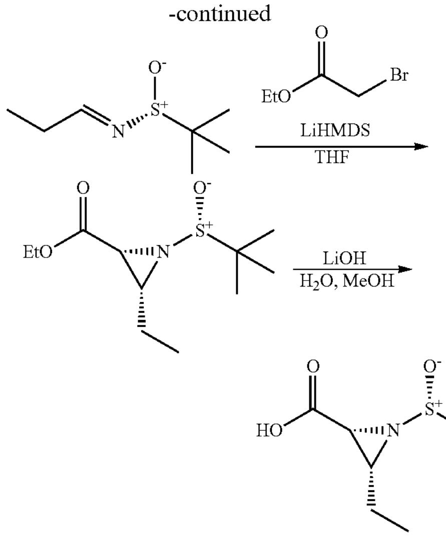

Step 1: Synthesis of (R,E)-2-methyl-N-propylidenepropane-2-sulfinamide

To a solution of propionaldehyde (6.27 mL, 86.1 mmol) in THE (200 mL) was added (R)-2-methylpropane-2-sulfinamide (10.4 g, 86.1 mmol) and titanium ethoxide (51 mL, 170 mmol). The reaction mixture was heated to 70° C. for 3 h then cooled to room temperature and quenched with $H_2O$ (50 mL), filtered, and extracted into EtOAc (3x30 mL). The combined organic layers were washed with brine (30 mL), dried over $Na_2SO_4$, filtered, and concentrated under reduced pressure. Purification by silica gel column chromatography (9→17% EtOAc/pet. ether) afforded the desired product (4.0 g, 29% yield).

Step 2: Synthesis of ethyl (2R,3R)-1-(tert-butylsulfinyl)-3-ethylaziridine-2-carboxylate To a solution of ethyl 2-bromoacetate (2.74 mL, 24.8 mmol) in THE (40 mL) at −78° C. was added LiHMDS (24.80 mL, 1 M in THF). After 30 min (R,E)-2-methyl-N-propylidenepropane-2-sulfinamide (2.0 g, 12.4 mmol) in THE (20 mL) was added to the reaction mixture. The mixture was stirred for 1 h then warmed to room temperature, quenched with $H_2O$ (50 mL), and extracted into EtOAc (3x50 mL). The combined organic layers were washed with brine (2x50 mL), dried over $Na_2SO_4$, filtered, and concentrated under reduced pressure. Purification by silica gel column chromatography (17→25% EtOAc/pet. ether) afforded product (1.34 g, 44% yield). LCMS (ESI) m/z: [M+H] calcd for $C_{11}H_{21}NO_3S$: 248.13; found 248.1.

Step 3: Synthesis of (2R,3R)-1-(tert-butylsulfinyl)-3-ethylaziridine-2-carboxylic acid To a solution of ethyl (2R,3R)-1-(tert-butylsulfinyl)-3-ethylaziridine-2-carboxylate (600 mg, 2.4 mmol) in MeOH (3 mL) and $H_2O$ (3 mL) was added LiOH (70 mg, 2.9 mmol). The resulting mixture was stirred for 16 h then diluted with $H_2O$ (20 mL) and washed with DCM (3x10 mL). Lyophilization of the aqueous layer afforded product (600 mg, crude). LCMS (ESI) m/z: [M+H] calcd for $C_9H_{17}NO_3S$: 220.10; found 220.3.

Intermediate A-40. Synthesis of (2S,3S)-1-(tert-butylsulfinyl)-3-ethylaziridine-2-carboxylic acid

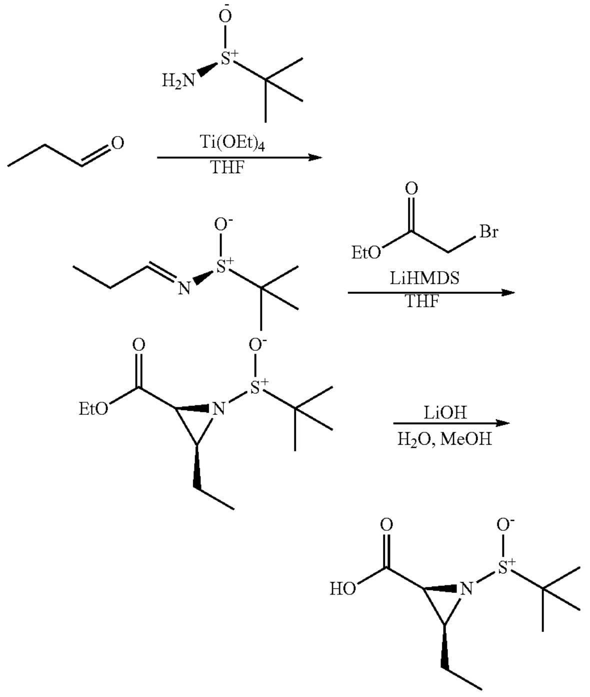

Step 1: Synthesis of (S,E)-2-methyl-N-propylidenepropane-2-sulfinamide

To a solution of propionaldehyde (6.27 mL, 86.1 mmol) in THE (50 mL) was added (S)-2-methylpropane-2-sulfinamide (10.4 g, 86.1 mmol) and titanium ethoxide (51 mL, 170 mmol). The reaction mixture was heated to 70° C. for 3 h then cooled to room temperature and quenched with $H_2O$ (30 mL), filtered, and extracted into DCM (3x100 mL). The combined organic layers were washed with brine (10 mL), dried over $Na_2SO_4$, filtered, and concentrated under reduced pressure. Purification by silica gel column chromatography (25% EtOAc/pet. ether) afforded product (4.6 g, 33% yield).

Step 2: Synthesis of ethyl (2S,3S)-1-(tert-butylsulfinyl)-3-ethylaziridine-2-carboxylate To a solution of ethyl 2-bromoacetate (2.74 mL, 24.8 mmol) in THE (40 mL) at −78° C. was added LiHMDS (24.80 mL, 1 M in THF). After 30 min (S,E)-2-methyl-N-propylidenepropane-2-sulfinamide (2.0 g, 12.4 mmol) in THE (20 mL) was added to the reaction mixture. The mixture was stirred for 1 h then warmed to room temperature, quenched with $H_2O$ (20 mL), and extracted into EtOAc (3x20 mL). The combined organic layers were washed with brine (2x25 mL), dried over $Na_2SO_4$, filtered, and concentrated under reduced pressure. Purification by reverse phase chromatography (31→51% MeCN/$H_2O$, 10 mM $NH_4HCO_3$) afforded product (600 mg, 20% yield). LCMS (ESI) m/z: [M+H] calcd for $C_{11}H_{21}NO_3S$: 248.13; found 248.1.

Step 3: Synthesis of (2S,3S)-1-(tert-butylsulfinyl)-3-ethylaziridine-2-carboxylic acid To a solution of ethyl (2S,3S)-1-(tert-butylsulfinyl)-3-ethylaziridine-2-carboxylate (600 mg, 2.4 mmol) in MeOH (300 μL) and $H_2O$ (300 μL) was added LiOH (87 mg, 3.6 mmol). The resulting mixture was stirred for 12 h then diluted with $H_2O$ (20 mL) and washed with DCM (3×10 mL). Lyophilization of the aqueous layer afforded product (600 mg, crude). LCMS (ESI) m/z: [M+H] calcd for $C_9H_{17}NO_3S$: 220.10; found 220.2.

Intermediate A-41. Synthesis of (2R,3R)-3-isopropyl-1-tritylaziridine-2-carboxylic acid

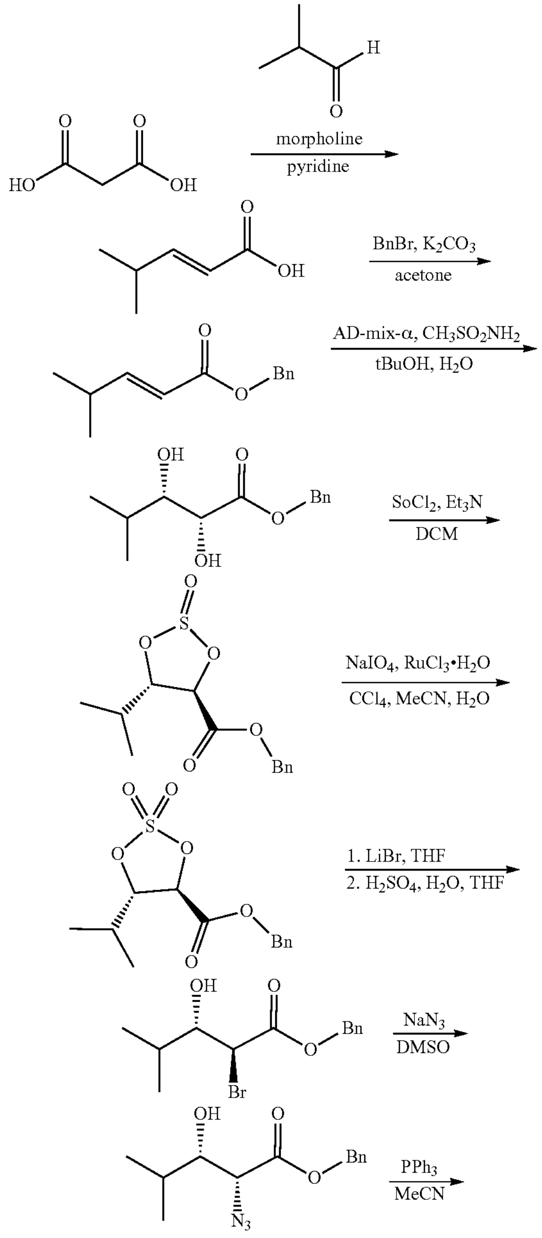

-continued

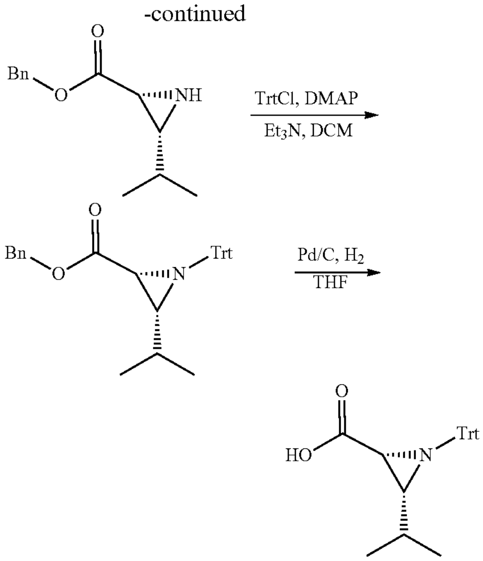

Step 1: Synthesis of (E)-4-methylpent-2-enoic acid

Two batches of a solution of malonic acid (25.0 mL, 240 mmol), isobutyraldehyde (34.7 mL, 380 mmol) and morpholine (380 μL, 4.32 mmol) in pyridine (75 mL) were stirred for 24 h then were heated to 115° C. and stirred for 12 h. The combined reaction mixtures were poured into $H_2SO_4$ (1M, 800 mL) and extracted into EtOAc (3×300 mL). The combined organic layers were washed with brine (300 mL), dried over $Na_2SO_4$, filtered, and concentrated under reduced pressure. The residue was dissolved in NaOH (1 M, 500 mL), washed with EtOAc (2×200 mL), acidified to pH=4-2 with HCl (4M), and extracted into EtOAc (3×300 mL). The combined organic layers were washed with brine (300 mL), dried over $Na_2SO_4$, filtered, and concentrated under reduced pressure which afforded product (54 g, 98% yield).

Step 2: Synthesis of benzyl (E)-4-methylpent-2-enoate

To two batches of a solution of (E)-4-methylpent-2-enoic acid (6.25 mL, 52.6 mmol) in acetone (90 mL) was added $K_2CO_3$ (13.8 g, 100 mmol) and the mixtures were stirred for 30 min. Then a solution of benzyl bromide (6.31 mL, 53.1 mmol) in acetone (10 mL) was added and the mixtures were heated to 75° C. for 5 h. The reaction mixtures were cooled to room temperature and concentrated under reduced pressure. The residue was dissolved in EtOAc (200 mL) and $H_2O$ (200 mL) then extracted into EtOAc (2×200 mL). The combined organic layers were washed with brine (300 mL), dried over $Na_2SO_4$, filtered, and concentrated under reduced pressure. Purification by silica gel chromatography (0→10% EtOAc/pet. ether) afforded product (9.0 g, 42% yield).

Step 3: Synthesis of benzyl (2R,3S)-2,3-dihydroxy-4-methylpentanoate

To a solution of AD-mix-α (61.7 g) and methanesulfonamide (4.19 g, 44.1 mmol) in tert-BuOH (225 mL) and $H_2O$ (225 mL) was added benzyl (E)-4-methylpent-2-enoate (9 g, 44.1 mmol). The mixture was stirred at room temperature for 12 h then $Na_2SO_3$ (67.5 g) was added and stirred for 30 min. The reaction mixture was diluted with EtOAc (300 mL) and $H_2O$ (300 mL) and extracted into EtOAc (3×300 mL), washed with brine (300 mL), dried over $Na_2SO_4$, filtered, and concentrated under reduced pressure. Purification by silica gel chromatography (0→25% EtOAc/pet. ether) afforded product (8.3 g, 79% yield). LCMS (ESI) m/z: [M+Na] calcd for $C_{13}H_{18}O_4$: 261.11; found 261.0.

Step 4: Synthesis of benzyl (4R,5S)-5-isopropyl-1,3,2-dioxathiolane-4-carboxylate 2-oxide To a solution of benzyl (2R,3S)-2,3-dihydroxy-4-methylpentanoate (10 g, 42.0 mmol) in DCM (100 mL) at 0° C. was added $Et_3N$ (17.5 mL, 126 mmol) and $SOCl_2$ (4.26 mL, 58.8 mmol). The reaction mixture was stirred 30 min then was diluted with DCM (30 mL) and $H_2O$ (100 mL), extracted into DCM (3×50 mL), washed with brine (100 mL), dried over $Na_2SO_4$, filtered, and concentrated under reduced pressure which afforded product (11.0 g, 92% yield).

Step 5: Synthesis of benzyl (4R,5S)-5-isopropyl-1,3,2-dioxathiolane-4-carboxylate 2,2-dioxide To a solution of benzyl (4R,5S)-5-isopropyl-1,3,2-dioxathiolane-4-carboxylate 2-oxide (11 g, 38.7 mmol) in $H_2O$ (250 mL), MeCN (125 mL), and $CCl_4$ (125 mL) was added $NaIO_4$ (3.22 mL, 58.0 mmol) and $RuCl_3 \cdot H_2O$ (872 mg, 3.87 mmol). The mixture was stirred at room temperature for 1 h then was diluted with EtOAc (200 mL) and $H_2O$ (50 mL), filtered, and the filtrate was extracted into EtOAc (3×200 mL). The combined organic layers were washed sequentially with brine (200 mL) and sat. aq. $Na_2CO_3$ (300 mL), dried over $Na_2SO_4$, filtered, and concentrated under reduced pressure. Purification by silica gel chromatography (0→17% EtOAc/pet. ether) afforded product (11 g, 95% yield).

Step 6: Synthesis of benzyl (2S,3S)-2-bromo-3-hydroxy-4-methylpentanoate

To a solution of benzyl (4R,5S)-5-isopropyl-1,3,2-dioxathiolane-4-carboxylate 2,2-dioxide (11 g, 36.6 mmol) in THE (520 mL) was added LiBr (3.49 mL, 139 mmol). The reaction mixture was stirred at room temperature for 5 h and then concentrated under reduced pressure. The residue was diluted in THE (130 mL) and $H_2O$ (65 mL), cooled to 0° C., then $H_2SO_4$ solution (20% aq., 1.3 L) was added and the mixture was warmed to room temperature and stirred for 24 h. The mixture was diluted with EtOAc (1.0 L), extracted into EtOAc (2×300 mL), washed sequentially with $Na_2CO_3$ (sat. aq., 300 mL) and brine (300 mL), then was concentrated under reduced pressure. Purification by silica gel chromatography (0→17% EtOAc/pet. ether) afforded product (10 g, 81% yield).

Step 7: Synthesis of benzyl (2R,3S)-2-azido-3-hydroxy-4-methylpentanoate

To a solution of benzyl (2S,3S)-2-bromo-3-hydroxy-4-methylpentanoate (10 g, 33.2 mmol) in DMSO (100 mL) was added $NaN_3$ (4.32 g, 66.4 mmol). The reaction mixture was stirred at room temperature for 12 h then was diluted with EtOAc (300 mL) and $H_2O$ (200 mL). The aqueous phase was extracted into EtOAc (2×200 mL), washed with brine (200 mL), dried over $Na_2SO_4$, filtered, and concentrated under reduced pressure. Purification by silica gel chromatography (0→17% EtOAc/pet. ether) afforded product (7.5 g, 79% yield).

Step 8: Synthesis of benzyl (2R,3R)-3-isopropylaziridine-2-carboxylate

To a solution of benzyl (2R,3S)-2-azido-3-hydroxy-4-methylpentanoate (7.5 g, 28.5 mmol) in MeCN (150 mL) was added $PPh_3$ (7.70 g, 29.3 mmol). The reaction mixture was stirred at room temperature for 1 h and then heated to 70° C. and stirred for 4 h. The reaction mixture was concentrated under reduced pressure and purification by silica gel chromatography (0→17% EtOAc/pet. ether) afforded product (4.5 g, 66% yield).

LCMS (ESI) m/z: [M+H] calcd for $C_{13}H_{17}NO_2$: 220.13; found 220.0.

Step 9: Synthesis of benzyl (2R,3R)-3-isopropyl-1-tritylaziridine-2-carboxylate

To a solution of benzyl (2R,3R)-3-isopropylaziridine-2-carboxylate (2 g, 9.12 mmol) in DCM (30 mL) at 0° C. was added $Et_3N$ (3.81 mL, 27.4 mmol) and trityl chloride (3.05 g, 10.9 mmol) followed by DMAP (111 mg, 912 μmol). The reaction mixture was stirred at 0° C. for 1 h and then was diluted with DCM (50 mL) and $H_2O$ (50 mL) then extracted into DCM (2×30 mL). The combined organic layers were washed with brine (50 mL), dried over $Na_2SO_4$, filtered, and concentrated under reduced pressure. Purification by silica gel chromatography (0→25% DCM/pet. ether) afforded product (3.1 g, 72% yield).

Step 10: Synthesis of (2R,3R)-3-isopropyl-1-tritylaziridine-2-carboxylic acid

Two solutions of benzyl (2R,3R)-3-isopropyl-1-tritylaziridine-2-carboxylate (200 mg, 430 μmol) and Pd/C (100 mg) in THE (4 mL) were stirred for 1 h at room temperature under $H_2$ atmosphere. The reaction mixtures were combined, filtered, and concentrated under reduced pressure. Purification by silica gel chromatography (0→50% EtOAc/pet. ether) afforded product (160 mg, 51% yield).

Intermediate A-42. Synthesis of (2S,3S)-1-benzyl-3-isopropylaziridine-2-carboxylic acid

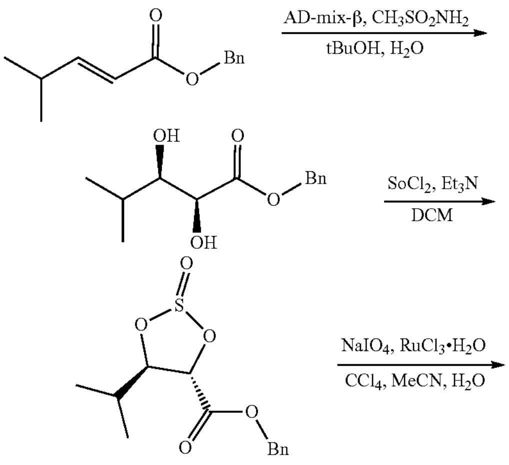

-continued

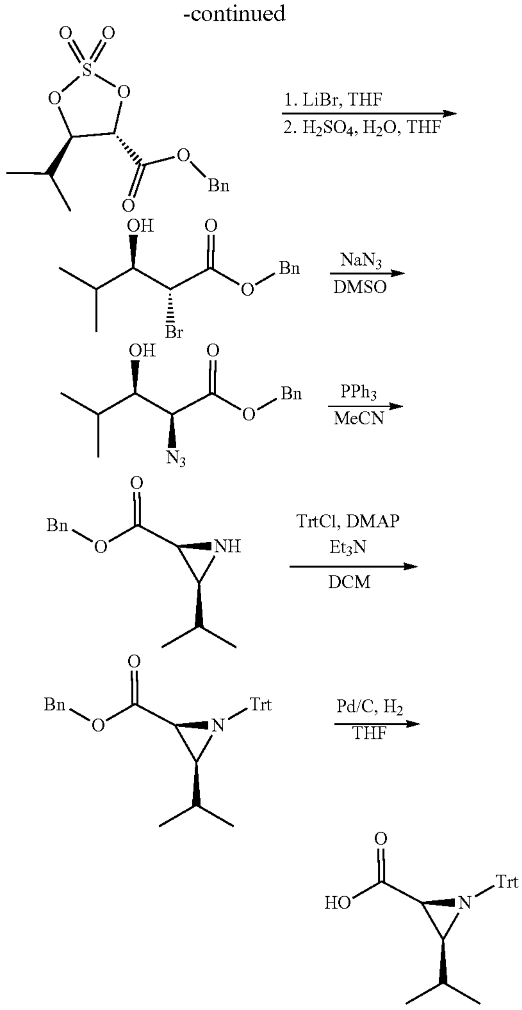

Step 1: Synthesis of benzyl (2S,3R)-2,3-dihydroxy-4-methylpentanoate

To a solution of AD-mix-β (61.7 g) and methanesulfonamide (4.19 g, 44.1 mmol) in tert-BuOH (225 mL) and $H_2O$ (225 mL) was added benzyl (E)-4-methylpent-2-enoate (9 g, 44.1 mmol). The mixture was stirred at room temperature for 12 h then $Na_2SO_3$ (67.5 g) was added and stirred for 30 min. The reaction mixture was diluted with EtOAc (300 mL) and $H_2O$ (300 mL) and extracted into EtOAc (3×300 mL), washed with brine (300 mL), dried over $Na_2SO_4$, filtered, and concentrated under reduced pressure. Purification by silica gel chromatography (0→25% EtOAc/pet. ether) afforded product (8.8 g, 84% yield). LCMS (ESI) m/z: [M+Na] calcd for $C_{13}H_{18}O_4$: 261.11; found 261.0.

Step 2: Synthesis of benzyl (4S,5R)-5-isopropyl-1,3,2-dioxathiolane-4-carboxylate 2-oxide To a solution of benzyl (2S,3R)-2,3-dihydroxy-4-methylpentanoate (11.6 g, 48.7 mmol) in DCM (116 mL) at 0° C. was added $Et_3N$ (20.3 mL, 146 mmol) and $SOCl_2$ (4.94 mL, 68.2 mmol). The reaction mixture was stirred 30 min then was diluted with DCM (100 mL) and $H_2O$ (100 mL), extracted into DCM (3×100 mL), washed with brine (200 mL), dried over $Na_2SO_4$, filtered, and concentrated under reduced pressure which afforded product (13.0 g, 94% yield).

Step 3: Synthesis of benzyl (4S,5R)-5-isopropyl-1,3,2-dioxathiolane-4-carboxylate 2,2-dioxide To a solution of benzyl (4S,5R)-5-isopropyl-1,3,2-dioxathiolane-4-carboxylate 2-oxide (13 g, 45.7 mmol) in $H_2O$ (290 mL), MeCN (145 mL), and $CCl_4$ (145 mL) was added $NaIO_4$ (3.80 mL, 68.6 mmol) and $RuCl_3 \cdot H_2O$ (1.03 g, 4.57 mmol). The mixture was stirred at room temperature for 1 h then was diluted with DCM (500 mL) and $H_2O$ (300 mL), filtered, and the filtrate was extracted into DCM (3×200 mL). The combined organic layers were washed sequentially with brine (500 mL) and sat. aq. $Na_2CO_3$ (300 mL), dried over $Na_2SO_4$, filtered, and concentrated under reduced pressure. Purification by silica gel chromatography (0→17% EtOAc/pet. ether) afforded product (11.5 g, 80% yield).

Step 4: Synthesis of benzyl (2R,3R)-2-bromo-3-hydroxy-4-methylpentanoate

To a solution of benzyl (4S,5R)-5-isopropyl-1,3,2-dioxathiolane-4-carboxylate 2,2-dioxide (11.5 g, 38.3 mmol) in THE (520 mL) was added LiBr (3.65 mL, 146 mmol). The reaction mixture was stirred at room temperature for 5 h and then concentrated under reduced pressure. The residue was diluted in THE (130 mL) and $H_2O$ (65 mL), cooled to 0° C., then $H_2SO_4$ solution (20% aq., 1.3 L) was added and the mixture was warmed to room temperature and stirred for 24 h. The mixture was diluted with EtOAc (1.0 L), washed with $Na_2CO_3$ (sat. aq., 300 mL), then was concentrated under reduced pressure. Purification by silica gel chromatography (0→17% EtOAc/pet. ether) afforded product (10 g, 83% yield).

Step 5: Synthesis of benzyl (2S,3R)-2-azido-3-hydroxy-4-methylpentanoate

To a solution of benzyl (2R,3R)-2-bromo-3-hydroxy-4-methylpentanoate (10 g, 33.2 mmol) in DMSO (100 mL) was added $NaN_3$ (4.33 g, 66.6 mmol). The reaction mixture was stirred at room temperature for 12 h then was diluted with EtOAc (300 mL) and $H_2O$ (200 mL). The mixture was extracted into EtOAc (2×200 mL), dried over $Na_2SO_4$, filtered, and concentrated under reduced pressure. Purification by silica gel chromatography (0→17% EtOAc/pet. ether) afforded product (7.5 g, 76% yield).

Step 6: Synthesis of benzyl (2S,3S)-3-isopropylaziridine-2-carboxylate

To a solution of benzyl (2S,3R)-2-azido-3-hydroxy-4-methylpentanoate (7.5 g, 28.5 mmol) in MeCN (150 mL) was added $PPh_3$ (7.70 g, 29.3 mmol). The reaction mixture was stirred at room temperature for 1 h and then heated to 70° C. and stirred for 3 h. The reaction mixture was concentrated under reduced pressure and purification by silica gel chromatography (0→17% EtOAc/pet. ether) afforded product (4.5 g, 64% yield).

LCMS (ESI) m/z: [M+H] calcd for $C_{13}H_{17}NO_2$: 220.13; found 220.1.

Step 7: Synthesis of benzyl (2S,3S)-1-benzyl-3-isopropylaziridine-2-carboxylate

To a solution of benzyl (2S,3S)-3-isopropylaziridine-2-carboxylate (1 g, 4.56 mmol) in MeCN (10 mL) was added $K_2CO_3$ (3.15 g, 22.8 mmol) and benzyl bromide (812 μL, 6.84 mmol). The reaction mixture was stirred at room temperature for 6 h then was diluted with EtOAc (30 mL) and $H_2O$ (30 mL), extracted into EtOAc (2×30 mL), washed with brine (50 mL), dried over $Na_2SO_4$, filtered, and concentrated under reduced pressure. Purification by silica gel chromatography (0→17% EtOAc/pet. ether) afforded product (1.3 g, 89% yield). LCMS (ESI) m/z: [M+H] calcd for $C_{20}H_{23}NO_2$: 310.18; found 310.1.

Step 8: Synthesis of (2S,3S)-1-benzyl-3-isopropylaziridine-2-carboxylic acid

To a solution of benzyl (2S,3S)-1-benzyl-3-isopropylaziridine-2-carboxylate (600 mg, 1.94 mmol) in THE (6 mL), MeCN (3 mL), and $H_2O$ (6 mL) at 0° C. was added $LiOH{\cdot}H_2O$ (163 mg, 3.88 mmol). The reaction mixture was stirred at room temperature for 1 h and was adjusted to pH=7-8 with HCl (0.5M). Lyophilization afforded product (750 mg, crude). LCMS (ESI) m/z: [M+H] calcd for $C_{13}H_{17}NO_2$: 220.13; found 220.1.

Intermediate A-43, A-44, A-45, and A-46. Synthesis of ethyl (2R,3R)-1-benzhydryl-3-(oxetan-3-yl)aziridine-2-carboxylate, ethyl (2S,3S)-1-benzhydryl-3-(oxetan-3-yl)aziridine-2-carboxylate, ethyl (2R,3S)-1-benzhydryl-3-(oxetan-3-yl)aziridine-2-carboxylate, and ethyl (2S,3R)-1-benzhydryl-3-(oxetan-3-yl)aziridine-2-carboxylate

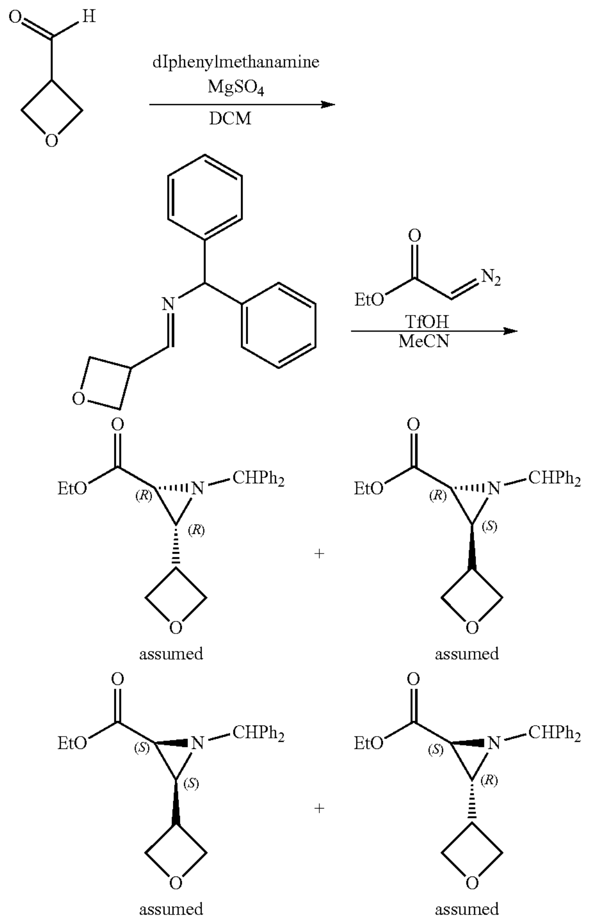

Step 1: Synthesis of N-benzhydryl-1-(oxetan-3-yl)methanimine

To a solution oxetane-3-carbaldehyde (5.0 g, 58 mmol) and $MgSO_4$ (6.99 g, 58.1 mmol) in DCM (120 mL) at 0° C. was added diphenylmethanamine (12.1 mL, 69.7 mmol). The mixture was stirred for 12 h at room temperature then filtered and concentrated under reduced pressure to afford the desired compound (14 g, 96% yield) which was used without further purification.

Step 2: Synthesis of ethyl cis-1-benzhydryl-3-(oxetan-3-yl)aziridine-2-carboxylate and ethyl trans-1-benzhydryl-3-(oxetan-3-yl)aziridine-2-carboxylate To a solution of N-benzhydryl-1-(oxetan-3-yl)methanimine (10 g, 39.79 mmol) in MeCN (150 mL) was added TfOH (878 mL, 9.95 mmol) and after 5 min ethyl diazoacetate (5.0 mL, 47.8 mmol) was added. The reaction mixture was stirred for 12 h at room temperature then cooled to 0° C. and quenched by the addition of saturated $NaHCO_3$ (300 mL). The aqueous layer was extracted with EtOAc (3×200 mL) and the combined organic layers were washed with brine, dried with $Na_2SO_4$, filtered, and concentrated under reduced pressure. Purification by reverse phase chromatography (50→65% MeCN/$H_2O$, 10 mM $NH_4HCO_3$) afforded racemic ethyl cis-1-benzhydryl-3-(oxetan-3-yl)aziridine-2-carboxylate (1.1 g, 8% yield) and racemic ethyl trans-1-benzhydryl-3-(oxetan-3-yl)aziridine-2-carboxylate (780 mg, 6% yield)

Step 3: Separation of racemic ethyl cis-1-benzhydryl-3-(oxetan-3-yl)aziridine-2-carboxylate: ethyl (2R,3R)-1-benzhydryl-3-(oxetan-3-yl)aziridine-2-carboxylate and ethyl (2S,3S)-1-benzhydryl-3-(oxetan-3-yl)aziridine-2-carboxylate Racemic ethyl cis-1-benzhydryl-3-(oxetan-3-yl)aziridine-2-carboxylate (800 mg, 2.37 mmol) was separated by chiral prep-SFC (25% MeOH/$CO_2$) to afford ethyl (2R,3R)-1-benzhydryl-3-(oxetan-3-yl) aziridine-2-carboxylate (320 mg, 40% yield) and ethyl (2S,3S)-1-benzhydryl-3-(oxetan-3-yl)aziridine-2-carboxylate (320 mg, 40% yield).

Step 4: Separation of racemic ethyl trans-1-benzhydryl-3-(oxetan-3-yl)aziridine-2-carboxylate: ethyl (2R,3S)-1-benzhydryl-3-(oxetan-3-yl)aziridine-2-carboxylate and ethyl (2S,3R)-1-benzhydryl-3-(oxetan-3-yl)aziridine-2-carboxylate Racemic ethyl trans1-benzhydryl-3-(oxetan-3-yl)aziridine-2-carboxylate (700 mg, 2.07 mmol) was separated by chiral prep-SFC (25% EtOH, 0.1% $NH_4OH/CO_2$) to afford ethyl (2R,3S)-1-benzhydryl-3-(oxetan-3-yl) aziridine-2-carboxylate (300 mg, 42% yield) and ethyl (2S,3R)-1-benzhydryl-3-(oxetan-3-yl)aziridine-2-carboxylate (320 mg, 43% yield).

Intermediate A-47 and A-48. Synthesis of (2R,3R)-1-benzhydryl-3-(oxetan-3-yl)aziridine-2-carboxylic acid and (2S,3S)-1-benzhydryl-3-(oxetan-3-yl)aziridine-2-carboxylic acid

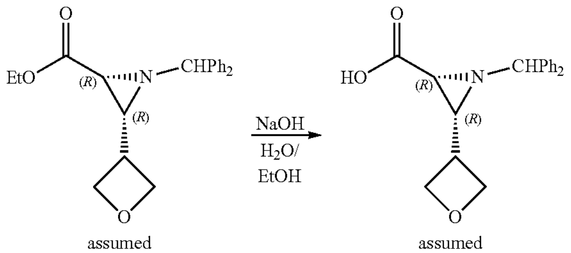

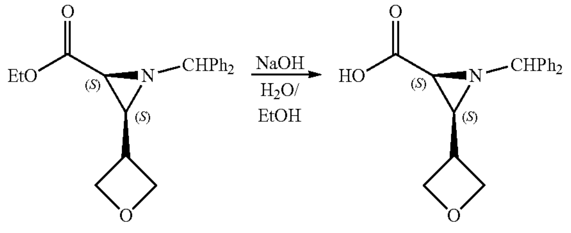

Step 1: Synthesis of (2R,3R)-1-benzhydryl-3-(oxetan-3-yl)aziridine-2-carboxylic acid To a solution of ethyl (2R,3R)-1-benzhydryl-3-(oxetan-3-yl)aziridine-2-carboxylate (156 mg, 463 mmol) in EtOH (3 mL) was added 2M NaOH (347 mL, 696 mmol). The reaction mixture was stirred for 3 h at room temperature and then concentrated under reduced pressure. The concentrate was acidified to pH 5 with 1M HCl and extracted with DCM (3×5 mL) and the combined organic layers were washed with brine, dried with $Na_2SO_4$, filtered and concentrated under reduced pressure to afford the desired compound (110 mg, 73% yield).

Step 2: Synthesis of (2S,3S)-1-benzhydryl-3-(oxetan-3-yl)aziridine-2-carboxylic acid To a solution of ethyl (2S,3S)-1-benzhydryl-3-(oxetan-3-yl)aziridine-2-carboxylate (150 mg, 444 mmol) in EtOH (5 mL) was added 2M NaOH (333 mL, 666 mmol). The reaction mixture was stirred for 3 h at room temperature and then acidified to pH 5 with 1 M HCl. The aqueous layer extracted with DCM (3×10 mL) and the combined organic layers were washed with brine, dried with $Na_2SO_4$, filtered, and concentrated under reduced pressure to afford the desired compound (120 mg, 86% yield).

Intermediate A-49 and A-50. Synthesis of sodium (2R,3S)-1-benzhydryl-3-(oxetan-3-yl)aziridine-2-carboxylate and sodium (2S,3R)-1-benzhydryl-3-(oxetan-3-yl)aziridine-2-carboxylate

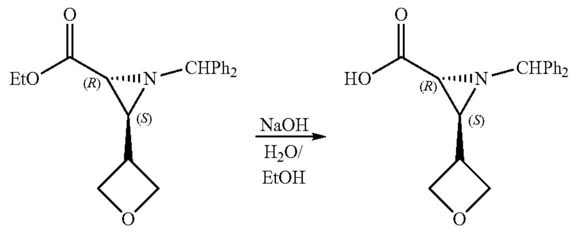

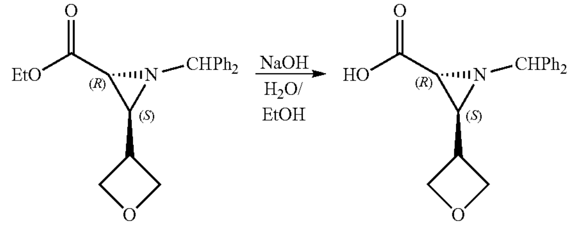

Step 1: Synthesis of sodium (2R,3S)-1-benzhydryl-3-(oxetan-3-yl)aziridine-2-carboxylate To a solution of ethyl (2R,3S)-1-benzhydryl-3-(oxetan-3-yl)aziridine-2-carboxylate (150 mg, 444 mmol) in EtOH (3 mL) was added 2M NaOH (333.42 mL, 666 mmol). The reaction mixture was stirred for 3 h at room temperature and then the pH was adjusted to pH 8 with 1M HCl. The resulting solution was lyophilized to afford the desired compound (165 mg, crude) which was used without further purification. LCMS (ESI) m/z: [M] calcd for $C_{19}H_{18}NO_3$: 308.13; found 308.0.

Step 2: Synthesis of sodium (2S,3R)-1-benzhydryl-3-(oxetan-3-yl)aziridine-2-carboxylate To a solution of ethyl (2S,3R)-1-benzhydryl-3-(oxetan-3-yl)aziridine-2-carboxylate (170 mg, 503 mmol) in EtOH (3 mL) was added 2M NaOH (378 mL, 754 mmol). The reaction mixture was stirred for 3 h at room temperature and then the pH was adjusted to pH 8 with 1 M HCl. The resulting solution was lyophilized to afford the desired compound (230 mg, crude) which was used without further purification. LCMS (ESI) m/z: [M] calcd for $C_{19}H_{18}NO_3$: 308.13; found 308.

Intermediate A-51—Synthesis of (S)-1-tritylaziridine-2-carbaldehyde

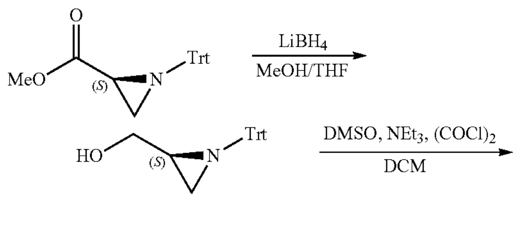

-continued

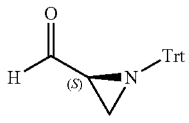

Step 1: Synthesis of (S)-(1-tritylaziridin-2-yl)methanol

To a solution of methyl (S)-1-tritylaziridine-2-carboxylate (2 g, 5.82 mmol) in THE (20 mL) at 0° C. was added $LiBH_4$ (634.3 mg, 29.1 mmol) followed by the dropwise addition of MeOH (3.54 mL). The resulting mixture was warmed to room temperature and was stirred for 3 h. The reaction mixture was quenched with $H_2O$ (50 mL), extracted into EtOAc (3×50 mL), dried over $Na_2SO_4$, filtered, and concentrated under reduced pressure to afford the crude product (1.8 g, 98% yield) as solid, which was used without further purification.

Step 2: Synthesis of (S)-1-tritylaziridine-2-carbaldehyde

To a solution of oxalyl chloride (167 μL, 1.9 mmol) in DCM (2.5 mL) at −78° C. was added a solution of DMSO (310 μL, 3.96 mmol) in DCM (2.5 mL), dropwise. After 30 min a solution of (S)-(1-tritylaziridin-2-yl)methanol (500 mg, 3.8 mmol) in DCM (5 mL) was added dropwise to the reaction mixture. After 30 min, $NEt_3$ (1.10 mL, 0.789 mmol) was added. After 45 min the reaction was quenched with $H_2O$ (50 mL) and extracted with DCM (3×20 mL). The combined organic layers were washed with sat. aq. brine, dried over $Na_2SO_4$, filtered, and concentrated under reduced pressure to afford the desired product (480 mg, 97% yield) as solid, which was used without further purification.

Intermediate A-52—Synthesis of (R)-1-tritylaziridine-2-carbaldehyde

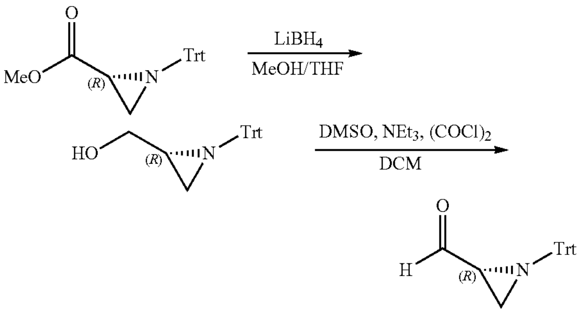

Step 1: Synthesis of (R)-(1-tritylaziridin-2-yl)methanol

To a solution of methyl (R)-1-tritylaziridine-2-carboxylate (2 g, 5.82 mmol) in THE (20 mL) at 0° C. was added $LiBH_4$ (634.2 mg, 29.1 mmol) followed by the dropwise addition of MeOH (4.0 mL). The resulting mixture was warmed to room temperature and was stirred for 3 h. The reaction mixture was quenched with $H_2O$ (60 mL) at 0° C., extracted into EtOAc (3×60 mL), washed with brine (20 mL), dried over $Na_2SO_4$, filtered, and concentrated under reduced pressure to afford the crude product (1.8 g, crude) as solid, which was used without further purification.

Step 2: Synthesis of (R)-1-tritylaziridine-2-carbaldehyde

To a solution of oxalyl chloride (600 μL, 6.85 mmol) in DCM (4.5 mL) at −78° C. was added a solution of DMSO (1.1 mL, 14.27 mmol) in DCM (5.5 mL), dropwise. After 30 min a solution of (R)-(1-tritylaziridin-2-yl)methanol (1.8 g, 5.71 mmol) in DCM (19.5 mL) was added dropwise to the reaction mixture. After 30 min, $NEt_3$ (2.89 mL, 28.5 mmol) was added. After 1 h the reaction was quenched with $H_2O$ (30 mL) and extracted with DCM (3×30 mL). The combined organic layers were dried over $Na_2SO_4$, filtered, and concentrated under reduced pressure to afford the desired product (1.7 g, 95% yield) as solid, which was used without further purification.

Example B1: Synthesis of ((R)-aziridin-2-yl)((1R,5S)-3-(8-fluoro-7-(8-fluoro-3-hydroxynaphthalen-1-yl)-2-(((2R,7aS)-2-fluorotetrahydro-1H-pyrrolizin-7a(5H)-yl)methoxy)pyrido[4,3-d]pyrimidin-4-yl)-3,8-diazabicyclo[3.2.1]octan-8-yl)methanone

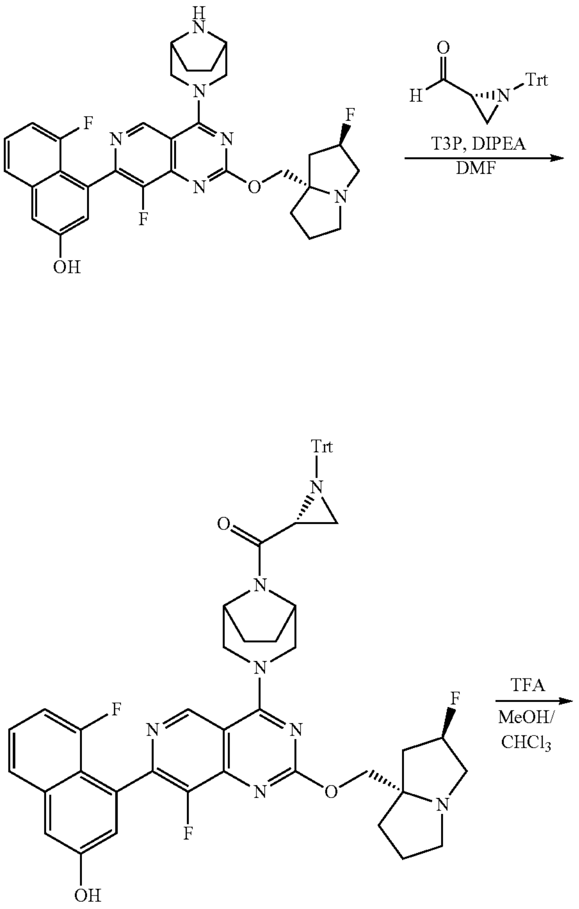

-continued

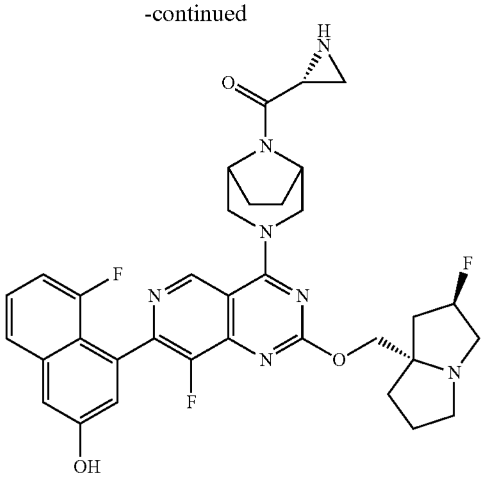

Step 1: Synthesis of ((1R,5S)-3-(8-fluoro-7-(8-fluoro-3-hydroxynaphthalen-1-yl)-2-(((2R,7aS)-2-fluorotetrahydro-1H-pyrrolizin-7a(5H)-yl)methoxy)pyrido[4,3-d]pyrimidin-4-yl)-3,8-diazabicyclo[3.2.1]octan-8-yl)((R)-1-tritylaziridin-2-yl)methanone To a solution of 4-(4-((1R,5S)-3,8-diazabicyclo[3.2.1]octan-3-yl)-8-fluoro-2-(((2R,7aS)-2-fluorotetrahydro-1H-pyrrolizin-7a(5H)-yl)methoxy)pyrido[4,3-d]pyrimidin-7-yl)-5-fluoronaphthalen-2-ol (100 mg, 173.4 μmol) and (R)-1-tritylaziridine-2-carboxylic acid (91.4 mg, 208.11 μmol) in DMF (5 mL) at 0° C. was added DIPEA (151.0 μL, 867.1 μmol) and $T_3P$ (113.5 μL, 190.8 μmol). The mixture was warmed to room temperature, stirred for 3 h, and was then added to $H_2O$ (30 mL). The mixture was extracted with EtOAc (3×30 mL), and the combined organic layers were washed with brine (50 mL), dried over $Na_2SO_4$, filtered, and concentrated under reduced pressure. The residue was purified by silica gel chromatography (0→17% MeOH/DCM) to afford the desired product (140 mg) as a solid. LCMS (ESI) m/z [M+H] calcd for $C_{53}H_{48}F_3N_7O_3$ 888.39; found: 888.3.

Step 2: Synthesis of ((R)-aziridin-2-yl)((1R,5S)-3-(8-fluoro-7-(8-fluoro-3-hydroxynaphthalen-1-yl)-2-(((2R,7aS)-2-fluorotetrahydro-1H-pyrrolizin-7a(5H)-yl)methoxy)pyrido[4,3-d]pyrimidin-4-yl)-3,8-diazabicyclo[3.2.1]octan-8-yl)methanon To a solution of ((1R,5S)-3-(8-fluoro-7-(8-fluoro-3-hydroxynaphthalen-1-yl)-2-(((2R,7aS)-2-fluorotetrahydro-1H-pyrrolizin-7a(5H)-yl)methoxy)pyrido[4,3-d]pyrimidin-4-yl)-3,8-diazabicyclo[3.2.1]octan-8-yl)((R)-1-tritylaziridin-2-yl)methanone (140 mg, 157.7 μmol) in $CHCl_3$ (0.7 mL) and MeOH (0.7 mL) at 0° C. was added TFA (233.5 μL, 3.2 mmol). The mixture was warmed to room temperature and stirred for 1 h and was then added to sat. aq. $NaHCO_3$ (20 mL). The mixture was extracted with DCM (3×5 mL) and the combined organic layers were washed with brine (10 mL), dried over $Na_2SO_4$, filtered, and concentrated under reduced pressure. The residue was purified by reverse phase chromatography (30→50% MeCN/$H_2O$) to afford the desired product (23.9 mg, 23% yield) as a solid. LCMS (ESI) m/z [M+H] calcd for $C_{34}H_{34}F_3N_7O_3$ 646.28; found: 646.3.

Example B2: Synthesis of ((S)-aziridin-2-yl)((1R,5S)-3-(8-fluoro-7-(8-fluoro-3-hydroxynaphthalen-1-yl)-2-(((2R,7aS)-2-fluorotetrahydro-1H-pyrrolizin-7a(5H)-yl)methoxy)pyrido[4,3-d]pyrimidin-4-yl)-3,8-diazabicyclo[3.2.1]octan-8-yl)methanone

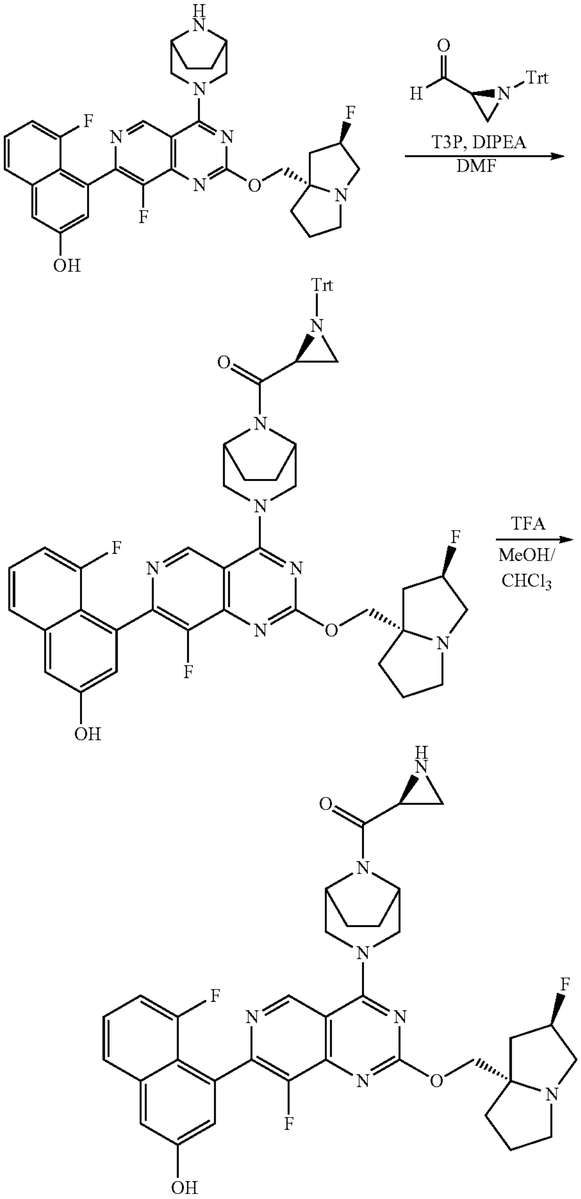

Step 1: Synthesis of ((1R,5S)-3-(8-fluoro-7-(8-fluoro-3-hydroxynaphthalen-1-yl)-2-(((2R,7aS)-2-fluorotetrahydro-1H-pyrrolizin-7a(5H)-yl)methoxy)pyrido[4,3-d]pyrimidin-4-yl)-3,8-diazabicyclo[3.2.1]octan-8-yl)((S)-1-tritylaziridin-2-yl)methanone To a solution of 4-(4-((1R,5S)-3,8-diazabicyclo[3.2.1]octan-3-yl)-8-fluoro-2-(((2R,7aS)-2-fluorotetrahydro-1H-pyrrolizin-7a(5H)-yl)methoxy)pyrido[4,3-d]pyrimidin-7-yl)-5-fluoronaphthalen-2-ol (250 mg, 433.57 μmol) and (S)-1-tritylaziridine-2-carboxylic acid (248 mg, 563.64 μmol) in DMF (5 mL) at 0° C. was added DIPEA (528.6 μL, 3.03 mmol) and $T_3P$ (515.7 μL, 867.14 μmol). The mixture was warmed to room temperature, stirred for 30 min, and was then added to sat. aq. $NH_4Cl$ (50 mL). The mixture was extracted with EtOAc (3×20 mL) and the combined organic layers were washed with brine (3×18 mL), dried over $Na_2SO_4$, filtered and concentrated under reduced pressure. The residue was purified by silica gel chromatography (0→100% EtOAc/Pet. ether) to afford the desired product (190 mg, 49% yield) as a solid. LCMS (ESI) m/z [M+H] calcd for $C_{53}H_{48}F_3N_7O_3$ 888.39; found: 888.6.

Step 2: Synthesis of ((S)-aziridin-2-yl)((1R,5S)-3-(8-fluoro-7-(8-fluoro-3-hydroxynaphthalen-1-yl)-2-(((2R,7aS)-2-fluorotetrahydro-1H-pyrrolizin-7a(5H)-yl)methoxy)pyrido[4,3-d]pyrimidin-4-yl)-3,8-diazabicyclo[3.2.1]octan-8-yl)methanone To a solution of ((1R,5S)-3-(8-fluoro-7-(8-fluoro-3-hydroxynaphthalen-1-yl)-2-(((2R,7aS)-2-fluorotetrahydro-1H-pyrrolizin-7a(5H)-yl)methoxy)pyrido[4,3-d]pyrimidin-4-yl)-3,8-diazabicyclo[3.2.1]octan-8-yl)((S)-1-tritylaziridin-2-yl)methanone (190 mg, 213.97 μmol) in $CHCl_3$ (1 mL) and MeOH (1 mL) at 0° C. was added TFA (475.3 μL, 6.42 mmol). The mixture was stirred at 0° C. for 30 min and was then added dropwise to sat. aq. $NaHCO_3$ (60 mL) at 0° C. The mixture was extracted with DCM (3×15 mL) and the combined organic layers were washed with brine (2×10 mL), dried over $Na_2SO_4$, filtered, and concentrated under reduced pressure. The residue was purified by reverse phase chromatography (25→45% $MeCN/H_2O$) to afford the desired product (24.7 mg, 18% yield) as a solid. LCMS (ESI) m/z [M+H] calcd for $C_{34}H_{34}F_3N_7O_3$ 646.28; found: 646.3.

Example B3: Synthesis of 4-(4-((1R,5S)-8-(((R)-aziridin-2-yl)methyl)-3,8-diazabicyclo[3.2.1]octan-3-yl)-8-fluoro-2-(((2R,7aS)-2-fluorotetrahydro-1H-pyrrolizin-7a(5H)-yl)methoxy)pyrido[4,3-d]pyrimidin-7-yl)-5-fluoronaphthalen-2-ol

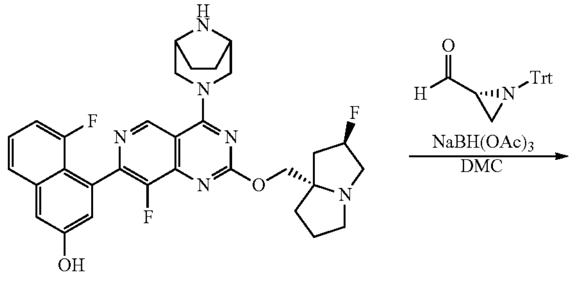

-continued

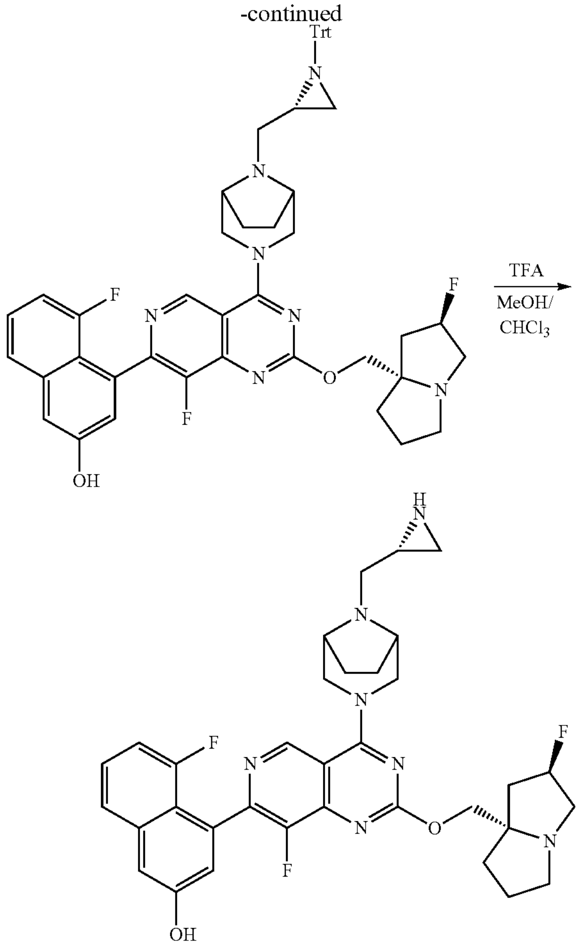

Step 1: Synthesis of 5-fluoro-4-(8-fluoro-2-(((2R,7aS)-2-fluorotetrahydro-1H-pyrrolizin-7a(5H)-yl)methoxy)-4-((1R,5S)-8-(((S)-1-tritylaziridin-2-yl)methyl)-3,8-diazabicyclo[3.2.1]octan-3-yl)pyrido[4,3-d]pyrimidin-7-yl)naphthalen-2-ol To a solution of 4-(4-((1R,5S)-3,8-diazabicyclo[3.2.1]octan-3-yl)-8-fluoro-2-(((2R,7aS)-2-fluorotetrahydro-1H-pyrrolizin-7a(5H)-yl)methoxy)pyrido[4,3-d]pyrimidin-7-yl)-5-fluoronaphthalen-2-ol (500 mg, 867.1 μmol) and (R)-1-tritylaziridine-2-carbaldehyde (312.5 mg, 997.2 μmol) in DCM (5 mL) was added $NaBH(OAc)_3$ (275.7 mg, 1.3 mmol). The reaction mixture was stirred at room temperature for 1 h and was then poured into $H_2O$ (10 mL). The mixture was extracted with DCM (3×5 mL) and the combined organic layers were washed with brine (10 mL), dried over $Na_2SO_4$, filtered, and concentrated under reduced pressure. The residue was purified by prep-HPLC (75→95% $MeCN/H_2O$) to afford the desired product (380 mg, 50% yield) as a solid. LCMS (ESI) m/z [M+H] calcd for $C_{53}H_{50}F_3N_7O_2$ 874.41; found: 874.3.

Step 2: Synthesis of 4-(4-((1R,5S)-8-(((R)-aziridin-2-yl)methyl)-3,8-diazabicyclo[3.2.1]octan-3-yl)-8-fluoro-2-(((2R,7aS)-2-fluorotetrahydro-1H-pyrrolizin-7a(5H)-yl)methoxy)pyrido[4,3-d]pyrimidin-7-yl)-5-fluoronaphthalen-2-ol To a solution of 5-fluoro-4-(8-fluoro-2-(((2R,7aS)-2-fluorotetrahydro-1H-pyrrolizin-7a(5H)-yl)methoxy)-4-((1R, 5S)-8-(((S)-1-tritylaziridin-2-yl)methyl)-3,8-diazabicyclo[3.2.1]octan-3-yl)pyrido[4,3-d]pyrimidin-7-yl)naphthalen-2-ol (330 mg, 377.6 μmol) in MeOH (2 mL) and $CHCl_3$ (1.7 mL) at 0° C. was added TFA (1.4 mL, 18.9 mmol). The mixture was stirred at 0° C. for 1 h and was then added dropwise to sat. aq. $NaHCO_3$ (15 mL) at 0° C. The mixture was extracted with DCM (3×8 mL) and the combined organic layers were washed with brine (10 mL), dried over $Na_2SO_4$, filtered, and concentrated under reduced pressure. The residue was purified by reverse phase chromatography (25→55% MeCN/$H_2O$) to afford the desired product (81.5 mg, 34% yield) as a solid. LCMS (ESI) m/z [M+H] calcd for $C_{34}H_{36}F_3N_7O_2$ 632.30; found: 632.3.

Example B4: Synthesis of 4-(4-((1R,5S)-8-(((S)-aziridin-2-yl)methyl)-3,8-diazabicyclo[3.2.1]octan-3-yl)-8-fluoro-2-(((2R,7aS)-2-fluorotetrahydro-1H-pyrrolizin-7a(5H)-yl)methoxy)pyrido[4,3-d]pyrimidin-7-yl)-5-fluoronaphthalen-2-ol

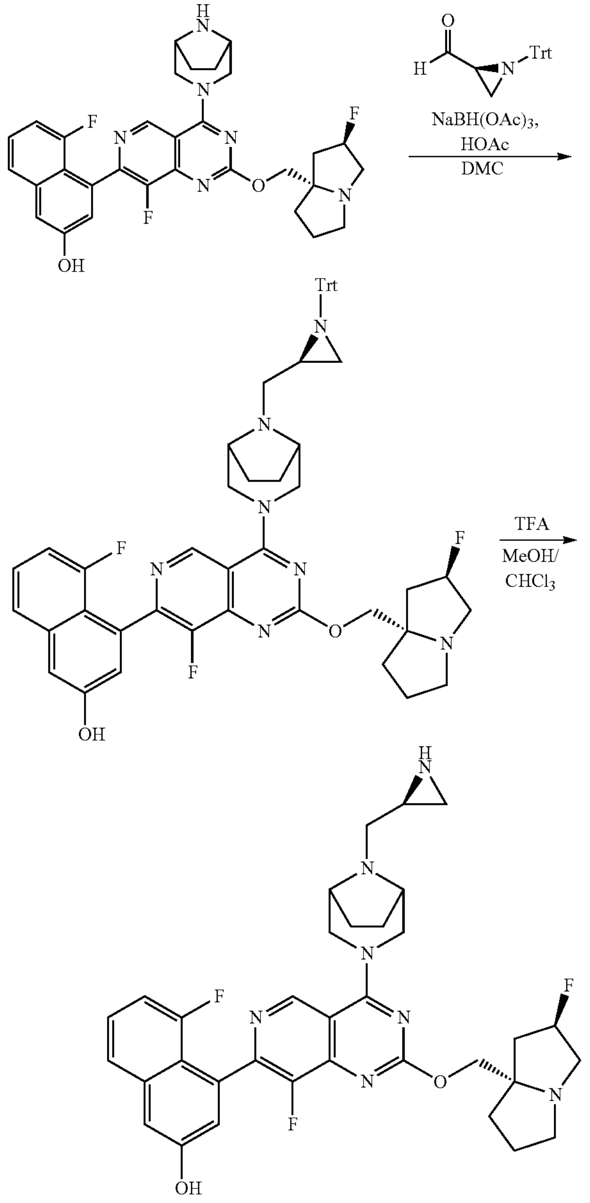

Step 1: Synthesis of 5-fluoro-4-(8-fluoro-2-(((2R,7aS)-2-fluorotetrahydro-1H-pyrrolizin-7a(5H)-yl)methoxy)-4-((1R,5S)-8-(((R)-1-tritylaziridin-2-yl)methyl)-3,8-diazabicyclo[3.2.1]octan-3-yl)pyrido[4,3-d]pyrimidin-7-yl)naphthalen-2-ol To a solution of 4-(4-((1R,5S)-3,8-diazabicyclo[3.2.1]octan-3-yl)-8-fluoro-2-(((2R,7aS)-2-fluorotetrahydro-1H-pyrrolizin-7a(5H)-yl)methoxy)pyrido[4,3-d]pyrimidin-7-yl)-5-fluoronaphthalen-2-ol (208.7 mg, 666.0 μmol) and (S)-1-tritylaziridine-2-carbaldehyde (240.0 mg, 765.9 μmol) in DCM (3.2 mL) was added $NaBH(OAc)_3$ (48.8 mg, 777.0 μmol) and HOAc (95 mL, 1.66 mmol). The reaction mixture was stirred at room temperature for 1 h and was then poured into $H_2O$ (10 mL). The mixture was extracted with DCM (3×10 mL) and the combined organic layers were washed with brine (10 mL), dried over $Na_2SO_4$, filtered, and concentrated under reduced pressure. The residue was purified by silica gel chromatography (50% EtOAc/Pet. ether to 9% MeOH/EtOAc) to afford the desired product (200 mg, 41% yield) as a solid. LCMS (ESI) m/z [M+H] calcd for $C_{53}H_{50}F_3N_7O_2$ 874.41; found: 874.2.

Step 2: Synthesis of 4-(4-((1R,5S)-8-(((S)-aziridin-2-yl)methyl)-3,8-diazabicyclo[3.2.1]octan-3-yl)-8-fluoro-2-(((2R,7aS)-2-fluorotetrahydro-1H-pyrrolizin-7a(5H)-yl)methoxy)pyrido[4,3-d]pyrimidin-7-yl)-5-fluoronaphthalen-2-ol To a solution of 5-fluoro-4-(8-fluoro-2-(((2R,7aS)-2-fluorotetrahydro-1H-pyrrolizin-7a(5H)-yl)methoxy)-4-((1R,5S)-8-(((R)-1-tritylaziridin-2-yl)methyl)-3,8-diazabicyclo[3.2.1]octan-3-yl)pyrido[4,3-d]pyrimidin-7-yl)naphthalen-2-ol (200 mg, 228.8 μmol) in MeOH (1 mL) and $CHCl_3$ (1 mL) at 0° C. was added TFA (339 μL, 4.58 mmol). The mixture was stirred at 0° C. for 30 min and was then added dropwise to sat. aq. $NaHCO_3$ (40 mL) at 0° C. The mixture was extracted with DCM (3×20 mL) and the combined organic layers were washed with brine (10 mL), dried over $Na_2SO_4$, filtered, and concentrated under reduced pressure. The residue was purified by reverse phase chromatography (30→55% MeCN/$H_2O$) to afford the desired product (32 mg, 22% yield) as a solid. LCMS (ESI) m/z [M+H] calcd for $C_{34}H_{36}F_3N_7O_2$ 632.30; found: 632.2.

Example B23: Synthesis of (4-(4-((1R,5S)-3,8-diazabicyclo[3.2.1]octan-3-yl)-8-fluoro-2-(((2R,7aS)-2-fluorotetrahydro-1H-pyrrolizin-7a(5H)-yl)methoxy)pyrido[4,3-d]pyrimidin-7-yl)-5-fluoroisoquinolin-2(1H)-yl)((R)-aziridin-2-yl)methanone

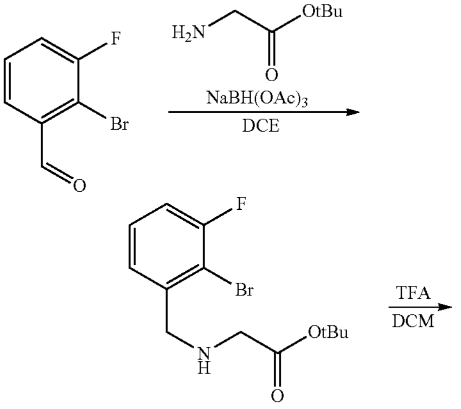

-continued

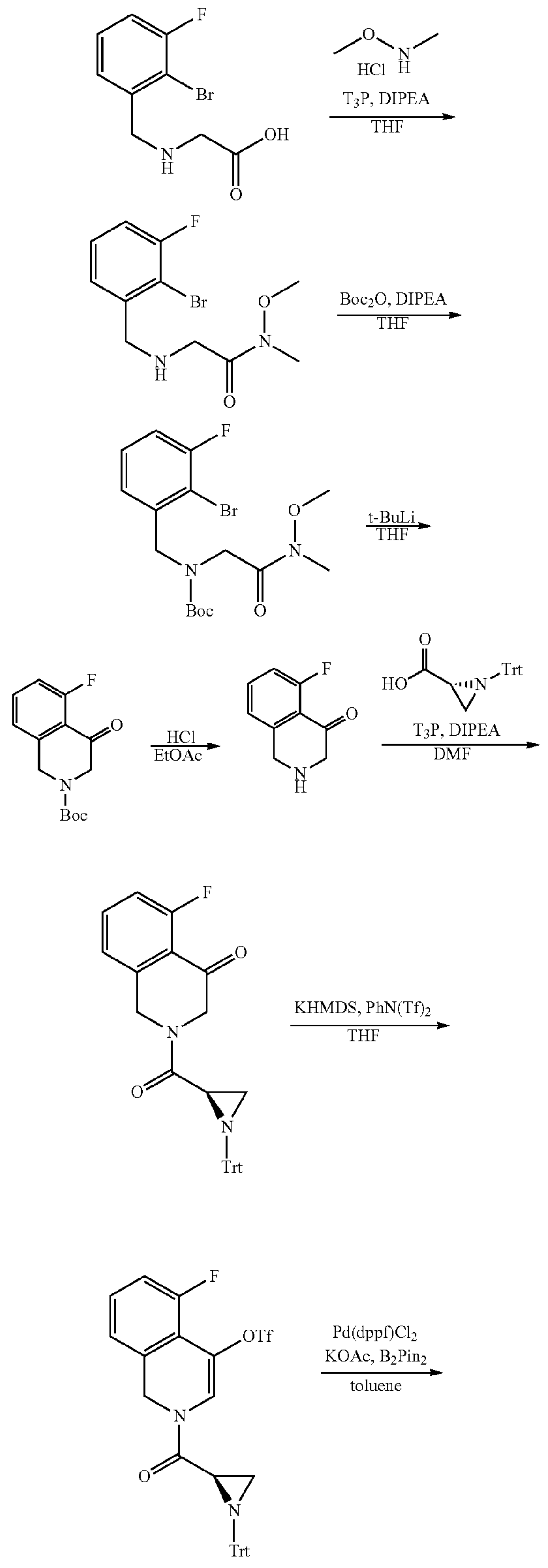

-continued

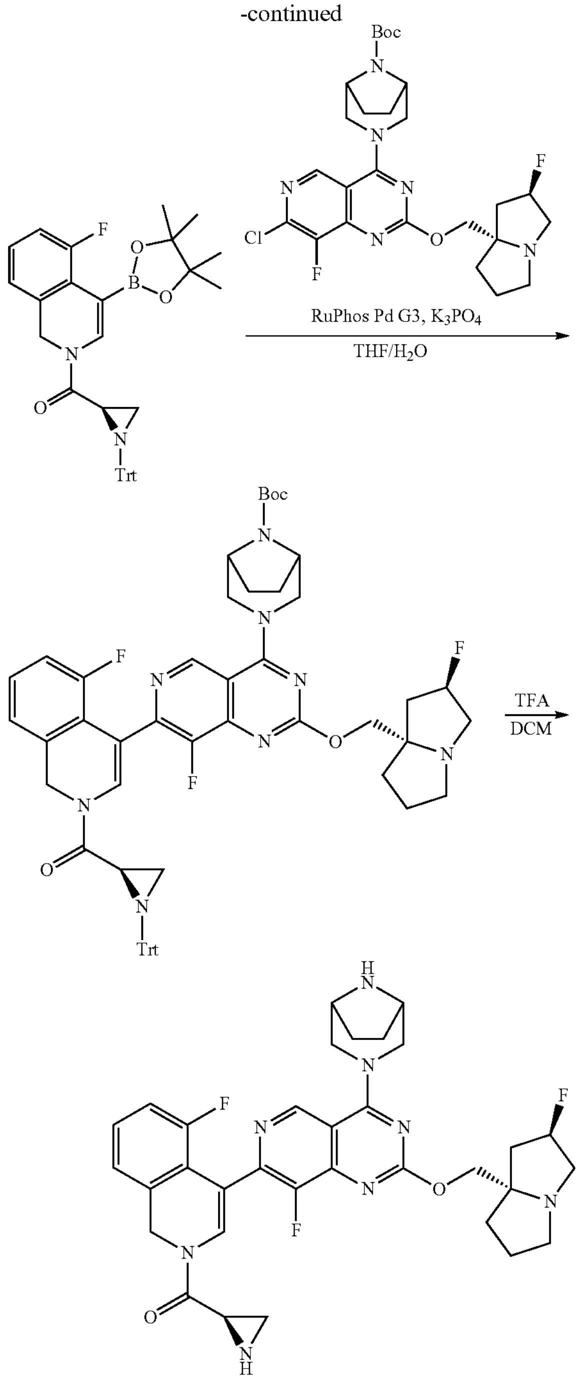

Step 1: Synthesis of tert-butyl (2-bromo-3-fluorobenzyl)glycinate

To a solution of tert-butyl glycinate (38.77 g, 295.6 mmol) and 2-bromo-3-fluorobenzaldehyde (40 g, 197.0 mmol) in DCE (400 mL) was added $NaBH(OAc)_3$ (125.28 g, 591.11 mmol). The reaction mixture was stirred at room temperature for 10 h and was then quenched with cold $H_2O$ (200 mL). The aqueous phase was extracted with DCM (3×300 mL) and the combined organic layers were washed with brine (300 mL), dried with $Na_2SO_4$, filtered, and concentrated under reduced pressure. The residue was purified by silica gel chromatography (9%→50% EtOAc/pet. ether) to afford the desired product (40 g, 64% yield) as an oil.

Step 2: Synthesis of (2-bromo-3-fluorobenzyl)glycine

To a solution of tert-butyl (2-bromo-3-fluorobenzyl)glycinate (19.5 g, 61.29 mmol) in DCM (195 mL) was added TFA (195 mL, 2.63 mol) at room temperature. The mixture was stirred for 2 h and was then concentrated under reduced pressure to afford the crude product (30 g) as an oil, which was used in the next step without purification. LCMS (ESI) m/z [M+H] calcd for $C_9H_9BrFNO_2$ 261.99; found: 262.0.

Step 3: Synthesis of 2-((2-bromo-3-fluorobenzyl) amino)-N-methoxy-N-methylacetamide To a solution of (2-bromo-3-fluorobenzyl)glycine (20 g, 76.31 mmol) and N,O-dimethylhydroxylamine hydrochloride (37.22 g, 381.6 mmol) in THE (1 L) at 0° C. was added DIPEA (132.9 mL, 763.1 mmol) and $T_3P$ (90.8 mL, 152.6 mmol). The reaction mixture was stirred for 1 h and then the mixture was warmed to room temperature, stirred for 4 h, and was added to $H_2O$ (300 mL). The aqueous phase was extracted with EtOAc (3×150 mL), and the combined organic layers were washed with brine (200 mL), dried with $Na_2SO_4$, filtered and concentrated under reduced pressure. The residue was purified by silica gel chromatography (17%→100% EtOAc/pet. ether) to afford the desired product (20 g) as a solid. LCMS (ESI) m/z [M+H] calcd for $C_1H_{14}BrFN_2O_2$ 305.03; found: 305.2.

Step 4: Synthesis of tert-butyl (2-bromo-3-fluorobenzyl)(2-(methoxy(methyl)amino)-2-oxoethyl) carbamate To a solution of 2-((2-bromo-3-fluorobenzyl)amino)-N-methoxy-N-methylacetamide (40 g, 131.1 mmol) in THE (400 mL) was added DIPEA (114.2 mL, 655.4 mmol) and $Boc_2O$ (60.2 mL, 262.2 mmol). The mixture was stirred at room temperature for 10 h and was then added to $H_2O$ (250 mL). The aqueous phase was extracted with EtOAc (3×100 mL) and the combined organic layers were washed with brine (100 mL), dried with $Na_2SO_4$, filtered and concentrated under reduced pressure. The residue was purified by silica gel chromatography eluted with (17%→100% EtOAc/pet. ether) to afford the desired product (34 g, 64% yield) as a solid.

Step 5: Synthesis of tert-butyl 5-fluoro-4-oxo-3,4-dihydroisoquinoline-2(1H)-carboxylate To a solution of tert-butyl (2-bromo-3-fluorobenzyl)(2-(methoxy(methyl)amino)-2-oxoethyl)carbamate (3 g, 7.40 mmol) in THE (90 mL) at −75° C. was added tBuLi (1.3 M, 8.0 mL). The reaction mixture was stirred for 30 min and was then poured into $H_2O$ (100 mL). The aqueous phase was extracted with EtOAc (3×50 mL) and the combined organic layers were washed with brine (50 mL), dried with $Na_2SO_4$, filtered and concentrated under reduced pressure. The residue was purified by silica gel chromatography (3%→9% EtOAc/pet. ether) to afford the desired product (1.4 g, 71% yield) as an oil.

Step 6: Synthesis of 5-fluoro-2,3-dihydroisoquinolin-4(1H)-one tert-butyl 5-fluoro-4-oxo-3,4-dihydroisoquinoline-2(1H)-carboxylate (1.4 g, 5.28 mmol) was stirred in a solution of HCl in EtOAc (4 M, 14 mL) at room temperature for 1 h. The mixture was then concentrated under reduced pressure to afford the desired product (1.6 g, crude, HCl) as a solid, which was used the next step directly.

Step 7: Synthesis of (R)-5-fluoro-2-(1-tritylaziridine-2-carbonyl)-2,3-dihydroisoquinolin-4(1H)-one To a solution of 5-fluoro-2,3-dihydroisoquinolin-4(1H)-one (1.5 g, 7.44 mmol, HCl) in DMF (20 mL) at 0° C. was added (R)-1-tritylaziridine-2-carboxylic acid (4.9 g, 14.9 mmol) and $T_3P$ (6.6 mL, 11.2 mmol) and DIPEA (6.5 mL, 37.2 mmol). The mixture was stirred at room temperature for 10 h and then the reaction mixture was quenched by the addition $H_2O$ (50 mL). The aqueous phase was extracted with EtOAc (3×15 mL) and then combine organic layers were washed with brine (15 mL), dried over $Na_2SO_4$, filtered, and concentrated under reduced pressure. The residue was purified by silica gel chromatography (1%→50% EtOAc/pet. ether) to afford the desired product (1.8 g, 51% yield) as a solid.

Step 8: Synthesis of (R)-5-fluoro-2-(1-tritylaziridine-2-carbonyl)-1,2-dihydroisoquinolin-4-yl trifluoromethanesulfonate To a solution of (R)-5-fluoro-2-(1-tritylaziridine-2-carbonyl)-2,3-dihydroisoquinolin-4(1H)-one (338 mg, 709.3 μmol) in THE (7 mL) at −78° C. was added KHMDS (1 M, 1.1 mL), dropwise, followed by a solution of N-phenyl-bis(trifluoromethanesulfonimide) (380.1 mg, 1.06 mmol) in THE (4 mL). The reaction mixture was stirred at −78° C. for 30 min and then was quenched by addition $H_2O$ (15 mL). The aqueous layer was extracted with EtOAc (3×4 mL) and the combined organic layers were washed with brine (7 mL), dried over $Na_2SO_4$, filtered, and concentrated under reduced pressure. The residue was purified by silica gel chromatography (50%→100% EtOAc/pet. ether) to afford the desired product (300 mg, 70% yield) as a solid.

Step 9: Synthesis of (R)-(5-fluoro-4-(4,4,5,5-tetramethyl-1,3,2-dioxaborolan-2-yl)isoquinolin-2(1H)-yl) (1-tritylaziridin-2-yl)methanone To a solution of bis(pinacolato)diboron (917.9 mg, 3.61 mmol) in toluene (12 mL) was added (R)-5-fluoro-2-(1-tritylaziridine-2-carbonyl)-1,2-dihydroisoquinolin-4-yl trifluoromethanesulfonate (1.1 g, 1.81 mmol), potassium acetate (443.5 mg, 4.52 mmol) and [1,1'-bis(diphenylphosphino)ferrocene]dichloropalladium(II) (132.3 mg, 180.7 μmol). The mixture was degassed and purged with $N_2$ 3 times. The mixture was stirred at 90° C. for 12 h and was then cooled and filtered. The filter cake was washed with EtOAc (3×10 mL) and the organic layer was concentrated under reduced pressure. The residue was purified by silica gel chromatography (1%→16% EtOAc/pet. ether) to afford the desired product (0.9 g, 85% yield) as an oil.

Step 10: Synthesis of tert-butyl (1R,5S)-3-(8-fluoro-7-(5-fluoro-2-((R)-1-tritylaziridine-2-carbonyl)-1,2-dihydroisoquinolin-4-yl)-2-(((2R,7aS)-2-fluorotetrahydro-1H-pyrrolizin-7a(5H)-yl)methoxy) pyrido[4,3-d]pyrimidin-4-yl)-3,8-diazabicyclo[3.2.1] octane-8-carboxylate To a solution of tert-butyl (1R,5S)-3-(7-chloro-8-fluoro-2-(((2R,7aS)-2-fluorotetrahydro-1H-pyrrolizin-7a(5H)-yl)

methoxy)pyrido[4,3-d]pyrimidin-4-yl)-3,8-diazabicyclo [3.2.1]octane-8-carboxylate (319.4 mg, 579.7 μmol) in THE (8 mL) and $H_2O$ (2 mL) was added RuPhos Pd G3 (52.55 mg, 57.97 μmol), $K_3PO_4$ (246.1 mg, 1.16 mmol), (R)-(5-fluoro-4-(4,4,5,5-tetramethyl-1,3,2-dioxaborolan-2-yl)isoquinolin-2(1H)-yl)(1-tritylaziridin-2-yl)methanone (850 mg, 1.45 mmol). The mixture was stirred at 80° C. for 12 h and was then quenched by addition $H_2O$ (20 mL). EtOAc (5 mL) was added and then the aqueous layer was extracted with EtOAc (3×5 mL). The combined organic layers were washed with brine (10 mL), dried over $Na_2SO_4$, filtered, and concentrated under reduced. The residue was purified by silica gel chromatography (1%→50% EtOAc/pet. ether) to afford the desired product (350 mg, 62% yield) as a solid. LCMS (ESI) m/z [M+H] calcd for $C_{57}H_{57}F_3N_8O_4$ 975.46; found: 975.5.

Step 11: Synthesis of (4-(4-((1R,5S)-3,8-diazabicyclo[3.2.1]octan-3-yl)-8-fluoro-2-(((2R,7aS)-2-fluorotetrahydro-1H-pyrrolizin-7a(5H)-yl)methoxy)pyrido[4,3-d]pyrimidin-7-yl)-5-fluoroisoquinolin-2(1H)-yl)((R)-aziridin-2-yl)methanone To a solution of tert-butyl (1R,5S)-3-(8-fluoro-7-(5-fluoro-2-((R)-1-tritylaziridine-2-carbonyl)-1,2-dihydroisoquinolin-4-yl)-2-(((2R,7aS)-2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate (200 mg, 205.1 μmol) in DCM (5 mL) at 0° C. was added TFA (5 mL, 67.5 mmol). The mixture was stirred for 30 min and was then diluted with aq. $NaHCO_3$ until pH 7. The aqueous layer was extracted with DCM (3×5 mL) and the combined organic layers were washed with aqueous brine (10 mL), dried over $Na_2SO_4$, filtered, and concentrated under reduced pressure. The residue was purified by reverse phase chromatography (5%→30% $MeCN/H_2O$) to afford the desired product (20 mg, 39% yield) as a solid. LCMS (ESI) m/z [M+H] calcd for $C_{33}H_{35}F_3N_8O_2$ 633.29; found: 633.4.

Example B24: Synthesis of (4-(4-((1R,5S)-3,8-diazabicyclo[3.2.1]octan-3-yl)-8-fluoro-2-(((2R,7aS)-2-fluorotetrahydro-1H-pyrrolizin-7a(5H)-yl)methoxy)pyrido[4,3-d]pyrimidin-7-yl)-5-fluoroisoquinolin-2(1H)-yl)((S)-aziridin-2-yl)methanone

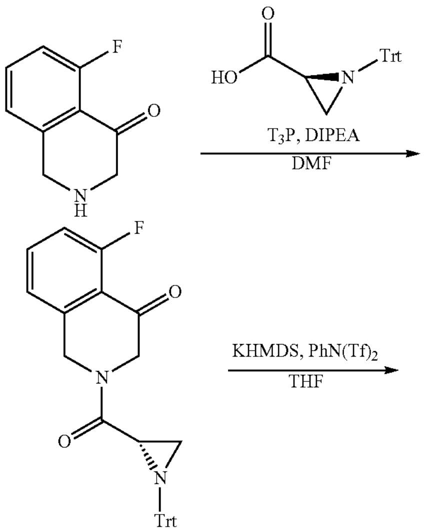

-continued

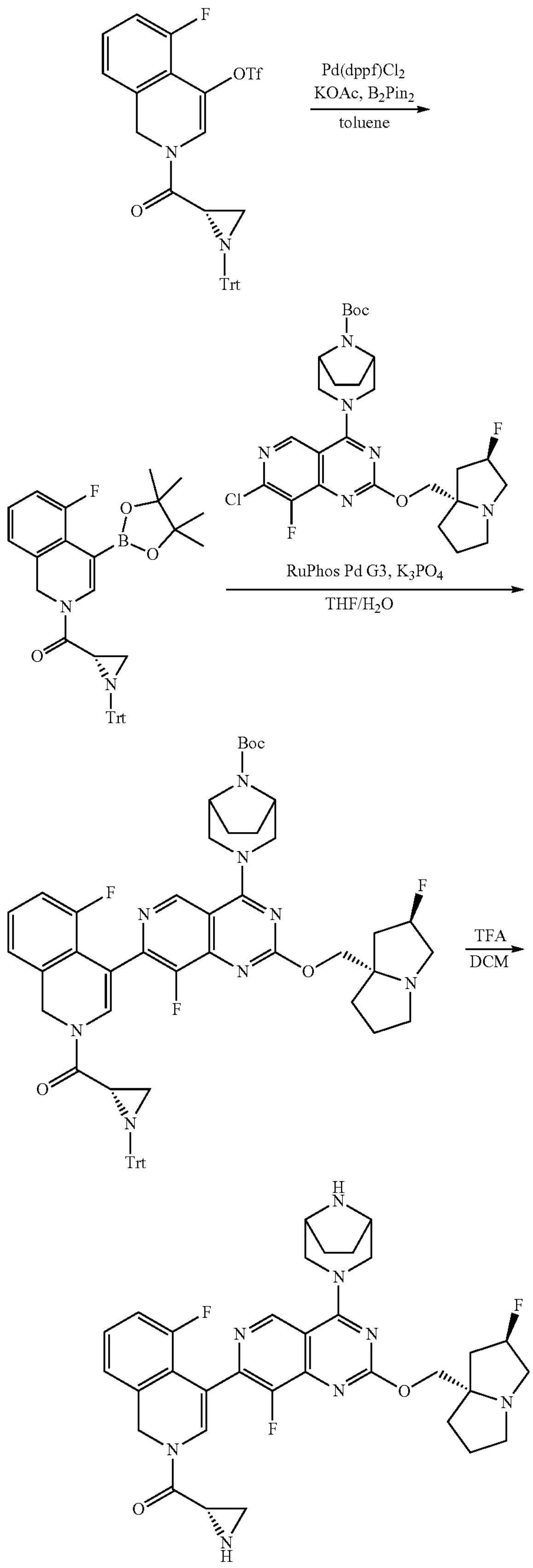

Step 1: Synthesis of (S)-5-fluoro-2-(1-tritylaziridine-2-carbonyl)-2,3-dihydroisoquinolin-4(1H)-one To a solution of 5-fluoro-2,3-dihydroisoquinolin-4(1H)-one (2 g, 9.92 mmol, HCl) in HMD (30 mL) at 0° C. was added (S)-1-tritylaziridine-2-carboxylic acid (6.53 g, 19.8 mmol) and $T_3P$ (9.47 g, 14.9 mmol) and DIPEA (8.6 mL, 49.6 mmol). The mixture was stirred at room temperature for 12 h and then the reaction mixture was quenched by the addition $H_2O$ (200 m. The aqueous phase was extracted with EtOAc (2×200 mL) and then combine organic layers were washed with brine (200 mL, dried over $Na_2SO_4$, filtered, and concentrated under reduced pressure. The residue was purified by silica gel chromatography (1% p50% EtOAc/pet. ether) to afford the desired product (950 mg, 71% yield) as a solid.

Step 2: Synthesis of (S)-5-fluoro-2-(1-tritylaziridine-2-carbonyl)-1,2-dihydroisoquinolin-4-yl trifluoromethanesulfonate Three reactions were run in parallel. To a solution of (S)-5-fluoro-2-(1-tritylaziridine-2-carbonyl)-2,3-dihydroisoquinolin-4(1H)-one (350 mg, 734.5 μmol) in THE (10 mL) at −78° C. was added KHMDS (1 M, 1.10 mL), dropwise, followed by a solution of N-phenyl-bis(trifluoromethanesulfonimide) (393.6 mg, 1.10 mmol) in THE (4 mL). The reaction mixture was stirred at −78° C. for 1 h and then the 3 reactions were combined and were quenched by addition $H_2O$ (70 mL). The aqueous layer was extracted with EtOAc (3×40 mL) and the combined organic layers were washed with brine (20 mL), dried over $Na_2SO_4$, filtered, and concentrated under reduced pressure. The residue was purified by silica gel chromatography (0%-*5% EtOAc/pet. ether) to afford the desired product (950 mg, 71% yield) as a solid.

Step 3: Synthesis of (S)-(5-fluoro-4-(4,4,5,5-tetramethyl-1,3,2-dioxaborolan-2-yl)isoquinolin-2(1H)-yl)(1-tritylaziridin-2-yl)methanone To a solution of bis(pinacolato)diboron (504.9 mg, 1.99 mmol) in toluene (20 mL) was added (S)-5-fluoro-2-(1-tritylaziridine-2-carbonyl)-1,2-dihydroisoquinolin-4-yl trifluoromethanesulfonate (1.1 g, 1.81 mmol), potassium acetate (443.5 mg, 4.5 mmol) and [1,1'-bis(diphenylphosphino)ferrocene]dichloropalladium(II) (132.3 mg, 180.7 μmol). The mixture was degassed and purged with $N_2$ 3 times. The mixture was stirred at 90° C. for 12 h and was then quenched by the addition of $H_2O$ (70 mL). The aqueous layer was extracted with EtOAc (3×40 mL) and the combined organic layers were washed with brine (1000 mL), dried over $Na_2SO_4$, filtered, and concentrated under reduced pressure. The residue was purified by silica gel chromatography (0%→5% EtOAc/pet. ether) to afford the desired product (1 g, 94% yield) as a solid.

Step 4: Synthesis of tert-butyl (1R,5S)-3-(8-fluoro-7-(5-fluoro-2-((S)-1-tritylaziridine-2-carbonyl)-1,2-dihydroisoquinolin-4-yl)-2-(((2R,7aS)-2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate To a solution of tert-butyl (1R,5S)-3-(7-chloro-8-fluoro-2-(((2R,7aS)-2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate (320 mg, 580.7 μmol) in THE (8 mL) and $H_2O$ (2 mL) was added RuPhos Pd G3 (52.6 mg, 58.1 μmol), $K_3PO_4$ (246.5 mg, 1.2 mmol), (S)-(5-fluoro-4-(4,4,5,5-tetramethyl-1,3,2-dioxaborolan-2-yl)isoquinolin-2(1H)-yl)(1-tritylaziridin-2-yl)methanone (851.5 mg, 1.45 mmol). The mixture was stirred at 80° C. for 12 h and was then quenched by addition $H_2O$ (15 mL). The aqueous layer was extracted with EtOAc (3×5 mL). The combined organic layers were washed with brine (10 mL), dried over $Na_2SO_4$, filtered, and concentrated under reduced. The residue was purified by silica gel chromatography (1%→50% EtOAc/pet. ether) to afford the desired product (330 mg, 58% yield) as a solid. LCMS (ESI) m/z [M+H] calcd for $C_{57}H_{57}F_3N_8O_4$ 975.46; found: 975.6.

Step 5: Synthesis of (4-(4-((1R,5S)-3,8-diazabicyclo[3.2.1]octan-3-yl)-8-fluoro-2-(((2R,7aS)-2-fluorotetrahydro-1H-pyrrolizin-7a(5H)-yl)methoxy)pyrido[4,3-d]pyrimidin-7-yl)-5-fluoroisoquinolin-2(1H)-yl)((S)-aziridin-2-yl)methanone Three reactions were run in parallel. To a solution of tert-butyl (1R,5S)-3-(8-fluoro-7-(5-fluoro-2-((R)-1-tritylaziridine-2-carbonyl)-1,2-dihydroisoquinolin-4-yl)-2-(((2R,7aS)-2-fluorotetrahydro-1H-pyrrolizin-7a(5H)-yl)methoxy)pyrido[4,3-d]pyrimidin-4-yl)-3,8-diazabicyclo[3.2.1]octane-8-carboxylate (100 mg, 102.55 μmol) in DCM (2.5 mL) at 0° C. was added TFA (2.5 mL, 33.77 mmol). The 3 reaction mixtures were stirred for 1 h and were then combined and diluted with aq. $NaHCO_3$ (10 mL) until pH 7. The aqueous layer was extracted with EtOAc (3×10 mL) and the combined organic layers were washed with aqueous brine (20 mL), dried over $Na_2SO_4$, filtered, and concentrated under reduced pressure. The residue was purified by reverse phase chromatography (5%→40% MeCN/$H_2O$) to afford the desired product (24 mg) as a solid. LCMS (ESI) m/z [M+H] calcd for $C_{33}H_{35}F_3N_8O_2$ 633.29; found: 633.4.

TABLE 2

Exemplary Compounds Prepared by Methods of the Present Invention

| Ex# | Molecular Formula | Calculated MW | Observed MW LCMS (ESI) m/z |
|---|---|---|---|
| B1 | $C_{34}H_{34}F_3N_7O_3$ | [M + H] = 646.28 | [M + H] = 646.3 |
| B2 | $C_{34}H_{34}F_3N_7O_3$ | [M + H] = 646.28 | [M + H] = 646.3 |
| B3 | $C_{34}H_{36}F_3N_7O_2$ | [M + H] = 632.30 | [M + H] = 632.3 |
| B4 | $C_{34}H_{36}F_3N_7O_2$ | [M + H] = 632.30 | [M + H] = 632.2 |
| B23 | $C_{33}H_{35}F_3N_8O_2$ | [M + H] = 633.29 | [M + H] = 633.4 |
| B24 | $C_{33}H_{35}F_3N_8O_2$ | [M + H] = 633.29 | [M + H] = 633.4 |

Example—Cross-Linking of Ras Proteins with Compounds of the Invention to Form Conjugates Protocol: K-Ras G12D(GDP) Cross-Linking Assay
Note: While the Following Protocol Outlines the Procedure for K-Ras G12D(GDP), a Person of Skill in the Art May Substitute Other Ras Proteins, and May Also Substitute a Non-Hydrolyzable GTP Analog for GDP to Study GTP Bound Ras Protein.

GDP-loaded K-Ras (1-169) G12D, C51S, C80L, C118S and GDP-loaded K-Ras (1-169) C51S, C80L, C118S were adjusted to 50 μM in K-Ras assay buffer (12.5 mM HEPES, 75 mM NaCl and 1 mM $MgCl_2$ at pH 7.4). A 5 μL aliquot of each protein solution was added to each well of a 96-well microplate containing 40 μL of assay buffer. Initial compound stocks were prepared in DMSO at 100 times their final assay concentration. Compounds were then diluted 10-fold into K-Ras assay buffer to 10 times their final concentration. A 5 μL aliquot of each diluted compound solution was added to each protein solution in the 96-well microplate to initiate the reaction, which then proceeded at room temperature. Typical final compound concentrations were 2, 10, and 25 μM. At each time point, the reactions were analyzed immediately or quenched with 5 μL of a 5% formic acid solution and kept at 4° C. until analysis. Typical assay endpoints were 1, 6 and 24 h.

Data collection took place on an Agilent 6230 TOF Mass Spectrometer. Complete reactions were injected onto a C4 reverse-phase column to separate protein from buffer components prior to entering the mass spectrometer. The proteins were eluted from the column by increasing acetonitrile fraction in the mobile phase and fed directly into the mass analyzer. Initial analysis of raw data took place on Agilent MassHunter BioConfirm software and consisted of deconvolution of multiple protein charge states with the maximum entropy algorithm, with a mass step of 1 Da. The heights of all deconvoluted protein masses were exported for further data analysis. The percent modification of each protein was then determined by calculating the peak height of the covalently modified K-Ras species as a percentage of the sum total of K-Ras protein peak height.

Compounds B1, B2, B4, B23 and B24 exhibited no cross-linking to K-Ras G12D at times up to 24 hours. Compound B3 exhibited greater than 0% cross-linking to K-Ras G12D at 24 hours.

Those skilled in the art will recognize or be able to ascertain, using no more than routine experimentation, many equivalents to the specific embodiments in accordance with the invention described herein. The scope of the present invention is not intended to be limited to the foregoing description, but rather is as set forth in the appended claims. Moreover, it is to be understood that while the present disclosure has been described in conjunction with the detailed description thereof, the foregoing description is intended to illustrate and not limit the scope of the present disclosure, which is defined by the scope of the appended claims. Other aspects, advantages, and alterations are within the scope of the following claims.

SEQUENCE LISTING

```
Sequence total quantity: 3
SEQ ID NO: 1          moltype = AA  length = 189
FEATURE               Location/Qualifiers
source                1..189
                      mol_type = protein
                      organism = Homo sapiens
SEQUENCE: 1
MTEYKLVVVG AGGVGKSALT IQLIQNHFVD EYDPTIEDSY RKQVVIDGET CLLDILDTAG  60
QEEYSAMRDQ YMRTGEGFLC VFAINNTKSF EDIHHYREQI KRVKDSEDVP MVLVGNKCDL  120
PSRTVDTKQA QDLARSYGIP FIETSAKTRQ RVEDAFYTLV REIRQYRLKK ISKEEKTPGC  180
VKIKKCIIM                                                          189

SEQ ID NO: 2          moltype = AA  length = 189
FEATURE               Location/Qualifiers
source                1..189
                      mol_type = protein
                      organism = Homo sapiens
SEQUENCE: 2
MTEYKLVVVG AGGVGKSALT IQLIQNHFVD EYDPTIEDSY RKQVVIDGET CLLDILDTAG  60
QEEYSAMRDQ YMRTGEGFLC VFAINNTKSF EDIHQYREQI KRVKDSDDVP MVLVGNKCDL  120
AARTVESRQA QDLARSYGIP YIETSAKTRQ GVEDAFYTLV REIRQHKLRK LNPPDESGPG  180
CMSCKCVLS                                                          189

SEQ ID NO: 3          moltype = AA  length = 189
FEATURE               Location/Qualifiers
source                1..189
                      mol_type = protein
                      organism = Homo sapiens
SEQUENCE: 3
MTEYKLVVVG AGGVGKSALT IQLIQNHFVD EYDPTIEDSY RKQVVIDGET CLLDILDTAG  60
QEEYSAMRDQ YMRTGEGFLC VFAINNSKSF ADINLYREQI KRVKDSDDVP MVLVGNKCDL  120
PTRTVDTKQA HELAKSYGIP FIETSAKTRQ GVEDAFYTLV REIRQYRMKK LNSSDDGTQG  180
CMGLPCVVM                                                          189
```

The invention claimed is:

1. A compound, or a pharmaceutically acceptable salt thereof, having the structure of Formula (I0), Formula (II0), Formula (III0) or Formula (IV0):

(I0)

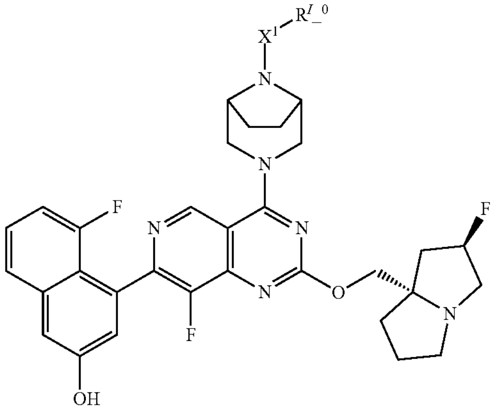

(II0)

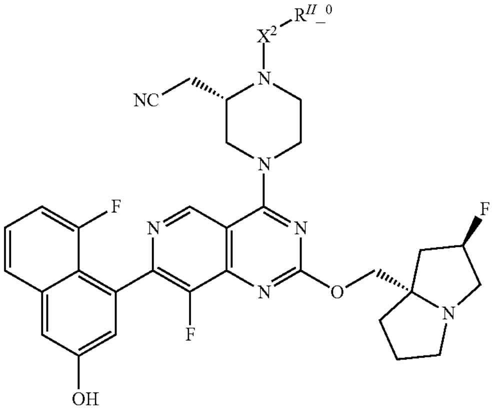

(III0)

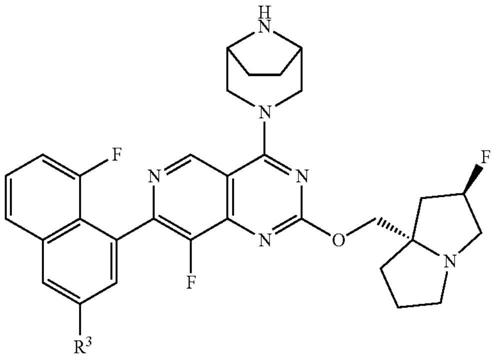

-continued (IV0)

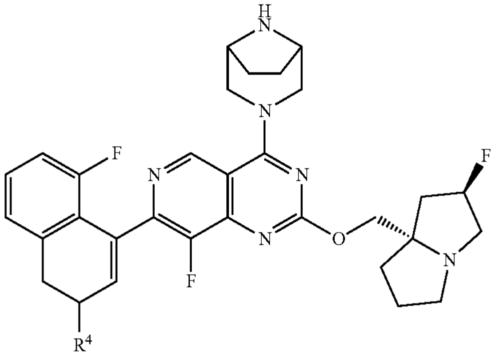

or a pharmaceutically acceptable salt thereof, wherein:

$R^{I\_0}$ is optionally substituted aziridine or optionally substituted epoxide;

$R^{II\_0}$ is optionally substituted aziridine or optionally substituted epoxide;

$X^1$ is selected from —C(O)— and —$CH_2$—;

$X^2$ is selected from —C(O)— and —$CH_2$—;

$Y^1$ is selected from —O— and —NH—;

$Y^2$ is selected from —O— and —NH—;

$R^3$ is optionally substituted aziridine or optionally substituted epoxide; and $R^4$ is optionally substituted aziridine or optionally substituted epoxide, wherein the compound is not

B1

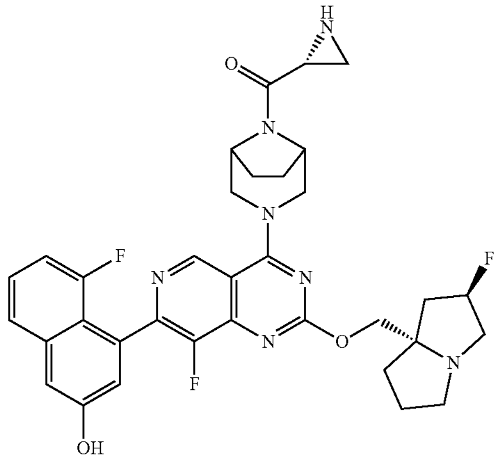

-continued
B2
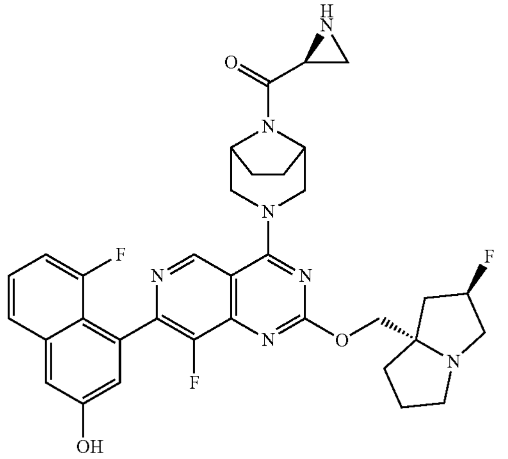
B4
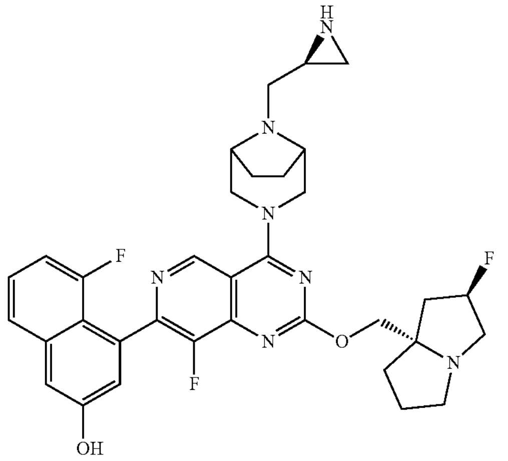
B23
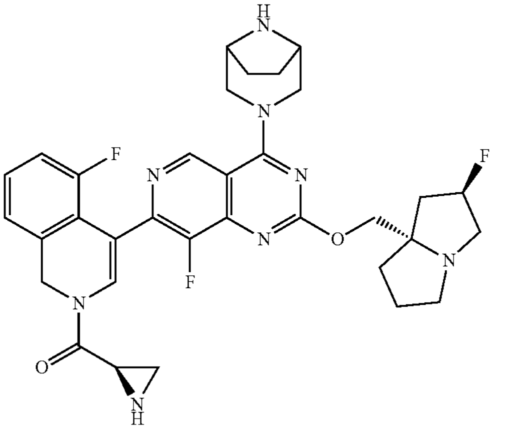
-continued
B24
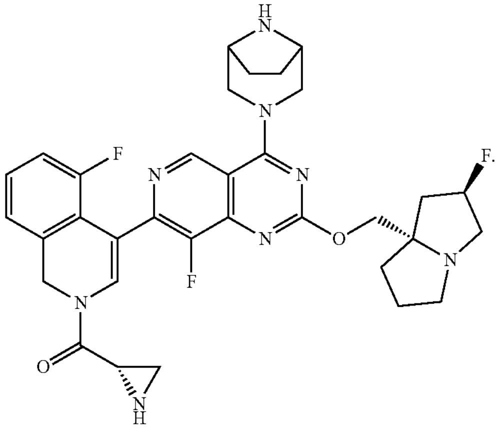
2. The compound of claim 1, or a pharmaceutically acceptable salt thereof, wherein $R^{I\_0}$, $R^{II\_0}$, $R^3$ and $R^4$ are each independently selected from the following, or a stereoisomer thereof:
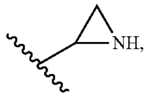,
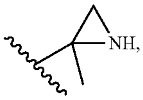,
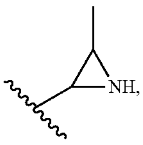,
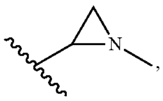,
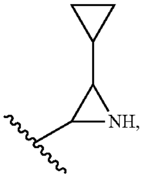,
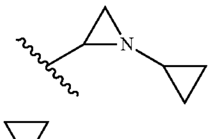,
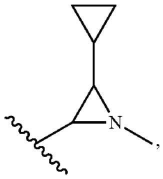,
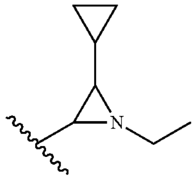,
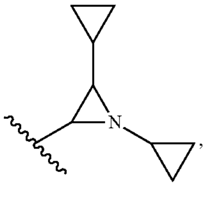,
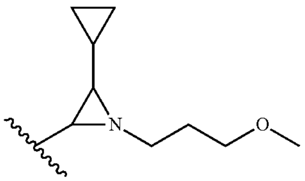,
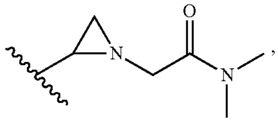,
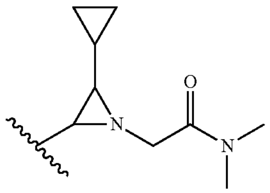,
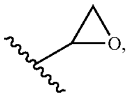,
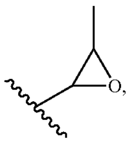, and
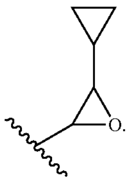.

3. The compound of claim 1 having the structure of Formula (I), Formula (II), Formula (III), or Formula (IV):

(I)

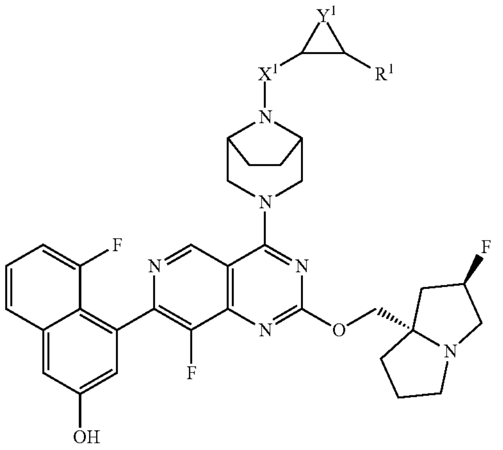

(II)

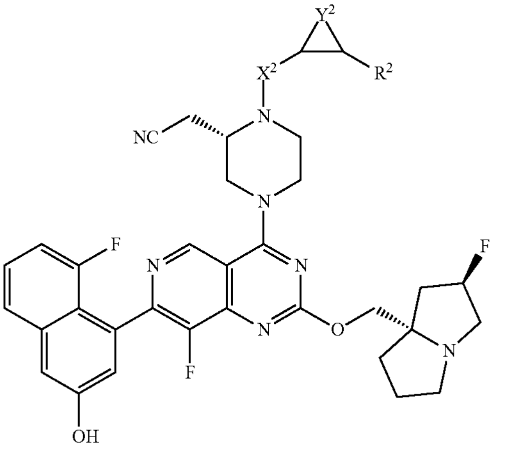

(III)

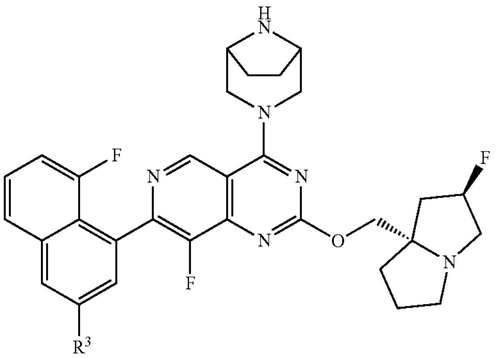

-continued (IV)

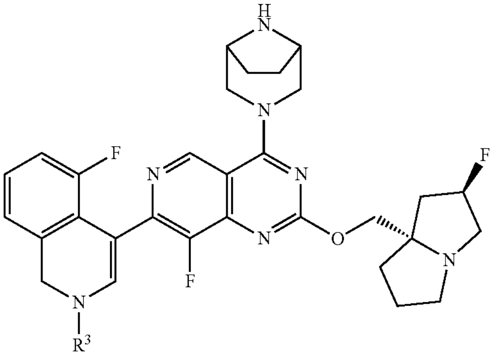

or a pharmaceutically acceptable salt thereof, wherein:

$R^1$ is selected from H and cyclopropyl;

$R^2$ is selected from H and cyclopropyl;

$X^1$ is selected from —C(O)— and —$CH_2$—;

$X^2$ is selected from —C(O)— and —$CH_2$—;

$Y^1$ is selected from —O—, —NH—, —$N(CH_3)$, —$N(CH_2CH_3)$, —N(cyclopropyl), and —N($C_1$-$C_6$ heteroalkyl);

$Y^2$ is selected from —O—, —NH—, —$N(CH_3)$, —$N(CH_2CH_3)$, —N(cyclopropyl), and —N($C_1$-$C_6$ heteroalkyl);

$R^3$ is selected from:

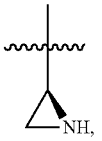 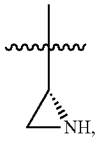 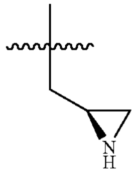 and 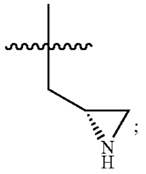 ;

and $R^4$ is selected from:

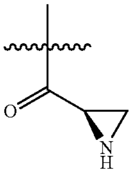 and 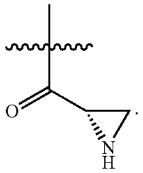 .

4. The compound of claim 3, or a pharmaceutically acceptable salt thereof, wherein $R^1$ and $R^2$ are each, independently, selected from

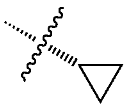 and 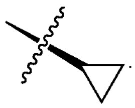 .

5. The compound of claim 1, or a pharmaceutically acceptable salt thereof, wherein the compound is selected from:

| # | Structure |
|---|---|
| B1 | 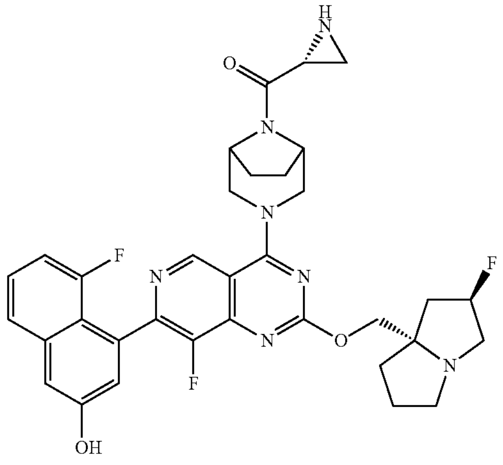 [SMILES: O=C([C@H]1CN1)N1C2CCC1CN(c1nc(OC[C@@]34CCCN3C[C@H](F)C4)nc3c(F)c(-c4cc(O)cc5cccc(F)c45)ncc13)C2] |
| B2 | 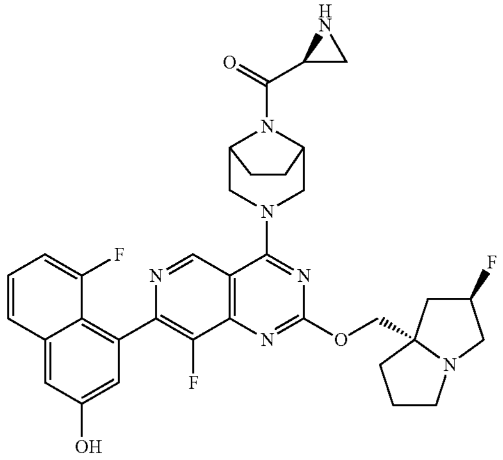 [SMILES: O=C([C@@H]1CN1)N1C2CCC1CN(c1nc(OC[C@@]34CCCN3C[C@H](F)C4)nc3c(F)c(-c4cc(O)cc5cccc(F)c45)ncc13)C2] |
| B3 | 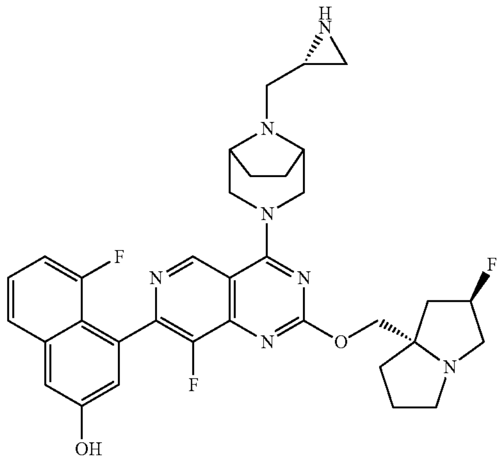 [SMILES: Oc1cc(-c2ncc3c(N4CC5CCC(C4)N5C[C@H]4CN4)nc(OC[C@@]45CCCN4C[C@H](F)C5)nc3c2F)c2c(F)cccc2c1] |
-continued
| # | Structure |
|---|---|
| B4 | 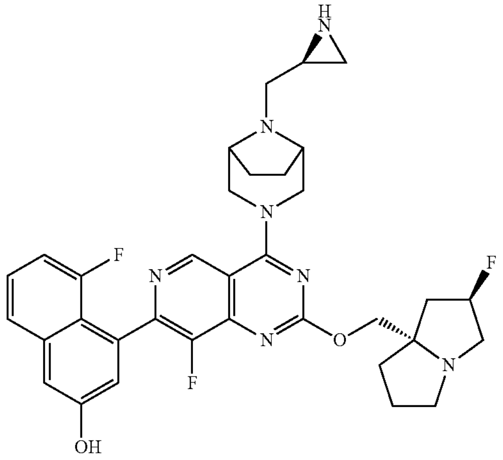 [SMILES: Oc1cc(-c2ncc3c(N4CC5CCC(C4)N5C[C@@H]4CN4)nc(OC[C@@]45CCCN4C[C@H](F)C5)nc3c2F)c2c(F)cccc2c1] |
| B5 | 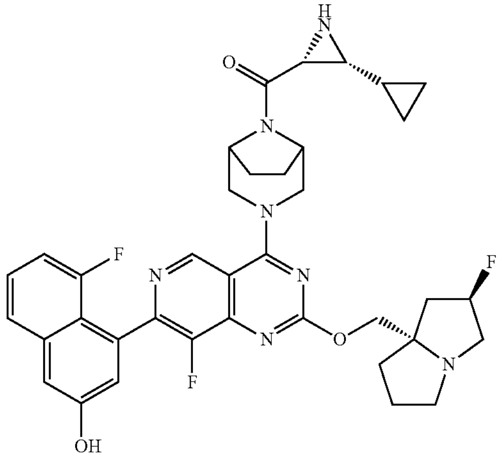 [SMILES: O=C([C@@H]1N[C@@H]1C1CC1)N1C2CCC1CN(c1nc(OC[C@@]34CCCN3C[C@H](F)C4)nc3c(F)c(-c4cc(O)cc5cccc(F)c45)ncc13)C2] |
| B6 | 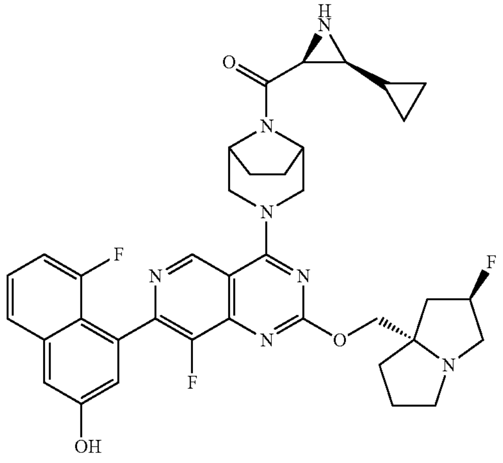 [SMILES: O=C([C@H]1N[C@H]1C1CC1)N1C2CCC1CN(c1nc(OC[C@@]34CCCN3C[C@H](F)C4)nc3c(F)c(-c4cc(O)cc5cccc(F)c45)ncc13)C2] |

-continued
| # | Structure |
| --- | --- |
| B7 | 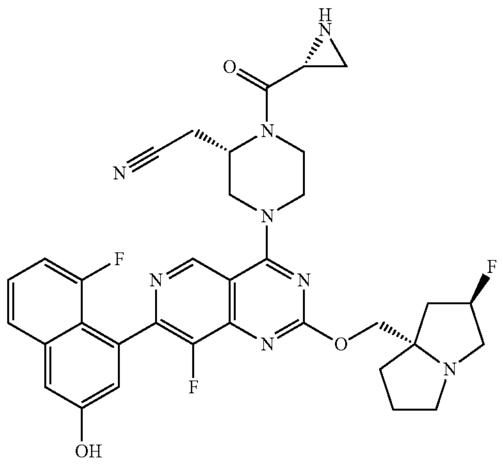 [SMILES: N#CC[C@H]1CN(c2nc(OC[C@@]34CCCN3C[C@H](F)C4)nc3c(F)c(-c4cc(O)cc5cccc(F)c45)ncc23)CCN1C(=O)[C@H]1CN1] |
| B8 | 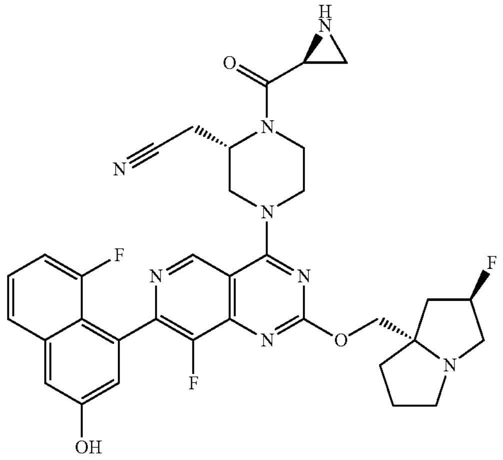 [SMILES: N#CC[C@H]1CN(c2nc(OC[C@@]34CCCN3C[C@H](F)C4)nc3c(F)c(-c4cc(O)cc5cccc(F)c45)ncc23)CCN1C(=O)[C@@H]1CN1] |
| B9 | 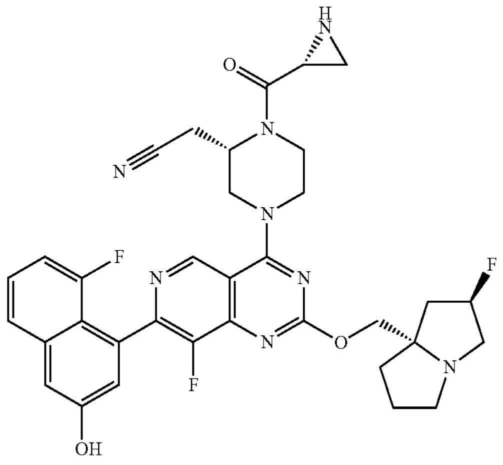 [SMILES: N#CC[C@H]1CN(c2nc(OC[C@@]34CCCN3C[C@H](F)C4)nc3c(F)c(-c4cc(O)cc5cccc(F)c45)ncc23)CCN1C(=O)[C@H]1CN1] |
-continued
| # | Structure |
| --- | --- |
| B10 | 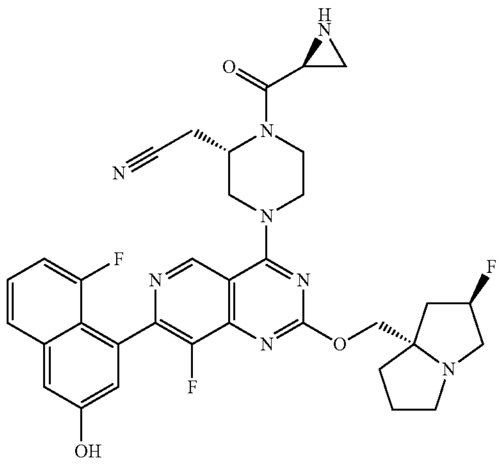 [SMILES: N#CC[C@H]1CN(c2nc(OC[C@@]34CCCN3C[C@H](F)C4)nc3c(F)c(-c4cc(O)cc5cccc(F)c45)ncc23)CCN1C(=O)[C@@H]1CN1] |
| B11 | 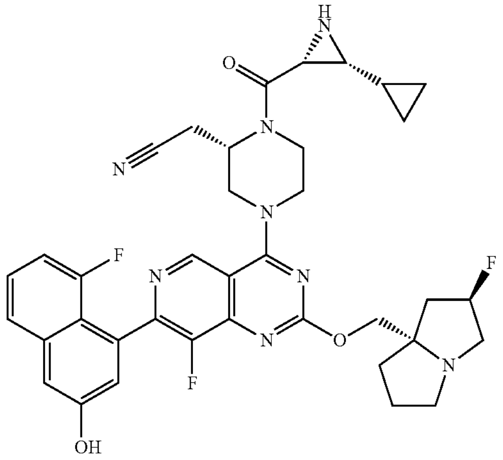 [SMILES: N#CC[C@H]1CN(c2nc(OC[C@@]34CCCN3C[C@H](F)C4)nc3c(F)c(-c4cc(O)cc5cccc(F)c45)ncc23)CCN1C(=O)[C@@H]1N[C@@H]1C1CC1] |
| B12 | 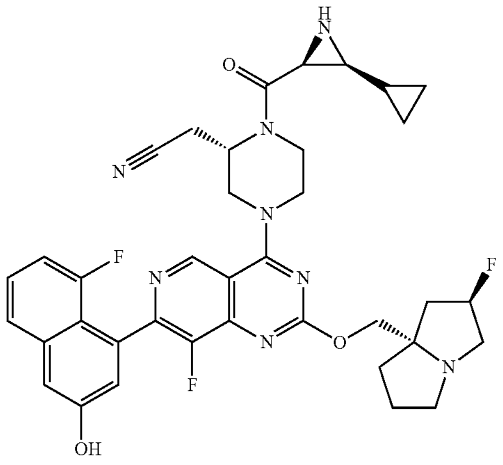 [SMILES: N#CC[C@H]1CN(c2nc(OC[C@@]34CCCN3C[C@H](F)C4)nc3c(F)c(-c4cc(O)cc5cccc(F)c45)ncc23)CCN1C(=O)[C@H]1N[C@H]1C1CC1] |

-continued
| # | Structure |
| --- | --- |
| B13 | 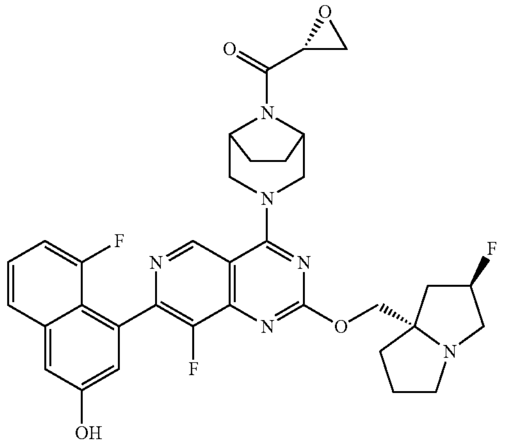 [SMILES: O=C([C@H]1CO1)N1C2CCC1CN(c1nc(OC[C@@]34CCCN3C[C@H](F)C4)nc3c(F)c(-c4cc(O)cc5cccc(F)c45)ncc13)C2] |
| B14 | 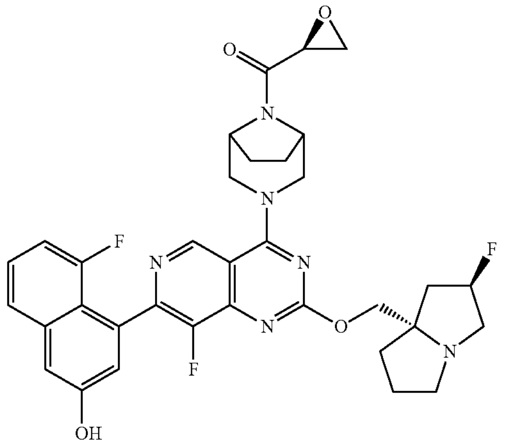 [SMILES: O=C([C@@H]1CO1)N1C2CCC1CN(c1nc(OC[C@@]34CCCN3C[C@H](F)C4)nc3c(F)c(-c4cc(O)cc5cccc(F)c45)ncc13)C2] |
| B15 | 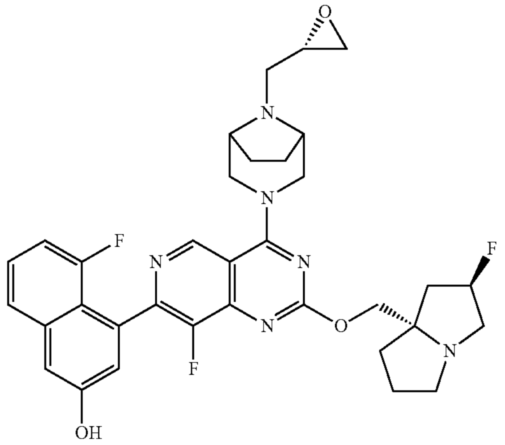 [SMILES: Oc1cc(-c2ncc3c(N4CC5CCC(C4)N5C[C@H]4CO4)nc(OC[C@@]45CCCN4C[C@H](F)C5)nc3c2F)c2c(F)cccc2c1] |
-continued
| # | Structure |
| --- | --- |
| B16 | 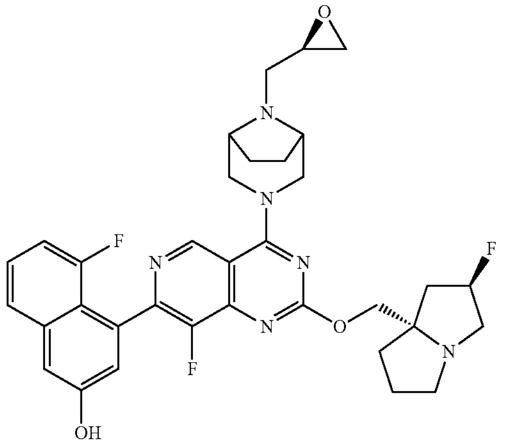 [SMILES: Oc1cc(-c2ncc3c(N4CC5CCC(C4)N5C[C@@H]4CO4)nc(OC[C@@]45CCCN4C[C@H](F)C5)nc3c2F)c2c(F)cccc2c1] |
| B17 | 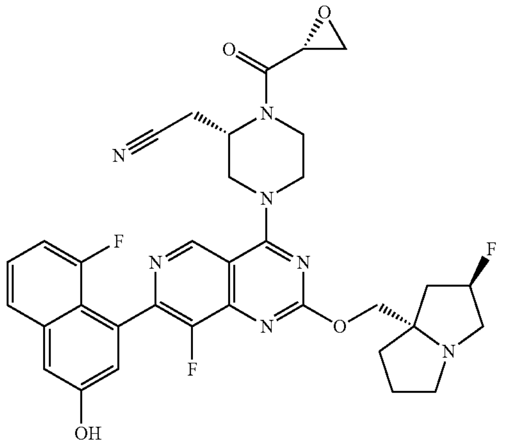 [SMILES: N#CC[C@H]1CN(c2nc(OC[C@@]34CCCN3C[C@H](F)C4)nc3c(F)c(-c4cc(O)cc5cccc(F)c45)ncc23)CCN1C(=O)[C@H]1CO1] |
| B18 | 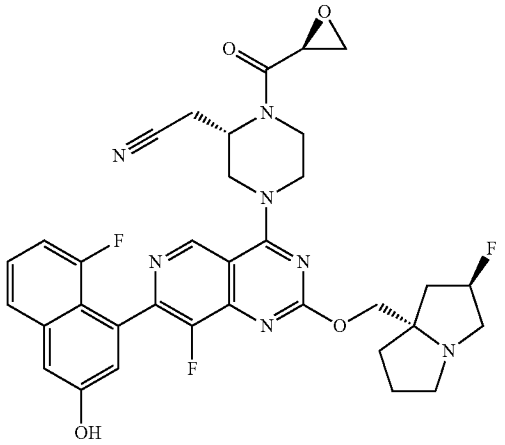 [SMILES: N#CC[C@H]1CN(c2nc(OC[C@@]34CCCN3C[C@H](F)C4)nc3c(F)c(-c4cc(O)cc5cccc(F)c45)ncc23)CCN1C(=O)[C@@H]1CO1] |

-continued
| # | Structure |
|---|---|
| B19 | 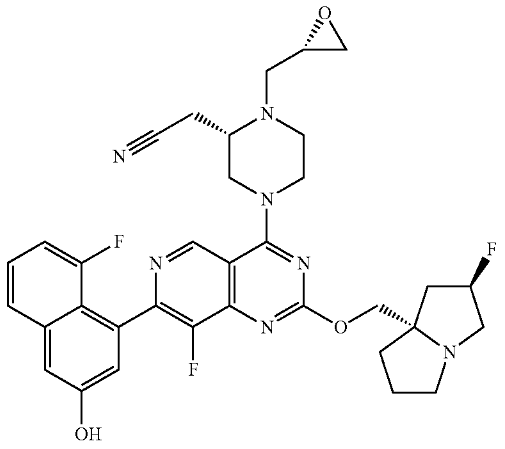 [SMILES: N#CC[C@H]1CN(c2nc(OC[C@@]34CCCN3C[C@H](F)C4)nc3c(F)c(-c4cc(O)cc5cccc(F)c45)ncc23)CCN1C[C@H]1CO1] |
| B20 | 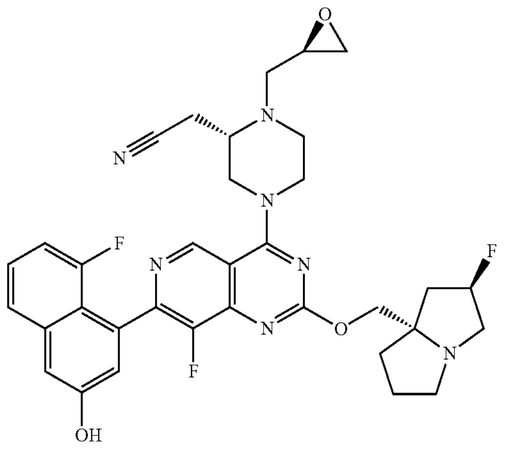 [SMILES: N#CC[C@H]1CN(c2nc(OC[C@@]34CCCN3C[C@H](F)C4)nc3c(F)c(-c4cc(O)cc5cccc(F)c45)ncc23)CCN1C[C@@H]1CO1] |
| B21 | 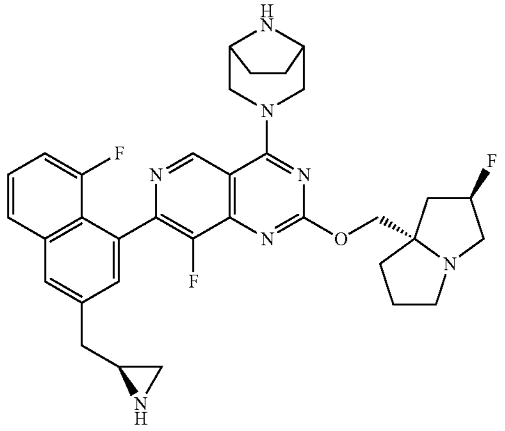 [SMILES: Fc1c(-c2cc(C[C@H]3CN3)cc3cccc(F)c23)ncc2c(N3CC4CCC(C3)N4)nc(OC[C@@]34CCCN3C[C@H](F)C4)nc12] |
-continued
| # | Structure |
|---|---|
| B22 | 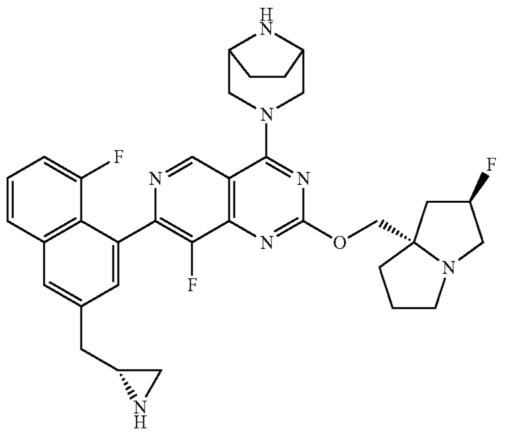 [SMILES: Fc1c(-c2cc(C[C@@H]3CN3)cc3cccc(F)c23)ncc2c(N3CC4CCC(C3)N4)nc(OC[C@@]34CCCN3C[C@H](F)C4)nc12] |
| B23 | 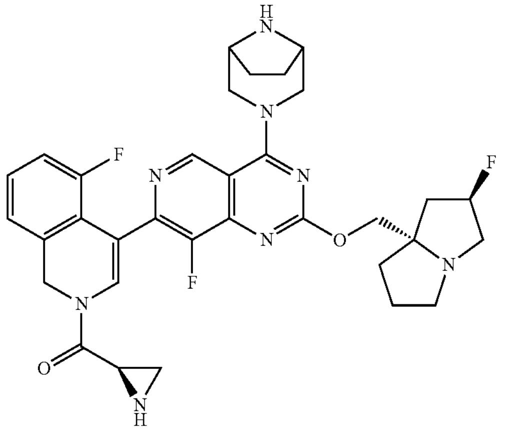 [SMILES: O=C([C@H]1CN1)N1C=C(c2ncc3c(N4CC5CCC(C4)N5)nc(OC[C@@]45CCCN4C[C@H](F)C5)nc3c2F)c2c(F)cccc2C1] |
| B24 | 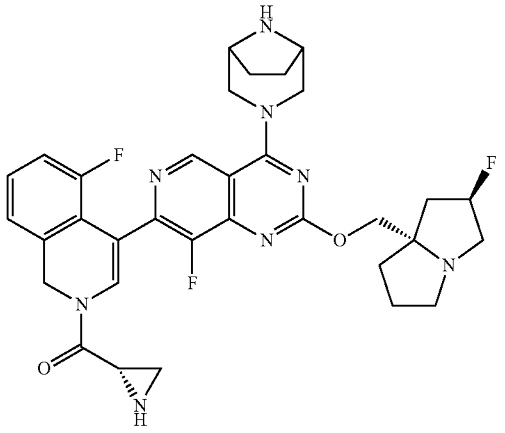 [SMILES: O=C([C@@H]1CN1)N1C=C(c2ncc3c(N4CC5CCC(C4)N5)nc(OC[C@@]45CCCN4C[C@H](F)C5)nc3c2F)c2c(F)cccc2C1] |

-continued

| # | Structure |
| --- | --- |
| B25 | 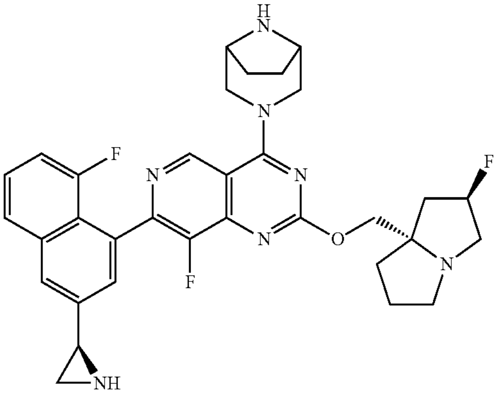 [SMILES: Fc1c(-c2cc([C@@H]3CN3)cc3cccc(F)c23)ncc2c(N3CC4CCC(C3)N4)nc(OC[C@@]34CCCN3C[C@H](F)C4)nc12] |
| B26 | 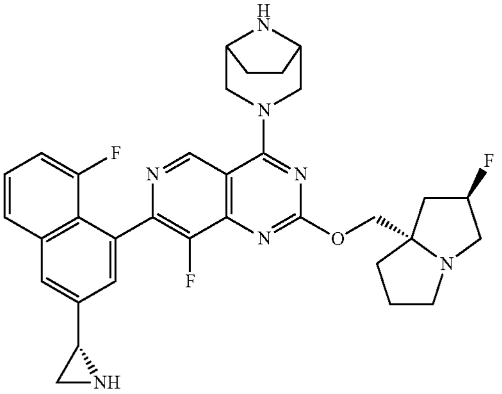 [SMILES: Fc1c(-c2cc([C@H]3CN3)cc3cccc(F)c23)ncc2c(N3CC4CCC(C3)N4)nc(OC[C@@]34CCCN3C[C@H](F)C4)nc12] |

6. A pharmaceutical composition comprising a compound, or a pharmaceutically acceptable salt thereof, of claim 1, or a pharmaceutically acceptable salt thereof, and a pharmaceutically acceptable excipient.

7. A conjugate, or a salt thereof, comprising a Ras protein covalently bound to a compound of claim 1.

8. The conjugate of claim 7, or a salt thereof, wherein the Ras protein is selected from an inhibited Ras protein, a wild-type Ras protein, or a mutated Ras protein.

9. A method of producing a conjugate, or a salt thereof, comprising contacting a Ras protein with a compound of claim 1, or a pharmaceutically acceptable salt thereof, under conditions sufficient for the compound to react covalently with the Ras protein, or under conditions suitable to permit conjugate formation.

10. The method of claim 9, wherein the compound forms a covalent bond with an aspartic acid or a glutamic acid at the 12 position or the 13 position of a mutant K-Ras, mutant H-Ras or mutant N-Ras protein.

11. The method of claim 10, wherein the compound forms a covalent bond with the aspartic acid residue at position 12 of K-Ras G12D.

12. The method of claim 10, wherein the compound forms a covalent bond with the aspartic acid residue at position 13 of K-Ras G13D.

13. The method of claim 10, wherein the compound forms a covalent bond with the glutamic acid residue at position 12 of K-Ras G12E.

14. The method of claim 10, wherein the compound forms a covalent bond with the glutamic acid residue at position 13 of K-Ras G13E.

* * * * *